(12) United States Patent
Nelson et al.

(10) Patent No.: US 8,961,516 B2
(45) Date of Patent: *Feb. 24, 2015

(54) STRAIGHT INTRAMEDULLARY FRACTURE FIXATION DEVICES AND METHODS

(75) Inventors: Charles L. Nelson, Santa Rosa, CA (US); Stephen R. McDaniel, San Francisco, CA (US); Vernon R. Hartdegen, Jr., Collierville, TN (US); Trung Ho Pham, Santa Rosa, CA (US); Darryll Leonard Charles Fletcher, Forestville, CA (US); Nathan D. Brown, Santa Rosa, CA (US)

(73) Assignee: Sonoma Orthopedic Products, Inc., Santa Rosa, CA (US)

( * ) Notice: Subject to any disclaimer, the term of this patent is extended or adjusted under 35 U.S.C. 154(b) by 161 days.

This patent is subject to a terminal disclaimer.

(21) Appl. No.: 13/615,078

(22) Filed: Sep. 13, 2012

(65) Prior Publication Data

US 2013/0116693 A1    May 9, 2013
US 2014/0074093 A9    Mar. 13, 2014

Related U.S. Application Data

(63) Continuation-in-part of application No. 13/203,713, filed as application No. PCT/US2009/058632 on Sep. 28, 2009, application No. 13/615,078, which is a continuation-in-part of application No. 12/965,480, (Continued)

(51) Int. Cl.
*A61B 17/56* (2006.01)
*A61B 17/72* (2006.01)
(Continued)

(52) U.S. Cl.
CPC .......... *A61B 17/7233* (2013.01); *A61B 17/1725* (2013.01); *A61B 17/7266* (2013.01); *A61B 17/7208* (2013.01); *A61B 2019/301* (2013.01)
USPC .......................................... 606/64

(58) Field of Classification Search
CPC ........... A61B 17/7266; A61B 17/7285; A61B 17/7233
USPC ..................................................... 606/62–68
See application file for complete search history.

(56) References Cited

U.S. PATENT DOCUMENTS 958,127 A    5/1910   Hufrud
1,169,635 A    1/1916   Grimes
(Continued)

FOREIGN PATENT DOCUMENTS

CA    2561552 A1    11/2005
EP    1582163 A1    11/2003
(Continued)

OTHER PUBLICATIONS

Andermahr et al., "Anatomy of the clavicle and the intramedullary nailing of midclavicular fractures," Clinical Anatomy, vol. 20; pp. 48-56; 2007.

(Continued)

*Primary Examiner* — Eduardo C Robert
*Assistant Examiner* — Stuart S Bray
(74) *Attorney, Agent, or Firm* — Knobbe, Martens, Olson & Bear, LLP

(57) ABSTRACT

A straight intramedullary bone fracture fixation device is provided with an elongate body having a longitudinal axis for deployment in a long bone, such as a clavicle. Methods of repairing a fracture of a bone are also disclosed. One such method comprises inserting a bone fixation device into an intramedullary space of the bone to place at least a portion of an elongate body of the fixation device on one side of the fracture and at least a portion of a hub on another side of the fracture, and engaging an inner surface of the intramedullary space to anchor the fixation device to the bone. Various configurations and designs may be used in combination with other fixation device components.

19 Claims, 82 Drawing Sheets

Related U.S. Application Data filed on Dec. 10, 2010, now abandoned, which is a continuation of application No. PCT/US2009/046951, filed on Jun. 10, 2009, application No. 13/615,078, which is a continuation-in-part of application No. 12/642,648, filed on Dec. 18, 2009, now Pat. No. 8,568,413, application No. 13/615,078, which is a continuation-in-part of application No. 12/482,406, filed on Jun. 10, 2009, now Pat. No. 8,287,541, and a continuation-in-part of application No. 11/944,366, filed on Nov. 21, 2007, now Pat. No. 7,909,825.

(60) Provisional application No. 61/553,059, filed on Oct. 28, 2011, provisional application No. 61/138,920, filed on Dec. 18, 2008, provisional application No. 61/122,563, filed on Dec. 15, 2008, provisional application No. 61/117,901, filed on Nov. 25, 2008, provisional application No. 61/100,652, filed on Sep. 26, 2008, provisional application No. 61/100,635, filed on Sep. 26, 2008, provisional application No. 61/060,450, filed on Jun. 10, 2008, provisional application No. 61/060,445, filed on Jun. 10, 2008, provisional application No. 61/060,440, filed on Jun. 10, 2008, provisional application No. 60/949,071, filed on Jul. 11, 2007, provisional application No. 60/867,011, filed on Nov. 22, 2006.

(51) Int. Cl.
*A61B 17/17* (2006.01)
*A61B 19/00* (2006.01)

(56) References Cited

U.S. PATENT DOCUMENTS

| | | |
|---|---|---|
| 1,790,841 A | 2/1931 | Rosen |
| 2,502,267 A | 3/1950 | McPherson |
| 2,685,877 A | 8/1954 | Dobelle |
| 2,998,007 A | 8/1961 | Herzog |
| 3,118,444 A | 1/1964 | Serrato, Jr. |
| 3,441,017 A | 4/1969 | Kaessmann |
| 3,626,935 A | 12/1971 | Pollock et al. |
| 3,710,789 A | 1/1973 | Ersek |
| 3,759,257 A | 9/1973 | Fischer et al. |
| 3,760,802 A | 9/1973 | Fischer et al. |
| 3,779,239 A | 12/1973 | Fischer et al. |
| 3,791,380 A | 2/1974 | Dawidowski |
| 3,846,846 A | 11/1974 | Fischer |
| 3,955,565 A | 5/1976 | Johnson, Jr. |
| 3,978,528 A | 9/1976 | Crep |
| 3,986,504 A | 10/1976 | Avila |
| 4,007,528 A | 2/1977 | Shea et al. |
| 4,011,602 A | 3/1977 | Rybicki et al. |
| 4,016,874 A | 4/1977 | Maffei et al. |
| 4,050,464 A | 9/1977 | Hall |
| 4,064,567 A | 12/1977 | Burstein et al. |
| 4,065,816 A | 1/1978 | Sawyer |
| 4,091,806 A | 5/1978 | Aginsky |
| 4,146,022 A | 3/1979 | Johnson et al. |
| 4,164,794 A | 8/1979 | Spector et al. |
| 4,190,044 A | 2/1980 | Wood |
| D255,048 S | 5/1980 | Miller |
| 4,204,531 A | 5/1980 | Aginsky |
| 4,227,518 A | 10/1980 | Aginsky |
| 4,236,512 A | 12/1980 | Aginsky |
| 4,237,875 A | 12/1980 | Termanini |
| 4,246,662 A | 1/1981 | Pastrick |
| 4,262,665 A | 4/1981 | Roalstad et al. |
| 4,275,717 A | 6/1981 | Bolesky |
| 4,293,962 A | 10/1981 | Fuson |
| 4,294,251 A | 10/1981 | Greenwald et al. |
| 4,312,336 A | 1/1982 | Danieletto et al. |
| 4,313,434 A | 2/1982 | Segal |
| 4,338,926 A | 7/1982 | Kummer et al. |
| 4,351,069 A | 9/1982 | Ballintyn et al. |
| 4,352,212 A | 10/1982 | Greene et al. |
| 4,353,358 A | 10/1982 | Emerson |
| 4,379,451 A | 4/1983 | Getscher |
| 4,409,974 A | 10/1983 | Freedland |
| 4,453,539 A | 6/1984 | Raftopoulos et al. |
| 4,457,301 A | 7/1984 | Walker |
| 4,459,708 A | 7/1984 | Buttazzoni |
| 4,462,394 A | 7/1984 | Jacobs |
| 4,467,794 A | 8/1984 | Maffei et al. |
| RE31,809 E | 1/1985 | Danieletto et al. |
| 4,492,226 A | 1/1985 | Belykh et al. |
| 4,503,847 A | 3/1985 | Mouradian |
| 4,519,100 A | 5/1985 | Wills et al. |
| 4,520,511 A | 6/1985 | Gianezio et al. |
| 4,522,200 A | 6/1985 | Stednitz |
| 4,541,423 A | 9/1985 | Barber |
| 4,552,136 A | 11/1985 | Kenna |
| 4,589,883 A | 5/1986 | Kenna |
| 4,590,930 A | 5/1986 | Kurth et al. |
| 4,604,997 A | 8/1986 | De Bastiani et al. |
| 4,621,627 A | 11/1986 | De Bastiani et al. |
| 4,622,959 A | 11/1986 | Marcus |
| 4,624,673 A | 11/1986 | Meyer |
| 4,628,920 A | 12/1986 | Mathys, Jr. et al. |
| 4,632,101 A | 12/1986 | Freedland |
| 4,643,177 A | 2/1987 | Sheppard et al. |
| 4,651,724 A | 3/1987 | Berentey et al. |
| 4,653,487 A | 3/1987 | Maale |
| 4,662,887 A | 5/1987 | Turner et al. |
| 4,667,663 A | 5/1987 | Miyata |
| D290,399 S | 6/1987 | Kitchens |
| 4,681,590 A | 7/1987 | Tansey |
| 4,697,585 A | 10/1987 | Williams |
| 4,705,027 A | 11/1987 | Klaue |
| 4,705,032 A | 11/1987 | Keller |
| 4,721,103 A | 1/1988 | Freedland |
| 4,735,625 A | 4/1988 | Davidson |
| 4,753,657 A | 6/1988 | Lee et al. |
| 4,776,330 A | 10/1988 | Chapman et al. |
| 4,781,181 A | 11/1988 | Tanguy |
| 4,805,595 A | 2/1989 | Kanbara |
| 4,805,607 A | 2/1989 | Engelhardt et al. |
| 4,813,963 A | 3/1989 | Hori et al. |
| 4,817,591 A | 4/1989 | Klaue et al. |
| 4,827,919 A | 5/1989 | Barbarito et al. |
| 4,828,277 A | 5/1989 | De Bastiani et al. |
| 4,854,312 A | 8/1989 | Raftopoulos et al. |
| 4,858,602 A | 8/1989 | Seidel et al. |
| 4,862,883 A | 9/1989 | Freeland |
| 4,871,369 A | 10/1989 | Muller |
| 4,875,474 A | 10/1989 | Border |
| 4,875,475 A | 10/1989 | Comte et al. |
| 4,896,662 A | 1/1990 | Noble |
| 4,921,499 A | 5/1990 | Hoffman et al. |
| 4,927,424 A | 5/1990 | McConnell et al. |
| 4,932,969 A | 6/1990 | Frey et al. |
| 4,943,291 A | 7/1990 | Tanguy |
| 4,946,179 A | 8/1990 | De Bastiani et al. |
| 4,959,066 A | 9/1990 | Dunn et al. |
| 4,969,889 A | 11/1990 | Greig |
| 4,976,258 A | 12/1990 | Richter et al. |
| 4,978,349 A | 12/1990 | Frigg |
| 4,978,358 A | 12/1990 | Bobyn |
| 4,988,349 A | 1/1991 | Pennig |
| 5,002,547 A | 3/1991 | Poggie et al. |
| 5,002,580 A | 3/1991 | Noble et al. |
| 5,006,120 A | 4/1991 | Carter et al. |
| 5,013,314 A | 5/1991 | Firica et al. |
| 5,019,077 A | 5/1991 | De Bastiani et al. |
| 5,026,374 A | 6/1991 | Dezza et al. |
| 5,027,799 A | 7/1991 | Laico et al. |
| 5,030,222 A | 7/1991 | Calandruccio et al. |
| 5,034,012 A | 7/1991 | Frigg |
| 5,034,013 A | 7/1991 | Kyle et al. |
| 5,035,697 A | 7/1991 | Frigg |
| 5,037,423 A | 8/1991 | Kenna |
| 5,041,114 A | 8/1991 | Chapman et al. |

(56) References Cited

U.S. PATENT DOCUMENTS

| | | |
|---|---|---|
| 5,041,115 A | 8/1991 | Frigg et al. |
| 5,053,035 A | 10/1991 | McLaren |
| 5,057,103 A | 10/1991 | Davis |
| 5,062,854 A | 11/1991 | Noble et al. |
| 5,066,296 A | 11/1991 | Chapman et al. |
| 5,084,050 A | 1/1992 | Draenert |
| 5,092,892 A | 3/1992 | Ashby |
| 5,098,433 A | 3/1992 | Freedland |
| 5,100,404 A | 3/1992 | Hayes |
| 5,102,413 A | 4/1992 | Poddar |
| 5,108,404 A | 4/1992 | Scholten et al. |
| 5,112,333 A | 5/1992 | Fixel |
| 5,116,335 A | 5/1992 | Hannon et al. |
| 5,116,380 A | 5/1992 | Hewka et al. |
| 5,122,141 A | 6/1992 | Simpson et al. |
| 5,122,146 A | 6/1992 | Chapman et al. |
| 5,124,106 A | 6/1992 | Morr et al. |
| 5,147,408 A | 9/1992 | Noble et al. |
| 5,152,766 A | 10/1992 | Kirkley |
| 5,163,963 A | 11/1992 | Hewka et al. |
| 5,171,324 A | 12/1992 | Campana et al. |
| 5,176,681 A | 1/1993 | Lawes et al. |
| 5,178,621 A | 1/1993 | Cook et al. |
| 5,190,544 A | 3/1993 | Chapman et al. |
| 5,190,546 A | 3/1993 | Jervis |
| 5,192,281 A | 3/1993 | de la Caffiniere |
| 5,197,966 A | 3/1993 | Sommerkamp |
| 5,197,990 A | 3/1993 | Lawes et al. |
| 5,201,735 A | 4/1993 | Chapman et al. |
| 5,201,767 A | 4/1993 | Caldarise et al. |
| 5,211,664 A | 5/1993 | Tepic et al. |
| 5,217,049 A | 6/1993 | Forsyth |
| 5,263,955 A | 11/1993 | Baumgart et al. |
| 5,268,000 A | 12/1993 | Ottieri et al. |
| 5,281,224 A | 1/1994 | Faccioli et al. |
| 5,281,225 A | 1/1994 | Vicenzi |
| 5,292,322 A | 3/1994 | Faccioli et al. |
| 5,295,991 A | 3/1994 | Frigg |
| 5,303,718 A | 4/1994 | Krajicek |
| 5,314,489 A | 5/1994 | Hoffman et al. |
| 5,320,622 A | 6/1994 | Faccioli et al. |
| 5,320,623 A | 6/1994 | Pennig |
| 5,326,376 A | 7/1994 | Warner et al. |
| 5,334,184 A | 8/1994 | Bimman |
| 5,342,360 A | 8/1994 | Faccioli et al. |
| 5,342,362 A | 8/1994 | Kenyon et al. |
| 5,346,496 A | 9/1994 | Pennig |
| 5,350,379 A | 9/1994 | Spievack |
| 5,352,227 A | 10/1994 | O'Hara |
| 5,358,534 A | 10/1994 | Dudasik et al. |
| 5,364,398 A | 11/1994 | Chapman et al. |
| 5,368,594 A | 11/1994 | Martin et al. |
| 5,376,090 A | 12/1994 | Pennig |
| 5,376,123 A | 12/1994 | Klaue et al. |
| 5,380,328 A | 1/1995 | Morgan |
| 5,383,932 A | 1/1995 | Wilson et al. |
| 5,387,243 A | 2/1995 | Devanathan |
| 5,397,328 A | 3/1995 | Behrens et al. |
| 5,403,321 A | 4/1995 | DiMarco |
| 5,411,503 A | 5/1995 | Hollstien et al. |
| 5,415,660 A | 5/1995 | Campbell et al. |
| 5,417,695 A | 5/1995 | Axelson, Jr. |
| RE34,985 E | 6/1995 | Pennig |
| 5,423,848 A | 6/1995 | Washizuka et al. |
| 5,423,850 A | 6/1995 | Berger |
| 5,433,718 A | 7/1995 | Brinker |
| 5,433,720 A | 7/1995 | Faccioli et al. |
| 5,441,500 A | 8/1995 | Seidel et al. |
| 5,443,477 A | 8/1995 | Marin et al. |
| 5,445,642 A | 8/1995 | McNulty et al. |
| 5,454,813 A | 10/1995 | Lawes |
| 5,454,816 A | 10/1995 | Ashby |
| 5,458,599 A | 10/1995 | Adobbati |
| 5,458,651 A | 10/1995 | Lawes |
| 5,458,653 A | 10/1995 | Davidson |
| 5,468,242 A | 11/1995 | Reisberg |
| 5,472,444 A | 12/1995 | Huebner et al. |
| 5,478,341 A | 12/1995 | Cook et al. |
| 5,480,400 A | 1/1996 | Berger |
| 5,484,438 A | 1/1996 | Pennig |
| 5,484,446 A | 1/1996 | Burke et al. |
| 5,488,761 A | 2/1996 | Leone |
| 5,490,852 A | 2/1996 | Azer et al. |
| 5,505,734 A | 4/1996 | Caniggia et al. |
| 5,514,137 A | 5/1996 | Coutts |
| 5,516,335 A | 5/1996 | Kummer et al. |
| 5,520,695 A | 5/1996 | Luckman |
| 5,527,316 A | 6/1996 | Stone et al. |
| 5,531,748 A | 7/1996 | de la Caffiniere |
| 5,534,004 A | 7/1996 | Santangelo |
| 5,545,162 A | 8/1996 | Huebner |
| 5,549,610 A | 8/1996 | Russell et al. |
| 5,549,706 A | 8/1996 | McCarthy |
| 5,554,192 A | 9/1996 | Crowninshield |
| 5,556,433 A | 9/1996 | Gabriel et al. |
| 5,562,667 A | 10/1996 | Shuler et al. |
| 5,562,673 A | 10/1996 | Koblish et al. |
| 5,562,674 A | 10/1996 | Stalcup et al. |
| 5,562,675 A | 10/1996 | McNulty et al. |
| 5,569,249 A | 10/1996 | James et al. |
| 5,571,189 A | 11/1996 | Kuslich |
| 5,571,204 A | 11/1996 | Nies |
| 5,573,536 A | 11/1996 | Grosse et al. |
| 5,578,035 A | 11/1996 | Lin |
| 5,586,985 A | 12/1996 | Putnam et al. |
| 5,591,169 A | 1/1997 | Benoist |
| 5,591,196 A | 1/1997 | Marin et al. |
| 5,593,451 A | 1/1997 | Averill et al. |
| 5,593,452 A | 1/1997 | Higham et al. |
| 5,605,713 A | 2/1997 | Boltong |
| 5,607,431 A | 3/1997 | Dudasik et al. |
| 5,613,970 A | 3/1997 | Houston et al. |
| 5,618,286 A | 4/1997 | Brinker |
| 5,618,300 A | 4/1997 | Marin et al. |
| 5,620,449 A | 4/1997 | Faccioli et al. |
| 5,624,440 A | 4/1997 | Huebner et al. |
| 5,624,447 A | 4/1997 | Myers |
| 5,626,580 A | 5/1997 | Brosnahan |
| 5,643,258 A | 7/1997 | Robioneck et al. |
| 5,645,545 A | 7/1997 | Bryant |
| 5,645,599 A | 7/1997 | Samani |
| 5,658,283 A | 8/1997 | Huebner |
| 5,658,287 A | 8/1997 | Hofmann et al. |
| 5,658,292 A | 8/1997 | Axelson, Jr. |
| 5,658,293 A | 8/1997 | Vanlaningham |
| 5,658,351 A | 8/1997 | Dudasik et al. |
| 5,662,648 A | 9/1997 | Faccioli et al. |
| 5,662,649 A | 9/1997 | Huebner |
| 5,662,712 A | 9/1997 | Pathak et al. |
| 5,665,090 A | 9/1997 | Rockwood et al. |
| 5,665,091 A | 9/1997 | Noble et al. |
| 5,681,289 A * | 10/1997 | Wilcox et al. ............... 604/175 |
| 5,681,316 A | 10/1997 | DeOrio et al. |
| 5,681,318 A | 10/1997 | Pennig et al. |
| 5,683,389 A | 11/1997 | Orsak |
| 5,683,460 A | 11/1997 | Persoons |
| 5,688,271 A | 11/1997 | Faccioli et al. |
| 5,688,279 A | 11/1997 | McNulty et al. |
| 5,690,634 A | 11/1997 | Muller et al. |
| 5,693,047 A | 12/1997 | Meyers et al. |
| 5,693,048 A | 12/1997 | Stalcup et al. |
| 5,695,729 A | 12/1997 | Chow et al. |
| 5,697,930 A | 12/1997 | Itoman et al. |
| 5,702,215 A | 12/1997 | Li |
| 5,702,481 A | 12/1997 | Lin |
| 5,702,487 A | 12/1997 | Averill et al. |
| 5,707,370 A | 1/1998 | Berki et al. |
| 5,718,704 A | 2/1998 | Medoff |
| 5,725,595 A | 3/1998 | Gustilo |
| 5,728,096 A | 3/1998 | Faccioli et al. |
| 5,741,256 A | 4/1998 | Bresina |
| 5,741,266 A | 4/1998 | Moran et al. |
| 5,749,872 A | 5/1998 | Kyle et al. |
| 5,749,880 A | 5/1998 | Banas et al. |

(56) References Cited

U.S. PATENT DOCUMENTS

| | | |
|---|---|---|
| 5,759,184 A | 6/1998 | Santangelo |
| 5,766,174 A | 6/1998 | Perry |
| 5,766,176 A | 6/1998 | Duncan |
| 5,766,178 A | 6/1998 | Michielli et al. |
| 5,766,179 A | 6/1998 | Faccioli et al. |
| 5,766,180 A | 6/1998 | Winquist |
| 5,772,662 A | 6/1998 | Chapman et al. |
| 5,772,663 A | 6/1998 | Whiteside et al. |
| 5,776,194 A | 7/1998 | Mikol et al. |
| 5,776,204 A | 7/1998 | Noble et al. |
| 5,779,703 A | 7/1998 | Benoist |
| 5,779,705 A | 7/1998 | Matthews |
| 5,782,921 A | 7/1998 | Colleran et al. |
| 5,785,057 A | 7/1998 | Fischer |
| 5,788,703 A * | 8/1998 | Mittelmeier et al. ............ 606/94 |
| 5,807,241 A | 9/1998 | Heimberger |
| 5,810,750 A | 9/1998 | Buser |
| 5,810,820 A | 9/1998 | Santori et al. |
| 5,810,826 A | 9/1998 | Åkerfeldt et al. |
| 5,810,830 A | 9/1998 | Noble et al. |
| 5,814,047 A | 9/1998 | Emilio et al. |
| 5,814,681 A | 9/1998 | Hino et al. |
| 5,816,812 A | 10/1998 | Kownacki et al. |
| 5,827,282 A | 10/1998 | Pennig |
| 5,827,289 A | 10/1998 | Reiley et al. |
| 5,829,081 A | 11/1998 | Pearce |
| 5,836,949 A | 11/1998 | Campbell, Jr. et al. |
| 5,837,909 A | 11/1998 | Bill et al. |
| 5,849,004 A | 12/1998 | Bramlet |
| 5,849,014 A | 12/1998 | Mastrorio et al. |
| 5,849,035 A | 12/1998 | Pathak et al. |
| 5,855,581 A | 1/1999 | Koblish et al. |
| 5,858,020 A | 1/1999 | Johnson et al. |
| 5,863,295 A | 1/1999 | Averill et al. |
| 5,876,459 A | 3/1999 | Powell |
| 5,879,352 A | 3/1999 | Filoso et al. |
| 5,881,878 A | 3/1999 | Faccioli et al. |
| 5,882,351 A | 3/1999 | Fox |
| 5,893,850 A | 4/1999 | Cachia |
| 5,895,390 A | 4/1999 | Moran et al. |
| 5,897,560 A | 4/1999 | Johnson |
| 5,902,302 A | 5/1999 | Berki et al. |
| 5,906,210 A | 5/1999 | Herbert |
| 5,908,422 A | 6/1999 | Bresina |
| 5,908,423 A | 6/1999 | Kashuba et al. |
| 5,912,410 A | 6/1999 | Cordell |
| 5,913,867 A | 6/1999 | Dion |
| 5,919,194 A | 7/1999 | Anderson |
| 5,925,048 A | 7/1999 | Ahmad et al. |
| 5,928,235 A | 7/1999 | Friedl |
| 5,928,240 A | 7/1999 | Johnson |
| 5,928,259 A | 7/1999 | Tovey |
| 5,931,830 A | 8/1999 | Jacobsen et al. |
| 5,931,839 A | 8/1999 | Medoff |
| 5,948,000 A | 9/1999 | Larsen et al. |
| 5,948,001 A | 9/1999 | Larsen |
| 5,951,556 A | 9/1999 | Faccioli et al. |
| 5,951,557 A | 9/1999 | Luter |
| 5,951,561 A | 9/1999 | Pepper et al. |
| 5,954,722 A | 9/1999 | Bono |
| 5,954,728 A | 9/1999 | Heller et al. |
| 5,961,553 A | 10/1999 | Coty et al. |
| 5,964,770 A | 10/1999 | Flomenblit et al. |
| 5,968,047 A | 10/1999 | Reed |
| 5,971,986 A | 10/1999 | Santori et al. |
| 5,976,134 A | 11/1999 | Huebner |
| 5,976,147 A | 11/1999 | LaSalle et al. |
| 5,976,188 A | 11/1999 | Dextradeur et al. |
| 5,989,260 A | 11/1999 | Yao |
| 5,989,261 A | 11/1999 | Walker et al. |
| 5,993,459 A | 11/1999 | Larsen et al. |
| 6,004,348 A | 12/1999 | Banas et al. |
| 6,010,505 A | 1/2000 | Asche et al. |
| 6,010,506 A | 1/2000 | Gosney et al. |
| 6,013,081 A | 1/2000 | Burkinshaw et al. |
| 6,015,413 A | 1/2000 | Faccioli et al. |
| 6,017,350 A | 1/2000 | Long |
| 6,018,094 A | 1/2000 | Fox |
| 6,019,761 A | 2/2000 | Gustilo |
| 6,019,762 A | 2/2000 | Cole |
| 6,020,396 A | 2/2000 | Jacobs |
| 6,024,745 A | 2/2000 | Faccioli et al. |
| 6,027,506 A | 2/2000 | Faccioli et al. |
| 6,027,534 A | 2/2000 | Wack et al. |
| 6,033,407 A | 3/2000 | Behrens |
| 6,039,742 A | 3/2000 | Krettek et al. |
| 6,045,556 A | 4/2000 | Cohen |
| 6,053,922 A | 4/2000 | Krause et al. |
| 6,056,756 A | 5/2000 | Eng et al. |
| 6,074,392 A | 6/2000 | Durham |
| 6,077,264 A | 6/2000 | Chemello |
| 6,080,159 A | 6/2000 | Vichard |
| 6,083,522 A | 7/2000 | Chu et al. |
| 6,093,209 A | 7/2000 | Sanders |
| 6,096,040 A | 8/2000 | Esser |
| 6,102,911 A | 8/2000 | Faccioli et al. |
| 6,106,528 A | 8/2000 | Durham et al. |
| 6,120,504 A | 9/2000 | Brumback et al. |
| 6,120,509 A | 9/2000 | Wheeler |
| 6,126,661 A | 10/2000 | Faccioli et al. |
| 6,126,691 A | 10/2000 | Kasra et al. |
| 6,127,597 A | 10/2000 | Beyar et al. |
| 6,129,756 A | 10/2000 | Kugler et al. |
| 6,129,762 A | 10/2000 | Li |
| 6,139,583 A | 10/2000 | Johnson |
| 6,143,012 A | 11/2000 | Gausepohl |
| 6,143,033 A | 11/2000 | Paul et al. |
| 6,162,223 A | 12/2000 | Orsak et al. |
| 6,162,226 A | 12/2000 | DeCarlo et al. |
| 6,168,595 B1 | 1/2001 | Durham et al. |
| 6,168,632 B1 | 1/2001 | Moser et al. |
| 6,171,309 B1 | 1/2001 | Huebner |
| 6,176,871 B1 | 1/2001 | Pathak et al. |
| 6,179,839 B1 | 1/2001 | Weiss et al. |
| 6,179,842 B1 | 1/2001 | Spotomo et al. |
| 6,183,470 B1 | 2/2001 | Booth, Jr. et al. |
| 6,197,029 B1 | 3/2001 | Fujimori et al. |
| 6,197,031 B1 | 3/2001 | Barrette et al. |
| 6,200,321 B1 | 3/2001 | Orbay et al. |
| 6,206,880 B1 | 3/2001 | Karladani |
| 6,221,036 B1 | 4/2001 | Lucas |
| 6,221,074 B1 | 4/2001 | Cole et al. |
| 6,224,600 B1 | 5/2001 | Protogirou |
| 6,224,609 B1 | 5/2001 | Ressemann et al. |
| 6,228,123 B1 | 5/2001 | Dezzani |
| 6,231,576 B1 | 5/2001 | Frigg et al. |
| 6,235,029 B1 | 5/2001 | Faccioli et al. |
| 6,235,043 B1 | 5/2001 | Reiley et al. |
| 6,241,734 B1 | 6/2001 | Scribner et al. |
| 6,248,110 B1 | 6/2001 | Reiley et al. |
| 6,261,289 B1 | 7/2001 | Levy |
| 6,270,499 B1 | 8/2001 | Leu et al. |
| 6,273,876 B1 | 8/2001 | Klima et al. |
| 6,273,892 B1 | 8/2001 | Orbay et al. |
| 6,280,456 B1 | 8/2001 | Scribner et al. |
| 6,280,474 B1 | 8/2001 | Cassidy et al. |
| 6,283,969 B1 | 9/2001 | Grusin et al. |
| 6,287,310 B1 | 9/2001 | Fox |
| 6,290,725 B1 | 9/2001 | Weiss et al. |
| 6,296,603 B1 | 10/2001 | Turnlund et al. |
| 6,296,645 B1 | 10/2001 | Hover et al. |
| 6,299,642 B1 | 10/2001 | Chan |
| 6,309,396 B1 | 10/2001 | Ritland |
| 6,319,253 B1 | 11/2001 | Ackeret et al. |
| 6,325,830 B1 | 12/2001 | Mastrorio et al. |
| 6,332,886 B1 | 12/2001 | Green et al. |
| 6,336,929 B1 | 1/2002 | Justin |
| 6,348,053 B1 | 2/2002 | Cachia |
| 6,355,042 B2 | 3/2002 | Winquist et al. |
| 6,355,044 B1 | 3/2002 | Hair |
| 6,355,069 B1 | 3/2002 | DeCarlo et al. |
| 6,358,250 B1 | 3/2002 | Orbay |
| 6,358,283 B1 | 3/2002 | Hogfors et al. |
| 6,364,824 B1 | 4/2002 | Fitzsimmons |

(56) References Cited

U.S. PATENT DOCUMENTS

| | | |
|---|---|---|
| 6,364,882 B1 | 4/2002 | Orbay |
| 6,364,909 B1 | 4/2002 | McGee |
| 6,379,359 B1 | 4/2002 | Dahners |
| 6,379,360 B1 | 4/2002 | Ackeret et al. |
| 6,383,188 B2 | 5/2002 | Kuslich et al. |
| 6,395,004 B1 | 5/2002 | Dye et al. |
| 6,402,753 B1 | 6/2002 | Cole et al. |
| 6,406,477 B1 | 6/2002 | Fujiwara |
| 6,416,516 B1 | 7/2002 | Stauch et al. |
| 6,423,083 B2 | 7/2002 | Reiley et al. |
| 6,423,096 B1 | 7/2002 | Musset et al. |
| 6,425,923 B1 | 7/2002 | Stalcup et al. |
| 6,436,148 B1 | 8/2002 | DeCarlo, Jr. et al. |
| 6,440,135 B2 | 8/2002 | Orbay et al. |
| 6,443,954 B1 | 9/2002 | Bramlet et al. |
| 6,443,992 B2 | 9/2002 | Lubinus |
| 6,447,513 B1 | 9/2002 | Griggs |
| 6,447,514 B1 | 9/2002 | Stalcup et al. |
| 6,447,515 B1 | 9/2002 | Meldrum |
| 6,447,518 B1 | 9/2002 | Krause et al. |
| 6,461,358 B1 | 10/2002 | Faccioli |
| 6,461,360 B1 | 10/2002 | Adam |
| 6,468,278 B1 | 10/2002 | Muckter |
| 6,488,684 B2 | 12/2002 | Bramlet et al. |
| 6,491,694 B1 | 12/2002 | Orsak |
| 6,500,209 B1 | 12/2002 | Kolb |
| 6,508,819 B1 | 1/2003 | Orbay |
| 6,508,820 B2 | 1/2003 | Bales |
| 6,511,481 B2 | 1/2003 | von Hoffmann et al. |
| 6,520,994 B2 | 2/2003 | Nogarin |
| 6,524,313 B1 | 2/2003 | Fassier et al. |
| 6,527,775 B1 | 3/2003 | Warburton |
| 6,530,925 B2 | 3/2003 | Boudard et al. |
| 6,533,788 B1 | 3/2003 | Orbay |
| 6,537,275 B2 | 3/2003 | Venturini et al. |
| 6,540,752 B1 | 4/2003 | Hicken et al. |
| 6,544,265 B2 | 4/2003 | Lieberman |
| 6,551,319 B2 | 4/2003 | Lieberman |
| 6,551,321 B1 | 4/2003 | Burkinshaw et al. |
| 6,554,833 B2 | 4/2003 | Levy et al. |
| 6,554,862 B2 | 4/2003 | Hays et al. |
| 6,558,388 B1 | 5/2003 | Bartsch et al. |
| 6,562,042 B2 | 5/2003 | Nelson |
| 6,565,573 B1 | 5/2003 | Ferrante et al. |
| 6,572,620 B1 | 6/2003 | Schon et al. |
| 6,575,973 B1 | 6/2003 | Shekalim |
| 6,575,986 B2 | 6/2003 | Overaker |
| 6,575,994 B1 | 6/2003 | Marin et al. |
| 6,582,453 B1 | 6/2003 | Tran et al. |
| 6,592,578 B2 | 7/2003 | Henniges et al. |
| 6,607,531 B2 | 8/2003 | Frigg |
| 6,613,052 B1 | 9/2003 | Kinnett |
| 6,616,667 B1 | 9/2003 | Steiger et al. |
| 6,616,742 B2 | 9/2003 | Lin et al. |
| 6,620,197 B2 | 9/2003 | Maroney |
| 6,623,487 B1 | 9/2003 | Goshert |
| 6,629,976 B1 | 10/2003 | Gnos et al. |
| 6,632,224 B2 | 10/2003 | Cachia et al. |
| 6,632,235 B2 | 10/2003 | Weikel et al. |
| 6,641,596 B1 | 11/2003 | Uzardi |
| 6,648,889 B2 | 11/2003 | Bramlet et al. |
| 6,648,890 B2 | 11/2003 | Culbert et al. |
| 6,648,893 B2 | 11/2003 | Dudasik |
| 6,652,529 B2 | 11/2003 | Swanson |
| 6,652,591 B2 | 11/2003 | Serbousek et al. |
| 6,656,189 B1 | 12/2003 | Wilson et al. |
| 6,663,647 B2 | 12/2003 | Reiley et al. |
| 6,679,890 B2 | 1/2004 | Margulies et al. |
| 6,682,568 B2 | 1/2004 | Despres, III et al. |
| 6,685,679 B2 | 2/2004 | Merdan |
| 6,685,706 B2 | 2/2004 | Padget et al. |
| 6,688,822 B2 | 2/2004 | Ritter et al. |
| 6,692,530 B2 | 2/2004 | Doubler et al. |
| 6,694,667 B2 | 2/2004 | Davis |
| 6,695,844 B2 | 2/2004 | Bramlet et al. |
| 6,699,251 B1 | 3/2004 | Venturini |
| 6,699,253 B2 | 3/2004 | McDowell et al. |
| 6,706,046 B2 | 3/2004 | Orbay et al. |
| 6,706,072 B2 | 3/2004 | Dwyer et al. |
| 6,709,436 B1 | 3/2004 | Hover et al. |
| 6,712,820 B2 | 3/2004 | Orbay |
| 6,719,793 B2 | 4/2004 | McGee |
| 6,722,368 B1 | 4/2004 | Shaikh |
| 6,723,129 B2 | 4/2004 | Dwyer et al. |
| 6,730,087 B1 | 5/2004 | Butsch |
| 6,730,090 B2 | 5/2004 | Orbay et al. |
| 6,736,818 B2 | 5/2004 | Perren et al. |
| 6,749,611 B2 | 6/2004 | Venturini et al. |
| 6,749,614 B2 | 6/2004 | Teitelbaum et al. |
| 6,755,831 B2 | 6/2004 | Putnam et al. |
| 6,755,862 B2 | 6/2004 | Keynan |
| 6,755,866 B2 | 6/2004 | Southworth |
| 6,767,350 B1 | 7/2004 | Lob |
| 6,767,351 B2 | 7/2004 | Orbay et al. |
| 6,780,185 B2 | 8/2004 | Frei et al. |
| 6,783,529 B2 | 8/2004 | Hover et al. |
| 6,783,530 B1 | 8/2004 | Levy |
| 6,783,533 B2 | 8/2004 | Green et al. |
| 6,786,908 B2 | 9/2004 | Hover et al. |
| 6,790,210 B1 | 9/2004 | Cragg et al. |
| 6,793,655 B2 | 9/2004 | Orsak |
| 6,793,659 B2 | 9/2004 | Putnam |
| 6,808,527 B2 | 10/2004 | Lower et al. |
| 6,821,277 B2 | 11/2004 | Teitelbaum |
| 6,821,299 B2 | 11/2004 | Kirking et al. |
| 6,827,739 B2 | 12/2004 | Griner et al. |
| 6,827,741 B2 | 12/2004 | Reeder |
| 6,840,939 B2 | 1/2005 | Venturini et al. |
| 6,855,146 B2 | 2/2005 | Frigg et al. |
| 6,855,167 B2 | 2/2005 | Shimp et al. |
| 6,863,692 B2 | 3/2005 | Meulink |
| 6,866,455 B2 | 3/2005 | Hasler |
| 6,866,665 B2 | 3/2005 | Orbay |
| 6,875,212 B2 | 4/2005 | Shaolian et al. |
| 6,887,243 B2 | 5/2005 | Culbert |
| 6,887,271 B2 | 5/2005 | Justin et al. |
| 6,887,276 B2 | 5/2005 | Gerbec et al. |
| 6,890,333 B2 | 5/2005 | von Hoffmann et al. |
| 6,893,444 B2 | 5/2005 | Orbay |
| 6,899,713 B2 | 5/2005 | Shaolian et al. |
| 6,899,719 B2 | 5/2005 | Reiley et al. |
| 6,902,583 B2 | 6/2005 | Gerbec et al. |
| 6,908,465 B2 | 6/2005 | von Hoffmann et al. |
| 6,916,323 B2 | 7/2005 | Kitchens |
| 6,921,397 B2 | 7/2005 | Corcoran et al. |
| 6,926,720 B2 | 8/2005 | Castaneda |
| 6,926,741 B2 | 8/2005 | Kolb |
| 6,929,692 B2 | 8/2005 | Tas |
| 6,942,666 B2 | 9/2005 | Overaker et al. |
| 6,942,668 B2 | 9/2005 | Padget et al. |
| 6,949,100 B1 | 9/2005 | Venturini |
| 6,949,124 B2 | 9/2005 | Serbousek et al. |
| 6,951,561 B2 | 10/2005 | Warren et al. |
| 6,974,482 B2 | 12/2005 | Zhu |
| 6,981,981 B2 | 1/2006 | Reiley et al. |
| 6,986,771 B2 | 1/2006 | Paul et al. |
| 6,999,819 B2 | 2/2006 | Swoyer et al. |
| 7,001,386 B2 | 2/2006 | Sohngen et al. |
| 7,001,388 B2 | 2/2006 | Orbay et al. |
| D518,174 S | 3/2006 | Venturini et al. |
| 7,008,425 B2 | 3/2006 | Phillips |
| 7,008,428 B2 | 3/2006 | Cachia et al. |
| 7,008,451 B2 | 3/2006 | Justin et al. |
| 7,011,664 B2 | 3/2006 | Haney et al. |
| 7,012,106 B2 | 3/2006 | Yuan et al. |
| 7,029,476 B2 | 4/2006 | Hansson |
| 7,029,478 B2 | 4/2006 | Hollstien et al. |
| 7,033,363 B2 | 4/2006 | Powell |
| 7,033,365 B2 | 4/2006 | Powell et al. |
| 7,041,104 B1 | 5/2006 | Cole et al. |
| 7,044,978 B2 | 5/2006 | Howie et al. |
| 7,052,498 B2 | 5/2006 | Levy et al. |
| 7,056,322 B2 | 6/2006 | Davison et al. |
| 7,060,075 B2 | 6/2006 | Govari et al. |

(56) References Cited

U.S. PATENT DOCUMENTS

| | | |
|---|---|---|
| 7,070,601 B2 | 7/2006 | Culbert et al. |
| 7,070,616 B2 | 7/2006 | Majercak et al. |
| 7,074,224 B2 | 7/2006 | Daniels et al. |
| 7,081,119 B2 | 7/2006 | Stihl |
| 7,083,624 B2 | 8/2006 | Irving |
| 7,090,676 B2 | 8/2006 | Huebner et al. |
| 7,097,648 B1 | 8/2006 | Globerman et al. |
| 7,097,664 B2 | 8/2006 | Despres, III et al. |
| RE39,301 E | 9/2006 | Bertin |
| 7,101,376 B2 | 9/2006 | Semet |
| 7,118,574 B2 | 10/2006 | Patel et al. |
| 7,122,056 B2 | 10/2006 | Dwyer et al. |
| 7,137,987 B2 | 11/2006 | Patterson et al. |
| 7,141,052 B2 | 11/2006 | Manderson |
| 7,141,067 B2 | 11/2006 | Jones et al. |
| 7,144,399 B2 | 12/2006 | Hayes et al. |
| 7,147,639 B2 | 12/2006 | Berki et al. |
| 7,147,640 B2 | 12/2006 | Huebner et al. |
| 7,153,309 B2 | 12/2006 | Huebner et al. |
| 7,156,852 B2 | 1/2007 | Dye et al. |
| 7,160,302 B2 | 1/2007 | Warburton |
| 7,160,333 B2 | 1/2007 | Plouhar et al. |
| 7,163,563 B2 | 1/2007 | Schwartz et al. |
| 7,175,625 B2 | 2/2007 | Culbert |
| 7,175,631 B2 | 2/2007 | Wilson et al. |
| 7,179,260 B2 | 2/2007 | Gerlach et al. |
| 7,188,687 B2 | 3/2007 | Rudd et al. |
| 7,189,237 B2 | 3/2007 | Huebner |
| 7,632,277 B2 | 12/2009 | Woll et al. |
| 7,846,162 B2 | 12/2010 | Nelson et al. |
| 7,909,825 B2 | 3/2011 | Saravia et al. |
| 7,914,533 B2 | 3/2011 | Nelson et al. |
| 7,942,875 B2 | 5/2011 | Nelson et al. |
| 8,287,541 B2 * | 10/2012 | Nelson et al. .................... 606/63 |
| 2001/0011174 A1 | 8/2001 | Reiley et al. |
| 2001/0034526 A1 | 10/2001 | Kuslich et al. |
| 2001/0049531 A1 | 12/2001 | Reiley et al. |
| 2002/0004685 A1 * | 1/2002 | White ........................ 623/23.15 |
| 2002/0029041 A1 * | 3/2002 | Hover et al. .................... 606/62 |
| 2002/0032444 A1 | 3/2002 | Mische |
| 2002/0041896 A1 | 4/2002 | Straub et al. |
| 2002/0068939 A1 * | 6/2002 | Levy et al. ...................... 606/63 |
| 2002/0068981 A1 * | 6/2002 | Hajianpour ................ 623/23.48 |
| 2002/0095214 A1 * | 7/2002 | Hyde, Jr. .................... 623/18.12 |
| 2002/0099385 A1 * | 7/2002 | Ralph et al. ...................... 606/92 |
| 2002/0103488 A1 * | 8/2002 | Lower et al. ...................... 606/62 |
| 2002/0143344 A1 * | 10/2002 | Taylor ............................ 606/105 |
| 2002/0161369 A1 | 10/2002 | Bramlet et al. |
| 2002/0165544 A1 * | 11/2002 | Perren et al. .................... 606/63 |
| 2002/0173792 A1 * | 11/2002 | Severns et al. .................. 606/62 |
| 2002/0177866 A1 * | 11/2002 | Weikel et al. .................. 606/192 |
| 2002/0188297 A1 | 12/2002 | Dakin et al. |
| 2002/0198526 A1 | 12/2002 | Shaolian et al. |
| 2003/0032960 A1 | 2/2003 | Dudasik |
| 2003/0040752 A1 | 2/2003 | Kitchens |
| 2003/0045919 A1 | 3/2003 | Swoyer et al. |
| 2003/0073999 A1 | 4/2003 | Putnam |
| 2003/0074075 A1 | 4/2003 | Thomas, Jr. et al. |
| 2003/0078669 A1 | 4/2003 | Martin et al. |
| 2003/0097136 A1 | 5/2003 | Hajianpour |
| 2003/0109932 A1 | 6/2003 | Keynan |
| 2003/0130660 A1 * | 7/2003 | Levy et al. ...................... 606/63 |
| 2003/0130664 A1 | 7/2003 | Boucher et al. |
| 2003/0139802 A1 | 7/2003 | Wulfman et al. |
| 2003/0181918 A1 | 9/2003 | Smothers et al. |
| 2003/0216738 A1 | 11/2003 | Azar |
| 2003/0236529 A1 | 12/2003 | Shluzas et al. |
| 2004/0006341 A1 | 1/2004 | Shaolian et al. |
| 2004/0010263 A1 | 1/2004 | Boucher et al. |
| 2004/0098017 A1 | 5/2004 | Saab et al. |
| 2004/0098134 A1 | 5/2004 | Meulink |
| 2004/0133204 A1 | 7/2004 | Davies |
| 2004/0133280 A1 | 7/2004 | Trieu |
| 2004/0153114 A1 | 8/2004 | Reiley et al. |
| 2004/0153115 A1 | 8/2004 | Reiley et al. |
| 2004/0167561 A1 | 8/2004 | Boucher et al. |
| 2004/0193255 A1 | 9/2004 | Shanley et al. |
| 2004/0193267 A1 | 9/2004 | Jones et al. |
| 2004/0213825 A1 | 10/2004 | Levy |
| 2004/0214311 A1 | 10/2004 | Levy |
| 2004/0215193 A1 | 10/2004 | Shaolian et al. |
| 2004/0230193 A1 | 11/2004 | Cheung et al. |
| 2004/0236327 A1 | 11/2004 | Paul et al. |
| 2004/0260398 A1 | 12/2004 | Kelman |
| 2004/0267269 A1 | 12/2004 | Middleton et al. |
| 2004/0267271 A9 | 12/2004 | Scribner et al. |
| 2005/0015154 A1 | 1/2005 | Lindsey et al. |
| 2005/0027294 A1 | 2/2005 | Woll et al. |
| 2005/0027301 A1 | 2/2005 | Stihl |
| 2005/0043737 A1 * | 2/2005 | Reiley et al. .................... 606/79 |
| 2005/0043757 A1 * | 2/2005 | Arad et al. .................... 606/200 |
| 2005/0047892 A1 | 3/2005 | Bremner |
| 2005/0055023 A1 * | 3/2005 | Sohngen et al. ................ 606/62 |
| 2005/0055024 A1 * | 3/2005 | James et al. .................... 606/64 |
| 2005/0080425 A1 | 4/2005 | Bhatnagar et al. |
| 2005/0090852 A1 | 4/2005 | Layne et al. |
| 2005/0107883 A1 | 5/2005 | Goodfried et al. |
| 2005/0119662 A1 | 6/2005 | Reiley et al. |
| 2005/0131386 A1 | 6/2005 | Freeman et al. |
| 2005/0143827 A1 | 6/2005 | Globerman et al. |
| 2005/0149022 A1 | 7/2005 | Shaolian et al. |
| 2005/0149024 A1 | 7/2005 | Ferrante et al. |
| 2005/0149025 A1 * | 7/2005 | Ferrante et al. ................ 606/62 |
| 2005/0159749 A1 | 7/2005 | Levy et al. |
| 2005/0165395 A1 | 7/2005 | Orbay et al. |
| 2005/0171552 A1 | 8/2005 | Johnson et al. |
| 2005/0171563 A1 | 8/2005 | Heinrich et al. |
| 2005/0177158 A1 | 8/2005 | Doubler et al. |
| 2005/0203510 A1 | 9/2005 | Sohngen |
| 2005/0209595 A1 | 9/2005 | Karmon |
| 2005/0216007 A1 | 9/2005 | Woll et al. |
| 2005/0228391 A1 | 10/2005 | Levy et al. |
| 2005/0234453 A1 * | 10/2005 | Shaolian et al. ................ 606/61 |
| 2005/0234559 A1 | 10/2005 | Fernandez et al. |
| 2005/0251140 A1 | 11/2005 | Shaolian et al. |
| 2005/0261781 A1 | 11/2005 | Sennett et al. |
| 2005/0267481 A1 | 12/2005 | Carl et al. |
| 2005/0267483 A1 | 12/2005 | Middleton |
| 2005/0267586 A1 | 12/2005 | Sidebotham |
| 2005/0283250 A1 | 12/2005 | Coon et al. |
| 2005/0288678 A1 | 12/2005 | Reiley et al. |
| 2006/0004465 A1 | 1/2006 | Bergin et al. |
| 2006/0015101 A1 | 1/2006 | Warburton et al. |
| 2006/0015123 A1 | 1/2006 | Fencl et al. |
| 2006/0030945 A1 | 2/2006 | Wright |
| 2006/0036248 A1 | 2/2006 | Ferrante |
| 2006/0052788 A1 * | 3/2006 | Thelen et al. .................... 606/72 |
| 2006/0064094 A1 | 3/2006 | Levy et al. |
| 2006/0084997 A1 | 4/2006 | Dejardin |
| 2006/0084998 A1 | 4/2006 | Levy et al. |
| 2006/0122601 A1 * | 6/2006 | Tandon ............................ 606/64 |
| 2006/0200143 A1 | 9/2006 | Warburton |
| 2006/0200144 A1 | 9/2006 | Warburton |
| 2006/0229617 A1 | 10/2006 | Meller et al. |
| 2006/0247638 A1 | 11/2006 | Trieu et al. |
| 2006/0264951 A1 | 11/2006 | Nelson et al. |
| 2007/0123878 A1 | 5/2007 | Shaver et al. |
| 2007/0142916 A1 | 6/2007 | Olson et al. |
| 2007/0260257 A1 | 11/2007 | Phan |
| 2008/0077154 A1 | 3/2008 | Edwards et al. |
| 2008/0132896 A1 | 6/2008 | Bowen et al. |
| 2008/0140078 A1 | 6/2008 | Nelson et al. |
| 2008/0149115 A1 | 6/2008 | Hauck et al. |
| 2008/0221620 A1 | 9/2008 | Krause et al. |
| 2008/0234678 A1 | 9/2008 | Gutierrez et al. |
| 2008/0243132 A1 | 10/2008 | Tipirneni et al. |
| 2008/0255560 A1 | 10/2008 | Myers et al. |
| 2008/0262495 A1 | 10/2008 | Coati et al. |
| 2008/0269745 A1 | 10/2008 | Justin |
| 2008/0269751 A1 | 10/2008 | Matityahu |
| 2008/0287951 A1 | 11/2008 | Stoneburner et al. |
| 2009/0018542 A1 | 1/2009 | Saravia et al. |
| 2009/0182336 A1 | 7/2009 | Brenzel et al. |
| 2009/0187116 A1 | 7/2009 | Noishiki et al. |

(56) References Cited

U.S. PATENT DOCUMENTS

| | | |
|---|---|---|
| 2009/0228007 A1 | 9/2009 | Justin et al. |
| 2009/0228008 A1 | 9/2009 | Justin et al. |
| 2010/0023010 A1 | 1/2010 | Nelson et al. |
| 2010/0094347 A1 | 4/2010 | Nelson et al. |
| 2011/0087227 A1 | 4/2011 | Mazur et al. |
| 2011/0144645 A1 | 6/2011 | Saravia et al. |
| 2011/0178520 A1 | 7/2011 | Taylor et al. |
| 2011/0190832 A1 | 8/2011 | Taylor et al. |
| 2011/0218585 A1 | 9/2011 | Krinke et al. |
| 2011/0218626 A1 | 9/2011 | Krinke et al. |
| 2011/0282346 A1 | 11/2011 | Pham et al. |
| 2014/0074093 A9 * | 3/2014 | Nelson et al. ............ 606/64 |

FOREIGN PATENT DOCUMENTS

| | | |
|---|---|---|
| EP | 1815813 A2 | 8/2007 |
| WO | WO 97/18769 | 5/1997 |
| WO | WO 98/27876 | 7/1998 |
| WO | WO98/56301 | 12/1998 |
| WO | WO 98/56301 | 12/1998 |
| WO | WO 99/20195 | 4/1999 |
| WO | WO 00/28906 | 5/2000 |
| WO | WO 01/28443 | 4/2001 |
| WO | WO01/28443 | 4/2001 |
| WO | WO 02/00270 | 1/2002 |
| WO | WO 02/00275 | 1/2002 |
| WO | WO 02/02158 | 1/2002 |
| WO | WO 2005/112804 | 12/2005 |
| WO | WO 2006/053210 | 5/2006 |
| WO | WO2007/009123 | 1/2007 |

OTHER PUBLICATIONS

The Titanium Flexible Humeral Nail System (Quick reference for surgical technique), Synthes, 1999.
The Titanium Flexible Humeral Nail System (Technique Guide), Synthes, 1999.
US 6,030,385, 02/2000, Faccioli et al. (withdrawn)

* cited by examiner

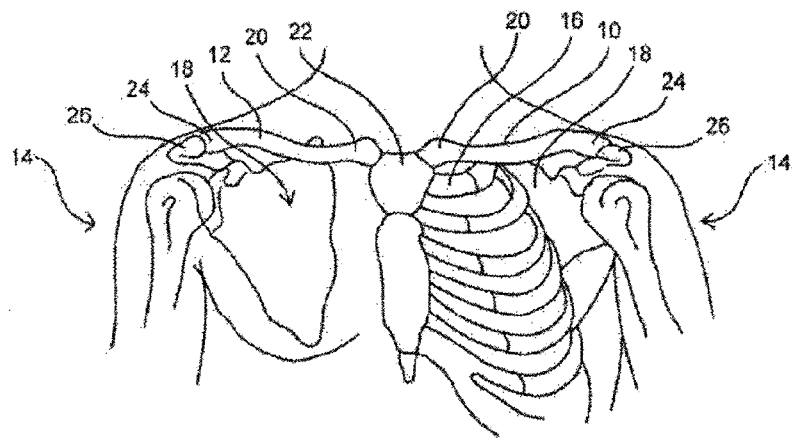
FIG. 1
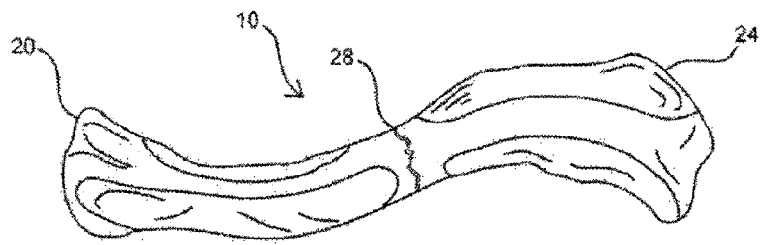
FIG. 2
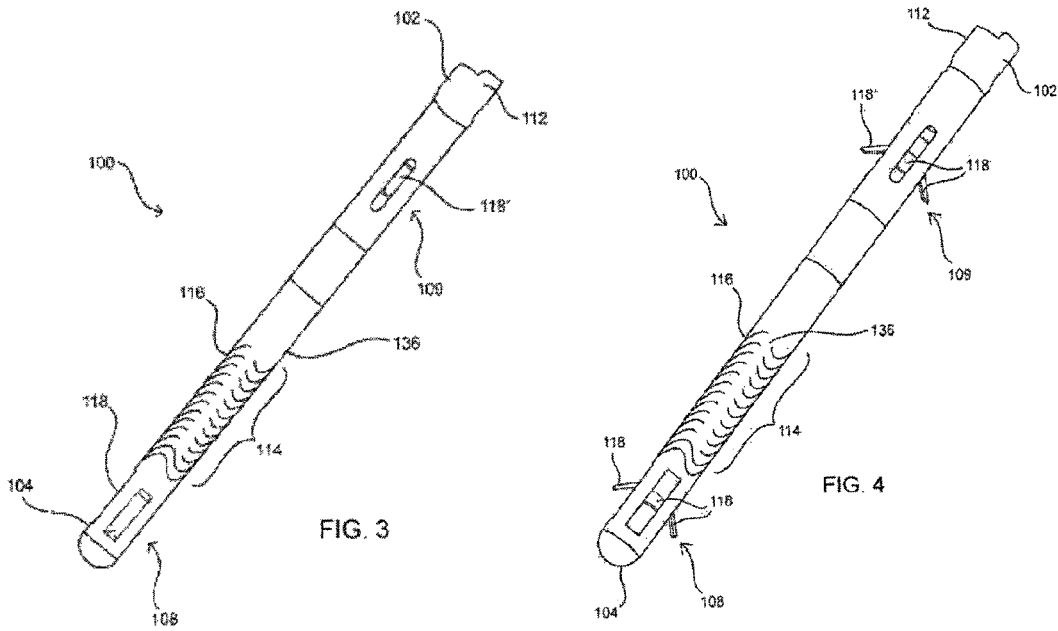
FIG. 3
FIG. 4

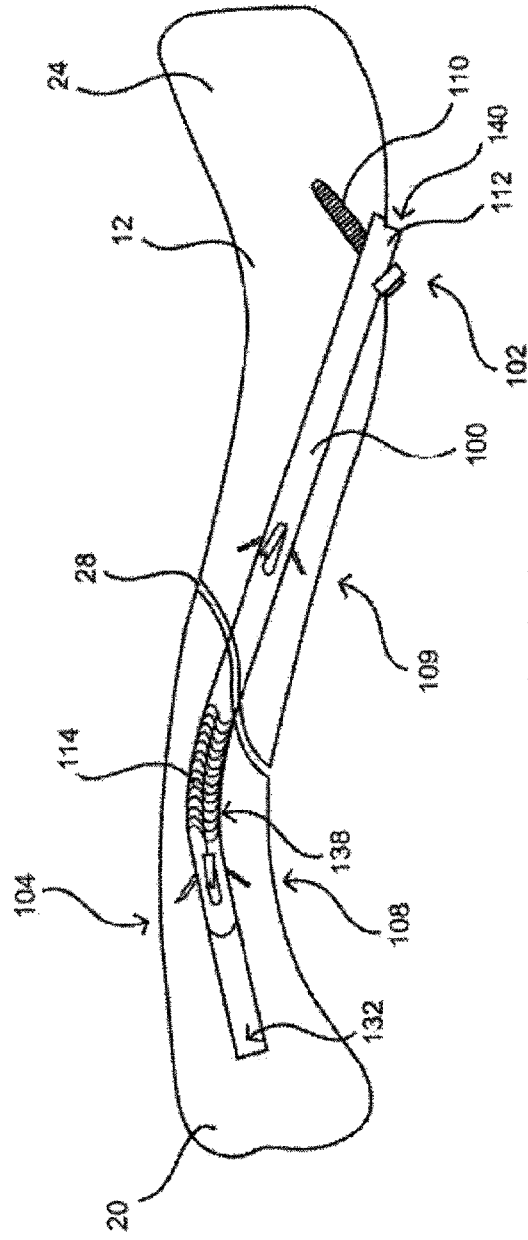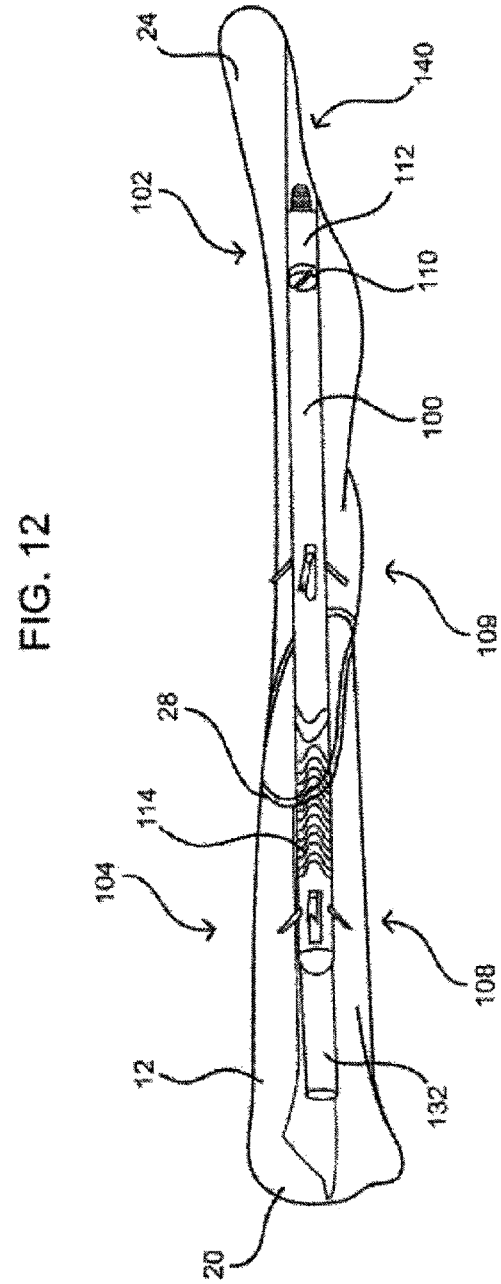
FIG. 11
FIG. 12

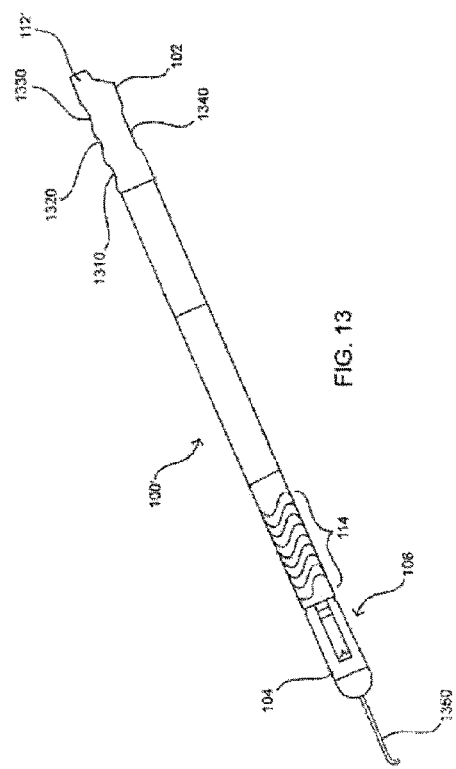
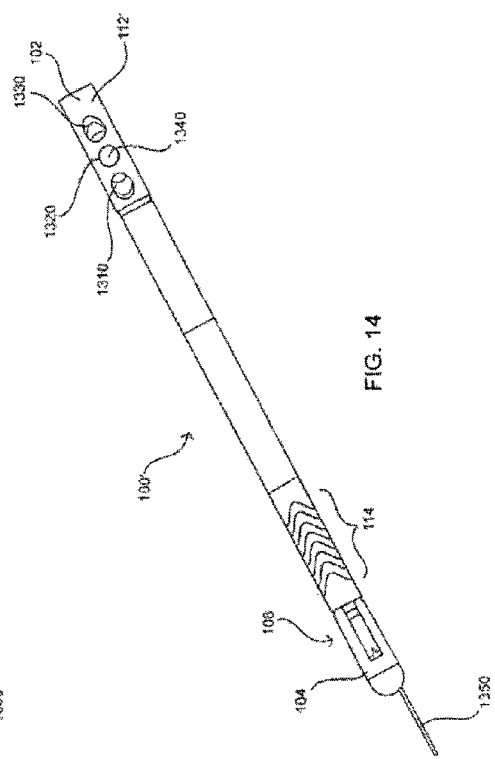

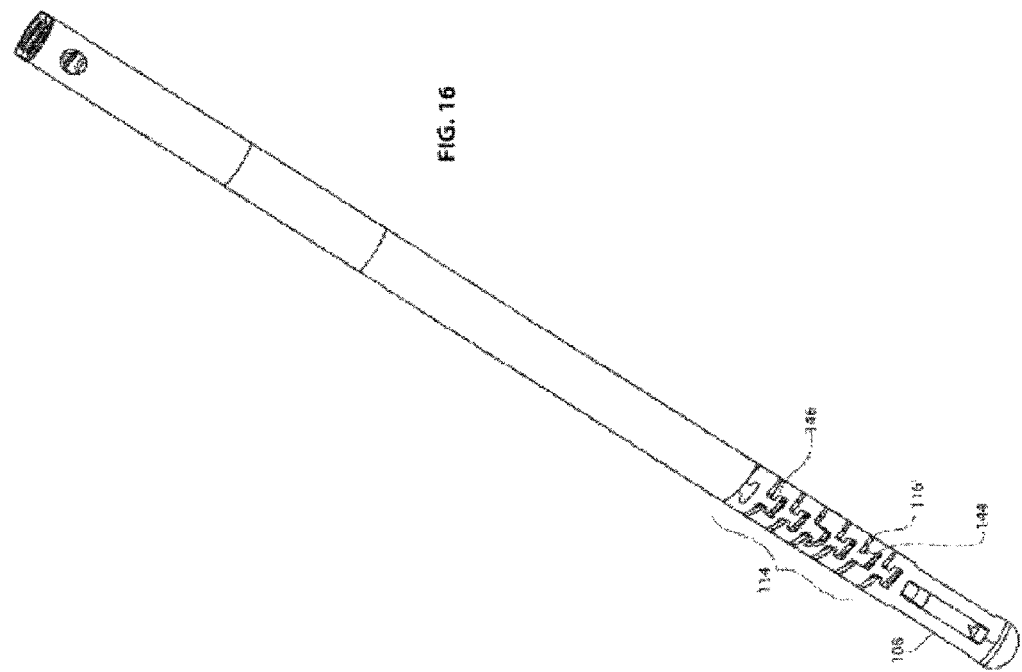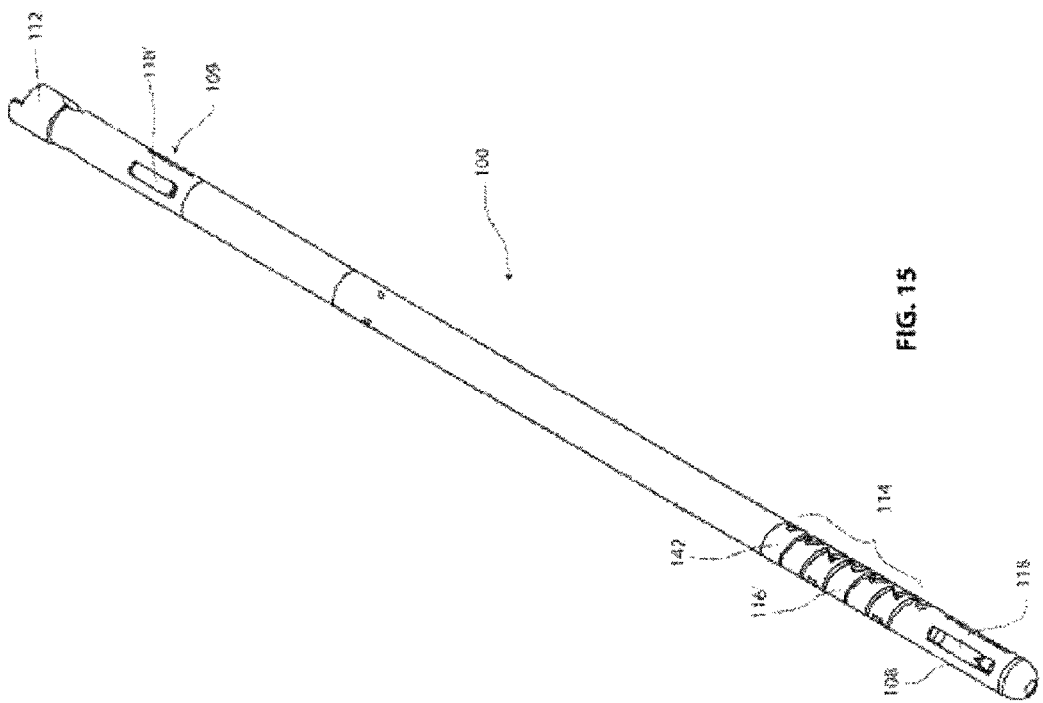

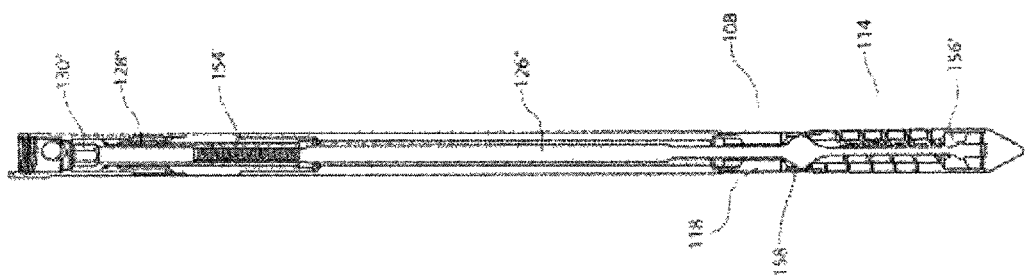
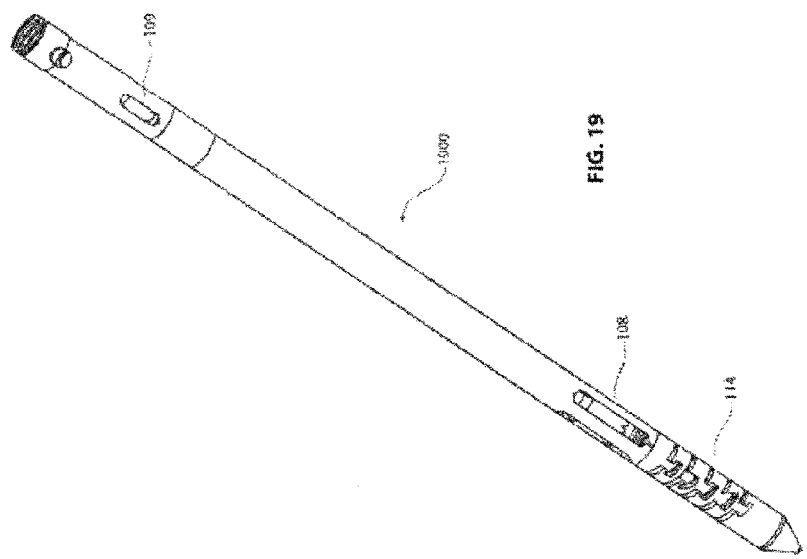

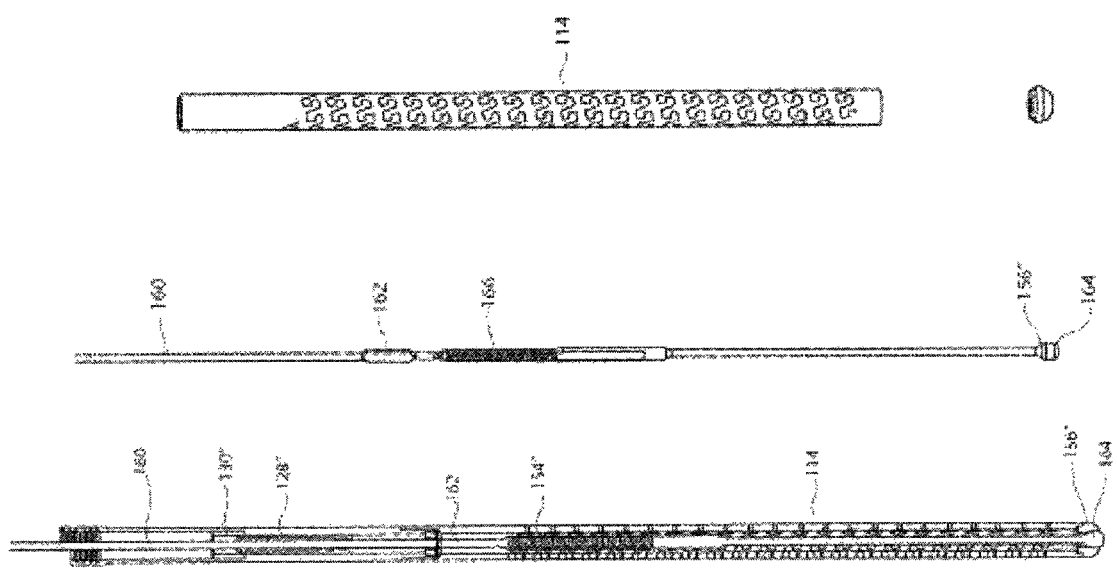
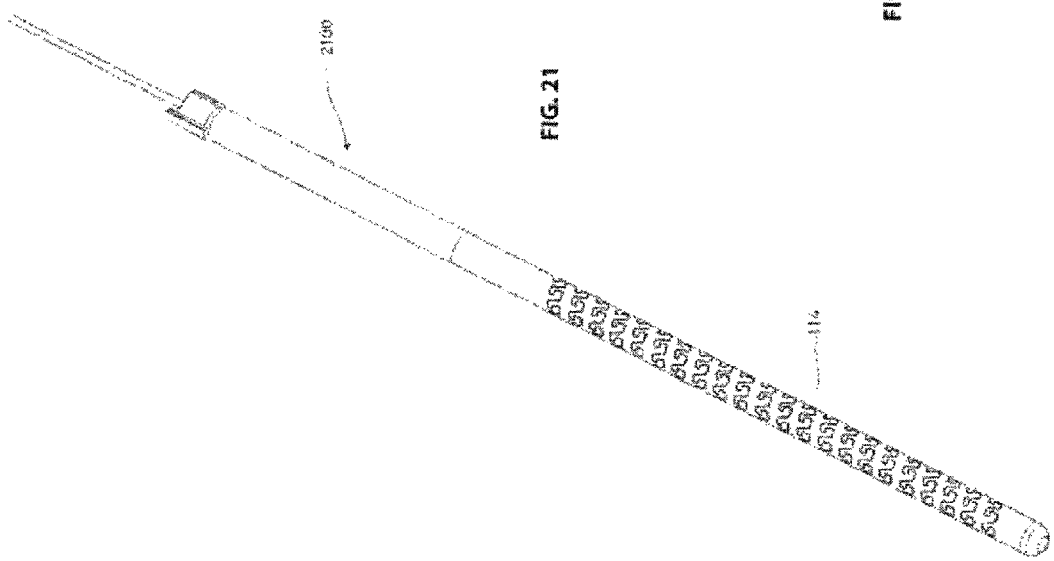

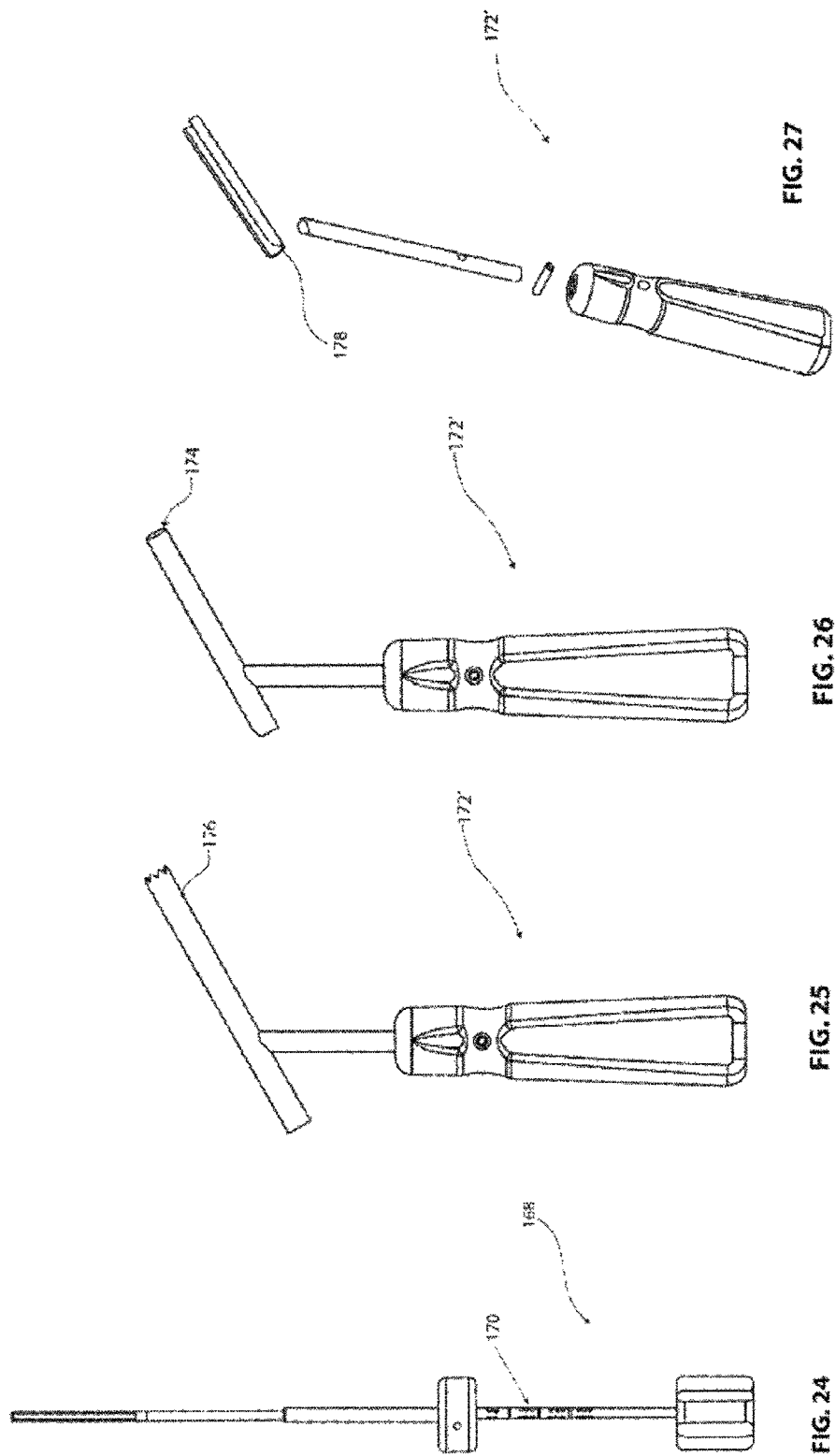

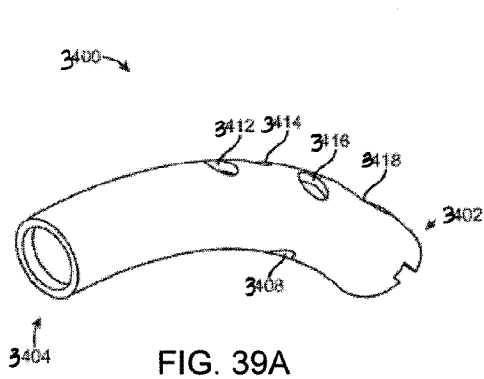
FIG. 39A
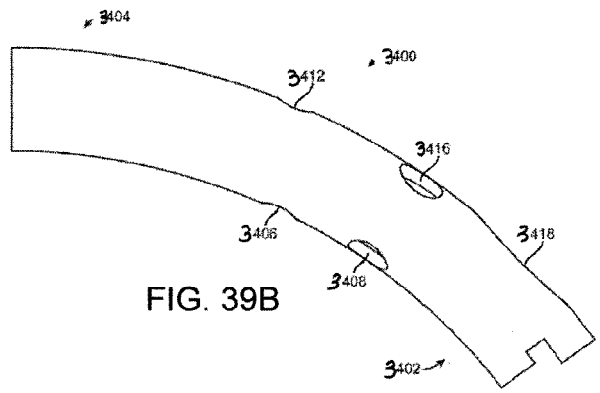
FIG. 39B
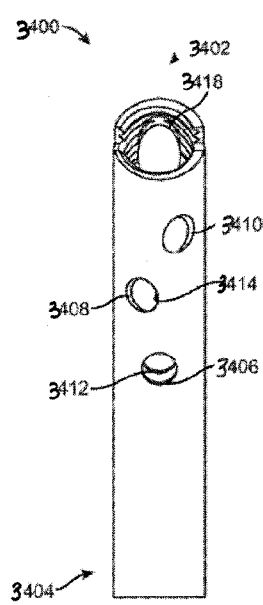
FIG. 39C
FIG. 39D
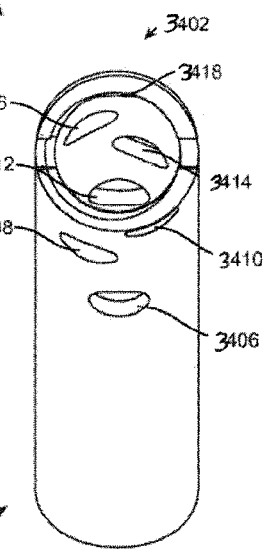
FIG. 39F
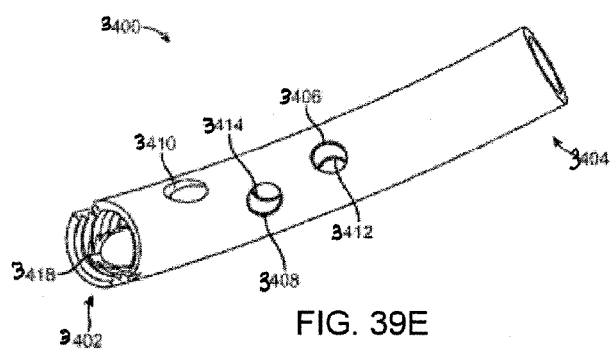
FIG. 39E

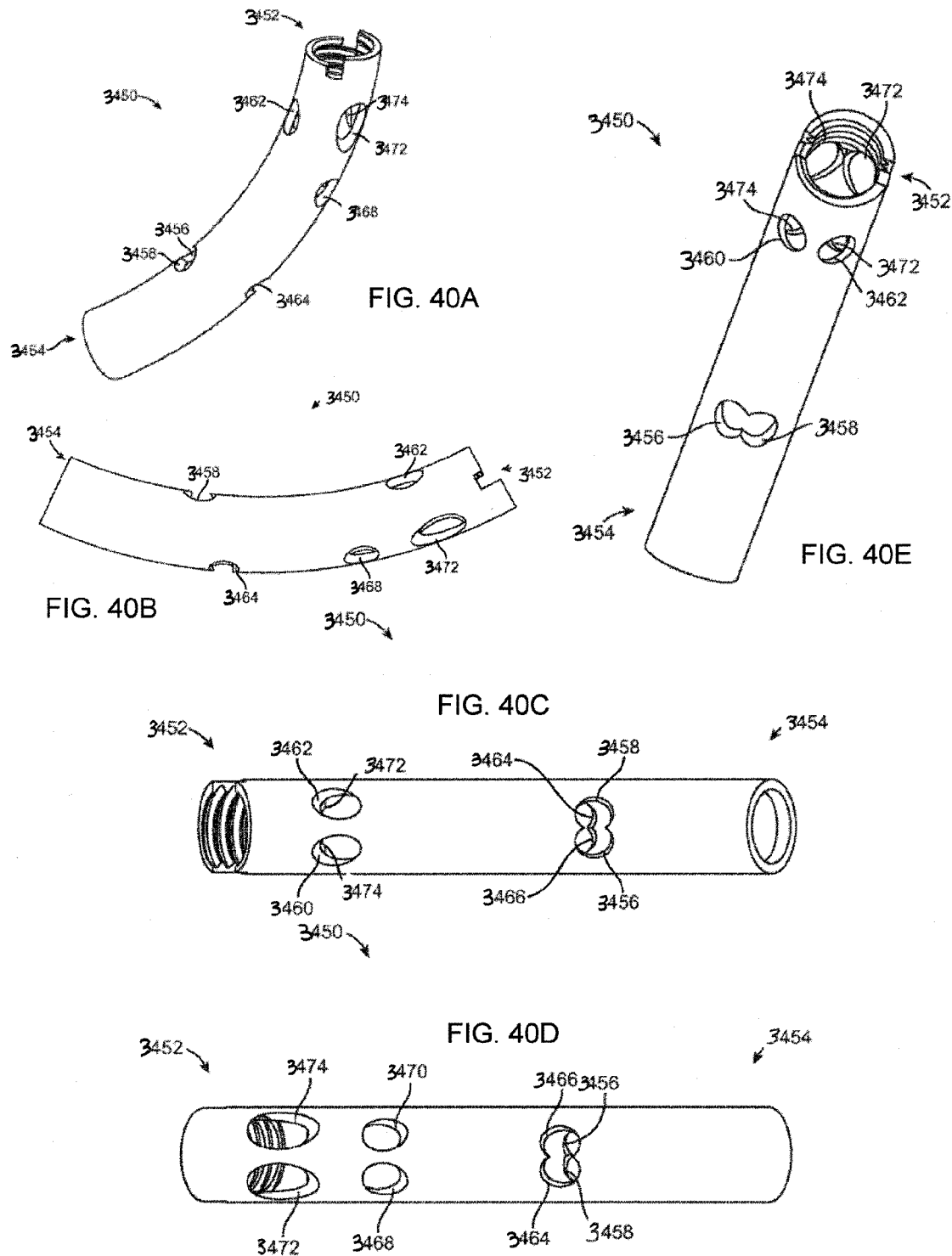

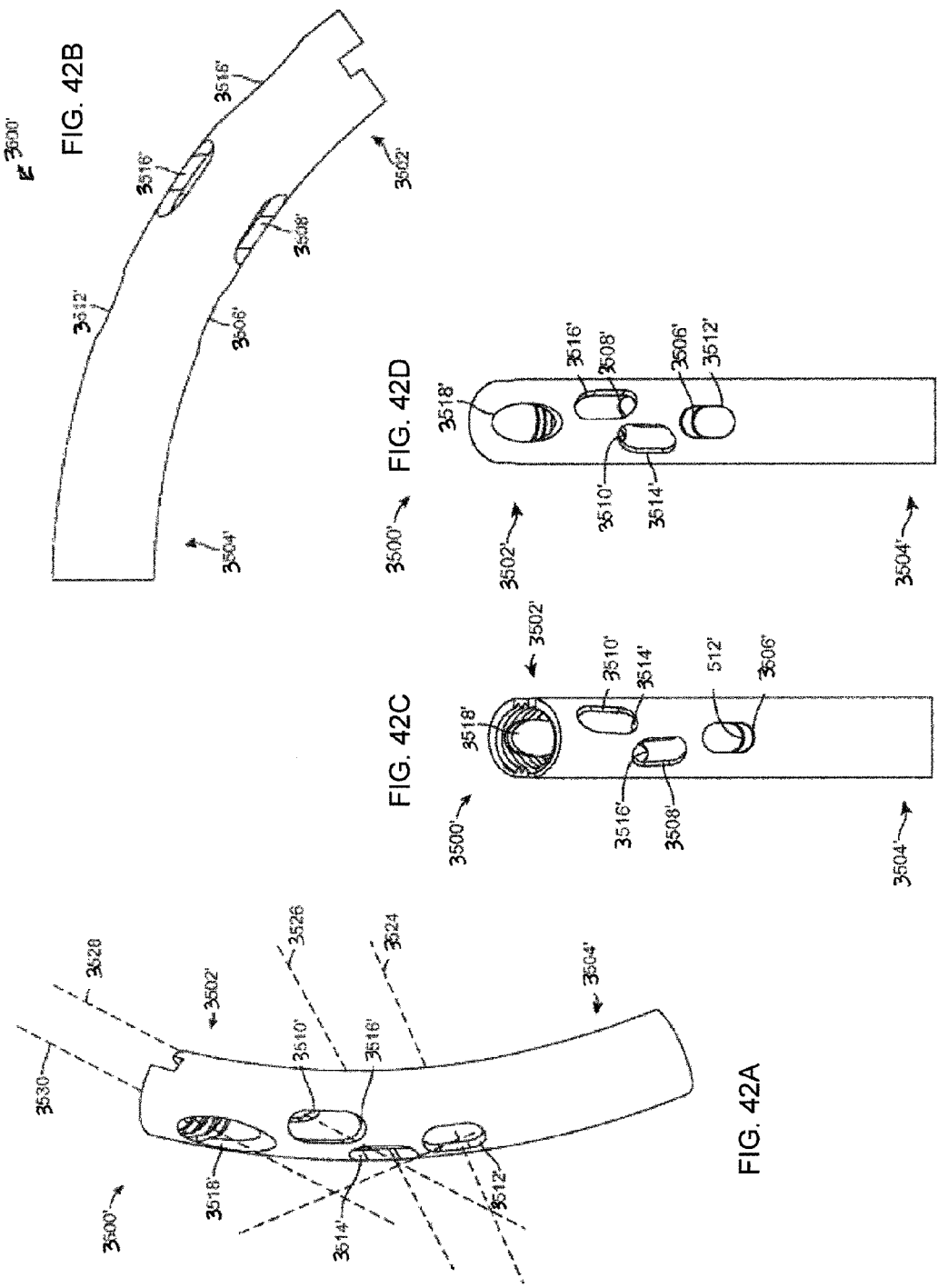

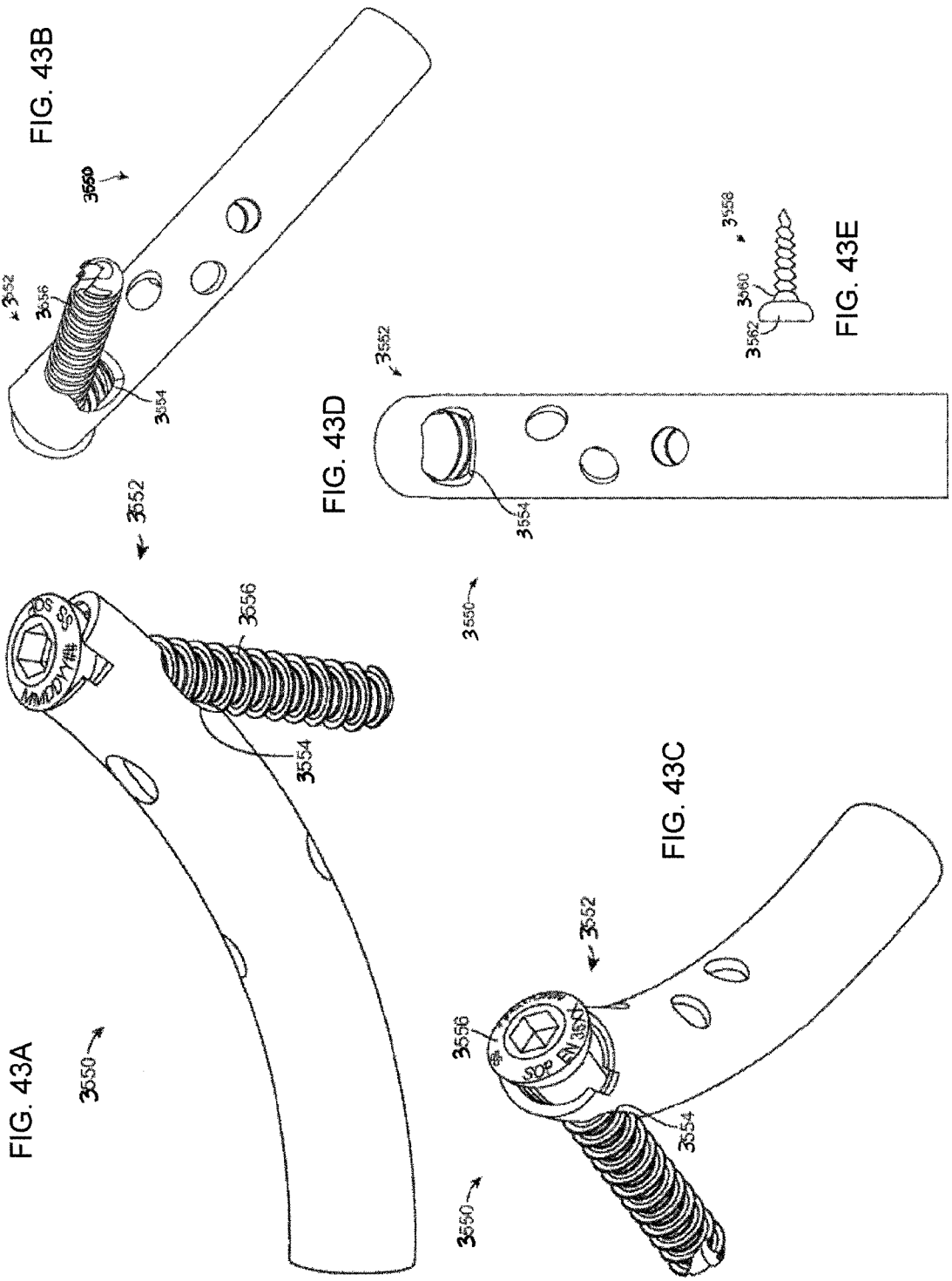

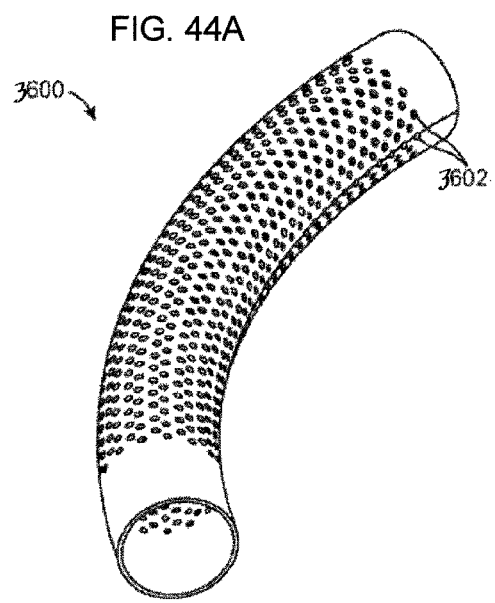
FIG. 44A
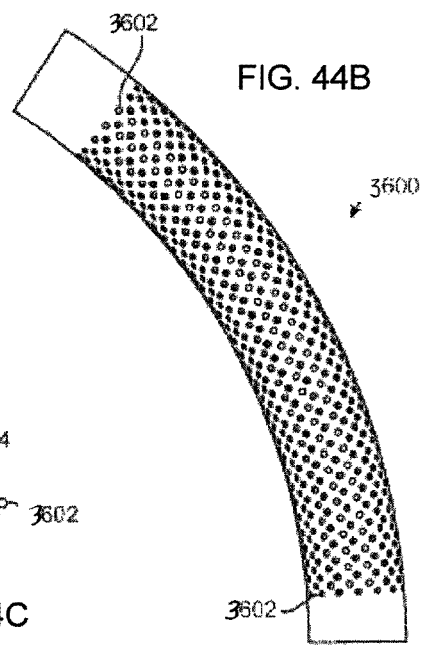
FIG. 44B
FIG. 44C
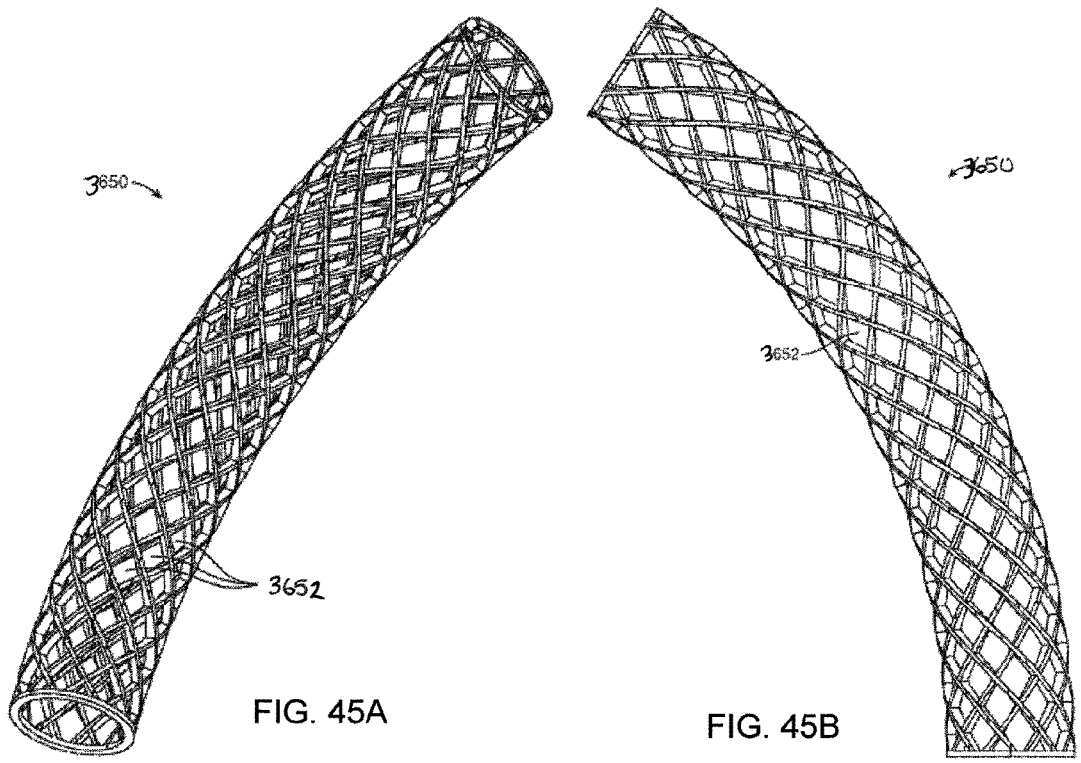
FIG. 45A
FIG. 45B

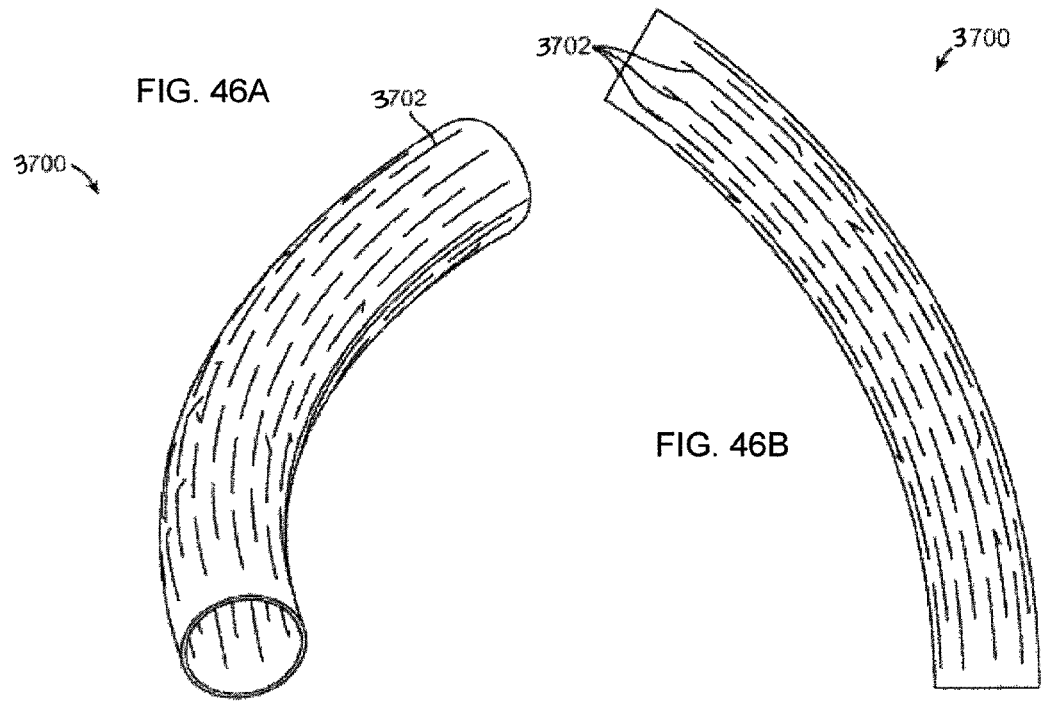
FIG. 46A
FIG. 46B
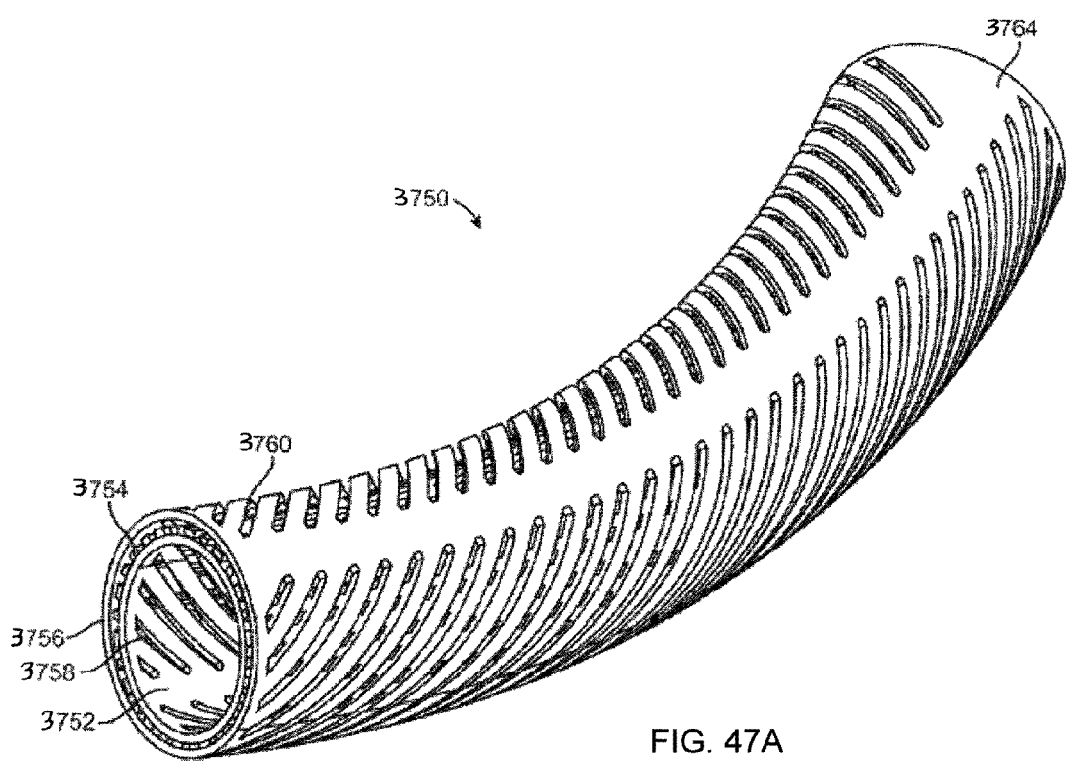
FIG. 47A

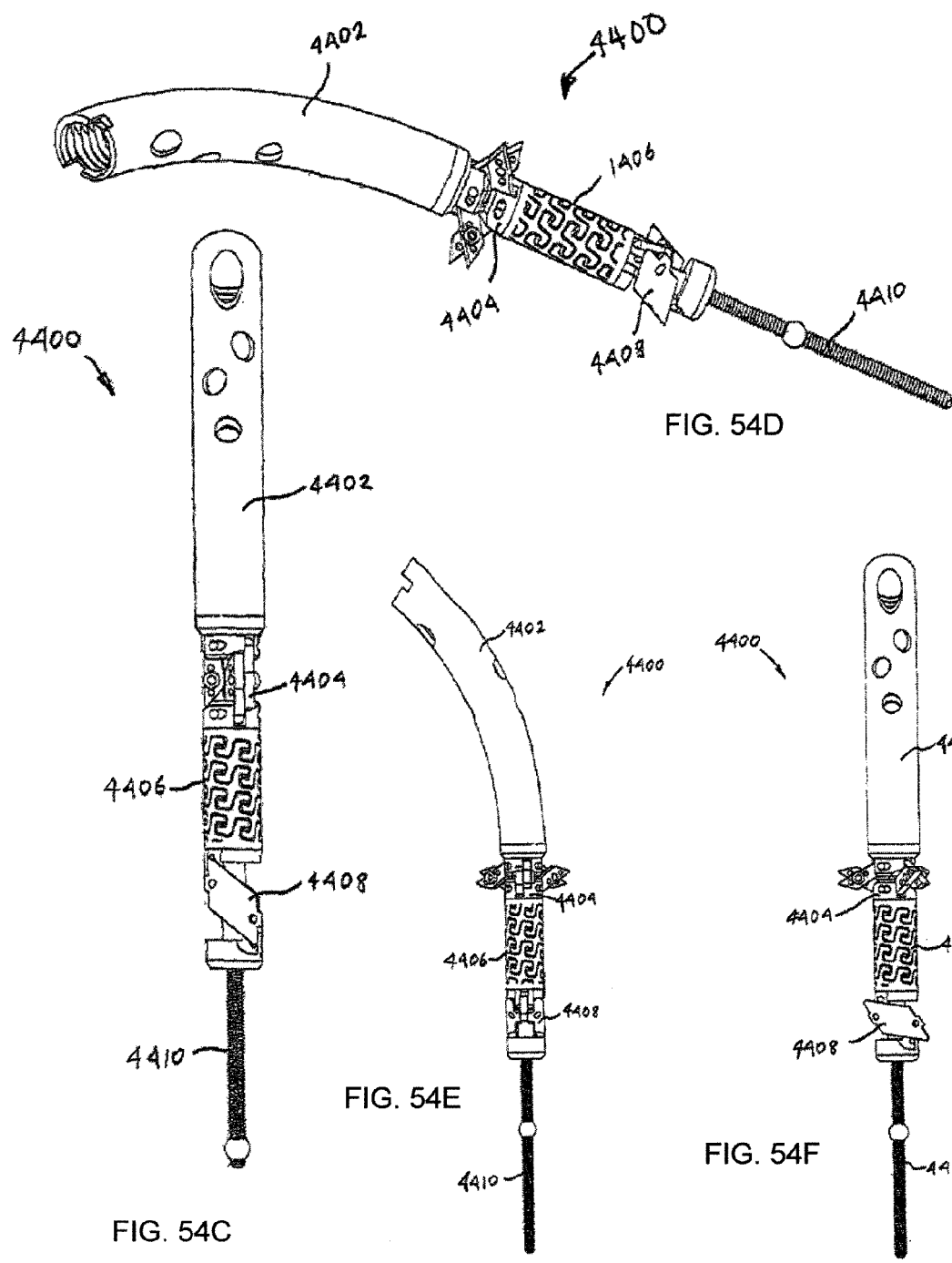

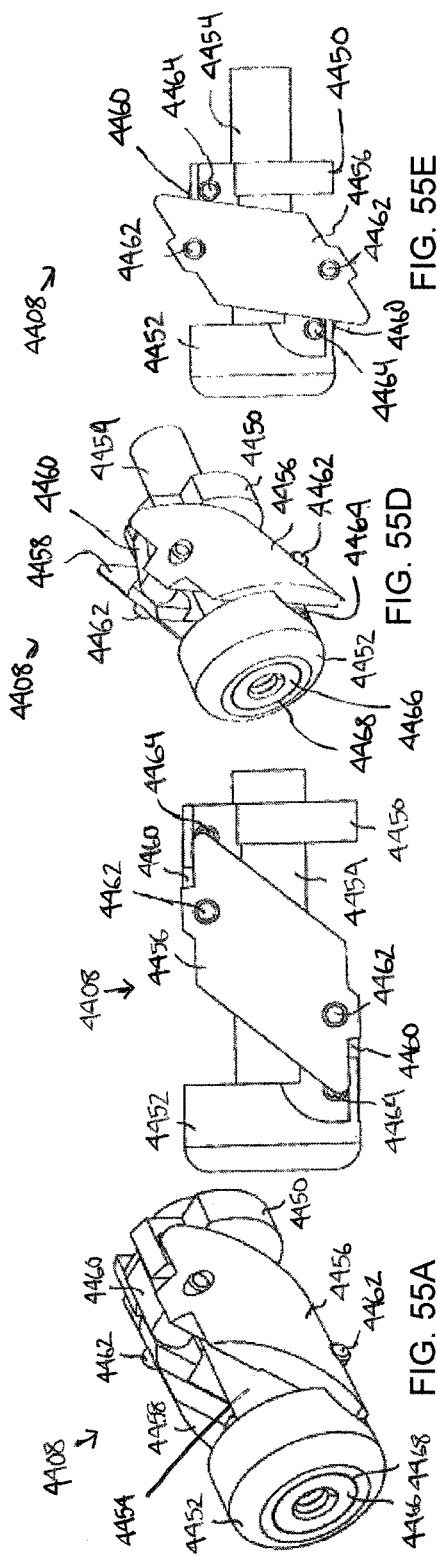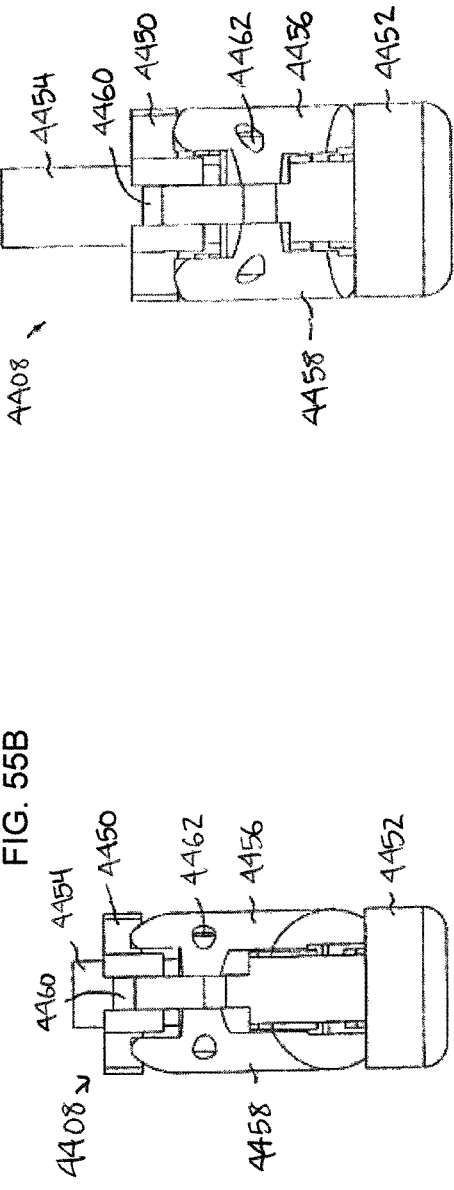

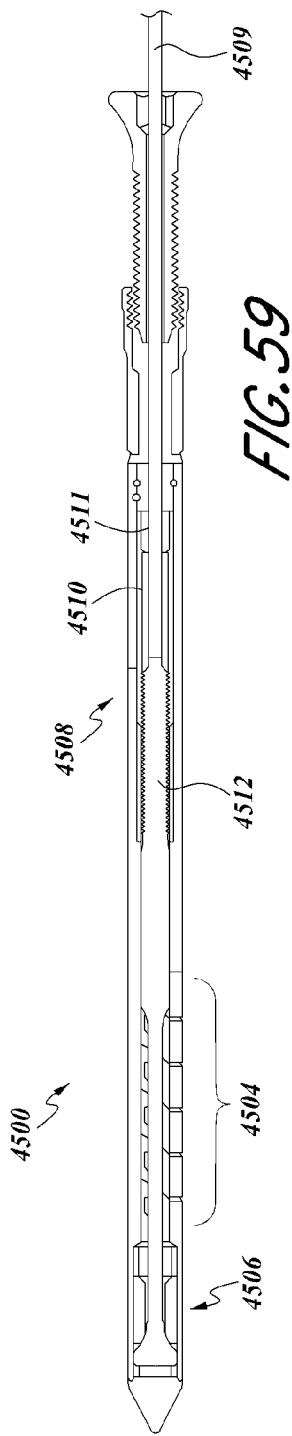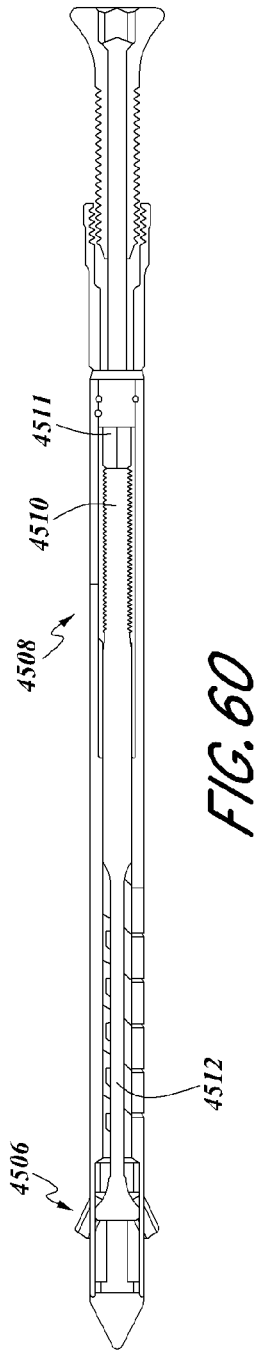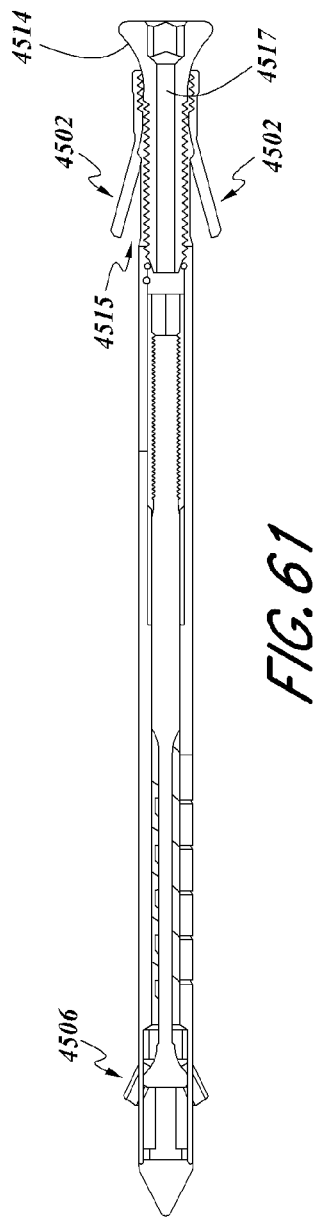

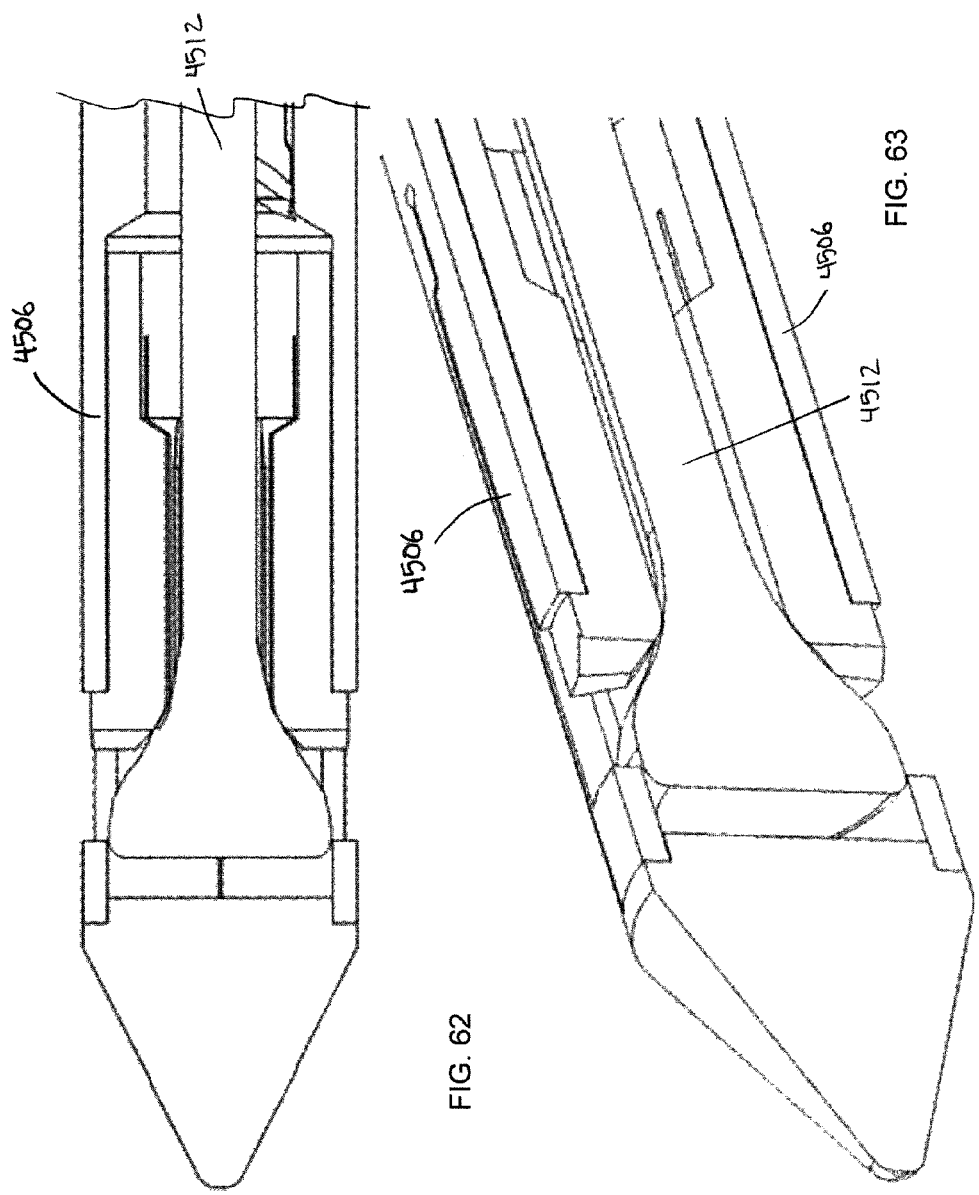

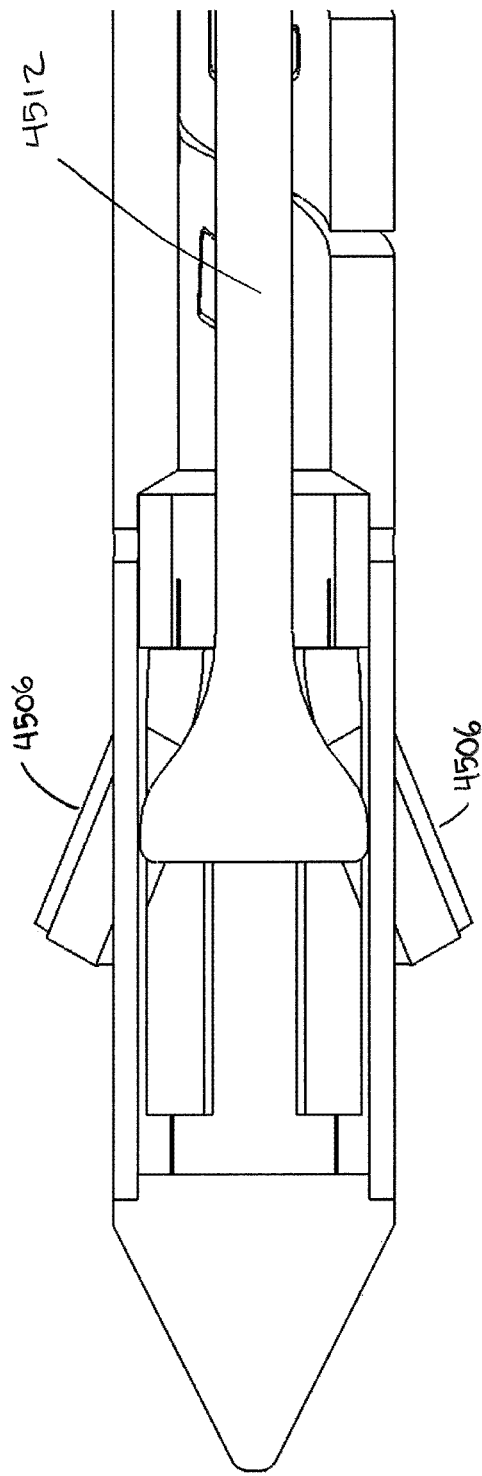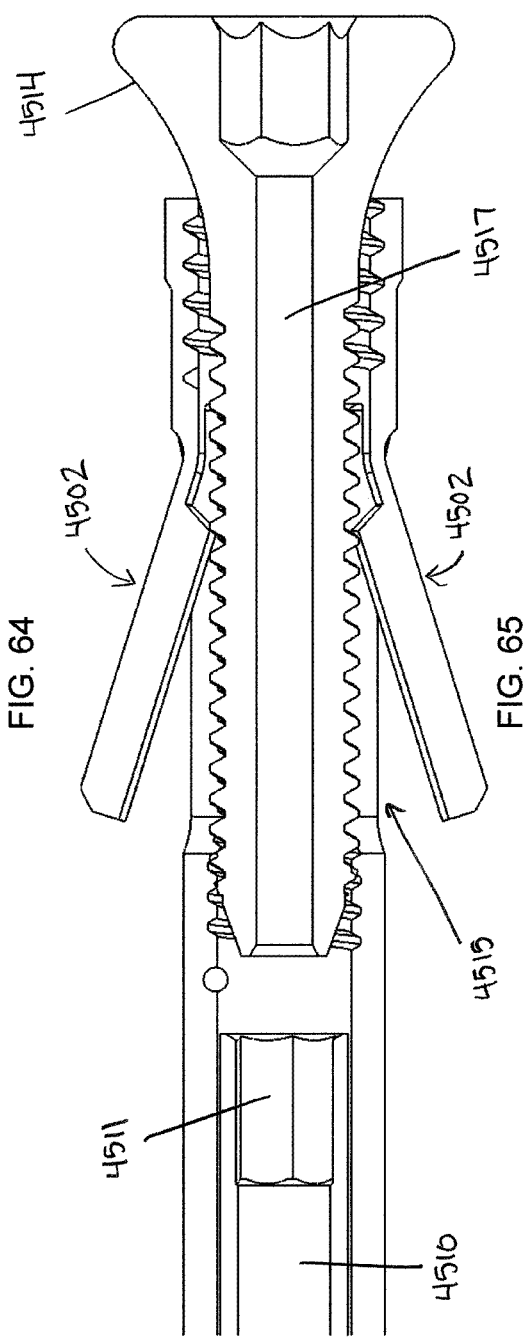

FIG. 96B
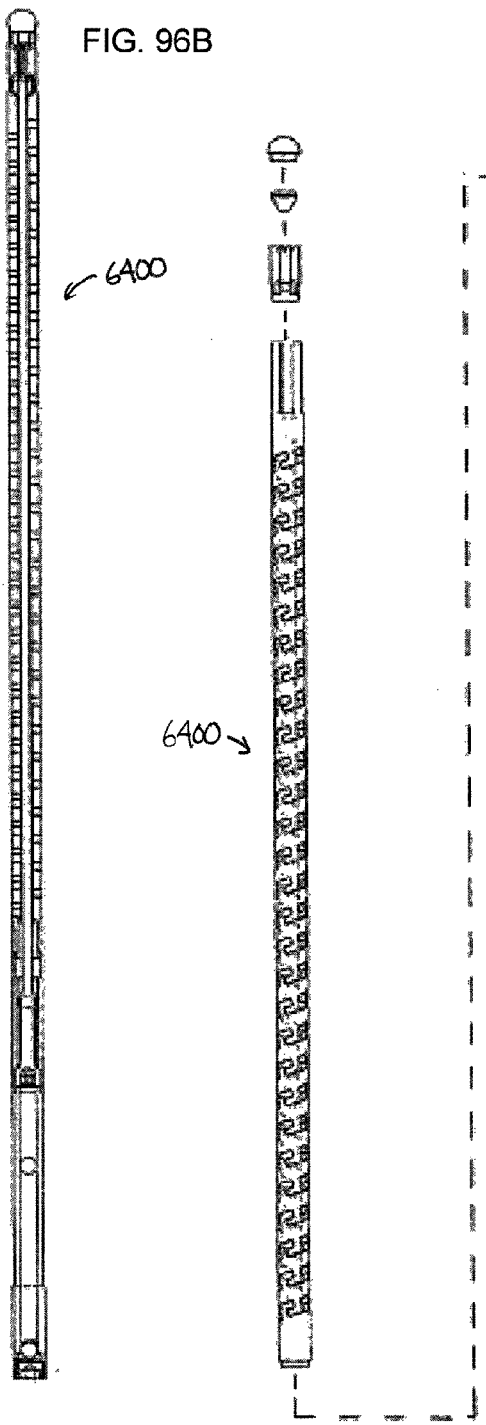
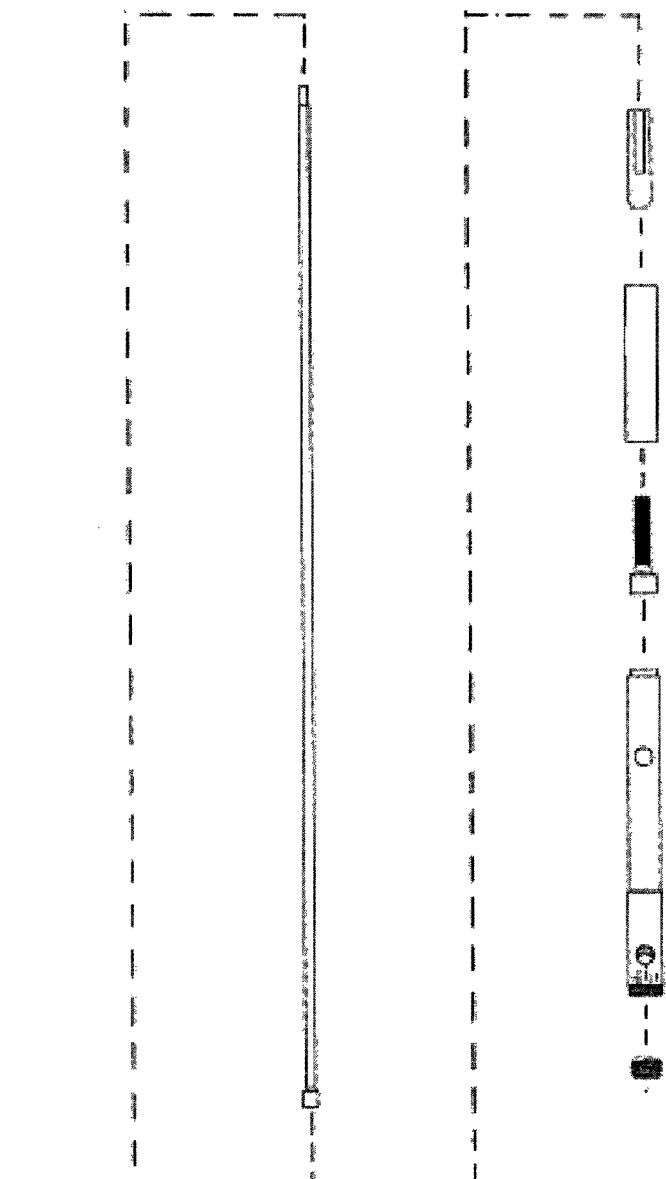
FIG. 96C

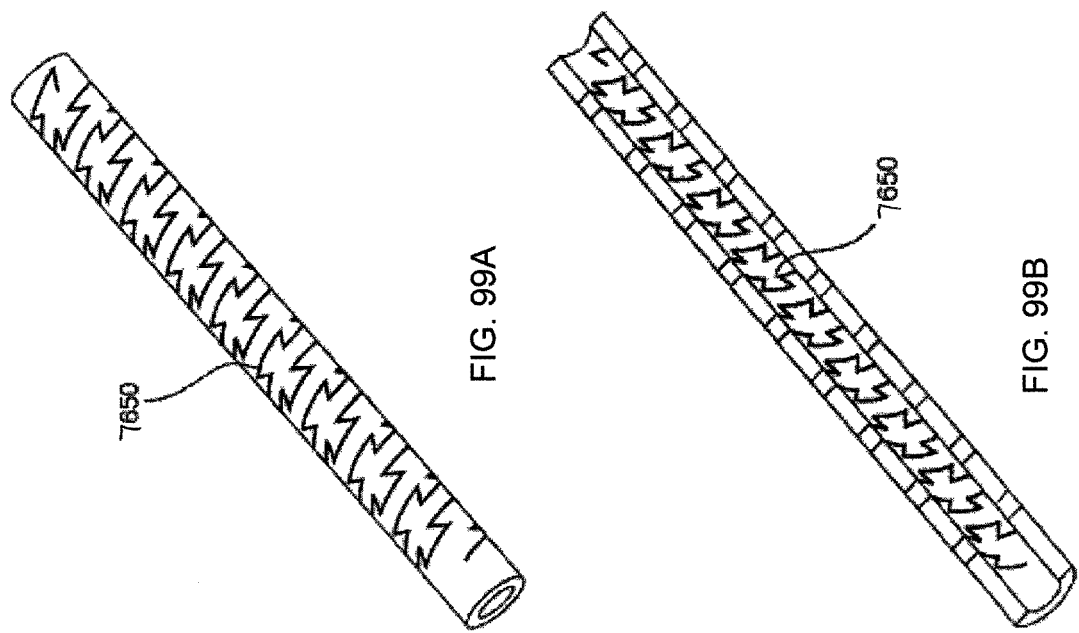
FIG. 99A
FIG. 99B
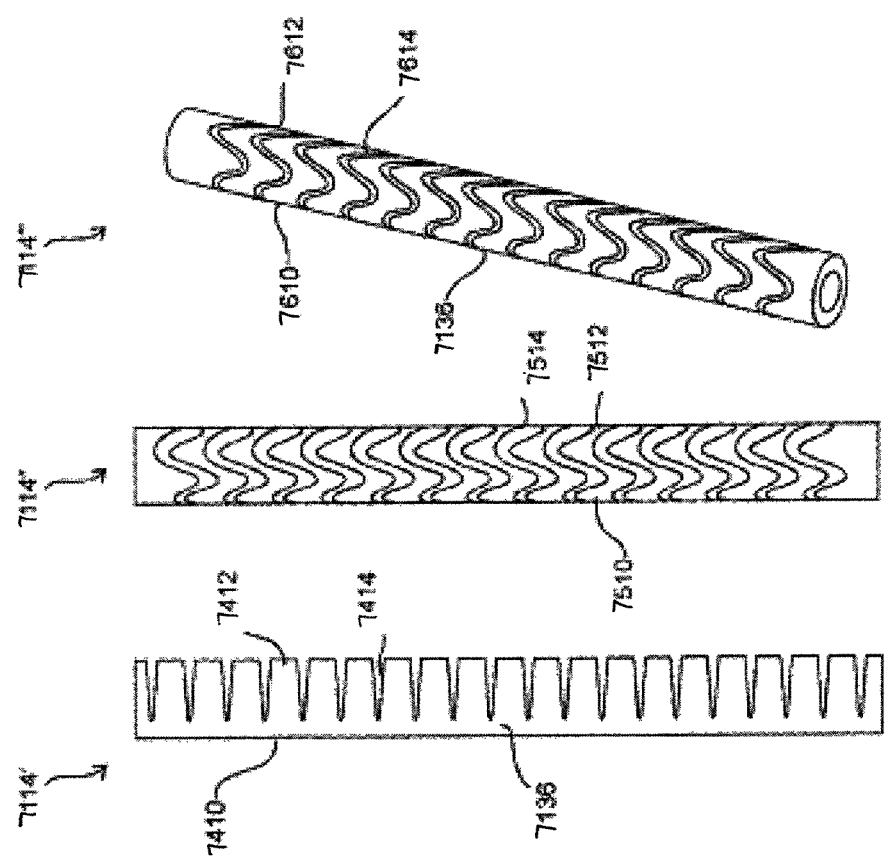
FIG. 98B
FIG. 98A
FIG. 97

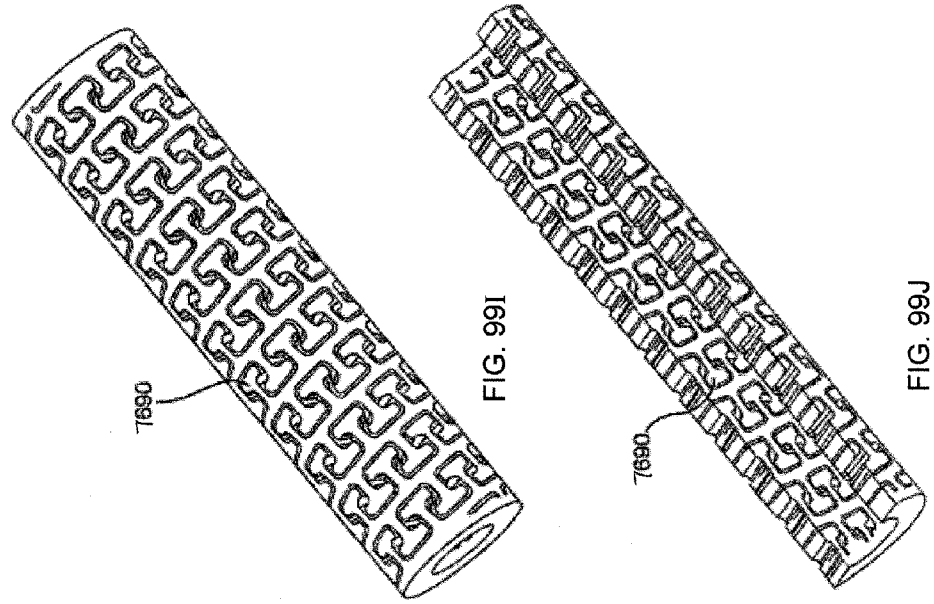
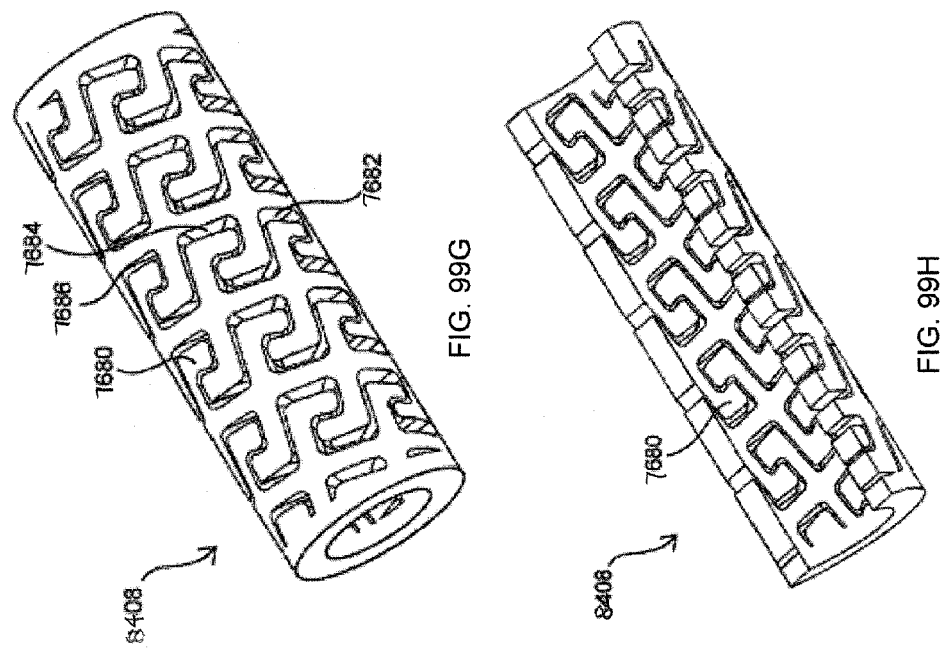

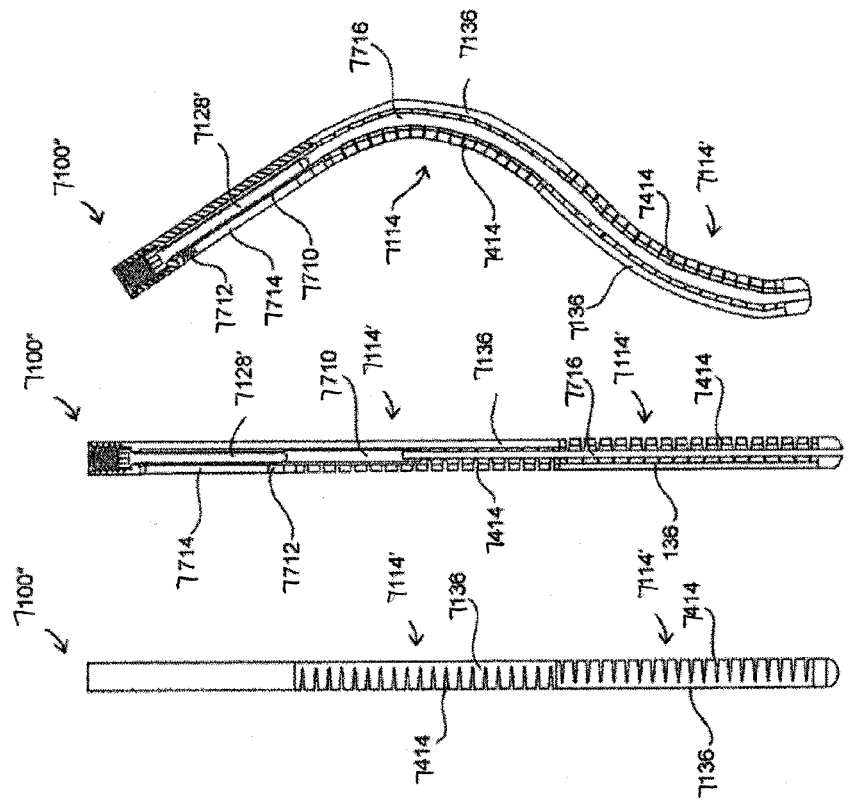
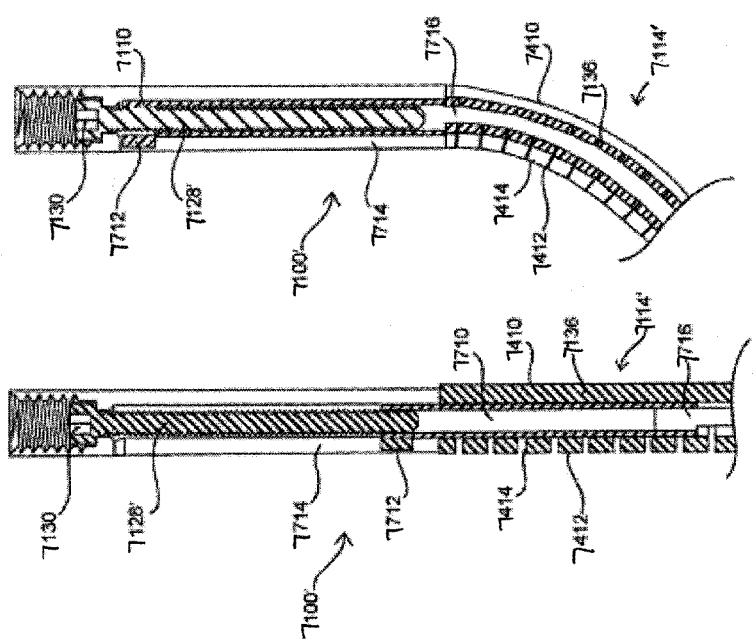
FIG. 100A  FIG. 100B  FIG. 101A  FIG. 101B  FIG. 101C

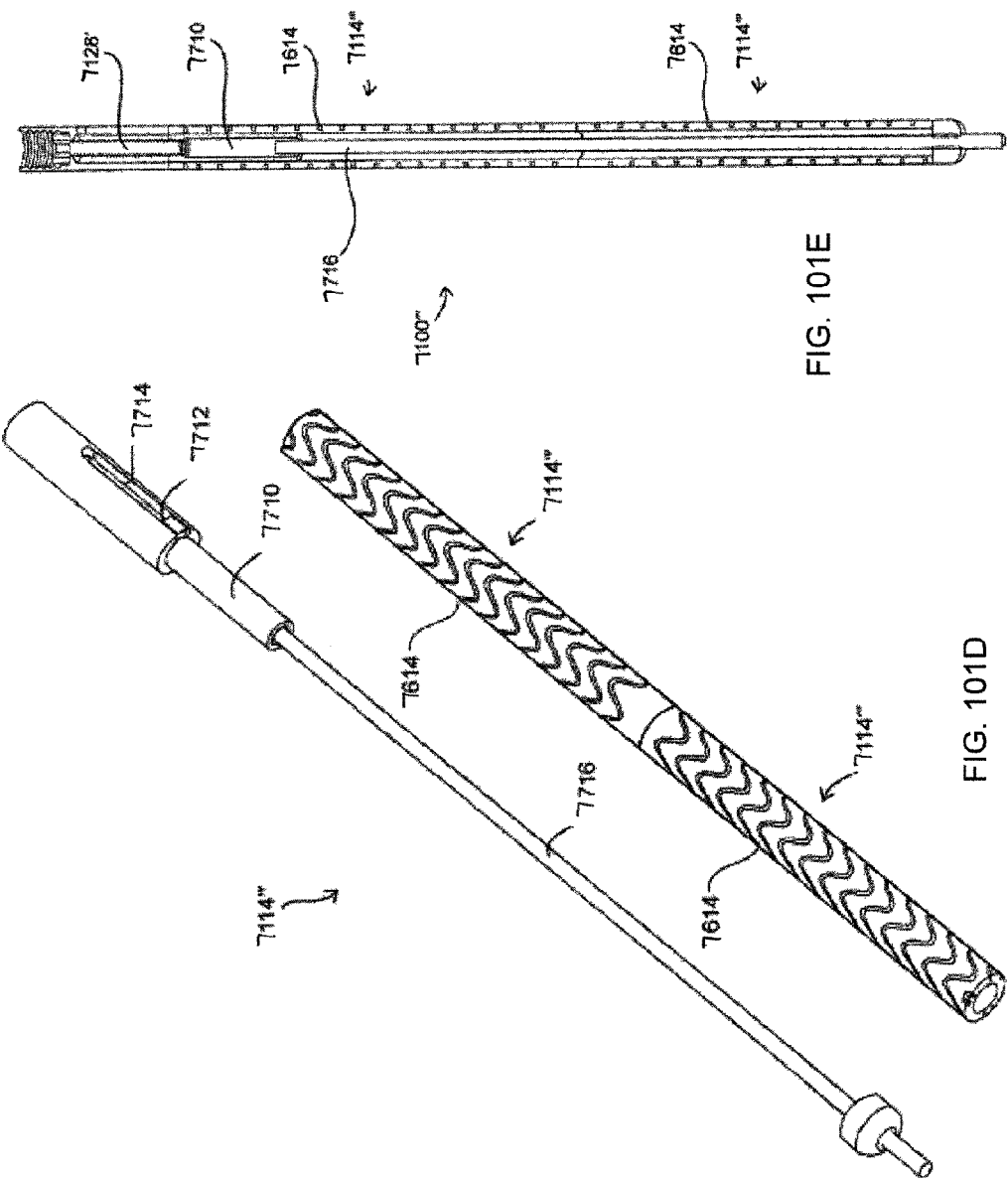

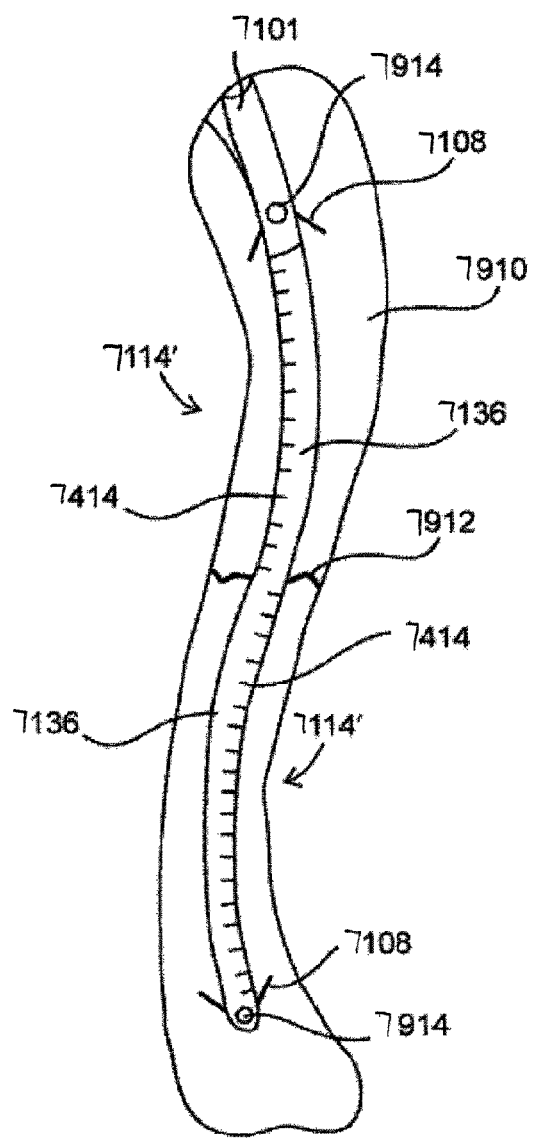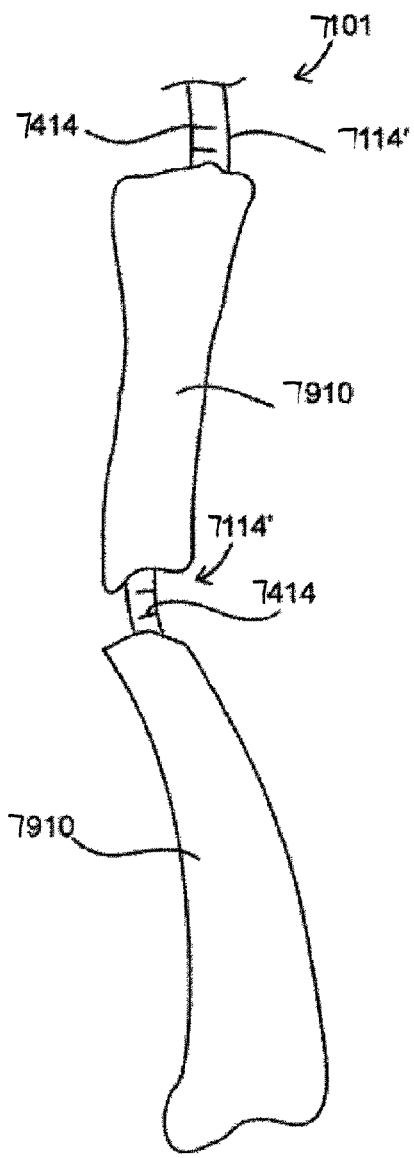
FIG. 102                    FIG. 103

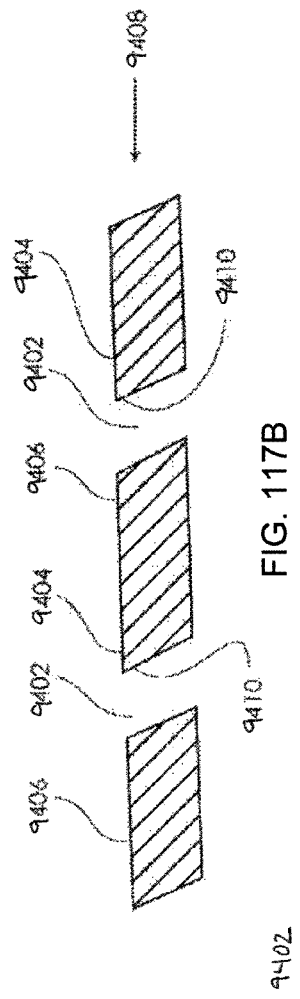
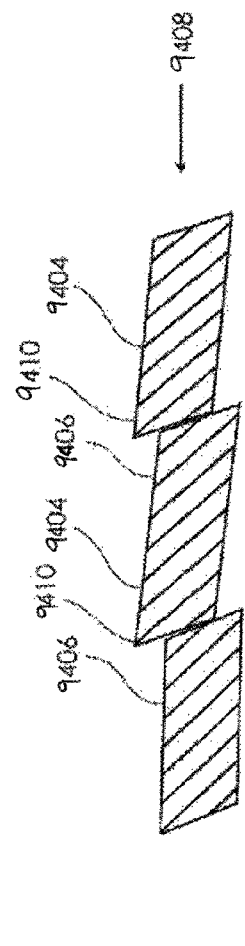
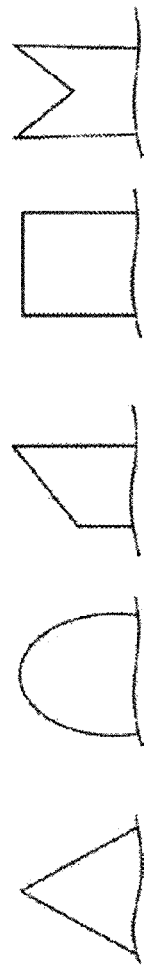
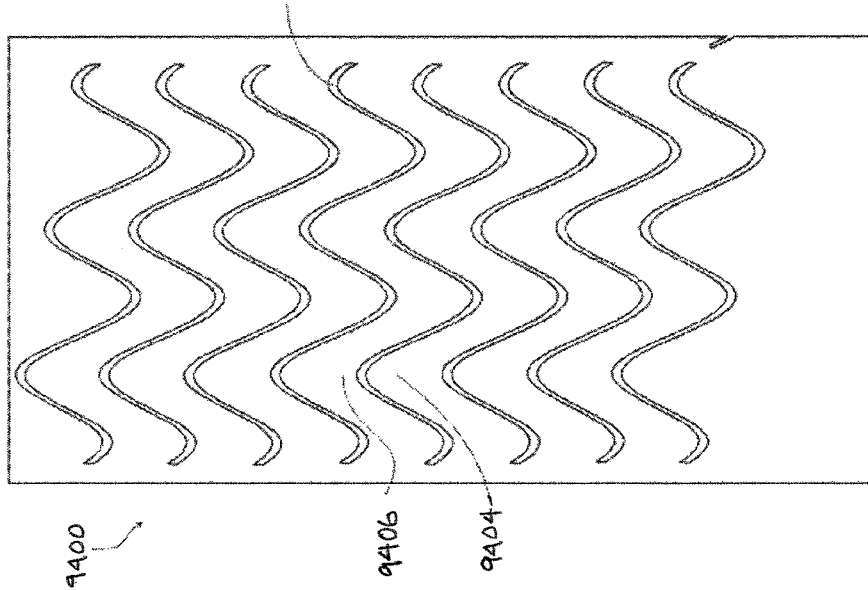
FIG. 117B  FIG. 117C
FIG. 117A
FIG. 117D  FIG. 117E  FIG. 117F  FIG. 117G  FIG. 117H

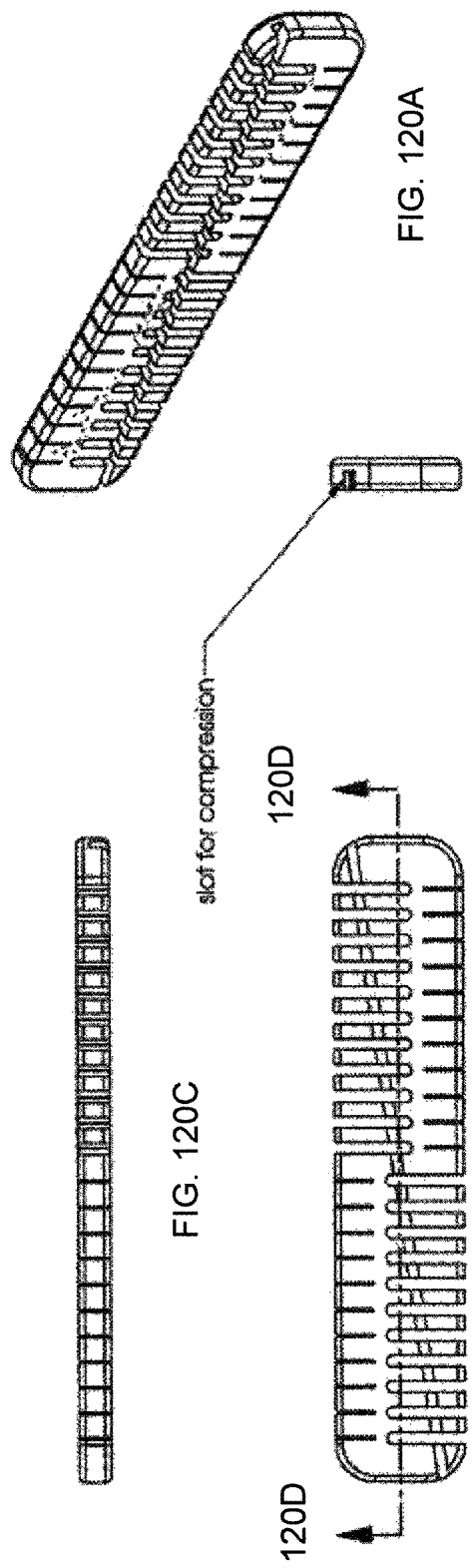
FIG. 120A
FIG. 120E
slot for compression
FIG. 120C
FIG. 120B
FIG. 120D

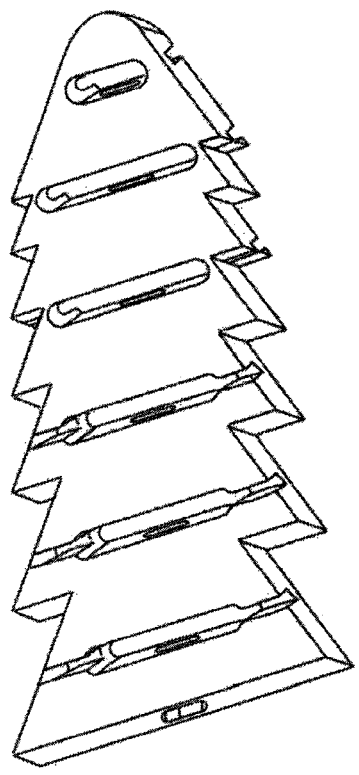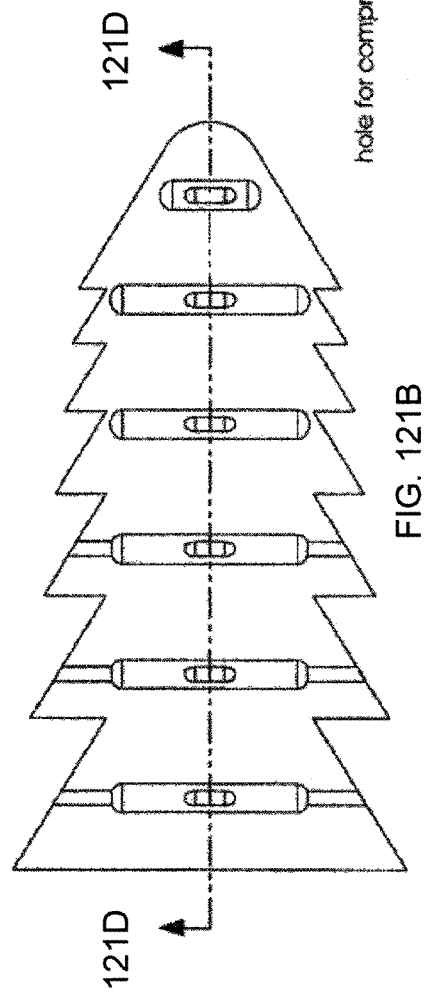
FIG. 121A
FIG. 121C
FIG. 121B
FIG. 121D
FIG. 121D
FIG. 121E
hole for compression

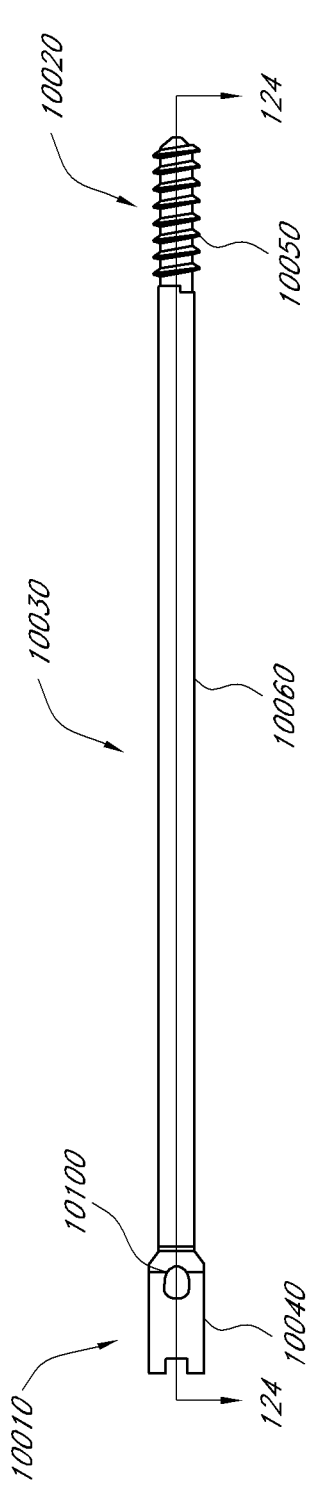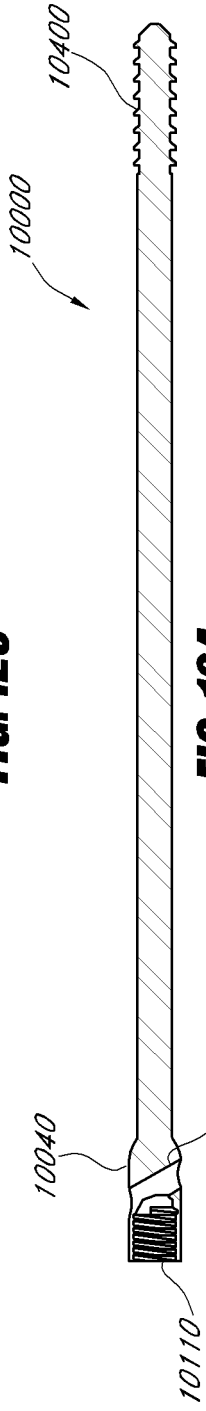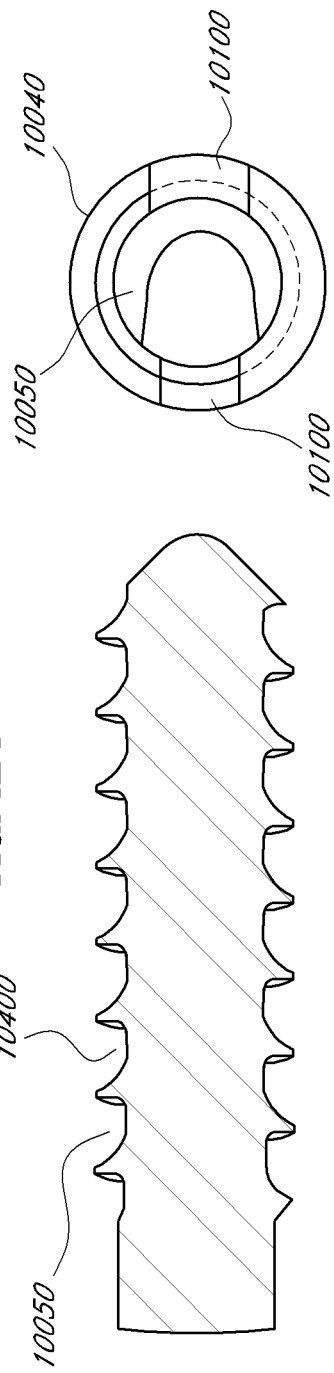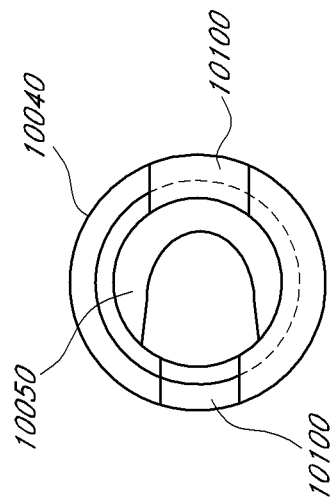
FIG. 123
FIG. 124
FIG. 125
FIG. 126

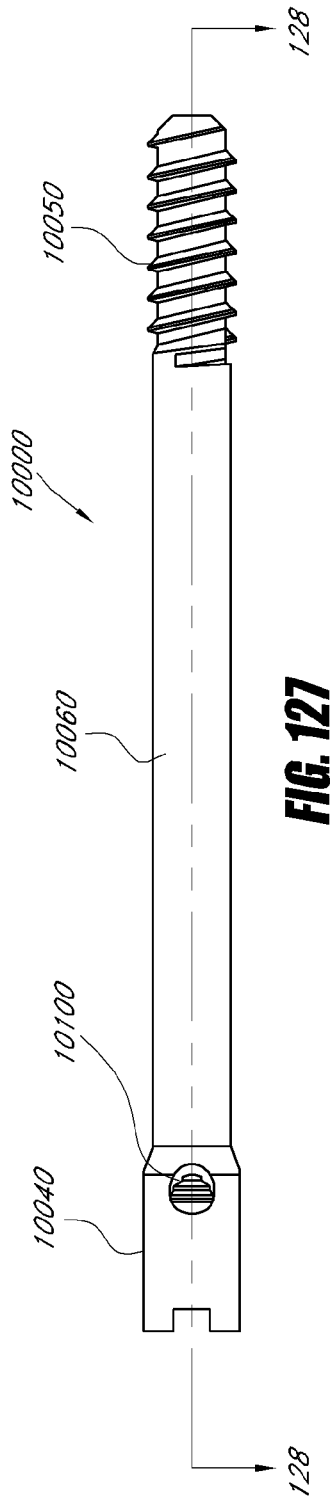
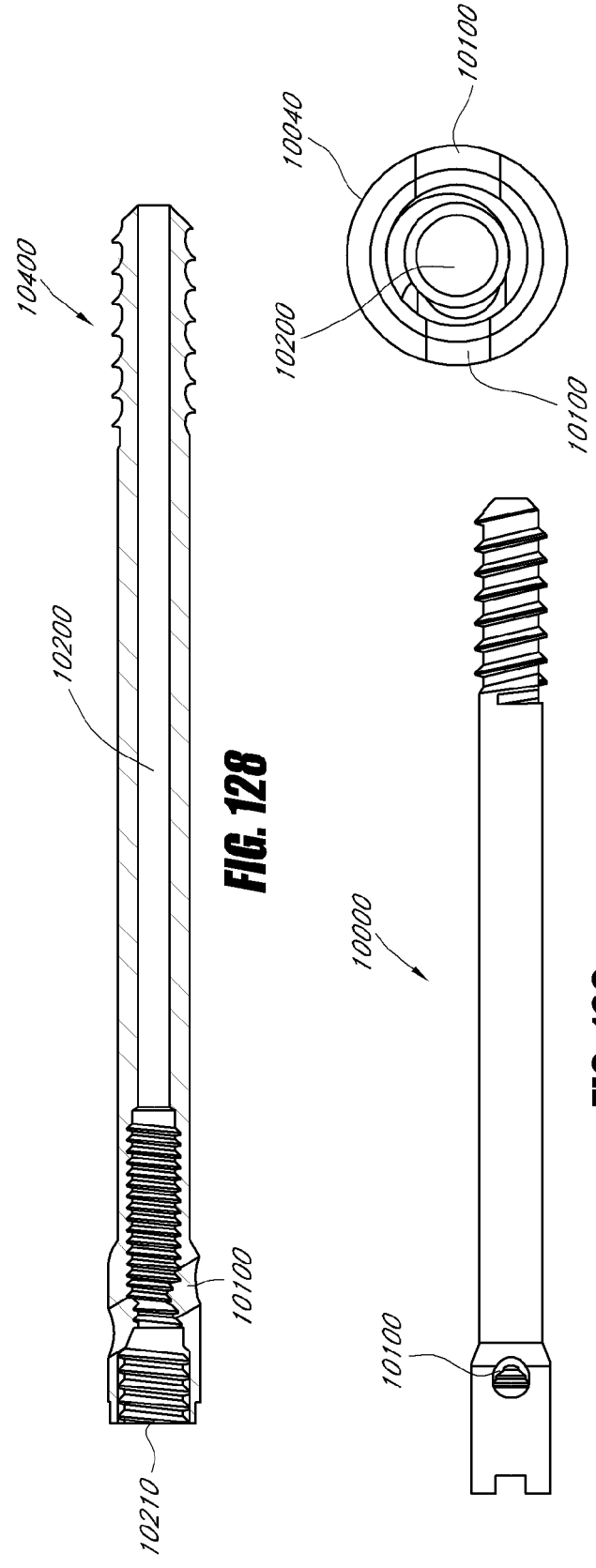
FIG. 127
FIG. 128
FIG. 129
FIG. 130

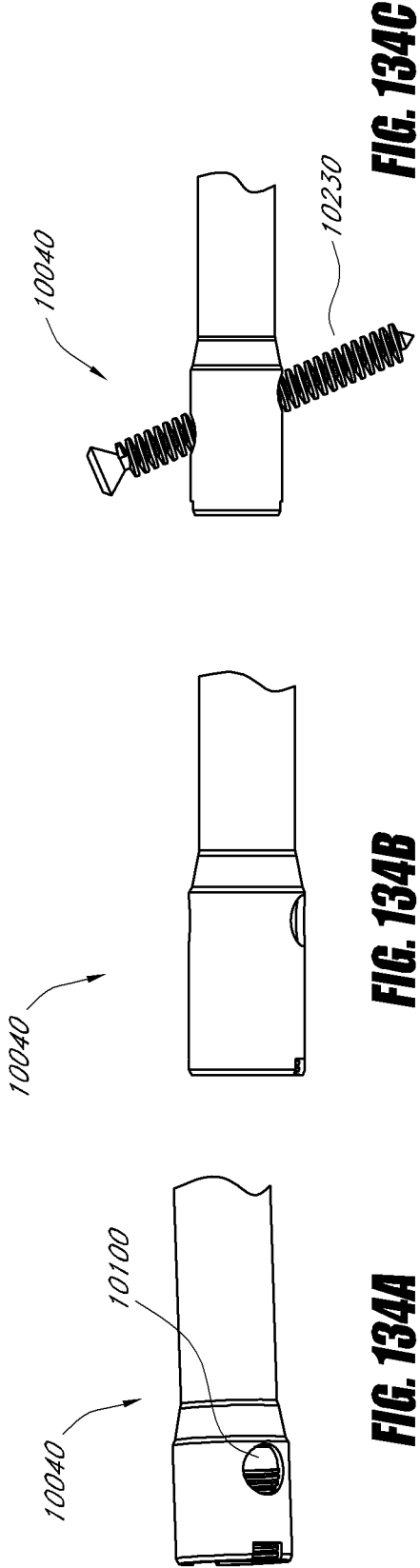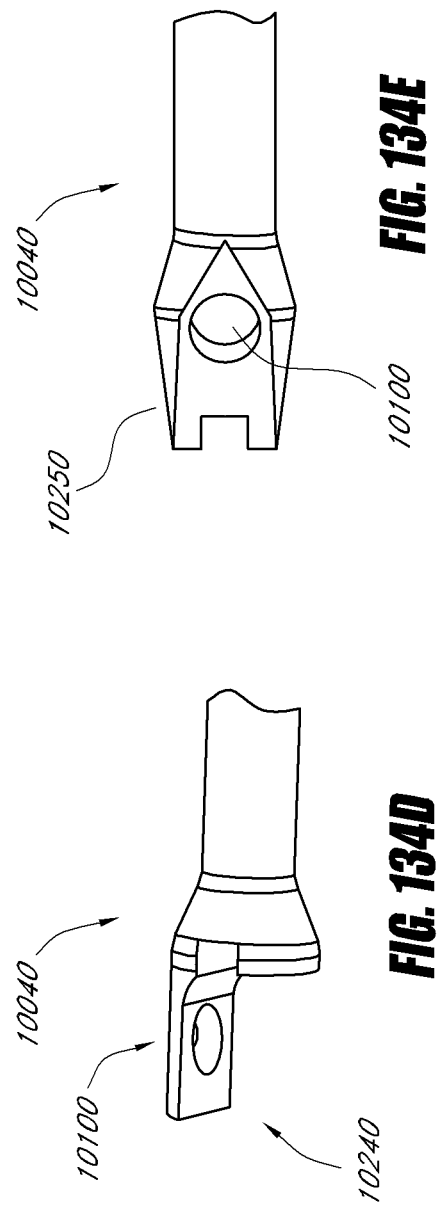

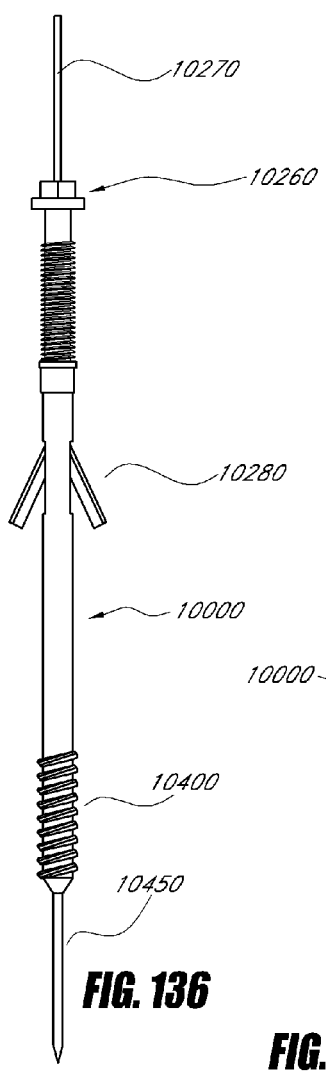
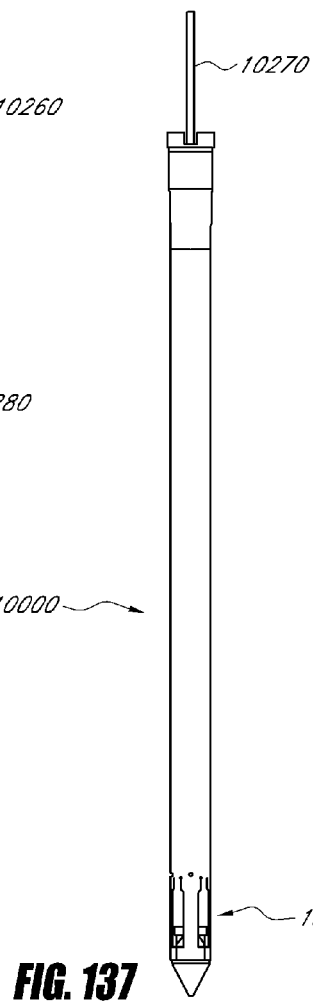
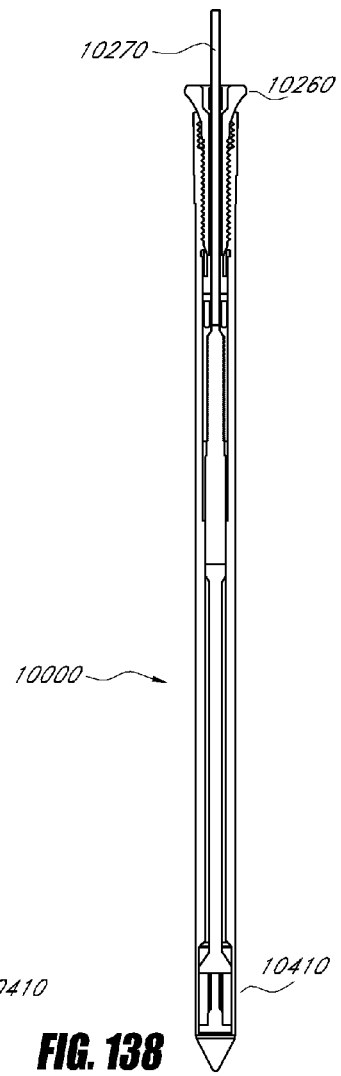
FIG. 136  FIG. 137  FIG. 138
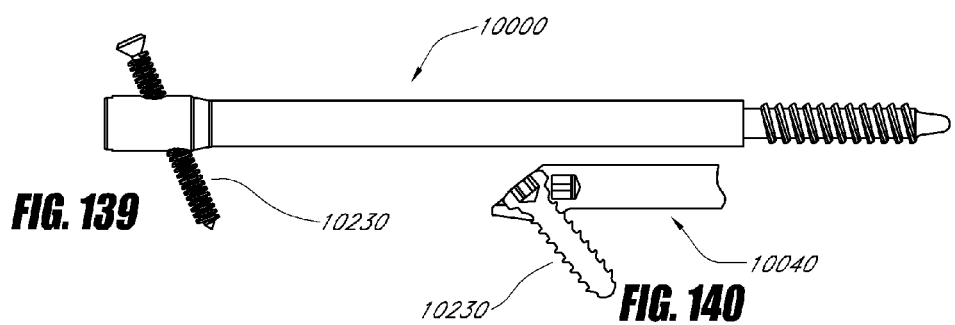
FIG. 139  FIG. 140

STRAIGHT INTRAMEDULLARY FRACTURE FIXATION DEVICES AND METHODS

CROSS-REFERENCE TO RELATED APPLICATIONS

This application claims the benefit of priority of U.S. Provisional Application 61/553,059, titled "STRAIGHT INTRAMEDULLARY FRACTURE FIXATION DEVICES AND METHODS", filed Oct. 28, 2011, which is incorporated by reference in its entirety herein.

This application is a Continuation-in-Part of U.S. application Ser. No. 12/482,388, filed Jun. 10, 2009, which claims the benefit of priority of U.S. Provisional Applications: No. 61/060,440, filed Jun. 10, 2008; No. 61/060,445, filed Jun. 10, 2008; No. 61/060,450, filed Jun. 10, 2008; No. 61/100,635, filed Sep. 26, 2008; No. 61/100,652, filed Sep. 26, 2008; No. 61/117,901, filed Nov. 25, 2008; No. 61/122,563, filed Dec. 15, 2008; and No. 61/138,920, filed Dec. 18, 2008. U.S. application Ser. No. 12/482,388 is also a Continuation-in-Part of U.S. application Ser. No. 11/383,269, filed May 15, 2006 which claims the benefit of priority of U.S. Provisional Application No. 60/682,652, filed May 18, 2005. U.S. application Ser. No. 12/482,388 is also a Continuation-in-part of U.S. application Ser. No. 11/383,800 filed May 17, 2006, which claims the benefit of priority of U.S. Provisional Application No. 60/682,652, filed May 18, 2005. U.S. application Ser. No. 12/482,388 is also a Continuation-in-Part of U.S. application Ser. No. 11/944,366, filed Nov. 21, 2007 which claims the benefit of priority of U.S. Provisional Applications: No. 60/867,011, filed Nov. 22, 2006; No. 60/866,976, filed Nov. 22, 2006; and No. 60/949,071, filed Jul. 11, 2007: all of which are incorporated by reference in their entireties herein.

This application is a Continuation-in-Part of U.S. application Ser. No. 12/482,406, filed Jun. 10, 2009. U.S. application Ser. No. 12/482,406 claims the benefit of priority of U.S. Provisional Applications: No. 61/060,440, filed Jun. 10, 2008; No. 61/060,445, filed Jun. 10, 2008; No. 61/060,450, filed Jun. 10, 2008; No. 61/100,635, filed Sep. 26, 2008; No. 61/100,652, filed Sep. 26, 2008; No. 61/117,901, filed Nov. 25, 2008; No. 61/122,563, filed Dec. 15, 2008; and No. 61/138,920, filed Dec. 18, 2008. U.S. application Ser. No. 12/482,406 is also a Continuation-in-Part of U.S. application Ser. No. 11/383,269, filed May 15, 2006 which claims the benefit of priority of U.S. Provisional Application No. 60/682,652, filed May 18, 2005. U.S. application Ser. No. 12/482,406 is also a Continuation-in-part of U.S. application Ser. No. 11/383,800, filed May 17, 2006, which claims the benefit of priority of U.S. Provisional Application No. 60/682,652, filed May 18, 2005. U.S. application Ser. No. 12/482,406 is also a Continuation-in-Part of U.S. application Ser. No. 11/944,366, filed Nov. 21, 2007 which claims the benefit of priority of U.S. provisional applications: No. 60/867,011, filed Nov. 22, 2006; No. 60/866,976, filed Nov. 22, 2006; and No. 60/949,071, filed Jul. 11, 2007: all of which are incorporated by reference in their entireties herein.

This application is a Continuation-in-Part of U.S. application Ser. No. 12/642,648, filed Dec. 18, 2009 which claims the benefit of priority of U.S. Provisional Application No. 61/138,920, filed Dec. 18, 2008: all of which are incorporated by reference in their entireties herein.

This application is a Continuation-in-Part of U.S. application Ser. No. 12/965,480, filed Dec. 10, 2010, which a Continuation of International Application PCT/US2009/046951, filed Jun. 10, 2009. International Application PCT/US2009/046951 claims the benefit of priority of U.S. Provisional Applications: No. 61/060,440, filed Jun. 10, 2008; No. 61/060,445, filed Jun. 10, 2008; No. 61/060,450, filed Jun. 10, 2008; No. 61/100,635, filed Sep. 26, 2008; No. 61/100,652, filed Sep. 26, 2008; No. 61/117,901, filed Nov. 25, 2008; No. 61/122,563, filed Dec. 15, 2008; and No. 61/138,920, filed Dec. 18, 2008: all of which are incorporated by reference in their entireties herein.

This application is a Continuation-in-Part of U.S. application Ser. No. 13/203,713, filed Aug. 26, 2011 which is a 371 National Phase application of PCT/US2009/058632, filed Sep. 28, 2009. International Application PCT/US2009/058632 priority of claims the benefit of priority of U.S. Provisional Application No. 61/100,635, filed Sep. 26, 2008; U.S. Provisional Application No. 61/100,652, filed Sep. 26, 2008; U.S. Provisional Application No. 61/117,901, filed Nov. 25, 2008; U.S. Provisional Application No. 61/122,563, filed Dec. 15, 2008; and U.S. Provisional Application No. 61/138,920, filed Dec. 18, 2008: all of which are incorporated by reference in their entireties herein.

INCORPORATION BY REFERENCE

All publications and patent applications mentioned in this specification are herein incorporated by reference to the same extent as if each individual publication or patent application was specifically and individually indicated to be incorporated by reference.

BACKGROUND

1. Field

Embodiments of the present invention relate to devices, tools and methods for providing reinforcement of bones. More specifically, the present invention relates to devices, tools and methods for providing reconstruction and reinforcement of bones, including diseased, osteoporotic and/or fractured bones.

2. Description of the Related Art

The number and diversity of sports and work related fractures are being driven by several sociological factors. The diversity of high energy sports has increased and the participation in these sports has followed the general trend of affluence and the resultant amount of time for leisure. High energy sports include skiing, motorcycle riding, snow mobile riding, snowboarding, mountain biking, road biking, kayaking, and all terrain vehicle (ATV) riding. As the general affluence of the economically developed countries has increased the number (or amount) and age of people participating in these activities has increased. Lastly, the acceptance and ubiquitous application of passive restraint systems, airbags, in automobiles has created greater numbers of non-life threatening fractures. In the past, a person that might expire from a serious automobile accident, now survives with multiple traumas and resultant fractures.

Bone fractures are a common medical condition both in the young and old segments of the population. However, with an increasingly aging population, osteoporosis has become more of a significant medical concern in part due to the risk of osteoporotic fractures. Osteoporosis and osteoarthritis are among the most common conditions to affect the musculoskeletal system, as well as frequent causes of locomotor pain and disability. Osteoporosis can occur in both human and animal subjects (e.g. horses). Osteoporosis (OP) and osteoarthritis (OA) occur in a substantial portion of the human population over the age of fifty. The National Osteoporosis Foundation estimates that as many as 44 million Americans are affected by osteoporosis and low bone mass, leading to fractures in more than 300,000 people over the age of 65. In 1997 the estimated cost for osteoporosis related fractures was $13 billion. That figure increased to $17 billion in 2002 and is projected to increase to $210-240 billion by 2040. Currently it is expected that one in two women, and one in four men, over the age of 50 will suffer an osteoporosis-related fracture. Osteoporosis is the most important underlying cause of fracture in the elderly. Also, sports and work-related accidents account for a significant number of bone fractures seen in emergency rooms among all age groups.

One current treatment of bone fractures includes surgically resetting the fractured bone. After the surgical procedure, the fractured area of the body (i.e., where the fractured bone is located) is often placed in an external cast for an extended period of time to ensure that the fractured bone heals properly. This can take several months for the bone to heal and for the patient to remove the cast before resuming normal activities.

In some instances, an intramedullary (IM) rod or nail is used to align and stabilize the fracture. In that instance, a metal rod is placed inside a canal of a bone and fixed in place, typically at both ends. See, for example, Fixion™ IM (Nail), www.disc-o-tech.com. Placement of conventional IM rods are typically a "line of sight" and require access collinear with the center line of the IM canal. Invariably, this line of sight access violates, disrupts, and causes damage to important soft tissue structures such as ligaments, tendons, cartilage, fascia, and epidermis. This approach requires incision, access to the canal, and placement of the IM nail. The nail can be subsequently removed or left in place. A conventional IM nail procedure requires a similar, but possibly larger, opening to the space, a long metallic nail being placed across the fracture, and either subsequent removal, and or when the nail is not removed, a long term implant of the IM nail. The outer diameter of the IM nail must be selected for the minimum inside diameter of the space. Therefore, portions of the IM nail may not be in contact with the canal. Further, micromotion between the bone and the IM nail may cause pain or necrosis of the bone. In still other cases, infection can occur. The IM nail may be removed after the fracture has healed. This requires a subsequent surgery with all of the complications and risks of a later intrusive procedure. In general, rigid IM rods or nails are difficult to insert, can damage the bone and require additional incisions for cross-screws to attach the rods or nails to the bone.

Some IM nails are inflatable. See, for example, Meta-Fix IM Nailing System, www.disc-o-tech.com. Such IM nails require inflating the rod with very high pressures, endangering the surrounding bone. Inflatable nails have many of the same drawbacks as the rigid IM nails described above.

External fixation is another technique employed to repair fractures. In this approach, a rod may traverse the fracture site outside of the epidermis. The rod is attached to the bone with trans-dermal screws. If external fixation is used, the patient will have multiple incisions, screws, and trans-dermal infection paths. Furthermore, the external fixation is cosmetically intrusive, bulky, and prone to painful inadvertent manipulation by environmental conditions such as, for example, bumping into objects and laying on the device.

Other concepts relating to bone repair are disclosed in, for example, U.S. Pat. No. 5,108,404 to Scholten for Surgical Protocol for Fixation of Bone Using Inflatable Device; U.S. Pat. No. 4,453,539 to Raftopoulos et al. for Expandable Intramedullary Nail for the Fixation of Bone Fractures; U.S. Pat. No. 4,854,312 to Raftopolous for Expanding Nail; U.S. Pat. No. 4,932,969 to Frey et al. for Joint Endoprosthesis; U.S. Pat. No. 5,571,189 to Kuslich for Expandable Fabric Implant for Stabilizing the Spinal Motion Segment; U.S. Pat. No. 4,522,200 to Stednitz for Adjustable Rod; U.S. Pat. No. 4,204,531 to Aginsky for Nail with Expanding Mechanism; U.S. Pat. No. 5,480,400 to Berger for Method and Device for Internal Fixation of Bone Fractures; U.S. Pat. No. 5,102,413 to Poddar for Inflatable Bone Fixation Device; U.S. Pat. No. 5,303,718 to Krajicek for Method and Device for the Osteosynthesis of Bones; U.S. Pat. No. 6,358,283 to Hogfors et al. for Implantable Device for Lengthening and Correcting Malpositions of Skeletal Bones; U.S. Pat. No. 6,127,597 to Beyar et al. for Systems for Percutaneous Bone and Spinal Stabilization, Fixation and Repair; U.S. Pat. No. 6,527,775 to Warburton for Interlocking Fixation Device for the Distal Radius; U.S. Patent Publication US2006/0084998 A1 to Levy et al. for Expandable Orthopedic Device; and PCT Publication WO 2005/112804 A1 to Myers Surgical Solutions, LLC et. al. for Fracture Fixation and Site Stabilization System. Other fracture fixation devices, and tools for deploying fracture fixation devices, have been described in: U.S. Patent Appl. Publ. No. 2006/0254950; U.S. Ser. No. 60/867,011 (filed Nov. 22, 2006); U.S. Ser. No. 60/866,976 (filed Nov. 22, 2006); and U.S. Ser. No. 60/866,920 (filed Nov. 22, 2006).

In view of the foregoing, it would be desirable to have a device, system and method for providing effective and minimally invasive bone reinforcement and fracture fixation to treat fractured or diseased bones, while improving the ease of insertion, eliminating cross-screw incisions and minimizing trauma.

SUMMARY

As used herein, the term "aspect" may be used interchangeably with the term "embodiment." Aspects of the invention relate to embodiments of a bone fixation device and to methods for using such a device for repairing a bone fracture. The bone fixation device may include an elongate body with a longitudinal axis, and/or having a flexible state and a rigid state. The device further may include a plurality of grippers disposed at longitudinally-spaced locations along the elongated body, a rigid hub connected to the elongated body, and an actuator that is operably-connected to the grippers to deploy the grippers from a first shape to an expanded second shape. In various embodiments, the elongate body and the rigid hub may or may not be collinear or parallel.

In one embodiment, a bone fixation device is provided with an elongate body having a longitudinal axis and having a first state in which at least a portion of the body is flexible and a second state in which the body is generally rigid, an actuatable bone engaging mechanism disposed on the elongate body, and an actuator operably connected to the bone engaging mechanism to actuate the bone engaging mechanism from a disengaged configuration to an engaged configuration. In one embodiment, a bone fixation device is provided with an elongate body having a longitudinal axis and having a first state in which at least a portion of the body is flexible and a second state in which the body is generally rigid, an actuatable gripper disposed at a distal location on the elongated body, a hub located on a proximal end of the elongated body, and an actuator operably connected to the gripper to deploy the gripper from a retracted configuration to an expanded configuration.

In one embodiment, a bone fixation device is provided with an elongate body having a longitudinal axis and having a first state in which at least a portion of the body is flexible and a second state in which the body is generally rigid, an actuatable gripper disposed at a location on the elongated body, a hub located on a proximal end of the elongated body, and an actuator operably connected to the gripper to deploy the gripper from a retracted configuration to an expanded configuration.

In one embodiment, a bone fixation device is provided with an elongate body having a longitudinal axis and having a first state in which at least a portion of the body is flexible and a second state in which the body is generally rigid, an actuatable gripper disposed at a distal location on the elongated body, a hub located on a proximal end of the elongated body, and an actuator operably connected to the gripper to deploy the gripper from a retracted configuration to an expanded configuration.

Methods of repairing a fracture of a bone are also disclosed. One such method comprises inserting a bone fixation device into an intramedullary space of the bone to place at least a portion of an elongate body of the fixation device in a flexible state on one side of the fracture and at least a portion of a hub on another side of the fracture, and operating an actuator to deploy at least one gripper of the fixation device to engage an inner surface of the intramedullary space to anchor the fixation device to the bone.

Another such method of repairing a fracture of a clavicle, the clavicle having a lateral segment adjacent to the acromion of a scapula and a medial segment adjacent to the manubrium of a sternum comprises creating an intramedullary channel, such that the channel traverses the fracture of the clavicle and comprises at least one segment that substantially follows a curved anatomical contour of the clavicle; and inserting a bone fixation device into the intramedullary channel and across the fracture of the clavicle, such that at least a portion of an elongate body of the fixation device in a flexible state is placed within the curved segment of the channel.

According to aspects of the present disclosure, similar methods involve repairing a fracture of a metatarsal, metacarpal, sternum, tibia, rib, midshaft radius, ulna, olecranon (elbow), humerus, or distal fibula. Each of these bones have a distal and proximal segment, farthest and closest to the heart, respectively, and on opposite ends of a fracture. The method comprises creating an intramedullary channel, such that the channel traverses the fracture of the bone and comprises at least one segment that substantially follows a curved anatomical contour of the bone; and inserting a bone fixation device into the intramedullary channel and across the fracture of the bone, such that at least a portion of an elongate body of the fixation device in a flexible state is placed within the curved segment of the channel.

One embodiment of the present invention provides a low weight to volume mechanical support for fixation, reinforcement and reconstruction of bone or other regions of the musculo-skeletal system in both humans and animals. The method of delivery of the device is another aspect of the invention. The method of delivery of the device in accordance with the various embodiments of the invention reduces the trauma created during surgery, decreasing the risks associated with infection and thereby decreasing the recuperation time of the patient. The framework may in one embodiment include an expandable and contractible structure to permit re-placement and removal of the reinforcement structure or framework.

In accordance with the various embodiments of the present invention, the mechanical supporting framework or device may be made from a variety of materials such as metal, composite, plastic or amorphous materials, which include, but are not limited to, steel, stainless steel, cobalt chromium plated steel, titanium, nickel titanium alloy (Nitinol), superelastic alloy, and polymethylmethacrylate (PMMA). The device may also include other polymeric materials that are biocompatible and provide mechanical strength, that include polymeric material with ability to carry and delivery therapeutic agents, that include bioabsorbable properties, as well as composite materials and composite materials of titanium and polyetheretherketone (PEEK), composite materials of polymers and minerals, composite materials of polymers and glass fibers, composite materials of metal, polymer, and minerals.

Within the scope of the present invention, each of the embodiments of types of devices may further be coated with proteins from synthetic or animal source, or include collagen coated structures, and radioactive or brachytherapy materials. Furthermore, the construction of the supporting framework or device may include radio-opaque markers or components that assist in their location during and after placement in the bone or other region of the musculo-skeletal systems.

Further, the reinforcement device may, in one embodiment, be osteo incorporating, such that the reinforcement device may be integrated into the bone.

In still another embodiment of the invention, a method of repairing a bone fracture is disclosed that comprises: accessing a fracture along a length of a bone through a bony protuberance at an access point at an end of a bone; advancing a bone fixation device into a space through the access point at the end of the bone; bending a portion of the bone fixation device along its length to traverse the fracture; and locking the bone fixation device into place within the space of the bone. The method can also include the step of advancing an obturator through the bony protuberance and across the fracture prior to advancing the bone fixation device into the space. In yet another embodiment of the method, the step of anchoring the bone fixation device within the space can be included.

In another embodiment of the invention, a method of repairing bone is disclosed whereby the area of the affected bone is remediated by advancing the device through an opening in the middle of the bone, below the metaphysis or at a point away from a joint or bony protuberance.

An aspect of the invention discloses a removable bone fixation device that uses a single port of insertion and has a single-end of remote actuation wherein a bone fixation device stabilizes bone after it has traversed the fracture. The bone fixation device is adapted to provide a single end in one area or location where the device initiates interaction with bone. The device can be deployed such that the device interacts with bone. Single portal insertion and single-end remote actuation enables the surgeon to insert and deploy the device, deactivate and remove the device, reduce bone fractures, displace or compress the bone, and lock the device in place. In addition, the single-end actuation enables the device to grip bone, compresses the rigidizable flexible body, permits axial, torsional and angular adjustments to its position during surgery, and releases the device from the bone during its removal procedure. A removable extractor can be provided in some embodiments of the device to enable the device to be placed and extracted by deployment and remote actuation from a single end. The device of the invention can be adapted and configured to provide at least one rigidizable flexible body or sleeve. Further the body can be configured to be flexible in all angles and directions. The flexibility provided is in selective planes and angles in the Cartesian, polar, or cylindrical coordinate systems. Further, in some embodiments, the body is configured to have a remote actuation at a single end. Additionally, the body can be configured to have apertures, windings, etc. The device may be configured to function with non-flexible bodies for use in bones that have a substantially straight segment or curved segments with a constant radius of curvature. Another aspect of the invention includes a bone fixation device in that has mechanical geometry that interacts with bone by a change in the size of at least one dimension of a Cartesian, polar, or spherical coordinate system. Further, in some embodiments, bioabsorbable materials can be used in conjunction with the devices, for example by providing specific subcomponents of the device configured from bioabsorbable materials. A sleeve can be provided in some embodiments where the sleeve is removable, has deployment, remote actuation, and a single end. Where a sleeve is employed, the sleeve can be adapted to provide a deployable interdigitation process or to provide an aperture along its length through which the deployable interdigitation process is adapted to engage bone. In some embodiments, the deployable interdigitation process is further adapted to engage bone when actuated by the sleeve. In some embodiments, the bone fixation device further comprises a cantilever adapted to retain the deployable bone fixation device within the space. The sleeve can further be adapted to be expanded and collapsed within the space by a user. One end of the device can be configured to provide a blunt obturator surface adapted to advance into the bone. A guiding tip may also be provided that facilitates guiding the device through the bone. The device may be hollow and accept a guide wire. The guiding tip may facilitate placement of the device thereby providing a means to remove bone in its path (a helical end, a cutting end, or ablative end). The guiding tip may allow capture, interaction, or insertion into or around a tube on its internal or external surface. Further, the deployable bone fixation device can be adapted to receive external stimulation to provide therapy to the bone. The device can further be adapted to provide an integral stimulator which provides therapy to the bone. In still other embodiments, the device can be adapted to receive deliver therapeutic stimulation to the bone.

The devices disclosed herein may be employed in various regions of the body, including: spinal, cranial, thoracic, lower extremities and upper extremities. Additionally, the devices are suitable for a variety of breaks including, epiphyseal, metaphyseal, diaphyseal cortical bone, cancellous bone, and soft tissue such as ligament attachment and cartilage attachment.

The fracture fixation devices of various embodiments of the invention are adapted to be inserted through an opening of a fractured bone, such as the radius (e.g., through a bony protuberance on a distal or proximal end or through the mid-shaft) into an intramedullary canal of the bone. The device can be inserted in one embodiment in a line of sight manner collinear or nearly collinear, or parallel to the central axis of the intramedullary canal. In another embodiment, the device can be inserted at an angle, radius, or tangency to the axis of the intramedullary canal. In another embodiment, the device can be inserted in a manner irrespective of the central axis of the intramedullary canal. In some embodiments, the fixation device has two main components, one configured component for being disposed on the side of the fracture closest to the opening and one component configured for being disposed on the other side of the fracture from the opening so that the fixation device traverses the fracture.

The device components cooperate to align, fix and/or reduce the fracture so as to promote healing. The device may be removed from the bone after insertion (e.g., after the fracture has healed or for other reasons), or it may be left in the bone for an extended period of time or permanently.

In some embodiments, the fracture fixation device has one or more actuatable bone engaging mechanisms such as anchors or grippers on its proximal and/or distal ends. These bone engaging mechanisms may be used to hold the fixation device to the bone while the bone heals. In another embodiment, the fracture fixation device has a plurality of actuatable bone engaging mechanisms such as grippers or anchors along its length. In another embodiment, the fracture fixation device has grippers or anchoring devices that interdigitate into the bone at an angle greater than zero degrees and less than 180 degrees to secure the bone segments of the fracture. In another embodiment the fracture fixation device has grippers or anchoring features that when activated from a state that facilitates insertion to a state that captures, aligns, and fixes the fracture, deploy in a geometry so that the resultant fixed bone is analogous or nearly identical, or identical to the geometry of the bone prior to the fracture. In one embodiment of the device, the flexible body allows insertion through tortuous paths within bone or created within bone. Upon activation from the state of insertion to the state of fixation, this device deforms so as to grip the bone upon multiple surfaces of the now collapsed, rigid, flexible body. In this collapsed state the device may be deform in such a way to re-achieve anatomical alignment of the bone. The device as described above can be fabricated so that it can have any cross sectional shape. Examples of cross sectional shapes include round, oval, square, rectangular, n-sided, where n is an integer from 1 to infinity, star shaped, spoke shaped.

In some embodiments, to aid in insertion of the device into the intramedullary canal, the main component of the fracture fixation device has a substantially flexible state. Thereby, the device, prior to activation, may not have a rigid section. Once in place, deployment of the device also causes the components to change from the flexible state to a rigid state to aid in proper fixation of the fracture. In some embodiments, at least one of the components may be semi-flexible. Placement of the device may be aided by a detachable rigid member such as a guide or outrigger. Placement of the device may be aided by removable rigid member such as a tube or guide wire. In some embodiments, at least one component may provide a bone screw attachment site for the fixation device. In some embodiments, at least one of the components of the device may allow a screw or compressive member to be attached along its axis to provide linear compression of one side of the fractured bone towards the other (e.g. compression of the distal segment towards the proximal segment or visa versa). In some embodiments, at least one of the components of the device may accept a screw at an acute angle, and angle less than 30 degrees from the axis of the device that would allow compression of one side of the fractured bone towards the other. In some embodiments, at least one of the components of the device may accept an alternately removable eyelet to accommodate a compressive device so as to compress one side of the fractured bone towards the other side.

In some embodiments, to aid in insertion into the intramedullary canal, at least one component of the fracture fixation device has a substantially flexible state and a substantially rigid state. Once in place, deployment of the device also causes the components to change from the flexible state to a rigid state to aid in proper fixation of the fracture. In some embodiments, at least one of the components may be substantially rigid or semi-flexible. In some embodiments, at least one component may provide a bone screw attachment site for the fixation device.

Embodiments of the invention also provide deployment tools with a tool guide for precise alignment of one or more bone screws with the fracture fixation device. These embodiments also provide bone screw orientation flexibility so that the clinician can select an orientation for the bone screw(s) that will engage the fixation device as well as any desired bone fragments or other bone or tissue locations.

These and other features and advantages of the present invention will be understood upon consideration of the following detailed description of the invention and the accompanying drawings.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 depicts the skeletal system of the pectoral girdles.

FIG. 2 show the superior surface of a left clavicle.

FIG. 3 is a side view of an embodiment of a bone repair device constructed according to aspects of the invention.

FIG. 4 shows the device of FIG. 3 in a deployed state.

FIG. 11 is a superior view showing the device of FIG. 3 implanted in a right clavicle.

FIG. 12 is a posterior view showing the device of FIG. 3 implanted in a right clavicle.

FIG. 13 is a side view of an alternative embodiment.

FIG. 14 is a top view of an alternative embodiment.

FIG. 15 is a perspective view of an alternative embodiment.

FIG. 16 is a side view of an alternative embodiment.

FIGS. 19 and 20 are a side view and a cross-section view, respectively, of an alternative embodiment.

FIGS. 21-23 are a perspective view, a cross-section view, and an exploded view respectively, of an alternative embodiment.

FIG. 24 is a side view of an embodiment of a depth gauge.

FIG. 25 is a side view of a first embodiment of a protection tool.

FIGS. 26 and 27 are a side view and an exploded view, respectively, of a second embodiment of a protection tool.

FIGS. 39A-39F show various views of an exemplary embodiment of a bone fixation device hub.

FIGS. 40A-40E show various views of another exemplary embodiment of a bone fixation device hub.

FIGS. 42A-42D show various views of another exemplary embodiment of a bone fixation device hub.

FIGS. 43A-43E show various views of another exemplary embodiment of a bone fixation device hub.

FIGS. 44A-44C show various views of another exemplary embodiment of a bone fixation device hub.

FIGS. 45A-45B show various views of another exemplary embodiment of a bone fixation device hub.

FIGS. 46A-46B show various views of another exemplary embodiment of a bone fixation device hub.

FIGS. 47A-47B show various views of another exemplary embodiment of a bone fixation device hub.

FIG. 54C is a side elevational view showing the device of FIG. 54A in a retracted or undeployed state.

FIG. 54D is a perspective view showing the device of FIG. 54A in a deployed state.

FIG. 54E is a top plan view showing the device of FIG. 54A in a deployed state.

FIG. 54F is a side elevational view showing the device of FIG. 54A in a deployed state.

FIG. 55A is an enlarged perspective view showing just the distal gripper of the device of FIG. 54A in a retracted or undeployed state.

FIG. 55B is a side elevational view showing the gripper of FIG. 55A in a retracted or undeployed state.

FIG. 55C is a top plan view showing the gripper of FIG. 55A in a retracted or undeployed state.

FIG. 55D is a perspective view showing the gripper of FIG. 55A in a deployed state.

FIG. 55E is a side elevational view showing the gripper of FIG. 55A in a deployed state.

FIG. 55F is a top plan view showing the gripper of FIG. 55A in a deployed state.

FIGS. 59-65 are schematic cross-sectional side and oblique views of an embodiment of a bone fixation device with a compression screw.

FIG. 96B is a cross-section view showing the device of FIG. 96A.

FIG. 96C is an exploded view showing the device of FIG. 96A.

FIG. 97 is a side view of one embodiment of a shape-conforming flexible-to-rigid body portion.

FIG. 98A is a side view of another embodiment of a shape-conforming flexible-to-rigid body portion.

FIG. 98B is a perspective view of yet another embodiment of a shape-conforming flexible-to-rigid body portion.

FIG. 99F is a longitudinal cross-sectional view of the body portion shown in FIG. 99E.

FIG. 99G is a perspective view showing another body portion embodiment having interlocking features.

FIG. 99H is a longitudinal cross-sectional view of the body portion shown in FIG. 99G.

FIG. 99I is a perspective view showing another body portion embodiment having interlocking features.

FIG. 99J is a longitudinal cross-sectional view of the body portion shown in FIG. 99I.

FIG. 100A is a cross-sectional view showing the proximal end of a device employing the body portion of FIG. 97, the device being shown in a flexible state.

FIG. 100B is a cross-sectional view showing the proximal end of a device employing the body portion of FIG. 97, the device being shown in a shape-conforming state.

FIG. 101A is a side view showing a device employing two body portions of FIG. 97, the device being shown in a flexible state.

FIG. 101B is a cross-sectional view showing a device employing two body portions of FIG. 97, the device being shown in a flexible state.

FIG. 101C is a cross-sectional view showing a device employing two body portions of FIG. 97, the device being shown in a shape-conforming state.

FIG. 101D is a partially exploded perspective view showing a device employing two body portions of FIG. 98B, the device being shown in a flexible state.

FIG. 101E is a cross-sectional view showing a device employing two body portions of FIG. 98B, the device being shown in a flexible state.

FIG. 102 is plan view depicting a device similar to that of FIGS. 101A-101C, the device being shown deployed in a clavicle.

FIG. 103 is a perspective view showing a device similar to that of FIGS. 101A-101C, the device being introduced into the intramedullary space of a clavicle.

Figures 104, 105:
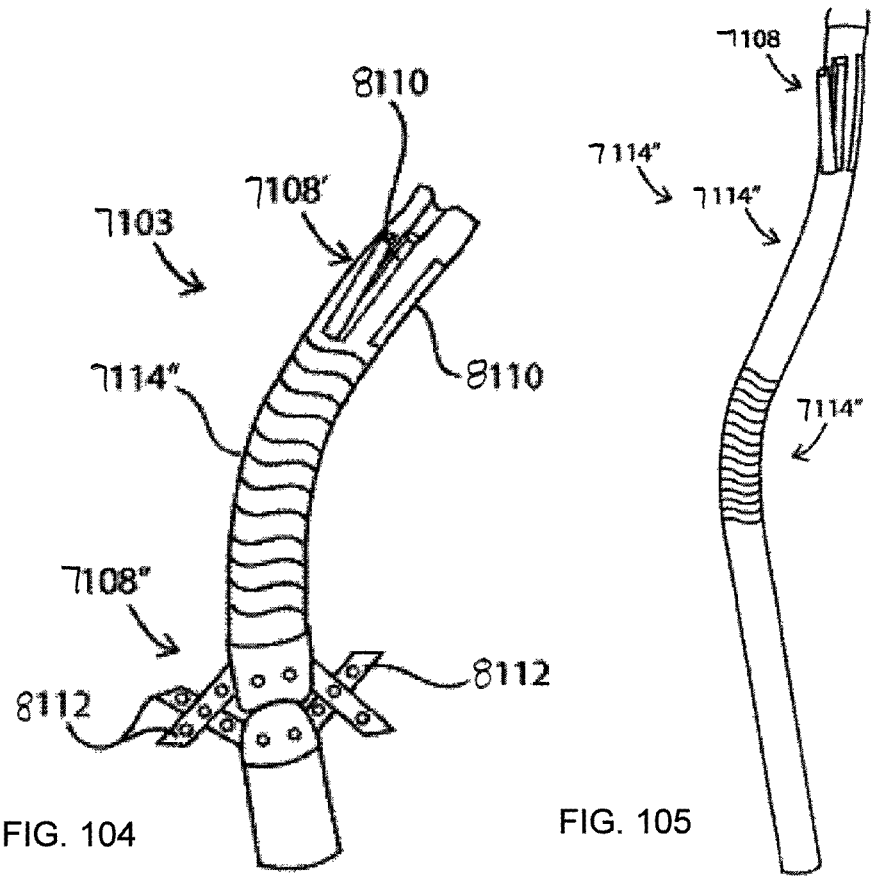

FIG. 104 is a side view showing an alternative embodiment device in a deployed, shape-conforming state and having alternative anchors.

FIG. 105 is a side view showing another alternative embodiment device in a deployed, shape-conforming state.

Figure 106:
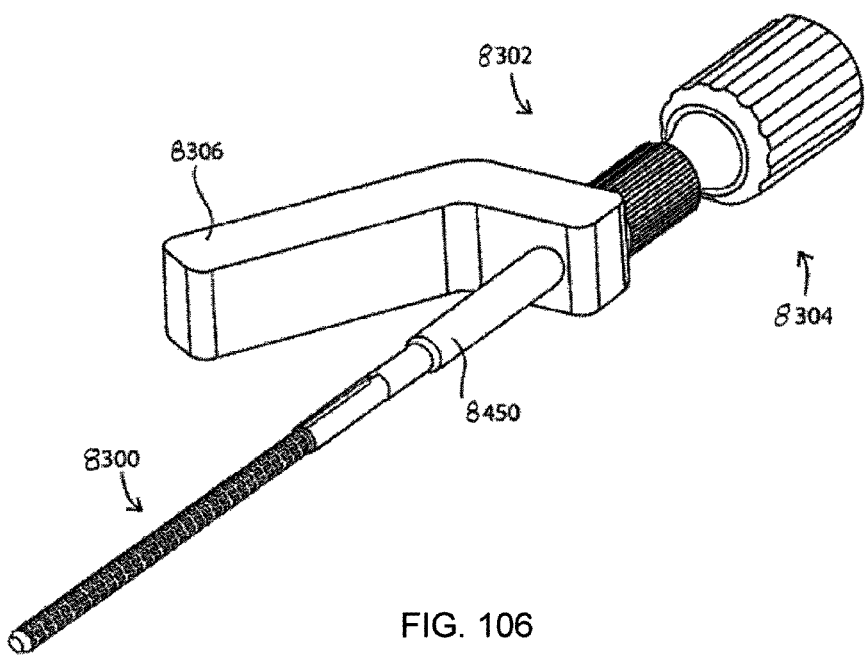

FIG. 106 is a perspective view showing another exemplary embodiment of a bone fixation device attached to tools that may be used for its insertion, deployment, and removal.

Figure 107:
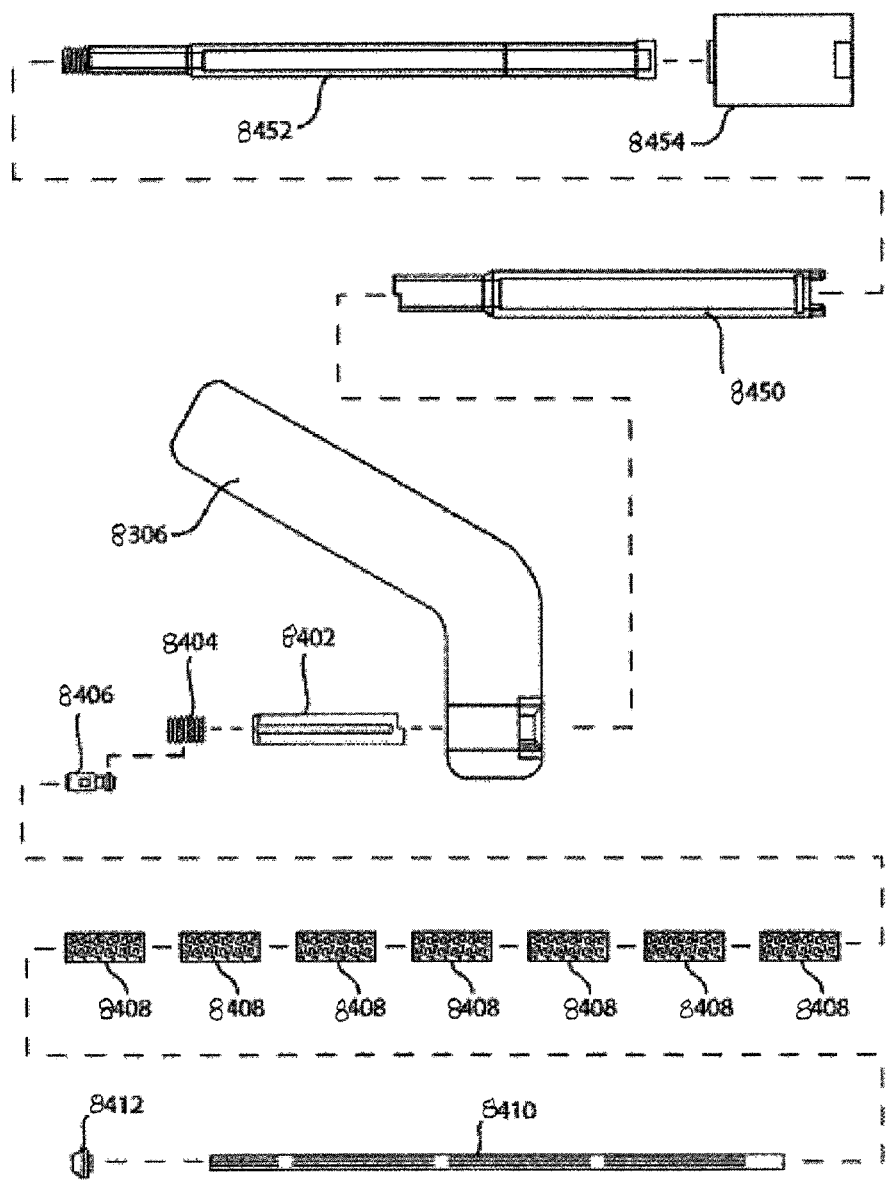

FIG. 107 is an exploded view showing the components of the bone fixation device and insertion/removal tool of FIG. 106.

Figure 108:
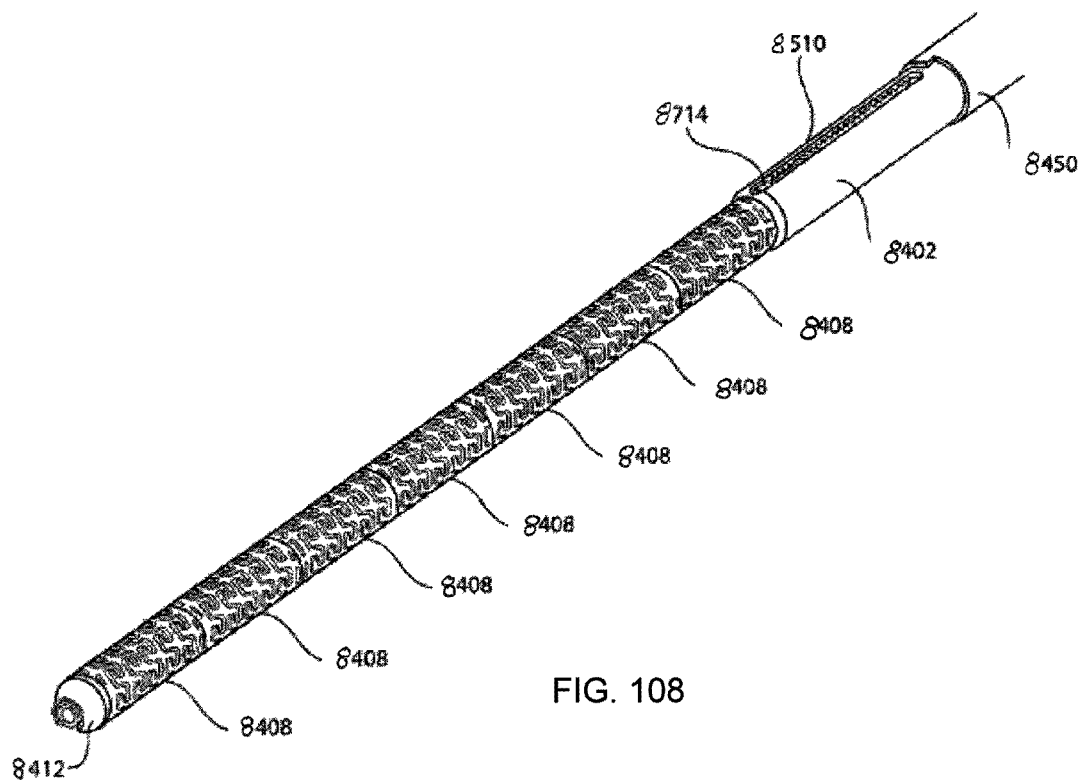

FIG. 108 is an enlarged perspective view showing the bone fixation device of FIG. 106.

Figure 109:
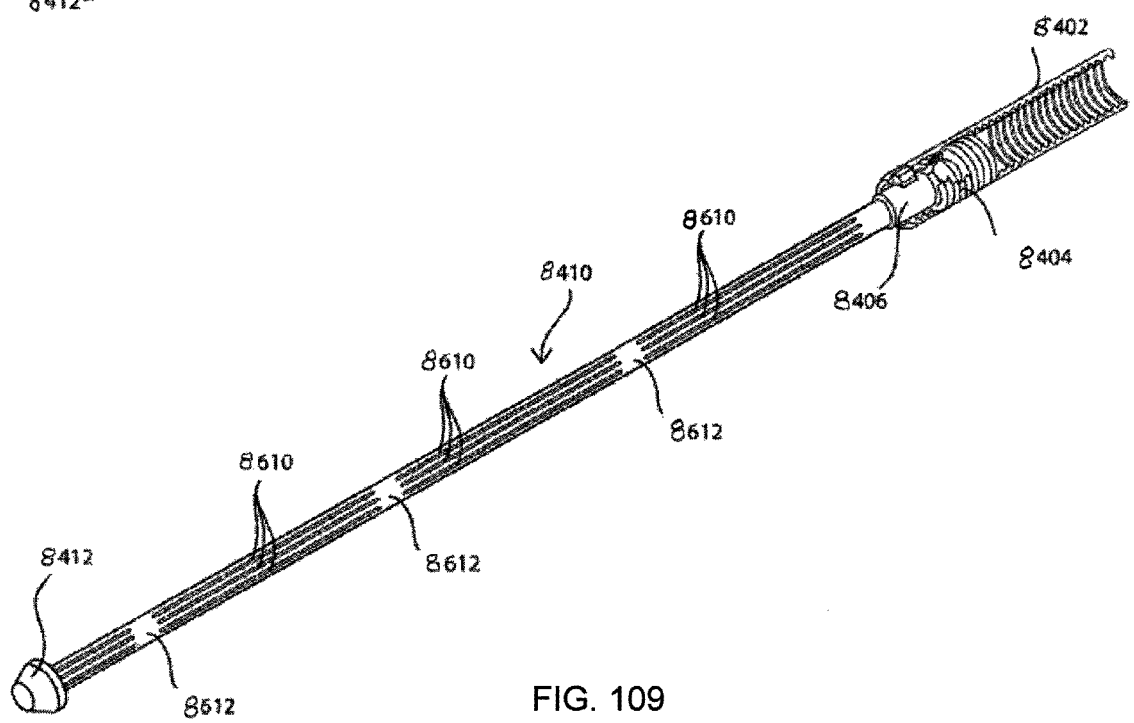

FIG. 109 is an enlarged, cut-away perspective view showing internal components of the device of FIG. 106.

FIGS. 110A-110D are enlarged perspective views showing details of various components of the device of FIG. 106.

Figure 110B:
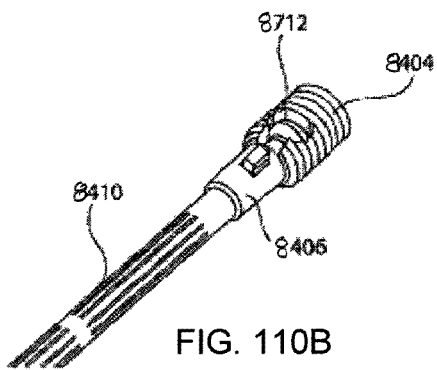
Figure 110C:
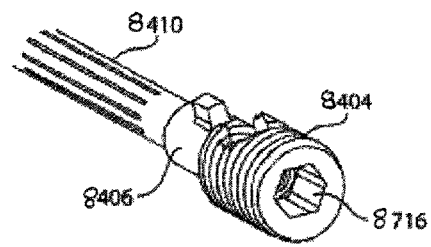
Figure 110A:
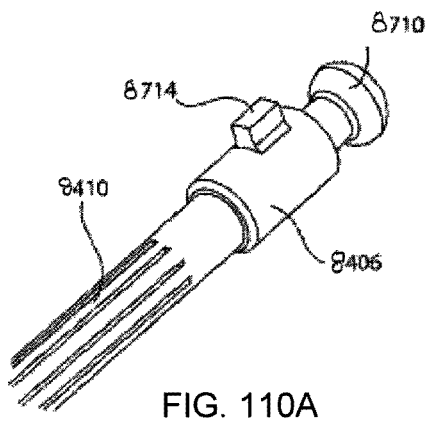
Figure 110D:
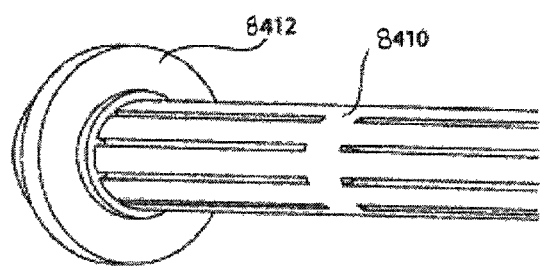
Figure 110E:
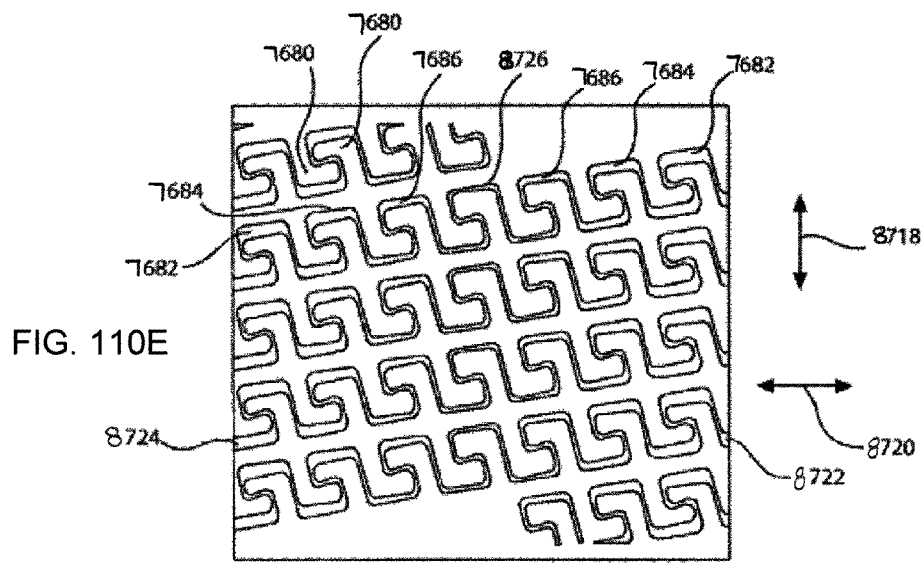

FIG. 110E is a plan view showing an exemplary interlocking pattern that may be used in the device of FIG. 106.

Figure 111:
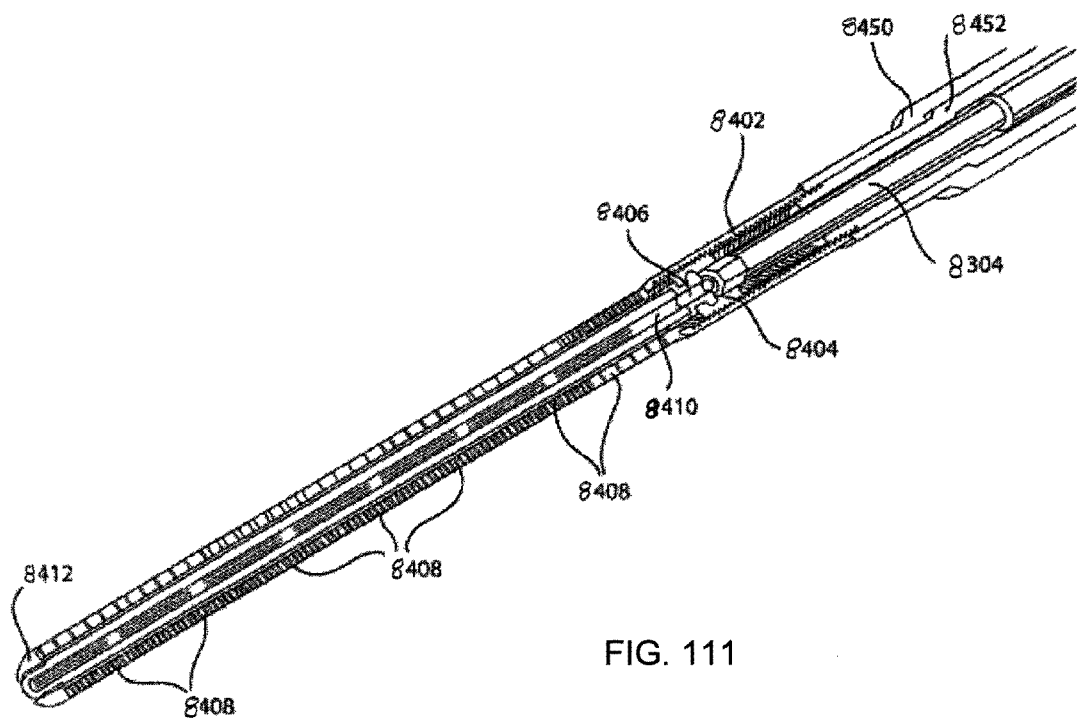

FIG. 111 is a longitudinal cross-section view showing the device and a portion of the tools of FIG. 106.

Figure 112:
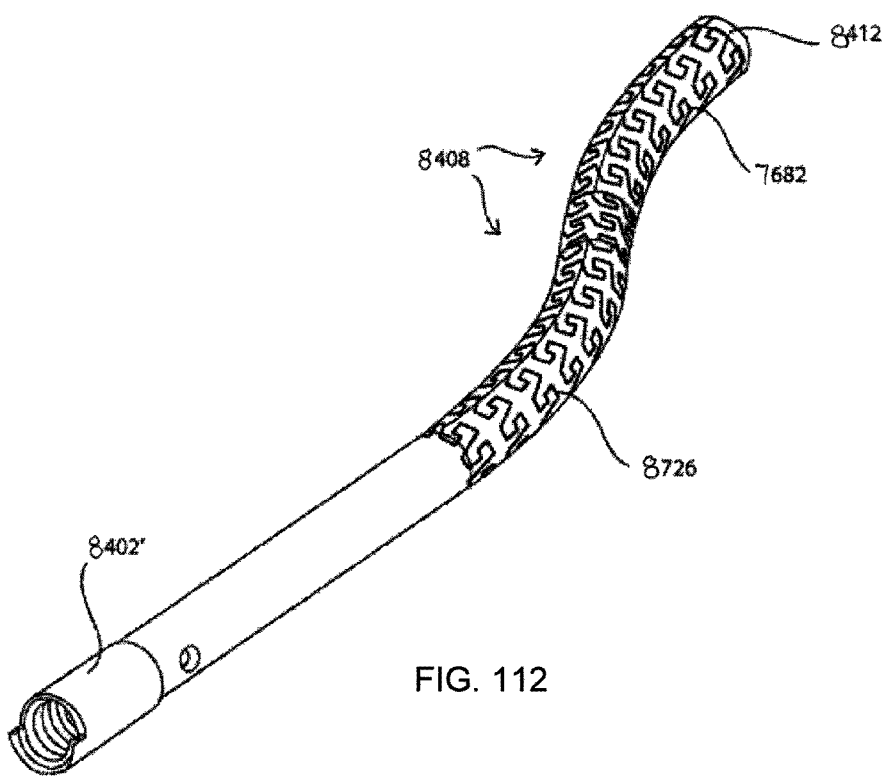

FIG. 112 is a perspective view showing the device of FIG. 106 in a deployed state.

Figure 113:
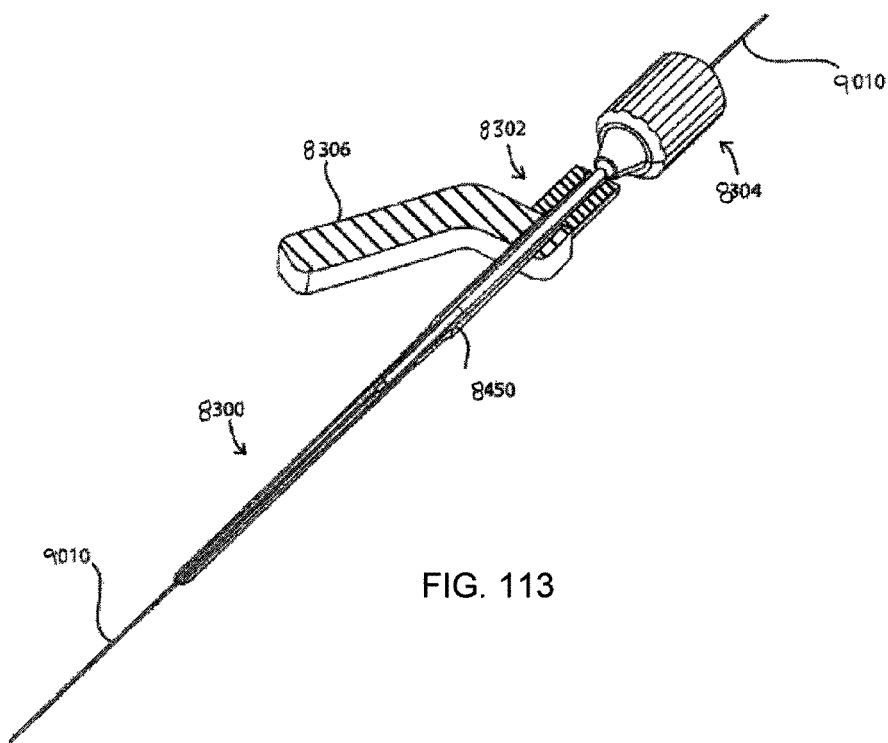

FIG. 113 is a cut-away perspective view showing the device and tools of FIG. 106 with a guide wire inserted therethrough.

Figure 114:
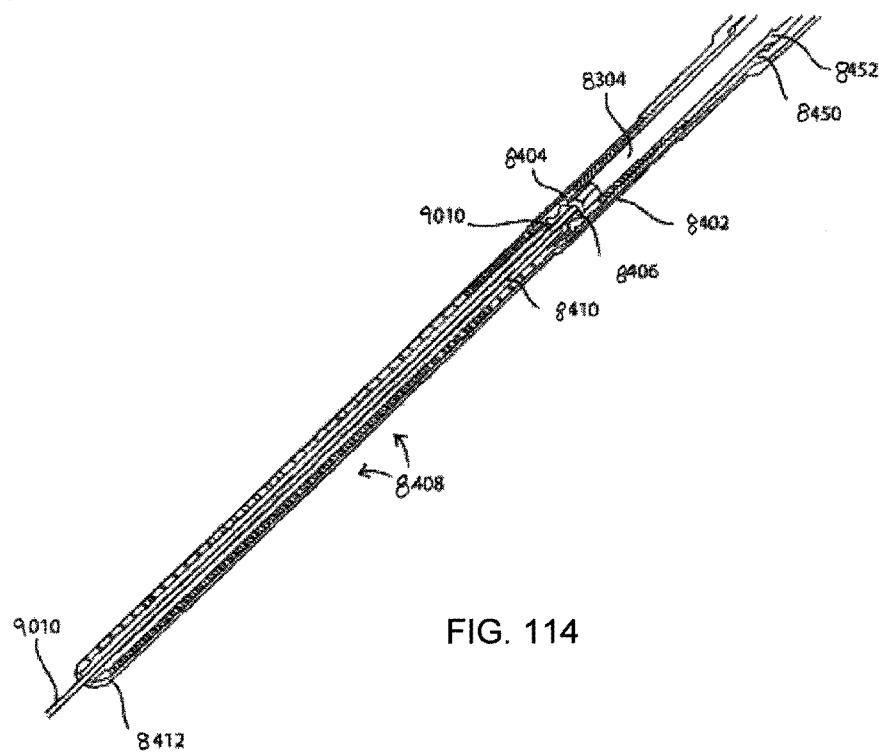

FIG. 114 is an enlarged cross-section view showing the device, tools and guide wire of FIG. 113.

Figure 115:
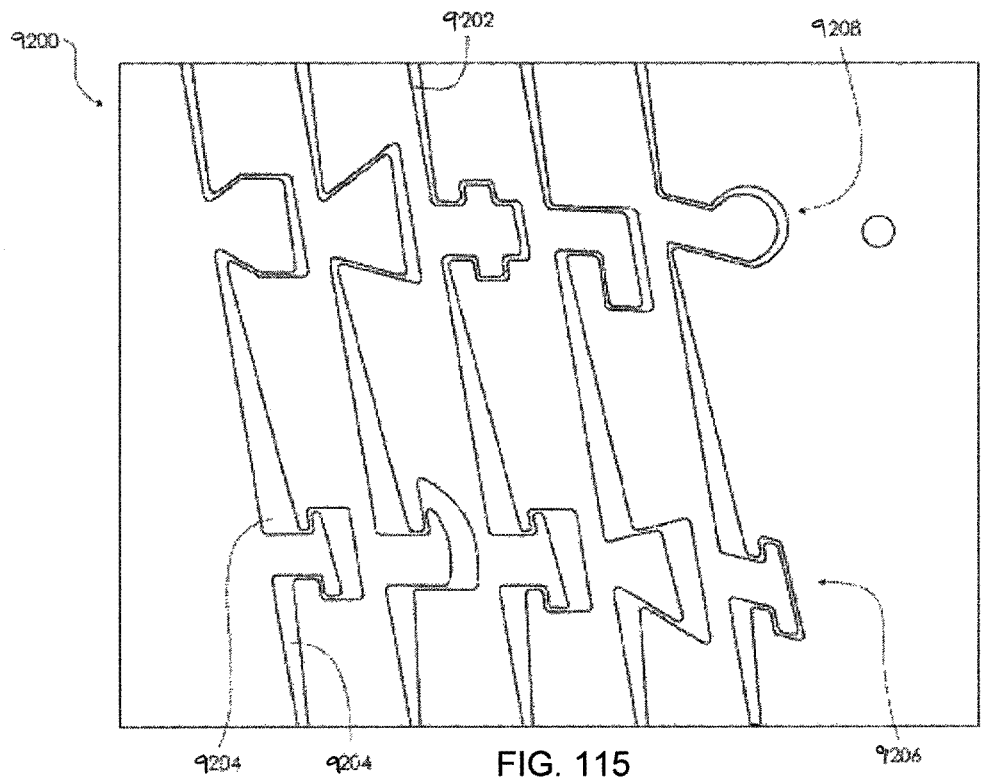
Figure 116:
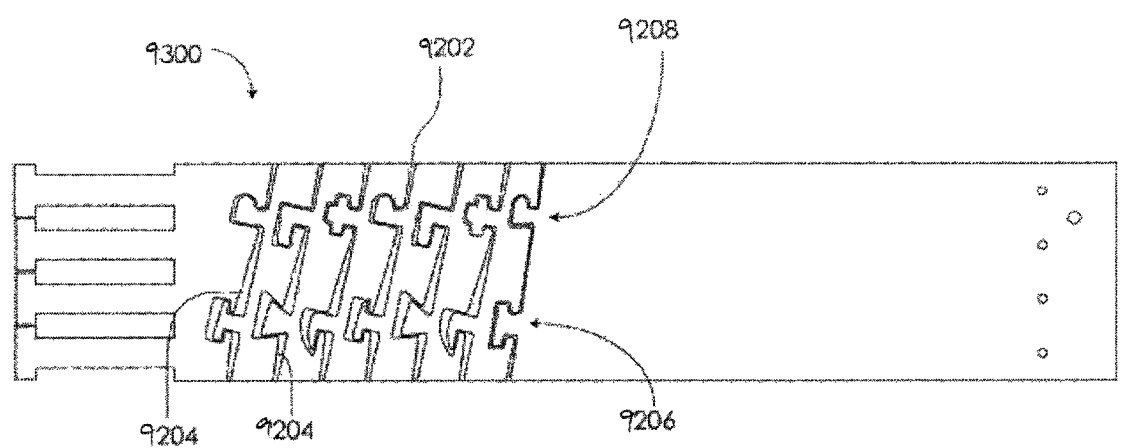

FIGS. 115 and 116 are plan views showing exemplary patterns that may be used in the flexible-to-rigid body portions of bone fixation devices.

FIGS. 117A-117H are views showing an overlapping flexible-to-rigid body portion, where FIG. 117A is a plan view, FIG. 117B is an enlarged cross-sectional side view of the body portion in an expanded, flexible state, FIG. 117C is an enlarged cross-sectional side view of the body portion in a compressed, rigid state, and FIGS. 117D-117H are enlarged plan views showing various tip configurations.

Figure 118B:
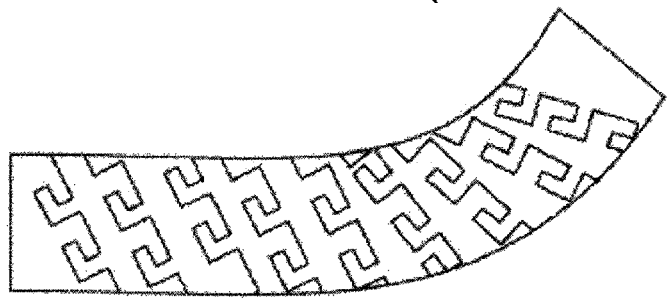
Figure 118C:
Figure 118A:
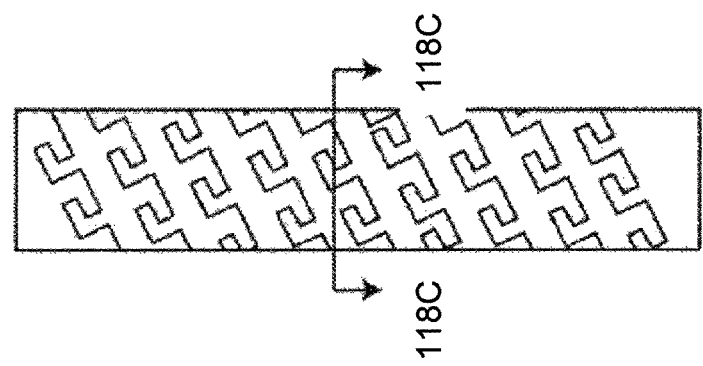

FIGS. 118A-118C are views showing an exemplary flexible-to-rigid body portion having an oval cross-section, where FIG. 118A is a side view showing the device in a flexible state, FIG. 118B is a side view showing the device in a rigid state, and FIG. 118C is a cross-section taken along line 118C-118C in FIG. 118A.

Figure 119B:
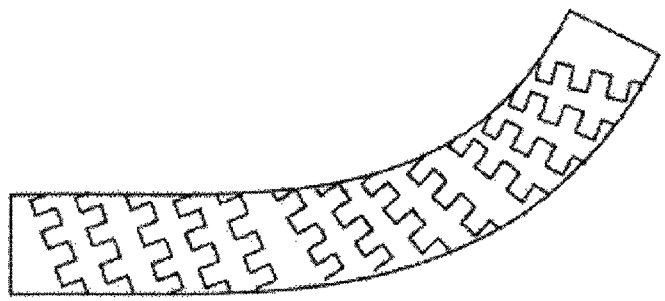
Figure 119C:
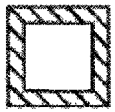
Figure 119A:
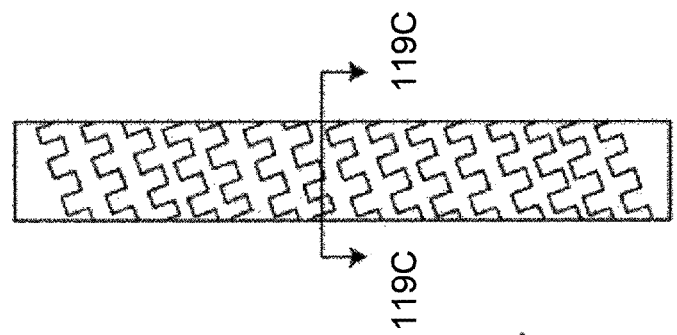

FIGS. 119A-119C are views showing an exemplary flexible-to-rigid body portion having a square cross-section, where FIG. 119A is a side view showing the device in a flexible state, FIG. 119B is a side view showing the device in a rigid state, and FIG. 119C is a cross-section taken along line 119C-119C in FIG. 119A.

FIGS. 120A-120E show an alternative embodiment of a bone fixation device.

FIGS. 121A-121E show an alternative embodiment of a bone fixation device.

Figure 122A:
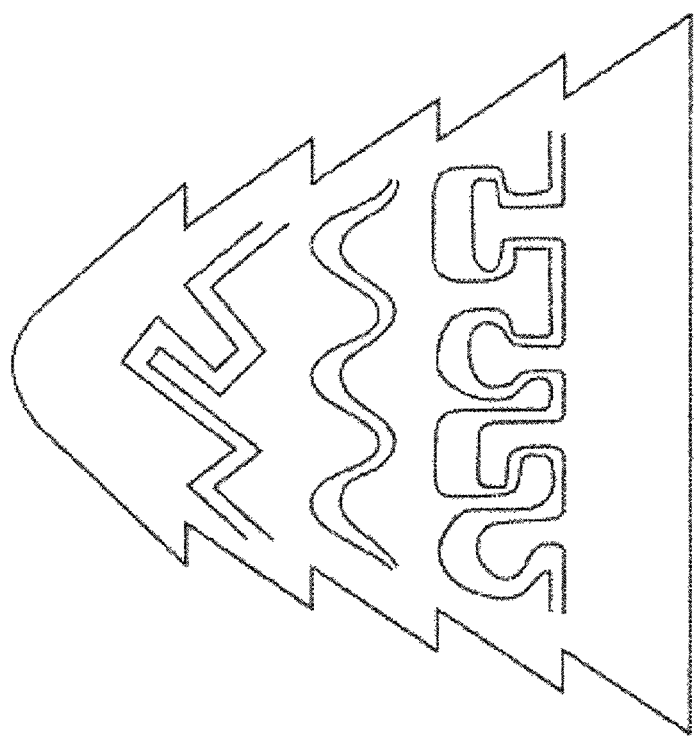
Figure 122B:

FIGS. 122A-122B show an alternative embodiment of a bone fixation device.

FIG. 123 is a schematic side view of a straight fixation implant configured for a cross locking screw according to an embodiment of the present invention.

FIG. 124 is a schematic side cross-section view of the fixation implant according to FIG. 123.

FIG. 125 is a schematic side cross-section view of a fixation region according to FIG. 124.

FIG. 126 is a schematic front view of the fixation implant according to FIG. 123.

FIG. 127 is a schematic side view of a cannulated straight fixation implant according to an embodiment of the present invention.

FIG. 128 is a schematic side cross-section view of the fixation implant according to FIG. 127.

FIG. 129 is a schematic isometric view of the fixation implant according to FIG. 127.

FIG. 130 is a schematic front view of the fixation implant according to FIG. 127.

Figure 131:
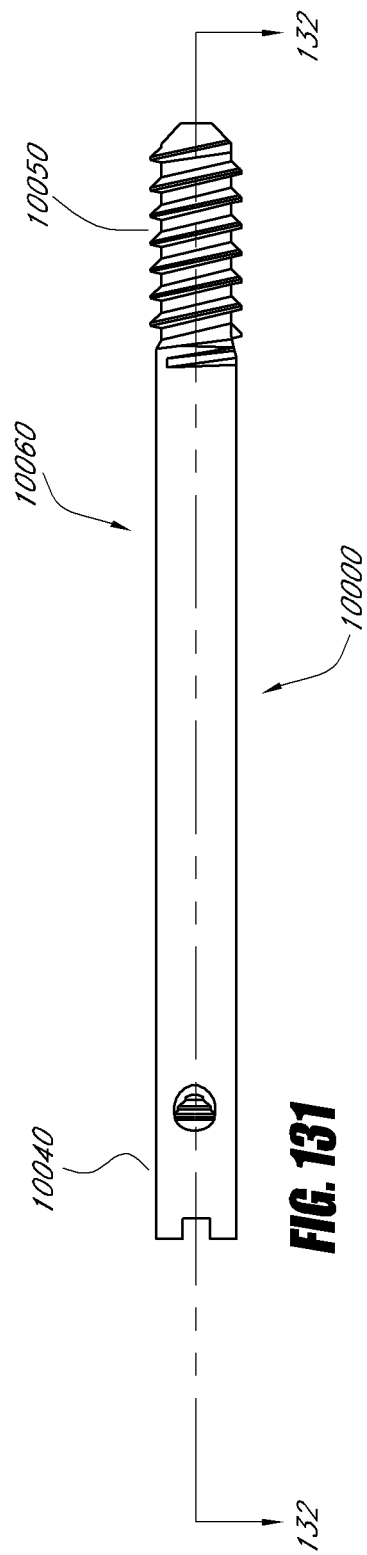

FIG. 131 is a schematic side view of a cannulated straight fixation implant according to an embodiment of the present invention.

Figure 132:
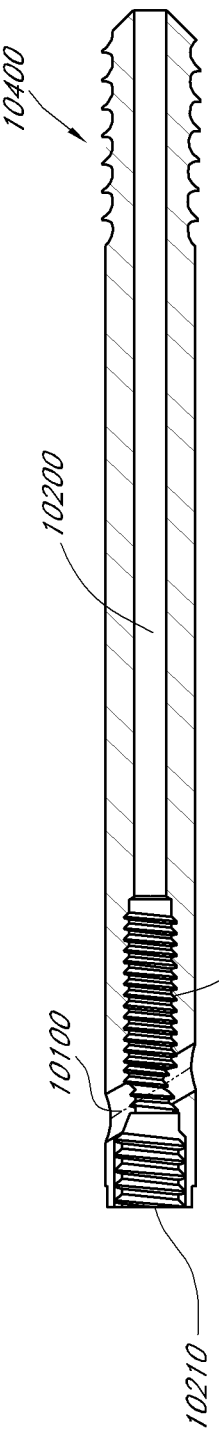

FIG. 132 is a schematic side cross-section view of the fixation implant according to FIG. 131.

Figure 133:
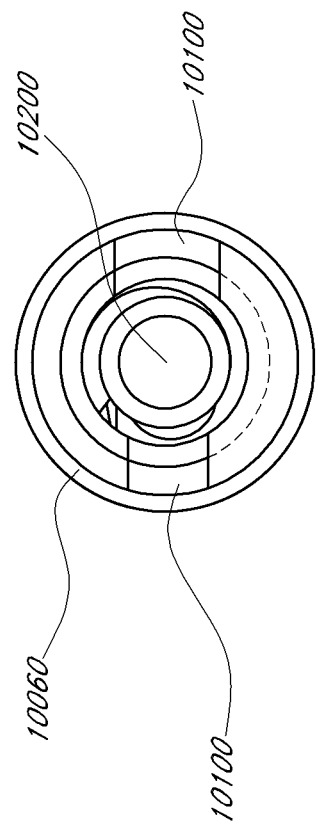

FIG. 133 is a schematic front view of the fixation implant according to FIG. 131.

Figure 134F:
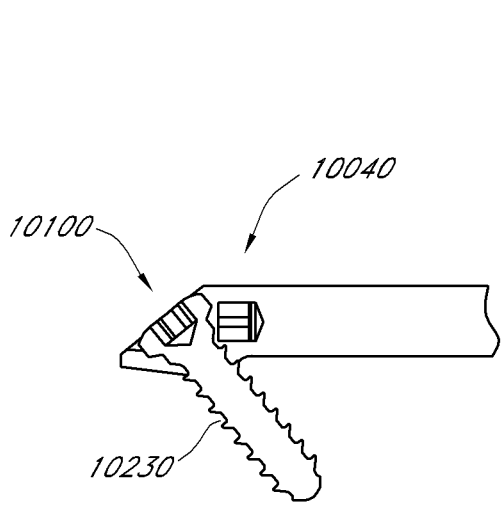
Figure 134G:
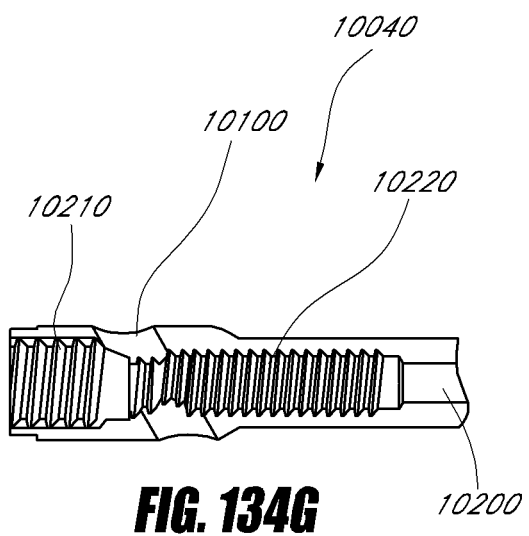
Figure 134H:
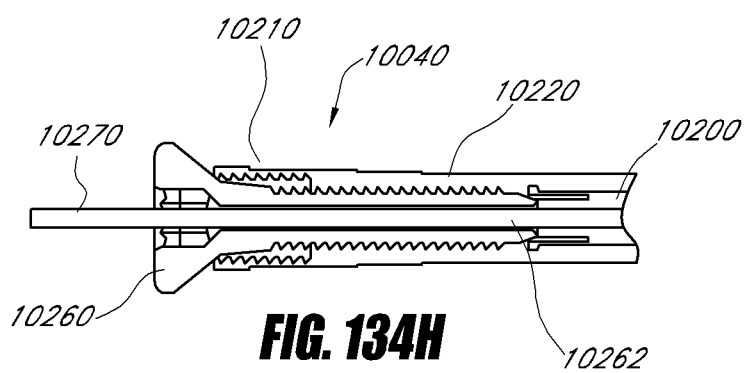
Figure 134I:
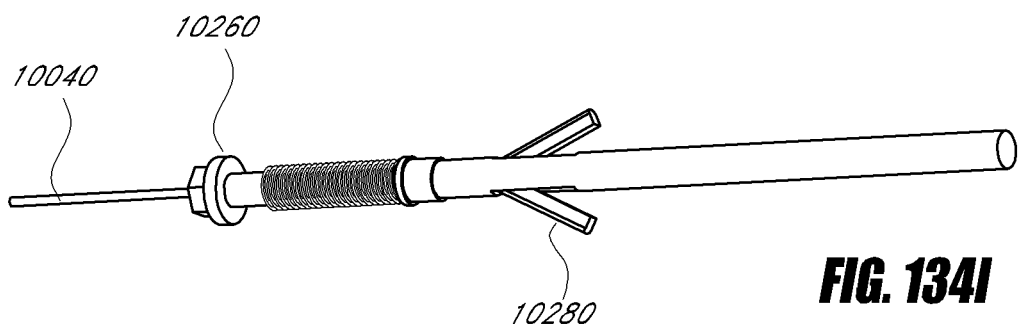
Figure 134J:
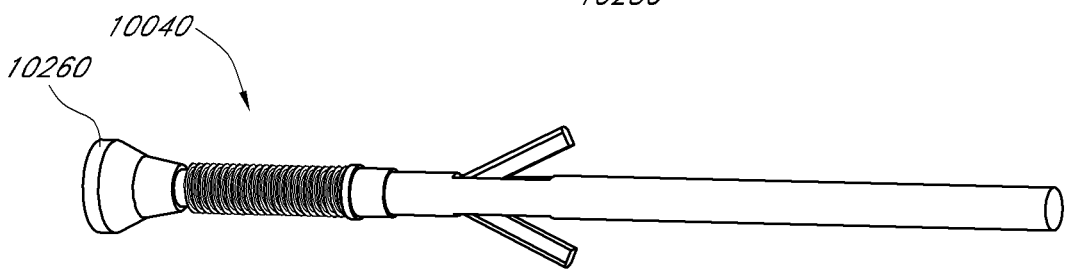
Figure 134K:
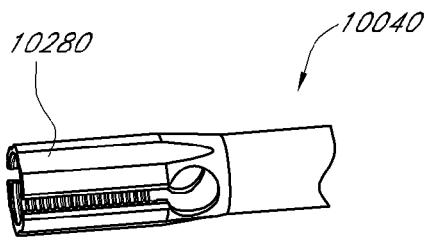
Figure 134M:
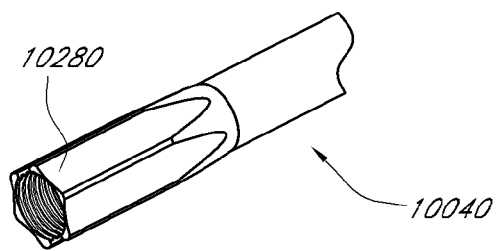
Figure 134L:
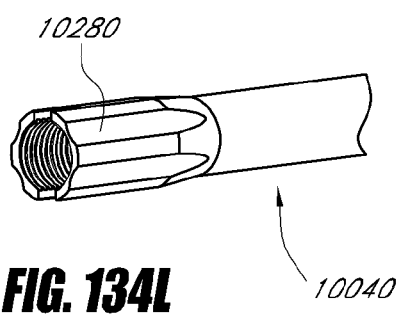
Figure 134N:
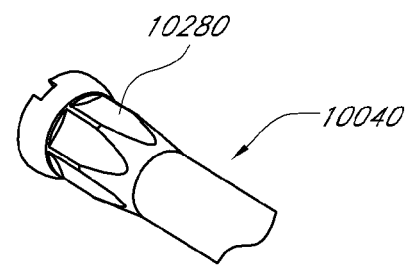
Figure 134O:
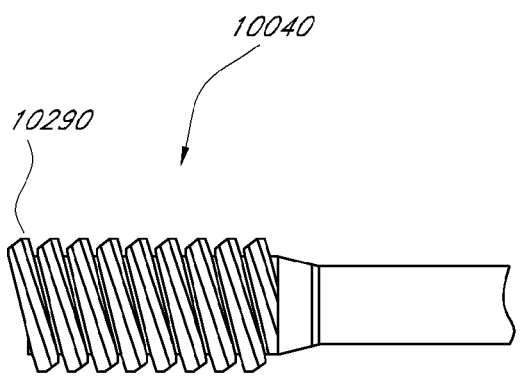
Figure 134P:
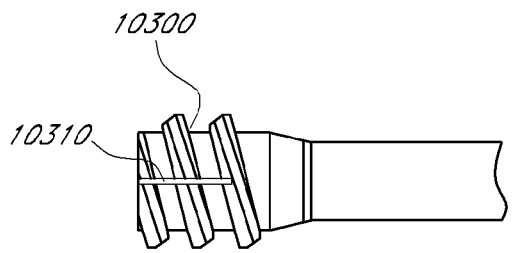
Figure 134Q:
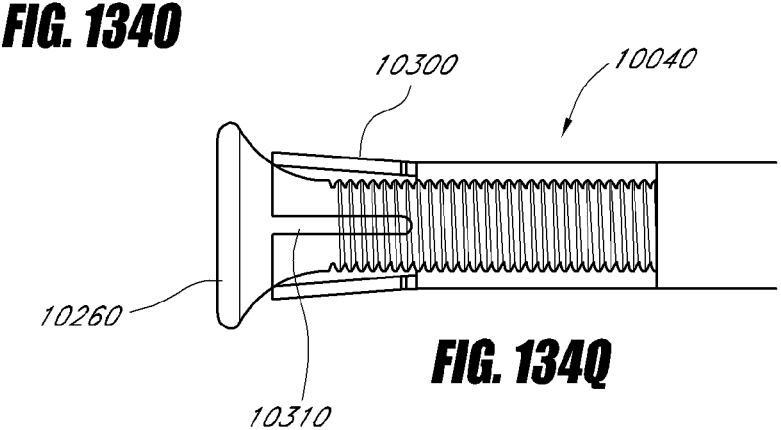

FIGS. 134A-134Q are schematic side and/or isometric views of hubs according to various embodiments of the present invention.

Figure 135A:
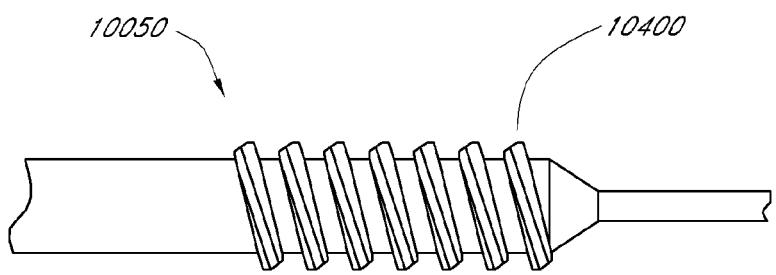
Figure 135B:
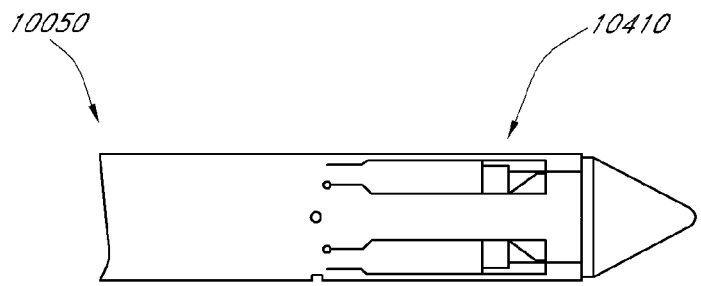
Figure 135C:
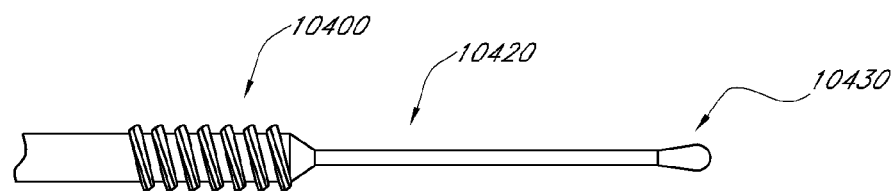
Figure 135D:
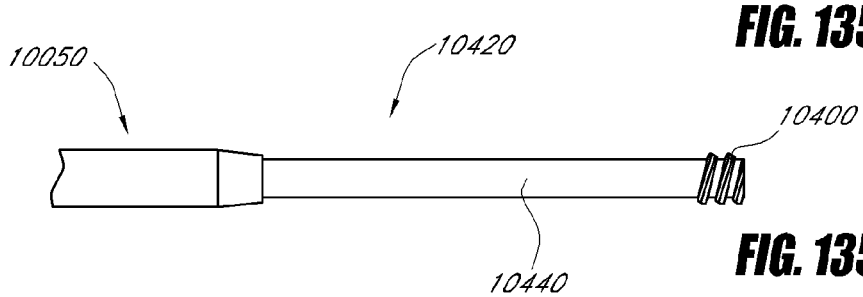
Figure 135E:
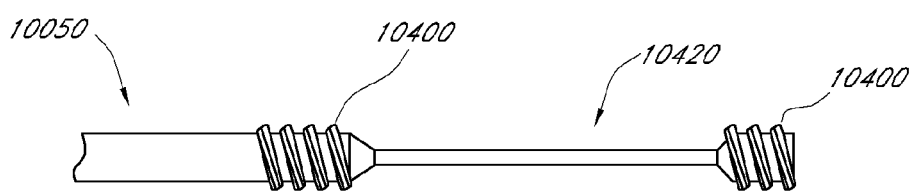
Figure 135F:
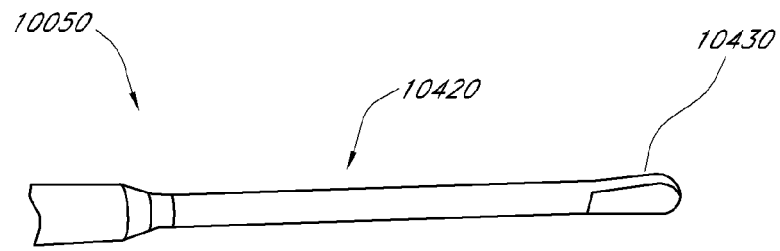
Figure 135G:
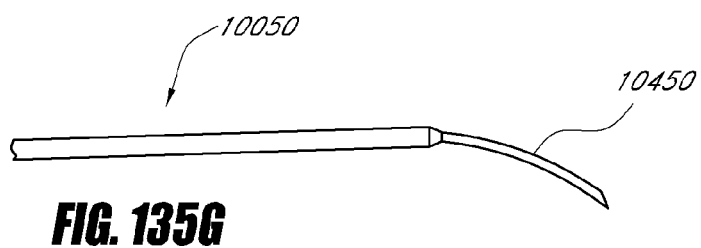
Figure 135H:
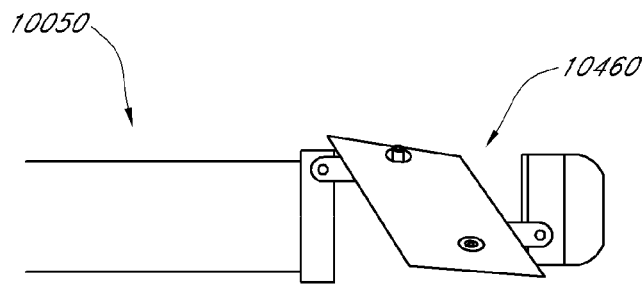
Figure 135J:
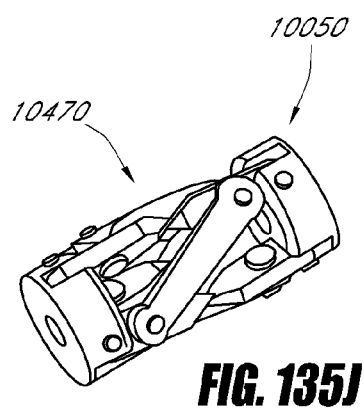
Figure 135I:
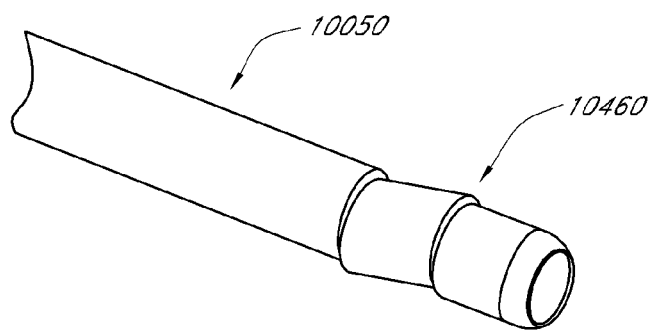
Figure 135K:
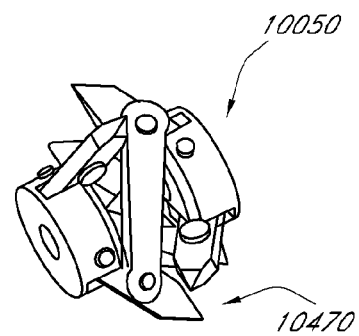
Figure 135L:
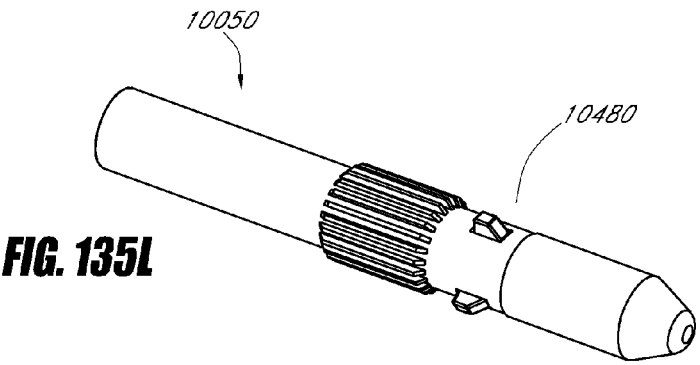
Figure 135M:
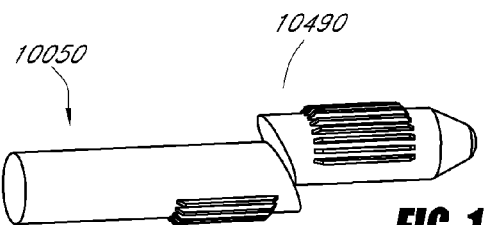
Figure 135N:
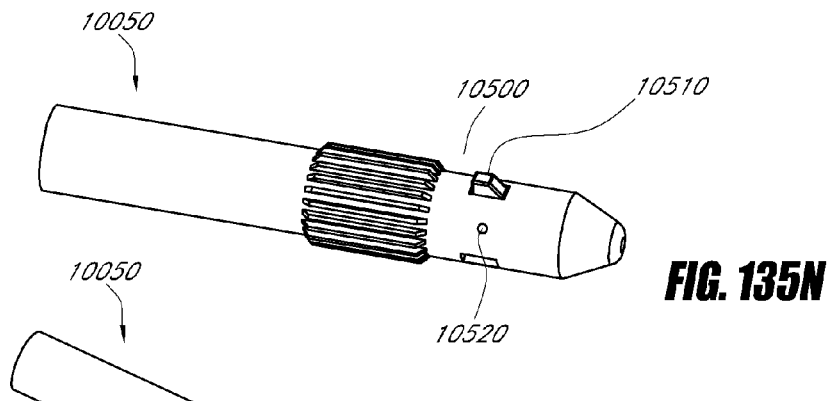
Figure 135O:
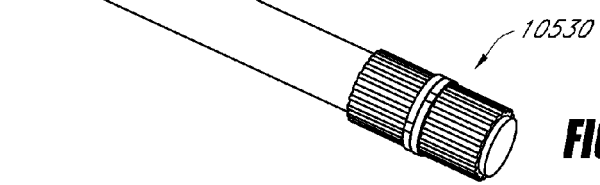
Figure 135P:
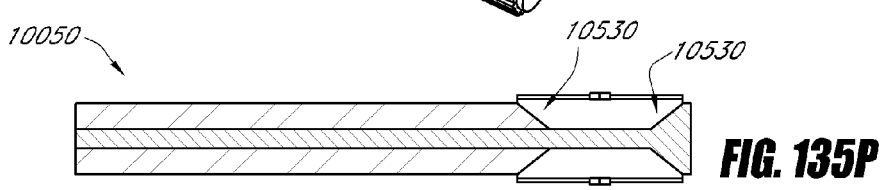

FIGS. 135A-135P are schematic side and/or isometric views of fixation regions according to various embodiments of the present invention.

FIG. 136 is a schematic side view of a straight fixation implant according to an embodiment of the present invention.

FIG. 137 is a schematic side view of a straight fixation implant according to an embodiment of the present invention.

FIG. 138 is a schematic side view of a straight fixation implant according to an embodiment of the present invention.

FIG. 139 is a schematic side view of a straight fixation implant according to an embodiment of the present invention.

FIG. 140 is a schematic side view of a straight fixation implant hub according to an embodiment of the present invention.

Figure 141:
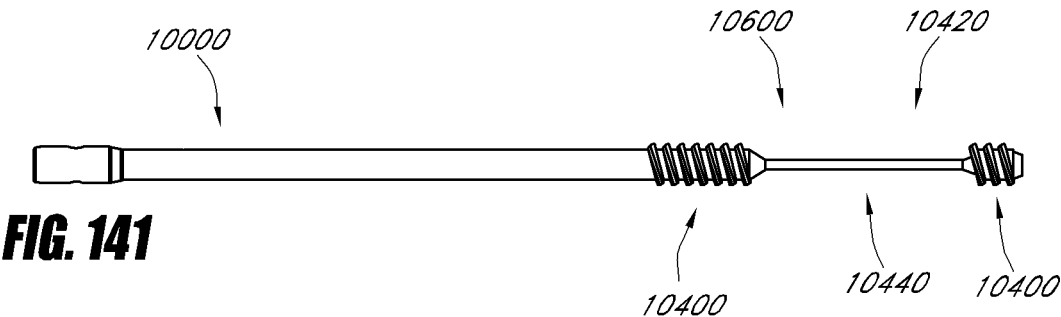

FIG. 141 is a schematic side view of a flexible fixation implant according to an embodiment of the present invention.

Figure 142:
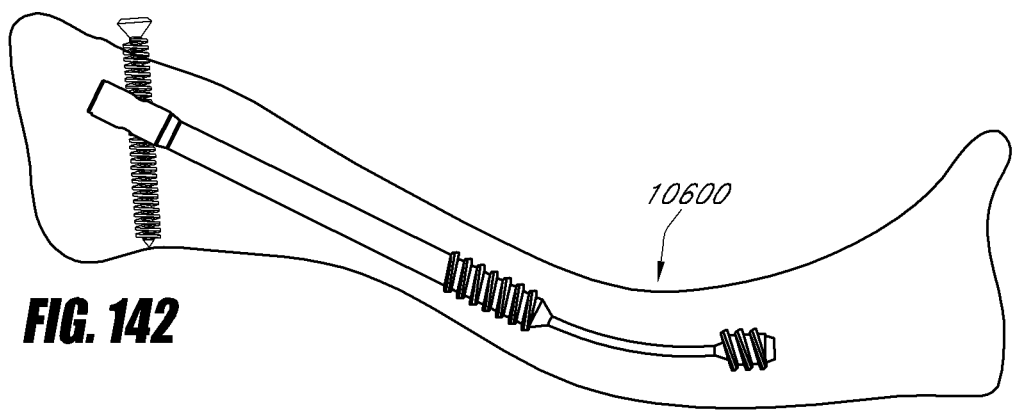

FIG. 142 is a side view of the flexible fixation implant according to FIG. 141 implanted in a clavicle.

Figure 143:
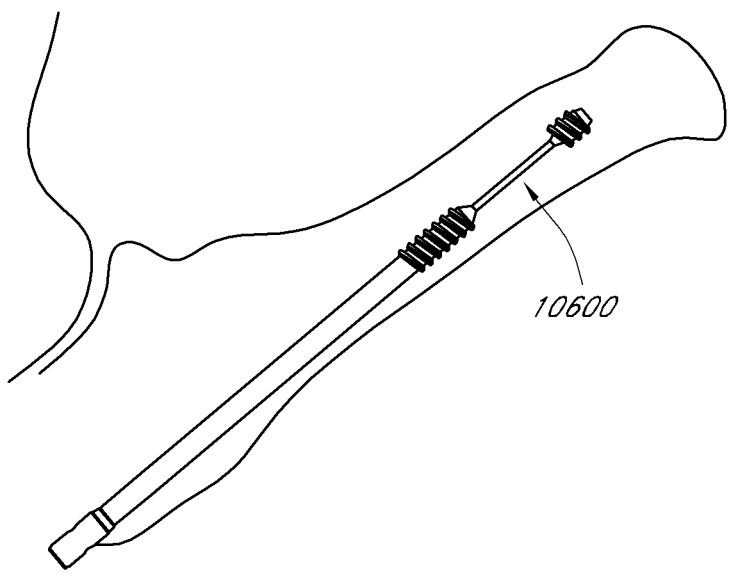

FIG. 143 is a side view of a straight fixation implant according to FIG. 141 implanted in a clavicle.

Figure 144:
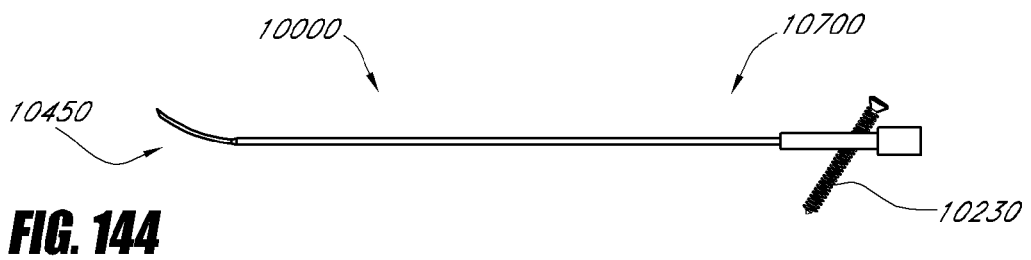

FIG. 144 is a schematic side view of a deployable fixation implant with a deployable member according to an embodiment of the present invention.

Figure 145:
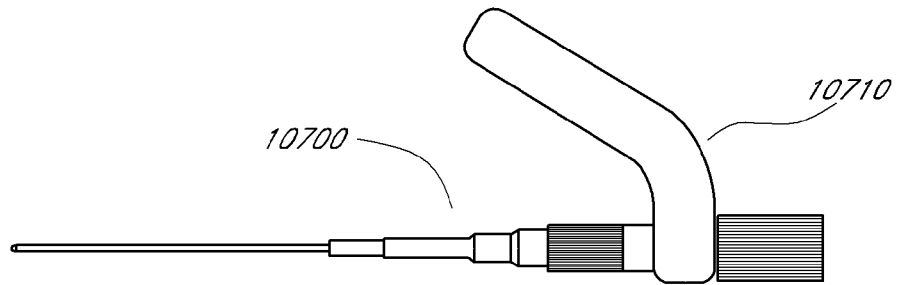

FIG. 145 is a schematic side view of the fixation implant with the deployable member retracted according to FIG. 144.

Figure 146:
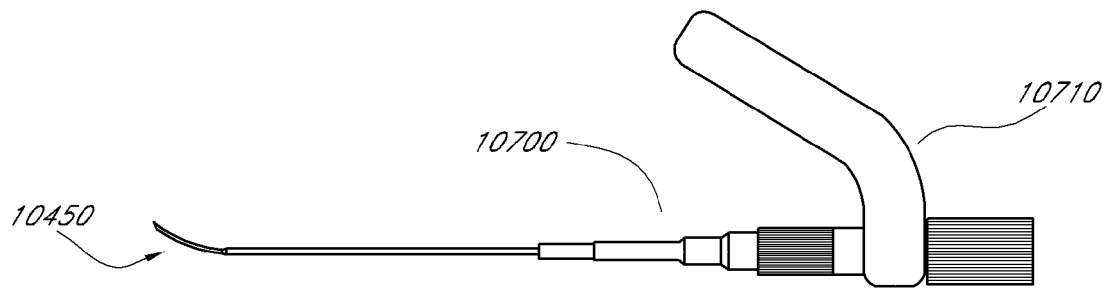

FIG. 146 is a schematic side view of the fixation implant with the deployable member deployed according to FIG. 144.

Figure 147:
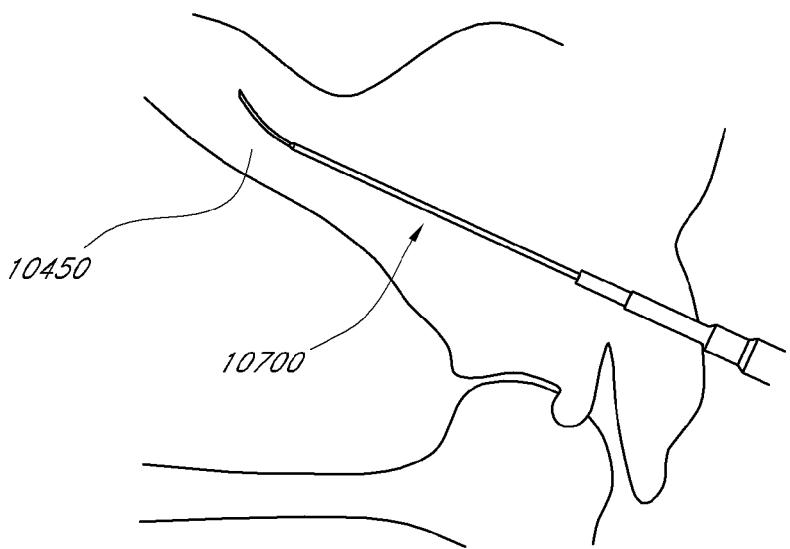

FIG. 147 is a side view of the fixation implant with the deployable member deployed in a clavicle according to FIG. 144.

Figure 148:
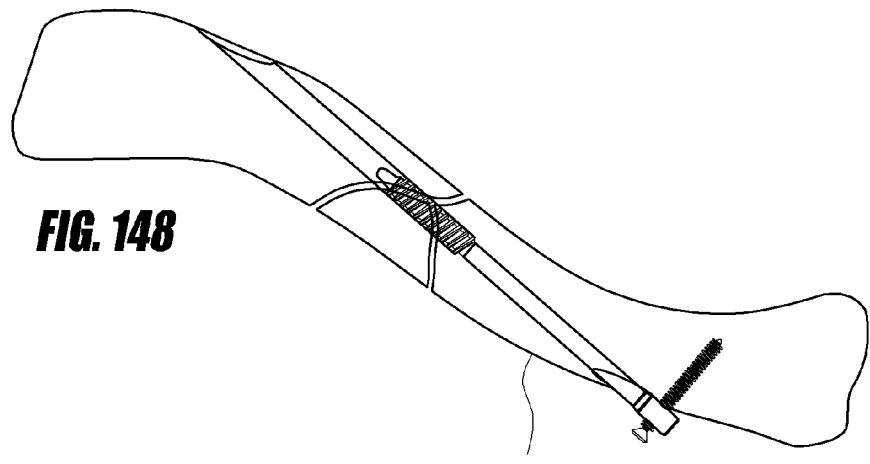

FIG. 148 is a schematic side view of a straight fixation implant with a medial approach according to an embodiment of the present invention.

Figure 149:
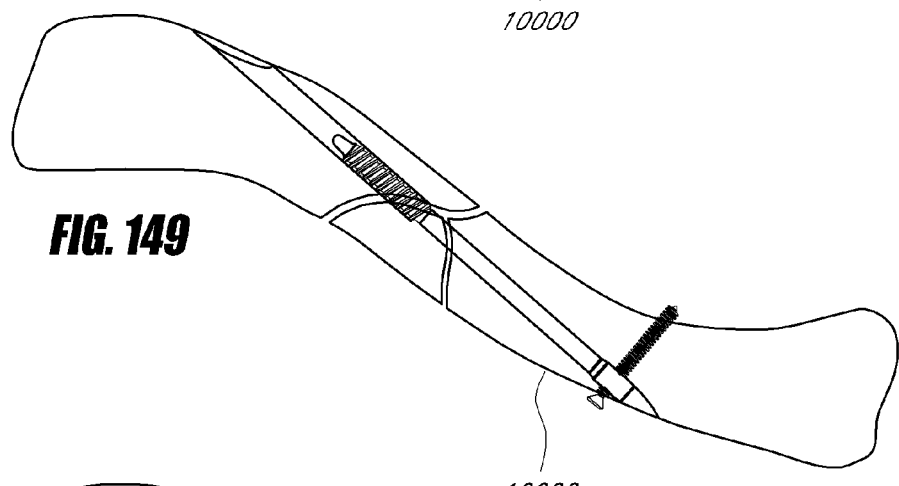

FIG. 149 is a schematic side view of a straight fixation implant with a medial approach according to an embodiment of the present invention.

Figure 150:
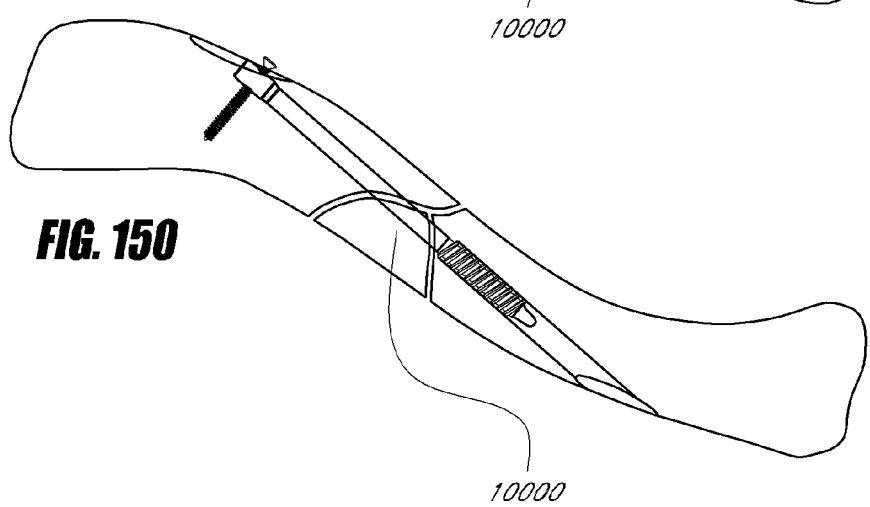

FIG. 150 is a schematic side view of a straight fixation implant with a lateral approach according to an embodiment of the present invention.

DETAILED DESCRIPTION

By way of background and to provide context for the invention, it may be useful to understand that bone is often described as a specialized connective tissue that serves three major functions anatomically. First, bone provides a mechanical function by providing structure and muscular attachment for movement. Second, bone provides a metabolic function by providing a reserve for calcium and phosphate. Finally, bone provides a protective function by enclosing bone marrow and vital organs. Bones can be categorized as long bones (e.g. radius, femur, tibia and humerus) and flat bones (e.g. skull, scapula and mandible). Each bone type has a different embryological template. Further each bone type contains cortical and trabecular bone in varying proportions. The devices of this invention can be adapted for use in any of the bones of the body as will be appreciated by those skilled in the art.

Cortical bone (compact) forms the shaft, or diaphysis, of long bones and the outer shell of flat bones. The cortical bone provides the main mechanical and protective function. The trabecular bone (cancellous) is found at the end of the long bones, or the epiphysis, and inside the cortex of flat bones. The trabecular bone consists of a network of interconnecting trabecular plates and rods and is the major site of bone remodeling and resorption for mineral homeostasis. During development, the zone of growth between the epiphysis and diaphysis is the metaphysis. Finally, woven bone, which lacks the organized structure of cortical or cancellous bone, is the first bone laid down during fracture repair. Once a bone is fractured, the bone segments are positioned in proximity to each other in a manner that enables woven bone to be laid down on the surface of the fracture. This description of anatomy and physiology is provided in order to facilitate an understanding of the invention. Persons of skill in the art will also appreciate that the scope and nature of the invention is not limited by the anatomy discussion provided. Further, it will be appreciated there can be variations in anatomical characteristics of an individual patient, as a result of a variety of factors, which are not described herein. Further, it will be appreciated there can be variations in anatomical characteristics between bones which are not described herein.

While the inventive devices, tools and methods described herein may be adapted for use with many regions of the musculo-skeletal system in both humans and animals, they are particularly well suited for addressing fractures in the human clavicle, also known as the collar bone. Clavicle fractures involve approximately 5% of all fractures seen in hospital emergency admissions. The clavicle is most commonly fractured between the proximal ⅔ and distal ⅓ of its length. Fractures often occur when a patient falls onto an outstretched upper extremity, falls onto a shoulder, or receives direct clavicular trauma.

FIG. 1 shows the location of the left clavicle 10 and right clavicle 12 in the human anatomy. The clavicle is classified as a membranous bone that makes up part of the pectoral girdles 14. The clavicle receives its name from the Latin claviculam, meaning "little key", because the bone rotates along its axis like a key when the shoulder is abducted. This movement is palpable with the opposite hand. The clavicle is a doubly curved short bone that connects the arm (upper limb) to the body (trunk), located directly above the first rib 16. It acts as a shunt to keep the scapula 18 in position so the arm can hang freely. At its medial end 20, the clavicle 10, 12 articulates with the manubrium of the sternum 22 (breast-bone) at the sterno-clavicular joint. At its lateral end 24, the clavicle 10, 12 articulates with the acromion 26 of the scapula (shoulder blade) at the acromioclavicular joint. As mentioned, the clavicle is a double curved bone, comprising a lateral segment having a lateral curve and a medial segment having a medical curve. It has been found by Jonas Andermahr et al. in "Anatomy of the clavicle and the Intramedullary Nailing of Midclavicular Fractures" (Clinical Anatomy 20 (2007): 48-56), that the medial curve radius is about 7.1.+−.1.3 cm overall (N=196) with women (N=106) having a slightly smaller curvature of 7.0.+−.1.2 cm and men (N=90) having a slightly larger curvature of 7.3.+−.1.3 cm. The lateral curve radius is about 3.9.+−.1.4 cm overall (N=196) with women (N=106) having a slightly larger curvature of 4.2.+−.1.6 cm and men (N=90) having a slightly smaller curvature of 3.6.+−.1.1 cm.

FIG. 2 is an enlarged view of the superior surface of the left clavicle 10. As can be seen, the clavicle 10 has a rounded medial end (sternal extremity) 20 and a flattened lateral end (acromial extremity) 24. From the roughly pyramidal sternal end 20, clavicle 10 curves laterally and posteriorly for roughly half its length. It then forms a smooth posterior curve to articulate with a process of the scapula (acromion), as described above. The flat, acromial end 24 of the clavicle 10 is broader than the sternal end 20. The acromial end 24 has a rough inferior surface that bears prominent lines and tubercles. These surface features are attachment sites for muscles and ligaments of the shoulder. The clavicle is made up of spongy (cancellous) bone with a shell of compact bone. It is a dermal bone derived from elements originally attached to the skull. An exemplary mid-shaft fracture site 28 is depicted in FIG. 2.

FIGS. 3 and 4 show an exemplary embodiment of a fracture fixation device according to aspects of the invention. As will be later described, device 100 may be implanted in a longitudinal intramedullary cavity of clavicle 10 shown in FIG. 2, or other bones, to approximate and/or secure fracture 28. FIG. 3 shows device 100 in a retracted state for insertion into or removal from a bone, while FIG. 4 shows the device in an expanded state as when it is anchored within a bone.

Bone repair device 100 has a proximal end 102 (nearest the surgeon) and a distal end 104 (further from surgeon) and positioned within the bone space of a patient according to the invention. The proximal end and distal end, as used in this context, refers to the position of an end of the device relative to the remainder of the device or the opposing end as it appears in the drawing. The proximal end can be used to refer to the end manipulated by the user or physician. The distal end can be used to refer to the end of the device that is inserted and advanced within the bone and is furthest away from the physician. As will be appreciated by those skilled in the art, the use of proximal and distal could change in another context, e.g. the anatomical context in which proximal and distal use the patient as reference. As described in most instances herein, the device will be implanted into a bone, such as a clavicle, such that the proximal end will be implanted in the lateral segment of the clavicle bone, and the distal end will be implanted in the medial segment of the clavicle bone.

When implanted within a patient, the device can be held in place with suitable fasteners such as wire, screws, nails, bolts, nuts and/or washers. The device 100 may be used for fixation of fractures of the proximal or distal end of long bones such as intracapsular, intertrochanteric, intercervical, supracondular, or condular fractures of the femur; for fusion of a joint; or for surgical procedures that involve cutting a bone. The devices 100 may be implanted or attached through the skin so that a pulling force (traction may be applied to the skeletal system).

In the embodiment shown in FIGS. 3, 4, and 15, the design of the repair device 100 depicted is adapted to provide two bone engaging mechanisms or grippers 108, 109, each adapted to engage target bone of a patient from the inside of the bone. As configured for this anatomical application, the device is designed to facilitate bone healing when placed in the intramedullary space within a post fractured bone. This device 100 has a gripper 108 positioned distally, and another gripper 109 positioned proximally. Both grippers are deployed radially outward against the wall of the intramedullary cavity. On entry into the cavity, grippers 108, 109 are flat and retracted as shown in FIG. 3. Upon deployment, grippers 108, 109 pivot radially outward, as shown in FIG. 4, and grip the diaphyseal bone in this embodiment from the inside of the bone. One or more screws 110, shown in FIG. 11, placed through apertures through the hub 112 lock the device 100 to the metaphyseal bone. Hence, the proximal end and or metaphysis and the distal end and or diaphysis are joined. The union between the proximal and distal ends may be achieved by the grippers 108 and 109 alone or in concert with screws 110 placed through hub 112. Hub 112 may be either at the distal or proximal end of the bone, in this case clavicle. A hub 112 may be at both ends of the device, there by allowing screws to be placed in the distal and proximal ends. A flexible-to-rigid body portion 114 may also be provided, and in this embodiment is positioned between grippers 108 and 109. The flexible-to-rigid body portion may be placed proximal or distal to both grippers, 108 and 109. It may be provided with cut 116 that is specific for the purpose and location of the device, as will be described in more detail below.

Figure 5:
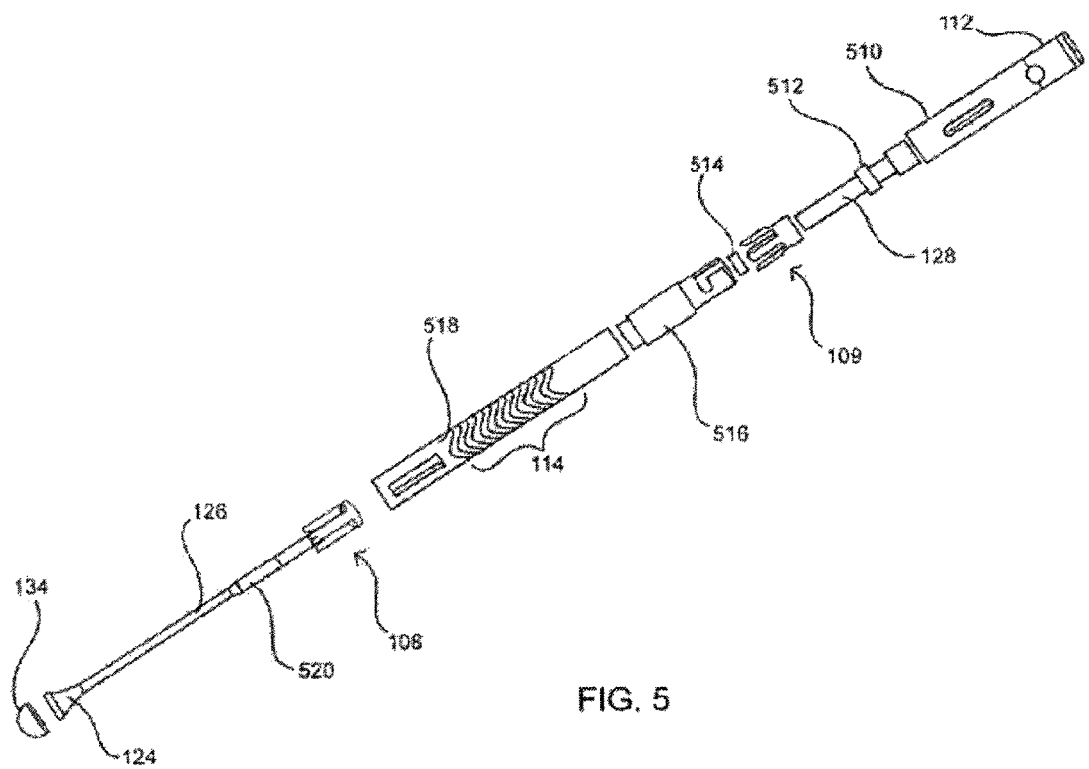
FIG. 5 is an exploded view showing the components of the device shown in FIG. 3.

FIG. 5 shows an exploded view of device 100. In this embodiment, device 100 (starting at the proximal end and moving towards the distal end) is formed from a proximal body member 510, drive member 128, keeper ring 512, proximal gripper 109, bushing 514, coupling member 516, distal body member 518, distal gripper 108, actuator 126, and tip cover 134. During assembly of device 100, proximal gripper 109 is rotatably received over the reduced diameter portion of drive member 128 until it abuts against the larger diameter proximal portion of drive member 128. Keeper ring 512 is then slid over the reduced diameter portion of drive member 128 to the position shown and is welded, pinned, press fit, swaged, adhered and/or otherwise secured in place such that it allows gripper 128 to rotate with respect to drive member 128 but not move axially relative to it. Bushing 514 is similarly slid over the reduced diameter portion of drive member 128 and secured in a position more distal than keeper ring 512. This drive member/gripper assembly is then placed within the axial bore of proximal body member 516.

Each end of coupling member 516 has a stepped portion of smaller outer diameter than the middle of coupling member 516. During assembly, the longer, proximal end of coupling member 516 is received within the distal end of proximal body member 510 (after the drive member/gripper assembly is inserted, as described above). The shorter, distal end of coupling member 516 is received within the proximal end of distal body member 518. The proximal and distal body members 510, 518 are secured to coupling member 516, such as by welding or other suitable means. When assembled, proximal body member 510, coupling member 516, and distal body member 518 form a smooth tube having a generally constant outer diameter, as shown in FIG. 3.

Distal gripper 108 is configured to fit within the distal end of distal body member 518. The proximal end of actuator 126 may be passed through the center of distal gripper 108, distal body member 518, and coupling member 516 until it reaches drive member 128, which is rotatably housed within proximal body member 510. The distal end of drive member 128 includes an internally threaded bore for receiving the externally threaded proximal end of actuator 126. As drive member 128 is rotated with respect to actuator 126, actuator 126 moves proximally and/or drive member 128 moves distally. Mating features of actuator 126 and coupling member 516, as will be later described, allow actuator 126 to move axially but prevent it from rotating.

Figure 17:
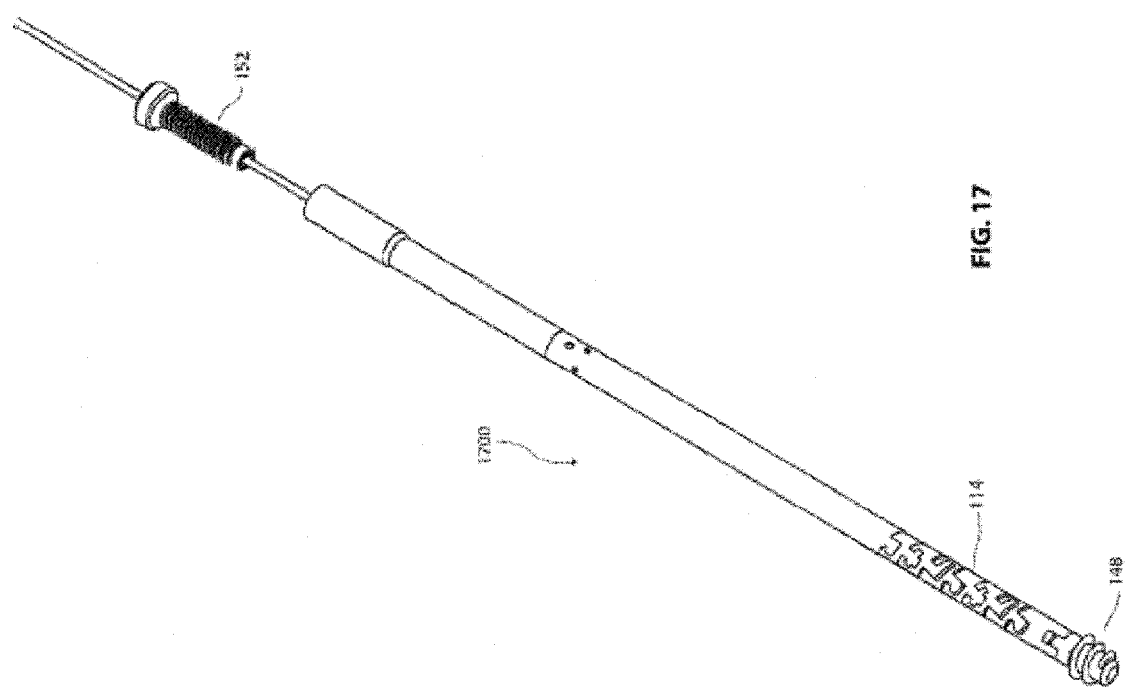

The assembly of device 100 may be completed by attaching hemispherical tip cover 134 to the distal end of distal body member 518, such as by welding or other suitable process. Tip cover 134 may be configured to act as a blunt obturator. This arrangement facilitates penetration of bone by device 100 while keeping the tip of device 100 from digging into bone during an insertion procedure. Alternatively, as shown in FIG. 17, the tip may include a screw or threaded tip or, as shown in FIG. 19, the tip may have a conical shape. The tip may have various geometrical configurations that adapt to enabling tools such as guide wires and guide tubes. The tip may be actively coupled to an electrical or mechanical source that removes or ablates bone to facilitate insertion. Variations or alternatives to the exemplary assembly procedure described above will be apparent to those skilled in the art.

Figure 6A:
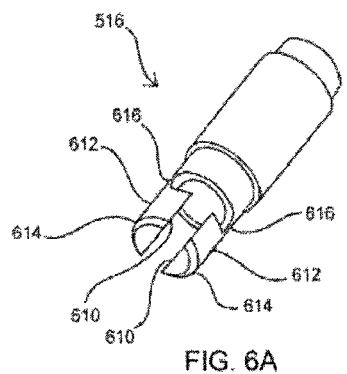
FIGS. 6A and 6B are perspective views showing a coupling member.
Figure 6B:
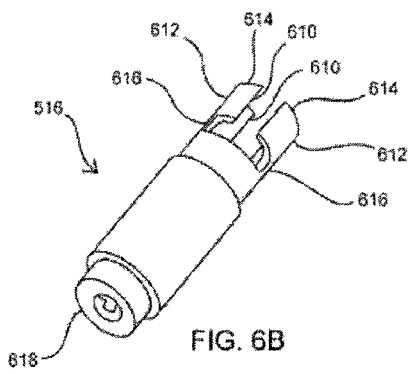

FIGS. 6A and 6B show detailed features of coupling member 516. T-shaped slots 610, 610 are formed on opposite sides of the proximal end of coupling member 516. This leaves two T-shaped appendages 612, 612 which extend in a proximal direction from coupling member 516 when it is assembled in device 100. The outer edges of each T-shaped appendage 612 include a ramped surface 614, 614, the purpose of which will be later described. The inner end of each T-shaped appendage 612 is connected to the main body of coupling member 516 by a necked down portion 616, 616. The necked down portions 616, 616 are configured and arranged to bend, allowing T-shaped appendages 612, 612 to pivot axially inward, as will be later described.

The distal end of coupling member 516 is provided with an oblong axial slot 618. The parallel sides of slot 618 mate with the flattened portion 520 of actuator 126 (shown in FIG. 5) to allow actuator 126 to move axially but prevent it from rotating.

Figure 7A:
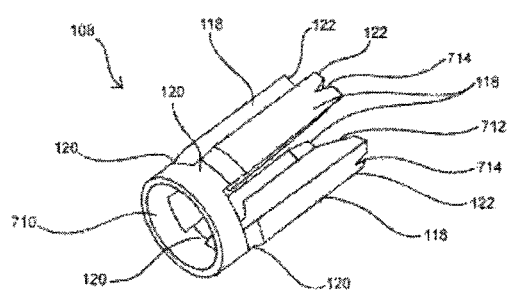
FIGS. 7A and 7B are perspective views showing a distal gripper.
Figure 7B:
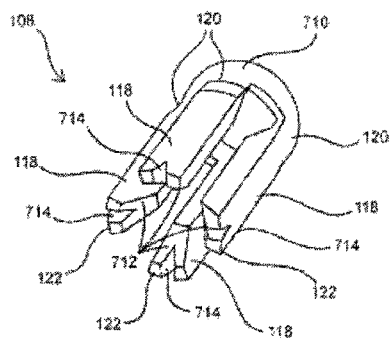

FIGS. 7A and 7B show detailed features of distal gripper 108. Gripper 108 includes two pairs of opposing bendable members 118. Each bendable member 118 has a thinned portion 120 that connects it to a common collar 710. Thinned portions 120 permit bending as the opposite distal ends 122 of members 118 are urged radially outward, such that members 118 may pivot about thinned portions 120. When radially extended, distal ends 122 of bendable members 118 contact the inside of the bone to anchor the distal portion of device 100 to the bone, as will be later described. As shown, each distal end 122 includes a ramped surface 712 to assist in radial deployment, and a notch 714 to assist in engaging the inner surface of the bone. In other embodiments, the notch 714 may be replaced with a point, radii, or rectangular geometry. In some embodiments ramped surface 712 is omitted. In other embodiments, it has an angle selected between 0 and 90 degrees. In other embodiments, this surface may have multiple angles between 0 and 90 degree, thereby faceting. This faceting may allow the expansion to be staged by tactile feedback. In still other embodiments, the ramped surface is curved and has a radius of between 0 and 1.0 inches. In other embodiments, there may be multiple radii. The ramped surface may be located on other surfaces of bendable member 118. Gripper 108 may have 1, 2, 3, 4, 5, 6, or some number of bendable members 118 that can be accommodated by the geometry of the device. In some embodiments, gripper 108 may be made of a nickel-titanium alloy.

Figures 8A, 8B:
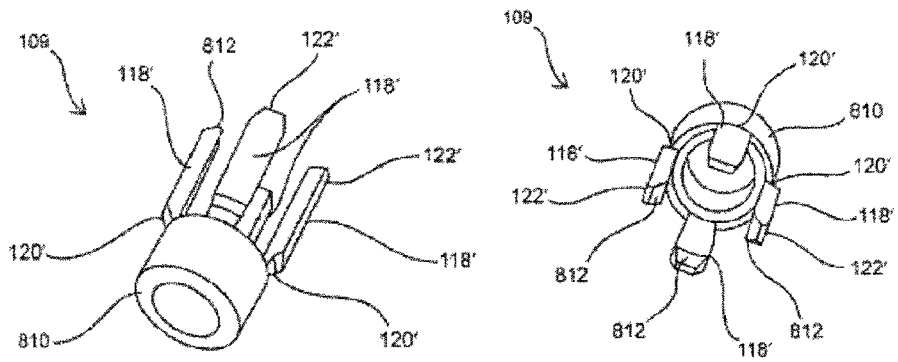
FIGS. 8A and 8B are perspective views showing a proximal gripper.

FIGS. 8A and 8B show detailed features of proximal gripper 109. Proximal gripper 109 has a construction and operation similar to those of distal gripper 108. Gripper 109 includes two pairs of opposing bendable members 118'. Each bendable member 118' has a thinned portion 120' that connects it to a common collar 810. Thinned portions 120' permit bending as the opposite distal ends 122' of members 118' are urged radially outward, such that members 118' may pivot about thinned portions 120'. When radially extended, distal ends 122' of bendable members 118' contact the inside of the bone to anchor the distal portion of device 100 to the bone, as will be later described. As shown, each distal end 122' includes a ramped surface 812 to assist in radial deployment. In some embodiments ramped surface 812 is omitted. In other embodiments, it has an angle selected between 0 and 90 degrees. In still other embodiments, the ramped surface is curved and has a radius of between 0 and 1.0 inches. The ramped surface may be located on other surfaces of bendable member 118'. In some embodiments, gripper 109 may be made of a nickel-titanium alloy. In some embodiments, one or more grippers may each comprise 1, 2, 3, 4, 5, 6 or more bendable members similar to members 118 or 118' shown. In some embodiments, gripper 109 may be made of a nickel-titanium alloy.

Figure 9:
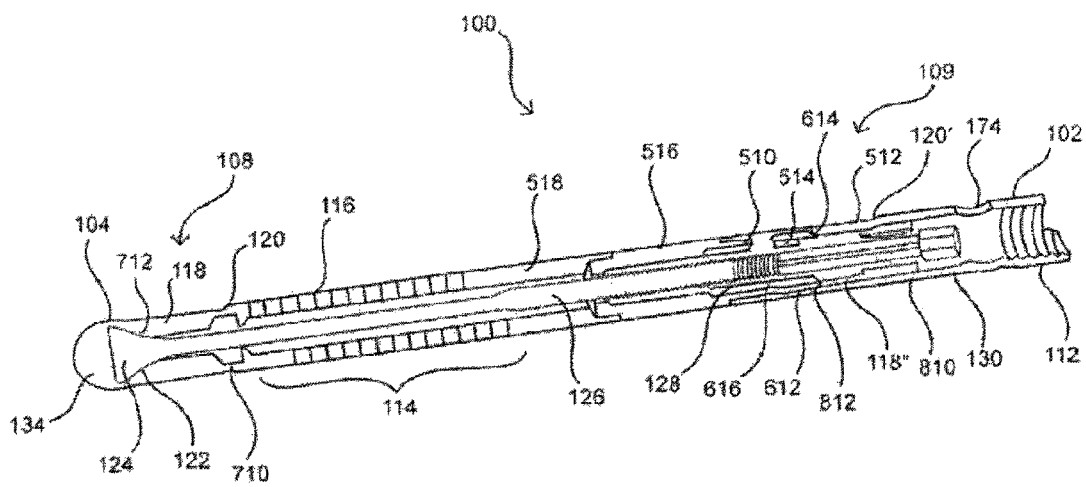
FIG. 9 is a cross-section view of the device of FIG. 3 in a retracted state.
Figure 10:
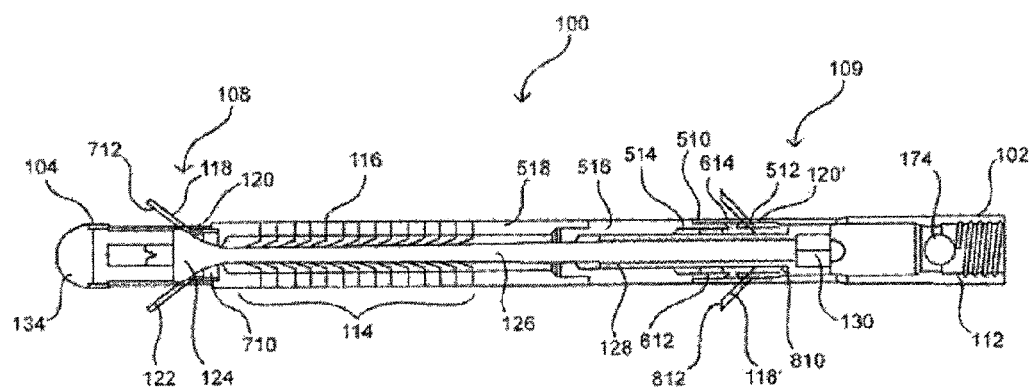
FIG. 10 is a cross-section view of the device of FIG. 3 in a deployed state.

FIGS. 9 and 10 show longitudinal cross-sections of device 100 with its components fully assembled as previously described. FIG. 9 shows device 100 in a retracted state, while FIG. 10 shows device 100 in a deployed state. To deploy grippers 108 and 109, a driver tool, such as one with a hexagonal tip (not shown) is inserted be axially into the proximal end 102 of device 100 until the tool tip is received within keyed socket 130 of drive member 128. When the driver tool is axially rotated, threadably engaged drive member 128 and actuator 126 are drawn together (i.e. drive member 128 moves left toward the distal end 104 and actuator 126 moves right toward the proximal end 102 of device 100). In alternative embodiments, a barbed, serrated wire may be used instead of actuator 126, and it may be ratcheted through a mating drive member. In an alternative embodiment, actuator 126 may be made of a super elastic alloy that when released from its insertion state it returns to its unstressed state thereby driving grippers 108 and 109 outward, shortening the device thereby compressing 518 into a rigid state.

During this actuation, bendable members 118 of proximal gripper 108 are urged radially outward by a ramped surface on actuator head 124. Actuator head 124 is formed on the distal end of actuator 126 and contacts ramped surfaces 712 on the distal ends of bendable members 118. As actuator head 124 is drawn proximally, thinned portions 120 bend and allow bendable members 118 to pivot outwardly through slots in distal body member 518. Gripper 108 and the actuator head 124 may be reversed in their geometrical layout of the device. The gripper 108 may be drawn by the actuator 126 over the actuator head 124, thereby deflecting the bendable members, 118, outward. Similarly, the bendable members, 118, may be made of a super elastic or elastic or spring alloy of metal whereby the bendable members are predisposed in their set state in the insertion configuration, that being their smallest diameter. When the actuator head, 124, engages the super elastic, elastic or spring alloy of steel bendable members 118, a continuous force is imparted upon actuator head 124 such that the bendable members 118 return to their insertion geometry after the actuator head 124 is removed. Typical super elastic, elastic, or spring alloys of metals include spring steels and NiTi or nitinol. Conversely, bendable members 118 may be made of super elastic, elastic, or spring alloys of metal and set in their maximum outside diameter, in their deployed state. Actuator 124 and the rectangular apertures in 518 would work cooperatively to expose the bendable members 118. Since the bendable members 118 would be set in their maximum outside dimension and constrained within 518, upon exposure of 118 to the rectangular apertures, the bendable members would be driven by the material properties into the bone.

At generally the same time that gripper 108 is being deployed, drive member 128 is moving distally, carrying proximal gripper 109 with it. This motion drives the ramped surfaces 812 at the end of bendable members 118' against the ramped surfaces 614 on the ends of T-shaped appendages 612 of coupling member 516, thereby urging the distal ends 122' of bendable members 118' radially outward. As gripper 109 continues to move distally, thinned portions 120' bend and allow bendable members 118' to pivot outwardly through slots in proximal body member 510. Gripper 109 and the coupling member 516 may be reversed in their geometrical layout of the device. The gripper 109 may be drawn by the drive member 128 over the coupling member 516, thereby deflecting the bendable members, 118', outward. Similarly, the bendable members, 118', may be made of a super elastic or elastic or spring alloy of metal where by the bendable members are predisposed in their set state in the insertion configuration, that being their smallest diameter. When the coupling member 516, engages the super elastic, elastic or spring alloy of steel bendable members, 118', a continuous force is imparted upon coupling member 516 such that the bendable members 118, return to their insertion geometry after the coupling member 516 is removed. Typical super elastic, elastic, or spring alloys of metals include spring steels and NiTi or nitinol. Conversely, bendable members 118' may be made of super elastic, elastic, or spring alloys of metal and set in their maximum outside diameter, in their deployed state. Coupling member 516 and the rectangular apertures in 510 would work cooperatively to expose the bendable members 118'. Since the bendable members 118' would be set in their maximum outside dimension and constrained within 510, upon exposure of 118' to the rectangular apertures, the bendable members would be driven by the material properties into the bone.

It can be seen in FIG. 9 that bushing 514 initially prevents T-shaped appendages 612 from collapsing radially inward. However, as drive member 128 carries bushing 514 far enough toward distal end 104, bushing 514 lines up with the circumferential portions of T-shaped slots 610 (shown in FIGS. 6A and 6B) and the necked down portions 616 of T-shaped appendages 612. Once bushing 514 has advanced this far distally, T-shaped appendages 612 are permitted to bend at necked down portions 616 and collapse radially inward as gripper 109 continues to advance distally. An advantage to this arrangement is that is allows grippers 108 and 109 to initially anchor themselves within the intramedullary cavity of the bone before T-shaped appendages 612 are permitted to collapse. Further rotation of drive member 128 allows bendable members 118' to further advance in the distal direction (by collapsing T-shaped appendages 612) rather than being forced to continue to expand only in the radial direction. This two-stage action allows grippers 108 and 109 to anchor on opposite sides of a bone fracture and then move closer together to approximate the fracture.

As previously mentioned, device 100 may include one or more flexible-to-rigid body portions 114. This feature is flexible upon entry into bone and rigid upon application of compressive axial force provided by tensioning actuator 126. Various embodiments may be used, including dual helical springs whose inner and outer tubular components coil in opposite directions, a chain of ball bearings with flats or roughened surfaces, a chain of cylinders with flats, features, cones, spherical or pointed interdigitating surfaces, wavy-helical cut tubes, two helical cut tubes in opposite directions, linear wires with interdigitating coils, and bellows-like structures. The flexible to rigid bodies may have a polygonal cross sectional geometry having any suitable number of sides from 1 to infinity. The flexible-to-rigid body may be cut in a specific way so that upon activation it conforms to a specific shape. The resultant shape may resemble or match the original anatomical shape of the bone. The resultant shape may provide specific translational actions so as to improve the healing of bone or create a resultant bone-implant construct that promotes a desired resultant geometry or effect. These resultant geometries may be bone lengthening where growth of the bone is improper, bone rotation to remediate poor pronation, supination, deflection, extension, deviation, or inclination of an appendage or joint. The shape of the flexible-to-rigid body may be devised or designed from x-ray or CT scans of the contralateral unaffected anatomy to return the affected anatomy to its original anatomical configuration or match the existing contralateral configuration.

The design of the flexible-to-rigid tubular body portion 114 allows a single-piece design to maximize the transformation of the same body from a very flexible member that minimizes strength in bending to a rigid body that maximizes strength in bending and torque. The flexible member transforms to a rigid member when compressive forces are applied in the axial direction at each end, such as by an actuator. The body portion 114 is made, for example as shown in FIG. 3, by a near-helical cut 116 on a tubular member at an angle of incidence to the axis somewhere between 0 and 180 degrees from the longitudinal axis of the tubular body portion 114. The near-helical cut or wavy-helical cut may be formed by the superposition of a helical curve added to a cyclic curve that produces waves of frequencies equal or greater than zero per turn around the circumference and with cyclic amplitude greater than zero. The waves of one segment nest with those on either side of it, thus increasing the torque, bending strength and stiffness of the tubular body when subjective to compressive forces. The tapered surfaces formed by the incident angle allow each turn to overlap with the segment on either side of it, thus increasing the bending strength when the body is in compression. Additionally, the cuts can be altered in depth and distance between the cuts (i.e. thickness) on the longitudinal axis along the length of body portion 114 to variably alter the flexible-to-rigid characteristics of the tubular body along its length. As shown in FIG. 15 or 16 for example, the body portion 114 is made by a patterned cut 116'. The pattern may be a repeating pattern, or it may be a non repeating pattern as shown in the Figures. As shown in FIG. 16, the patterned cut 116' may include a ramp 142, edges 144, and inter-digitations 146 (i.e. portions that are interlocking) The ramp 142 may function to dictate the radius of curvature and/or the chord length of the geometry of the elongate body in its rigid state. The ramp may be sized and configured such that the geometry in the rigid shape fits or matches the anatomical curvature of the specific bone into which it will be implanted. The edges 144 may function to prevent axial displacement or excessive elongation of the elongate body. The edges may function to prevent the elongate body from unraveling and allow for the removal of the device. In some embodiments, the edges may be sized and configured to withstand up to about 200 pounds-force. The inter-digitations 146 may also function to prevent axial displacement or excessive elongation of the elongate body and in some instances, they may provide torsional resistance, especially when the elongate body is curved and in a rigid state.

The cuts 116 in body portion 114 allow an otherwise rigid member to increase its flexibility to a large degree during deployment. The tubular member can have constant or varying internal and external diameters. This design reduces the number of parts of the flexible-to-rigid body portion of the device and allows insertion and extraction of the device through a curved entry port in the bone while maximizing its rigidity once inserted. Application and removal of compressive forces provided by a parallel member such as wire(s), tension ribbons, a sheath, or actuator 126 as shown will transform the body from flexible to rigid and vice versa.

In operation, as actuator 126 is tightened, gripper members 118 and 118' are extended radially outwardly. Once the distal ends of gripper members 118 contact bone and stop moving outward, continued rotation of actuator 126 draws grippers 108 and 109 together, as previously described, and also draws the proximal end 102 and the distal end 104 of device 100 closer together until cuts 116 are substantially closed. As this happens, body portion 114 changes from being flexible to rigid to better secure the bone fracture(s), as will be further described below. Rotating actuator 126 in the opposite direction causes body portion 114 to change from a rigid to a flexible state, such as for removing device 100 if needed in the initial procedure or during a subsequent procedure after the bone fracture(s) have partially or completely healed. Body portion 114 may be provided with a solid longitudinal portion 136 (as seen in FIGS. 3 and 4) such that cuts 116 are a series of individual cuts each traversing less than 360 degrees in circumference, rather than a single, continuous helical cut. This solid portion 136 can aid in removal of device 100 by keeping body portion 114 from undesirably extending like a spring.

If removal of device 100 is desired, keeper ring 512 also serves to help retract gripper 109. Keeper ring 512 pulls gripper 109 in the proximal direction as drive member 128 moves proximally, and also as device 100 is being withdrawn, to keep gripper 109 from sliding distally along drive member 128. With drive member 128 retracted to its original proximal position and actuator 126 extended to its original distal position (as both shown in FIG. 9), bendable gripper members 118, 118' are free to retract back within distal body member 518 and proximal body member 510, respectively, as device 100 is withdrawn from the bone in the proximal direction.

As shown in FIGS. 9 and 10, hub 112 at the proximal end 102 of device 100 may be provided with an angled hole 174 for receiving a bone screw, interlocking pin, or transverse bone attachment member to further anchor device 100 to a bone, as will be later described. Hole 174 may be tapped to interfere with the bone screw, interlocking pin, or transverse bone attachment member so that there is mechanical interference between the hub 112 and the attachment member, such that, over time, the attachment member does not back out or translate away or into the hub unexpectedly. Hub 112 may also be provided with an internally threaded bore as shown. This threaded bore can serve to attach an insertion and removal tool (not shown) to aid in placing or removing device 100 in the intramedullary space of a bone. A step may also be provided at the proximal end of hub 112 to mate with a similar step of the insertion tool to prevent device 100 from rotating with respect to the tool. The step can be semicircular or of any suitable geometrical configuration so that the insertion tool and hub are keyed relative to each other for alignment and secure positioning. After disengaging the tool from device 100, the threaded bore may also serve to receive an end plug (not shown) to prevent ingrowth of tissue into implanted device 100.

FIGS. 11 and 12 show device 100 implanted in a right clavicle 12. FIG. 11 shows clavicle 12 from a superior perspective, while FIG. 12 shows clavicle 12 from a posterior perspective. As shown, the clavicle has a lateral segment having a lateral end 24 and a medial segment having a medial end 20. In a patient, the lateral end is adjacent to the acromion of a scapula and the medial end is adjacent to the manubrium of a sternum. As shown in FIGS. 11 and 12, the lateral segment is between the fracture 28 and the lateral end 24 and the medial segment is between the fracture and the medial end 20.

A method of implanting the device 100 into a bone and of repairing the bone, such as a clavicle, may include the steps of creating an intramedullary channel 132 and inserting the bone fixation device into the channel. The channel may be created such that the channel traverses the fracture 28 of the bone and comprises at least one segment 138 that substantially follows the anatomical contour of the bone. The bone fixation device may be inserted into the channel such that the device transverses the fracture and at least a portion 114 of an elongate body of the fixation device in a flexible state is placed within the contoured segment of the channel. The method may further comprise the step of operating an actuator to deploy at least one gripper of the fixation device to engage an inner surface of the intramedullary channel to anchor the fixation device to the clavicle.

In a first embodiment, to implant bone fixation device 100 in clavicle 12, an incision is first made at the fracture 28, and tissue is retracted if needed to access the fracture. Fracture 28 is then distracted to gain access to the medial end of the lateral portion of the bone. A channel may then be drilled axially through the lateral portion of the bone from fracture site 28 outward toward the lateral end 24 until it surfaces at the lateral end as shown. A guidewire, such as a K-wire, may first be driven anterior to posterior thereby tenting the posterior skin and the drill guided over the guidewire anterior to posterior in the lateral clavicle segment.

A second incision may be made where the channel exits lateral end 24 of clavicle 12 in order to access the exit point. A guide wire may then be placed through the second incision and into the lateral exit point of the channel created in the lateral portion of clavicle 12. The guide wire may then be fed medially through the channel to the fracture site 28. With the fracture approximated, the guide wire may be advanced across the fracture site and into the medial portion of clavicle 12. Note that the path of the guide wire may need to bend to approximately follow the longitudinal axis of clavicle 12. The procedure may be done under fluoroscopy or other imaging technique to allow the surgeon to visualize the path of the guide wire as it is advanced, and/or to confirm its location once extended through clavicle 12. A guiding sheath or cannulated drill bit may alternatively be used to facilitate the placement of the guide wire from anterior to posterior in the lateral clavicle fragment, thereby allowing the guide wire to be passed either anterior to posterior in the lateral fragment or posterior to anterior in the lateral fragment.

A canulated drill, reamer, or other channel forming instrument may then be advanced over the guide wire to create a straight or curved channel in the medial portion of clavicle 12 as needed. Once the desired intramedullary channel is created on both sides of fracture 28, device 100 may be inserted into the channel through the lateral exit point.

As previously described, grippers 108 and 109 are in a retracted state during insertion, and flexible to rigid body portion 114 is in a flexible state. With fracture 28 roughly approximated, grippers 108, 109 may be deployed and body portion 114 converted to a rigid state by inserting a rotary drive tool through the second incision and into proximal end 102 of device 100, and rotating the tool as previously described. According to aspects of the invention, this action can further approximate fracture 28. One or more screws 110 may be inserted in the second incision and through hub 112 as shown to further secure proximal end 102 of device 100 to the lateral end 24 of clavicle 12. At this point, any insertion tool attached to device 100 may be removed and replaced with an end plug if desired, and the incisions are closed.

In a second embodiment, to implant bone fixation device 100 in clavicle 12, an incision is first made at the fracture 28. The patient may be positioned in the "beach chair" position or any other suitable position for surgery. The incision is made at the front (anterior side) of the patient adjacent to the fracture. Tissue is retracted if needed to access the fracture and the fracture 28 may then be distracted or elevated to gain access to each of the segments of the bone. The medial segment and lateral segment are then both prepared for the insertion of the device by creating a channel within them.

Any suitable combination of tools may be used to create the channels in both the medial segment and the lateral segment of the clavicle. The tools may include hand tools or power tools. The tools may also include awls, drill bits, guidewires, or any other suitable tools to create a channel within bone. The awls may be curved awls, straight awls, and/or malleable awls (i.e. the user may change the radius of curvature of the awl intraoperatively). The tools may have any suitable head geometry such as a pointed geometry, a blunted geometry, a fluted geometry, etc. In some cases, a blunted tip is preferably over a sharp tip as to avoid important nerves (such as the bracheoplexus) and vessels (such as the subclavian artery which supplies blood to the brain) that surround the clavicle bone. The tools may be cannulated (i.e. hollow) or solid. In the case that the tool is cannulated, it may be adapted to be inserted into the bone over a guidewire and/or the tool may function as a sheath or trocar like device and a guidewire may be inserted through the cannula of the cannulated tool.

The segments may be prepared in any suitable order. As an example, the medial segment may be prepared first. The channel is created in the medial segment by inserting a tool into the medial segment starting at the fractured end. The tool is then moved through the medial segment creating the channel. The channel substantially follows the anatomical contour of the bone. In the case of the clavicle, as shown in FIG. 11, this means following the curve of the bone through the medial segment. A curved tool may be used to create the curved or contoured segment of the channel. A straight tool may be used to create the substantially straight segments before and/or after the curved or contoured segment. As shown in FIG. 12, the channel 132 is created substantially along the midline of the bone. Furthermore, the channel 132 may run deeper into the medial segment of the bone than conventional channels can because it is a curved channel. Conventional channels cannot be curved, and therefore they cannot be created past the curved portion or bend in the medial segment of the clavicle bone without breaking out of the bone.

As an example, once the medial segment is prepared, the lateral segment may be prepared by creating a channel through the lateral segment of the clavicle. The channel is created in the lateral segment by inserting a tool into the lateral segment starting at the fractured end. The tool is then moved through the lateral segment creating the channel. As shown in FIG. 11, the channel through the lateral segment may be substantially straight, and may exit the lateral segment of the clavicle toward the lateral end 24 of the bone, creating a port 140 through which other tools and/or the device can be inserted. As shown in FIG. 12, the channel 132 is created substantially along the midline of the bone.

As described above, any suitable combination of tools may be used to prepare the medial segment and then the lateral segment. For example, a smaller diameter channel may initially be created by a guidewire and/or an awl. The channel may be made larger by then inserting a larger diameter tool such as a larger awl, a drill bit, and/or a reamer. Once the initial channel is created in both the lateral and the medial segments, a guidewire may be inserted into the channels. The guidewire may be inserted through the incision such that a first end is inserted into the medial segment, and then a second end is inserted into the lateral segment. The second end may be inserted through the lateral segment such that it exits the bone at the port 140. The guidewire may then "tent" or raise the skin of the patient at their back as the guidewire passes out of the bone. The guidewire may be used to puncture the skin at this point, or an additional incision may be made in the back of the patient, adjacent to the port at the lateral end of the bone. Alternatively, the incision at the back of the patient may be made first (or the guidewire may puncture the skin) and the guidewire may be inserted from the back of the patient, through the port, into the lateral segment of the bone, across the fracture, and into the medial segment of the bone. The fracture may be reduced (i.e. brought together) before or after the insertion of the guidewire. The fracture may be held together with conventional surgical bone clamps.

Once the guidewire is in place within the channel 132, tools may be inserted into the channel over the guidewire. For example, a cannulated reamer (stiff and/or flexible) or cannulated drill bit may be inserted through port 140 and into the clavicle by being threaded over the guidewire. A straight tool may be used to enlarge the diameter of the straight portions of the channel, and a curved or flexible tool may be used to enlarge the diameter of the curved and/or straight portions of the channel. The guidewire may function to guide the tools through the bone such that the tools follow the anatomical curvature of the bone (through at least a portion the medial segment), and stay substantially at the midline of the bone. In some instances, the initial channel of lateral segment will have a larger diameter than the initial channel of the medial segment, so tools may be used to only enlarge a portion (e.g. the medial segment) of the channel.

Additional tools may be inserted into the channel over the guidewire. For example, a depth gauge 168, as shown in FIG. 24, may be inserted into the channel. In some embodiments, the depth gauge includes markings 170 to indicate the depth of the channel created. The markings may be reverse scale markings such that the deeper that the gauge can be inserted into the channel, the higher the marking that will be legible. The depth reading may be used to determine the length of device needed to fit correctly within the channel. The flexible to rigid body portion 114 may rest substantially within the contoured portion 138 of the channel and the end of the device is just below the outer surface of the bone. Various lengths and diameters of devices may be provided for the surgeon to select from to suit the particular anatomy and fracture involved. For example, device 100 may be provided in 4, 5 and 6 mm diameters, and in 50, 75, 100 and 125 mm lengths. Dimensions and configurations can be altered for use in bones other than the clavicle.

The device may then be inserted through the port 140 and positioned within the intramedullary channel 132, as shown in FIGS. 11 and 12. In order to insert the device through the incision and the surrounding soft tissues, a tissue protection tool may be used. As shown in FIGS. 25-27, the tissue protection tool 172 or 172' may function to guide the device through the soft tissue to the port while protecting the soft tissue from being damaged by the device. In some embodiments, as shown in FIGS. 26 and 27, the protection tool comprises a tapered portion 174 at one end of the tool. The tapered portion may be sized and configured to fit at least partially within the entry port in the bone. The tapered portion may function to pilot or guide the fixation device into the channel in the bone. As shown in FIG. 25, the protection tool comprises a toothed portion 176 at one end of the tool. The toothed portion may be sized and configured to fit at least partially within the entry port in the bone or may alternatively be sized and configured to grip the end of the bone. In some embodiments, as shown in FIG. 27, the protection tool has a U-shaped cross section 178 that cradles the fixation device. Once the fixation device is in place and/or at least partially within the channel of the bone, the protection tool may simply be pulled off of the fixation device. In some embodiments, the fixation device may be sold or provided to a user already coupled to the protection tool. Alternatively, the protection tool may be sold or provided to a user coupled to a combination tool or other insertion, actuation, and/or alignment devices. The combination tool and insertion, actuation, and/ or alignment devices are described in further detail in U.S. Provisional Application 61/060,445, filed 10 Jun. 2008. Once inserted, the device may be actuated to anchor the fixation device to the bone, as described above.

In an alternative method, the entire implant procedure may be performed through a single incision at the lateral end 24 of clavicle 12. In this alternative procedure, a drill enters the lateral portion of clavicle 12 and is advanced to fracture site 28. A guide wire may then be advanced across the approximated fracture site and into the medial portion of the bone. A canulated drill or reamer may then be advanced over the guide wire to complete the intramedullary channel in the medial portion of clavicle 12. Device 100 is then inserted and deployed and described above. This alternative method may be referred to as a "closed" procedure and requires more work and skill to perform, but is less invasive than the first method described. In any method, it is envisioned that the use of a guide wire may be omitted if desired, particularly if device 100 is deployed in a relatively straight portion of bone.

In an alternative variation of the "closed" procedure, once an incision is made adjacent to an end portion of the lateral segment of the clavicle, the channel may be created in a clavicle bone by inserting a tool or a series of tools through the incision and into the end portion of the lateral segment of the of the clavicle. As described above, a tool is inserted into the bone and advanced through the bone such that it traverses the fracture of the bone. The tool may be a guidewire. The guidewire has a stiffness such that it may traverse the fracture. For example, a guidewire with adequate stiffness to traverse the fracture may be one that is stiff enough to maintain a substantially straight trajectory through the midline of the bone, and one that will not buckle or otherwise bend or fail within the bone or across the fracture. Once a tool has been inserted into the bone and across the fracture, a second tool may be inserted to create the medial segment of the channel. The channel within the medial segment of the clavicle substantially follows the anatomical curvature or contour of the clavicle bone. Any suitable tool may be used to create this contoured segment of the channel. For example, a second guidewire may be inserted (in some cases, after the first guidewire is removed) into the clavicle at the lateral end and moved through the bone, following the anatomical curvature of the bone. The second guidewire is less stiff than the first guidewire such that it may flex and bend around the curvature of the clavicle and create an anatomically matching (i.e. curved) channel within the bone. Any number of guidewires having any combination of stiffnesses may be used sequentially to create the channel within the clavicle such that at least a portion of the channel matches the anatomical contour of the clavicle.

In an alternative example, a cannulated reaming tool or drill bit may be advanced into the bone over one of the guidewires described above. The cannulated tool may be used to expand the diameter of the channel to a diameter large enough to accept the fixation device. The cannulated tool may be stiff or flexible. For example, if the tool is flexible, it may be advanced over the guidewire and follow the curve of the channel to create a contoured and anatomically matching channel. The cannulated tool may also function as a sheath or trocar-like device. For example, the cannulated tool may remain at least partially within the bone, and one or a series of guidewires may be inserted and removed through the cannulated tool. Alternatively, the guidewire may be removed, and a tool (cannulated or not) may be moved through the bone independently.

FIGS. 13 and 14 show an alternative embodiment similar to device 100 described above. Device 100' includes a distal gripper 108 but does not include a proximal gripper. The proximal end 102 of device 100' is secured to the bone by one or more bone screws. For this purpose, three through holes 1310, 1320 and 1330 are provided in hub 112' at various angles. Hole 1320 runs perpendicularly to hub 112, and holes 1310 and 1330 on either side angle toward hole 1320. The three holes share a common exit point, which is an elongated slot 1340 on the opposite side of hub 112. FIG. 16, shown an embodiment similar to that of FIGS. 13 and 14 that includes a patterned cut 116' as described above.

Figure 18:
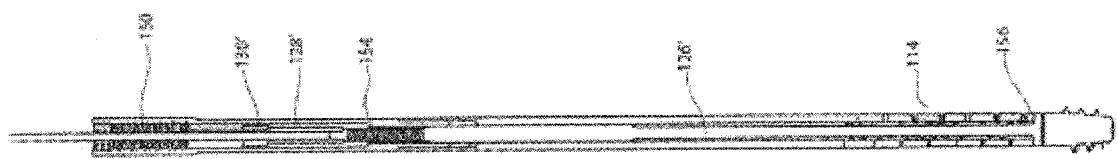
FIGS. 17 and 18 are a perspective view and a cross-section view, respectively, of an alternative embodiment.

FIGS. 17 and 18 show another alternative embodiment similar to device 100 described above. Device 1700 further includes a screw tip 148. The screw tip may be sized and configured to screw into bone. Additionally, the screw tip may be sized and configured to be a self tapping screw tip. In some variations, as shown in FIG. 17, the device 1700 may not need to include distal and/or proximal grippers due to the engagement of the screw tip into bone. Additionally, the flexible-to-rigid portion 114 of the elongate body may function as the actuatable bone engaging mechanism (either alone or in addition to the screw tip) by gripping the bone as the elongate body is changed from its flexible state to its rigid state. In some embodiments, a channel is created in the bone prior to inserting device 1700. The diameter of the channel may be about the same size as the major thread diameter of screw tip 148, or may be about the same size as the minor diameter of screw tip 148. In some embodiments, a proximal portion of the channel may be at least as large as the major diameter and a distal portion of the channel may be about the same size as the minor diameter. In other embodiments, little or no channel formation may be performed before inserting device 1700 into the bone, relying instead on the turning screw tip 148 to form its own channel as it is screwed into the bone. In some embodiments a guide wire is advanced into the bone first and device 1700 then threaded over the guide wire.

Additionally, as shown in FIG. 18, the device may further include threads 150 along a portion of the inner diameter of the elongate body, wherein the threads are sized and configured to receive a compression screw 152 (as shown in FIG. 17). The compression screw may function to compress the device 1700 against the screw tip 148 and/or to the inside walls of the channel within the bone. The compression screw may further function to approximate a fracture within the bone, in some instances by approximating the lateral segment of the bone (coupled to the compression screw) with the medial segment of the bone (coupled to the screw tip).

FIG. 18 also shows a drive member 128' positioned proximally to the flexible-to-rigid portion 114 of the elongate body and threadably engaged (as shown by threads 154) with the actuator 126'. As shown, the actuator is disposed along the length of the device, and has a surface 156 that couples to the distal end of the flexible-to-rigid portion 114. To actuate the device, as an example, a driver tool, such as one with a hexagonal tip (not shown) may be inserted axially into the proximal end of the device until the tool tip is received within keyed socket 130' of drive member 128'. When the driver tool is axially rotated, threadably engaged drive member and the distal end of the actuator are drawn together such that they apply a compressive force to the flexible-to-rigid portion the elongate body along the longitudinal axis thereby changing the elongate body from its flexible state to its rigid state.

FIGS. 19 and 20 also show another alternative embodiment similar to device 100 described above. Device 1900, like device 100, includes a distal gripper 108 and a proximal gripper 109. In this embodiment, the flexible-to-rigid portion 114 of the elongate body is disposed at a location on the elongate body distal to both the distal and proximal grippers.

FIG. 20 shows a drive member 128" positioned proximally to the flexible-to-rigid portion 114 of the elongate body and threadably engaged (as shown by threads 154') with the actuator 126". As shown, the actuator is disposed along the length of the device, has a surface 156' that couples to the distal end of the flexible-to-rigid portion 114, and has a surface 158 that contacts the bendable member 118 of the first gripper 108. To actuate the device, as an example, a driver tool, such as one with a hexagonal tip (not shown) may be inserted axially into the proximal end of the device until the tool tip is received within keyed socket 130" of drive member 128". When the driver tool is axially rotated, threadably engaged drive member and actuator are drawn together. The first surface of the actuator and the drive member are drawn together thereby applying a compressive force to at least a portion of the elongate body along the longitudinal axis changing the elongate body from its flexible state to its rigid state. Additionally, the second surface moves proximally against the bendable member, thereby pivoting the bendable member of the first gripper away from the longitudinal axis.

FIGS. 21-23 show yet another alternative embodiment similar to device 100 described above. Device 2100 may not include a distal gripper or a proximal gripper, but rather the flexible-to-rigid portion 114 of the elongate body may function as the actuatable bone engaging mechanism by gripping the bone as the elongate body is changed from its flexible state to its rigid state. The actuator of device 2100 is a guidewire 160. FIG. 22 shows how the elongate body is cannulated such that it is sized and configured to receive the guidewire 160. As shown, the guidewire is disposed along the length of the device. As shown in FIG. 23, the guidewire 160 includes a distal tip 164, which includes a surface 156" that couples to the distal end of the flexible-to-rigid portion 114. The guidewire also includes features such as a threaded portion 166 and a flat portion 162. The guidewire may further include any suitable combination of features such that it may function to actuate the flexible-to-rigid portion and/or an actuatable bone engaging mechanism.

As shown in FIGS. 22 and 23, device 2100 also includes a drive member 128' positioned proximally to the flexible-to-rigid portion 114 of the elongate body and threadably engaged with the guidewire 160 (as shown by threaded portion 154" in FIG. 22). To actuate device 2100, as an example, a driver tool, such as one with a hexagonal tip (not shown) may be inserted axially into the proximal end of the device until the tool tip is received within keyed socket 130''' of drive member 128'''. When the driver tool is axially rotated, threadably engaged drive member and guidewire distal tip 164 are drawn together such that the surface 156" applies a compressive force to the flexible-to-rigid portion the elongate body along the longitudinal axis and thereby changes the elongate body from its flexible state to its rigid state.

In some embodiments, a guide wire 1350 (FIG. 13) may be used to penetrate the bone prior to inserting device 100'. A canulated reamer and/or drill can be used over the guide wire to create an intramedullary space for the device. Device 100' can then be guided into place over guide wire 1350. In other embodiments, the intramedullary space may be prepared and device 100' inserted without the use of a guidewire.

In accordance with the various embodiments of the present invention, the device may be made from a variety of materials such as metal, composite, plastic or amorphous materials, which include, but are not limited to, steel, stainless steel, cobalt chromium plated steel, titanium, nickel titanium alloy (nitinol), superelastic alloy, and polymethylmethacrylate (PMMA). The device may also include other polymeric materials that are biocompatible and provide mechanical strength, that include polymeric material with ability to carry and delivery therapeutic agents, that include bioabsorbable properties, as well as composite materials and composite materials of titanium and polyetheretherketone (PEEK™), composite materials of polymers and minerals, composite materials of polymers and glass fibers, composite materials of metal, polymer, and minerals.

Within the scope of the present invention, each of the aforementioned types of device may further be coated with proteins from synthetic or animal source, or include collagen coated structures, and radioactive or brachytherapy materials. Furthermore, the construction of the supporting framework or device may include radio-opaque markers or components that assist in their location during and after placement in the bone or other region of the musculo-skeletal systems.

Further, the reinforcement device may, in one embodiment, be osteo incorporating, such that the reinforcement device may be integrated into the bone.

In a further embodiment, there is provided a low weight to volume device deployed in conjunction with other suitable materials to form a composite structure in-situ. Examples of such suitable materials may include, but are not limited to, bone cement, high density polyethylene, Kapton™, polyetheretherketone (PEEK), and other engineering polymers.

Once deployed, the device may be electrically, thermally, or mechanically passive or active at the deployed site within the body. Thus, for example, where the device includes nitinol, the shape of the device may be dynamically modified using thermal, electrical or mechanical manipulation. For example, the nitinol device may be expanded or contracted once deployed, to move the bone or other region of the musculo-skeletal system or area of the anatomy by using one or more of thermal, electrical or mechanical approaches.

It is contemplated that the inventive implantable device, tools and methods may be used in many locations within the body. Where the proximal end of a device in the anatomical context is the end closest to the body midline and the distal end in the anatomical context is the end further from the body midline, for example, on the humerus, at the head of the humerus (located proximal, or nearest the midline of the body) or at the lateral or medial epicondyle (located distal, or furthest away from the midline); on the radius, at the head of the radius (proximal) or the radial styloid process (distal); on the ulna, at the head of the ulna (proximal) or the ulnar styloid process (distal); for the femur, at the greater trochanter (proximal) or the lateral epicondyle or medial epicondyle (distal); for the tibia, at the medial condyle(proximal) or the medial malleolus (distal); for the fibula, at the neck of the fibula (proximal) or the lateral malleoulus (distal); the ribs; the clavicle; the phalanges; the bones of the metacarpus; the bones of the carpus; the bones of themetatarsus; the bones of the tarsus; the sternum and other bones, the device may be adapted and configured with adequate internal dimension to accommodate mechanical fixation of the target bone and to fit within the anatomical constraints. As will be appreciated by those skilled in the art, access locations other than the ones described herein may also be suitable depending upon the location and nature of the fracture and the repair to be achieved. Additionally, the devices taught herein are not limited to use on the long bones listed above, but can also be used in other areas of the body as well, without departing from the scope of the invention. It is within the scope of the invention to adapt the device for use in flat bones as well as long bones.

Figure 28:
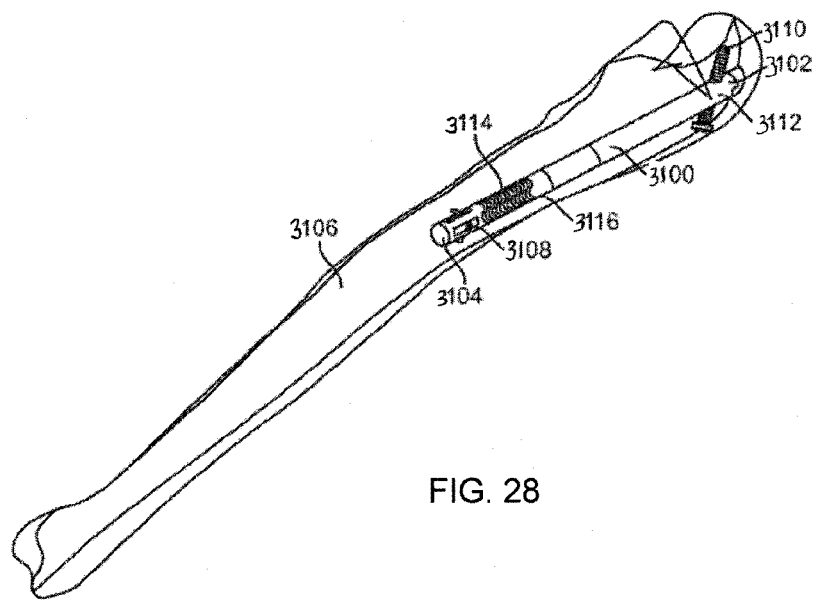
FIG. 28 is a perspective view of an embodiment of a bone fixation device implanted in a bone according to the invention.
Figure 29:
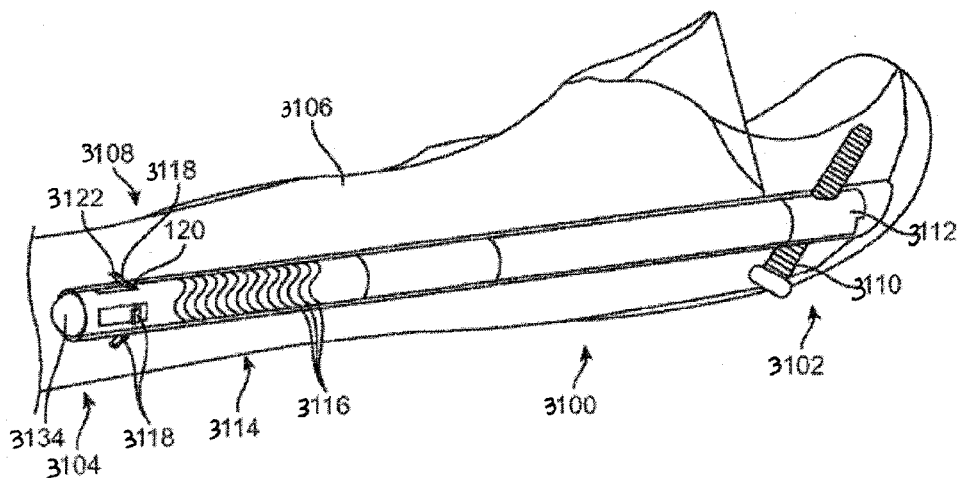
FIG. 29 is another perspective view of the implanted device of FIG. 28.

FIGS. 28 and 29 are perspective views of an embodiment of a bone fixation device 3100 having a proximal end 3102 (nearest the surgeon) and a distal end 3104 (further from surgeon) and positioned within the bone space of a patient according to the invention. In this example, device 3100 is shown implanted in the upper (or proximal) end of an ulna 3106. The proximal end and distal end, as used in this context, refers to the position of an end of the device relative to the remainder of the device or the opposing end as it appears in the drawing. The proximal end can be used to refer to the end manipulated by the user or physician. The distal end can be used to refer to the end of the device that is inserted and advanced within the bone and is furthest away from the physician. As will be appreciated by those skilled in the art, the use of proximal and distal could change in another context, e.g. the anatomical context in which proximal and distal use the patient as reference, or where the entry point is distal from the surgeon.

When implanted within a patient, the device can be held in place with suitable fasteners such as wire, screws, nails, bolts, nuts and/or washers. The device 3100 is used for fixation of fractures of the proximal or distal end of long bones such as intracapsular, intertrochanteric, intercervical, supracondular, or condular fractures of the femur; for fusion of a joint; or for surgical procedures that involve cutting a bone. The devices 3100 may be implanted or attached through the skin so that a pulling force (traction may be applied to the skeletal system).

Figure 30:
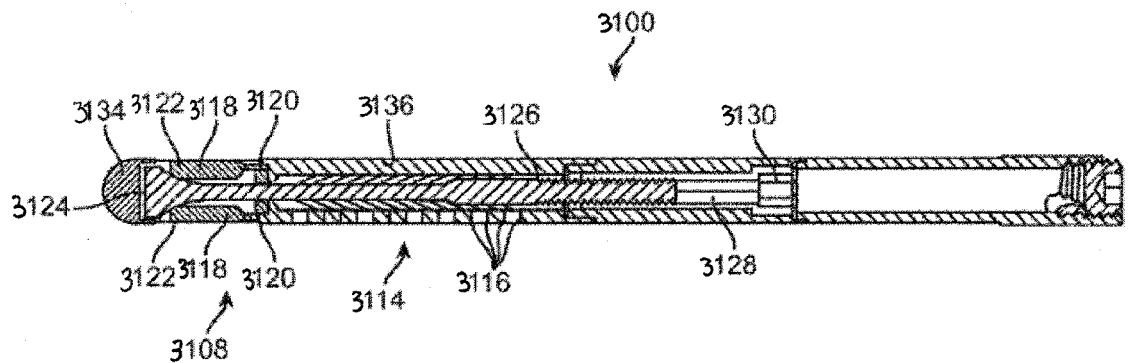
FIG. 30 is a longitudinal cross-section view of the bone fixation device of FIG. 28 in a non-deployed state.

In the embodiment shown in FIG. 28, the design of the metaphyseal fixation device 3100 depicted is adapted to provide a bone engaging mechanism or gripper 3108 adapted to engage target bone of a patient from the inside of the bone. As configured for this anatomical application, the device is designed to facilitate bone healing when placed in the intramedullary space within a post fractured bone. This device 3100 has a gripper 3108 positioned distally and shown deployed radially outward against the wall of the intramedullary cavity. On entry into the cavity, gripper 3108 is flat and retracted (FIG. 30). Upon deployment, gripper 3108 pivots radially outward and grips the diaphyseal bone from the inside of the bone. One or more screws 3110 placed through apertures through the hub 3112 lock the device 3100 to the metaphyseal bone. Hence, the metaphysis and the diaphysis are joined. A flexible-to-rigid body portion 3114 may also be provided, and in this embodiment is positioned between gripper 3108 and hub 3112. It may be provided with wavy spiral cuts 3116 for that purpose, as will be described in more detail below.

FIG. 30 shows a longitudinal cross-section of device 3100 in a non-deployed configuration. In this embodiment, gripper 3108 includes two pairs of opposing bendable gripping members 3118. Two of the bendable gripping members 3118 are shown in FIG. 30, while the other two (not shown in FIG. 30) are located at the same axial location but offset by 90 degrees. Each bendable gripping member 3118 has a thinned portion 3120 that permits bending as the opposite distal end 3122 of member 3118 is urged radially outward, such that member 3118 pivots about thinned portion 3120. When extended, distal ends 3122 of bendable members 3118 contact the inside of the bone to anchor the distal portion of device 3100 to the bone. In alternative embodiments (not shown), the gripper may comprise 1, 2, 3, 4, 5, 6 or more bendable members similar to members 3118 shown.

During actuation, bendable members 3118 of gripper 3108 are urged radially outward by a ramped surface on actuator head 3124. Actuator head 3124 is formed on the distal end of actuator 3126. The proximal end of actuator 3126 is threaded to engage a threaded bore of drive member 3128. The proximal end of drive member 3128 is provided with a keyed socket 3130 for receiving the tip of a rotary driver tool 3132 (shown in FIG. 32) through the proximal bore of device 3100. As rotary driver tool 3132 turns drive member 3128, actuator 3126 is drawn in a proximal direction to outwardly actuate gripper members 3118.

A hemispherical tip cover 3134 may be provided at the distal end of the device as shown to act as a blunt obturator. This arrangement facilitates penetration of bone (e.g. an intramedullary space) by device 3100 while keeping the tip of device 3100 from digging into bone during insertion.

As previously mentioned, device 3100 may include one or more flexible-to-rigid body portions 3114. This feature is flexible upon entry into bone and rigid upon application of compressive axial force provided by tensioning actuator 3126. Various embodiments of a flexible-to-rigid portion may be used, including dual helical springs whose inner and outer tubular components coil in opposite directions, a chain of ball bearings with flats or roughened surfaces, a chain of cylinders with flats, features, cones, spherical or pointed interdigitating surfaces, wavy-helical cut tubes, two helical cut tubes in opposite directions, linear wires with interdigitating coils, and bellows-like structures.

The design of the flexible-to-rigid tubular body portion 3114 allows a single-piece design to maximize the transformation of the same body from a very flexible member that minimizes strength in bending to a rigid body that maximizes strength in bending and torsion. The flexible member transforms to a rigid member when compressive forces are applied in the axial direction at each end, such as by an actuator similar to 3126. The body portion 3114 is made, for example, by a near-helical cut 3116 on a tubular member at an angle of incidence to the axis somewhere between 0 and 180 degrees from the longitudinal axis of the tubular body portion 3114. The near-helical cut or wavy-helical cut may be formed by the superposition of a helical curve added to a cyclic curve that produces waves of frequencies equal or greater than zero per turn around the circumference and with cyclic amplitude greater than zero. The waves of one segment nest with those on either side of it, thus increasing the torque, bending strength and stiffness of the tubular body when subjective to compressive forces. The tapered surfaces formed by the incident angle allow each turn to overlap or interdigitate with the segment on either side of it, thus increasing the bending strength when the body is in compression. Additionally, the cuts can be altered in depth and distance between the cuts on the longitudinal axis along the length of body portion 3114 to variably alter the flexible-to-rigid characteristics of the tubular body along its length.

The cuts 3116 in body portion 3114 allow an otherwise rigid member to increase its flexibility to a large degree during deployment. The tubular member can have constant or varying internal and external diameters. This design reduces the number of parts of the flexible-to-rigid body portion of the device and allows insertion and extraction of the device through a curved entry port in the bone while maximizing its rigidity once inserted. Application and removal of compressive forces provided by a parallel member such as wire(s), tension ribbons, a sheath, wound flexible cable, or actuator 3126 as shown will transform the body from flexible to rigid and vice versa.

Figure 36:
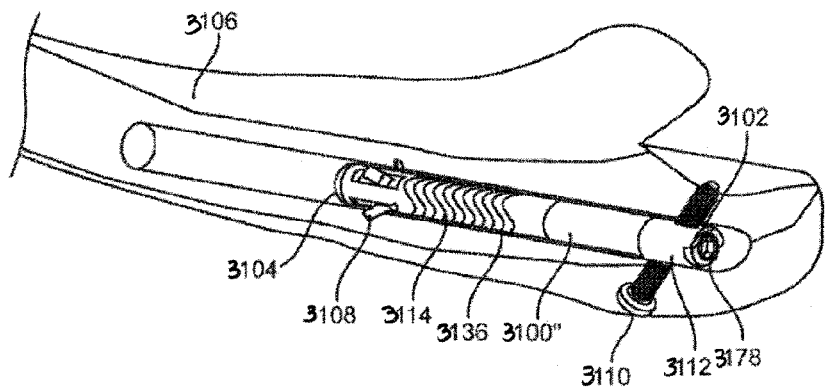
FIG. 36 is a perspective view of another alternative embodiment of the implanted device of FIG. 28.

In operation, as actuator 3126 is tightened, gripper members 3118 are extended radially outwardly. Once the distal ends of gripper members 3118 contact bone and stop moving outward, continued rotation of actuator 3126 draws the proximal end 3102 and the distal end 3104 of device 3100 closer together until cuts 3116 are substantially closed. As this happens, body portion 3114 changes from being flexible to rigid to better secure the bone fracture(s), as will be further described below. Rotating drive member 3128 in the opposite direction causes body portion 3114 to change from a rigid to a flexible state, such as for removing device 3100 if needed in the initial procedure or during a subsequent procedure after the bone fracture(s) have partially or completely healed. Body portion 3114 may be provided with a solid longitudinal portion 3136 (as seen in FIGS. 30 and 36) such that cuts 3116 are a series of individual cuts each traversing less than 360 degrees in circumference, rather than a single, continuous helical cut. This solid portion 3136 can aid in removal of device 3100 by keeping body portion 3114 from extending axially like a spring.

Figure 31:
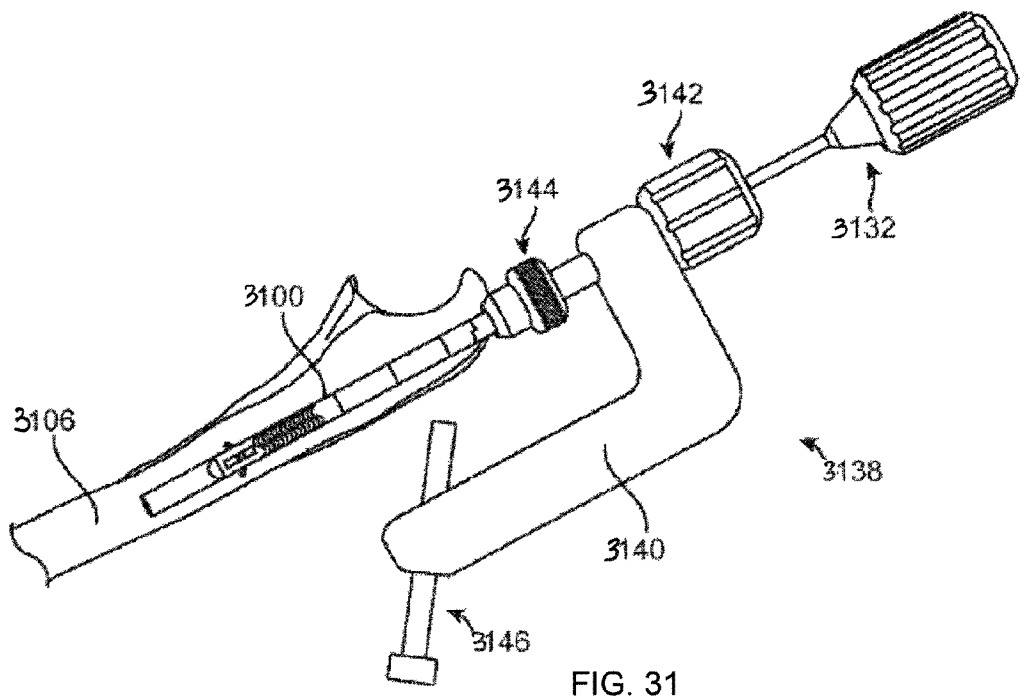
FIG. 31 is a plan view of a combination deployment tool that may be used with the bone fixation device of FIG. 28.

FIG. 31 illustrates a combination tool 3138 useful for inserting device 3100, actuating gripper 3108, compressing flexible-to-rigid body portion 3114, approximating the fracture in bone 3106, aligning anchor screw(s) 3110, and removing device 3100, if desired. In this exemplary embodiment, tool 3138 includes an L-shaped body 3140 that mounts the other components of the tool and also serves as a handle. The main components of tool 3138 are a device attachment portion 3142, a rotary driver 3132, an approximating driver 3144, and a screw alignment portion 3146.

Figure 32:
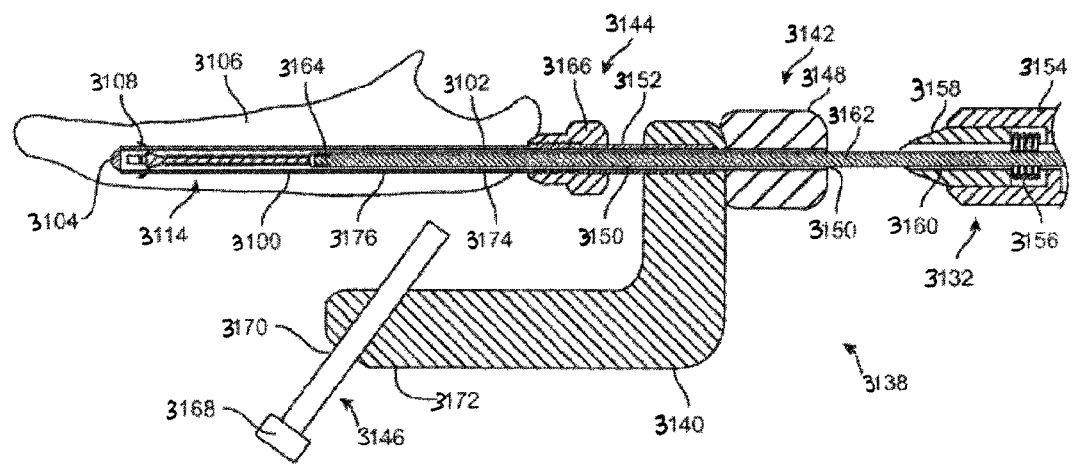
FIG. 32 is a cross-section view of the tool and device shown in FIG. 31.

FIG. 32 shows a cross-section of the tool 3138 and device 3100 illustrated in FIG. 31. As shown, device attachment portion 3142 includes a knob 3148 rigidly coupled to a tube 3150 which is rotatably mounted within sleeve 3152. Sleeve 3152 in turn is fixedly mounted to tool body 3140. The distal end of tube 3150 is provided with external threads for engaging the internal threads on the proximal end of device 3100. As seen in FIG. 31, both the distal end of sleeve 3152 and the proximal end of device 3100 may be provided with semicircular steps that inter-engage to prevent device 3100 from rotating with respect to sleeve 3152. With this arrangement, device 3100 can be prevented from rotating when it is secured to tool 3138 by tube 3150 of device attachment portion 3142.

The mating semicircular steps also serve to position device 3100 in a particular axial and angular orientation with respect to tool 3138 for aligning screws with screw holes, as will be later described.

Rotary driver 3132 may be used to actuate gripper 3108 and compress flexible-to-rigid body portion 3114 after device 3100 is inserted into bone 3106. Driver 3132 may also be used to allow body portion 3114 to decompress and gripper 3108 to retract if removal of device 3100 from bone 3106 is desired. In the embodiment shown, driver 3132 includes knob 3154, torsion spring 3156, hub 3158, bushing 3160 and shaft 3162. The distal end of shaft 3162 is provided with a mating tip 3164, such as one having a hex-key shape, for engaging with keyed socket 3130 of device 3100 (seen in FIG. 30), such that turning driver shaft 3162 turns drive member 3128 and axially actuates actuator 3126, as described above.

The proximal end of shaft 3162 may be fitted with a bushing 3160, such as with a press-fit. Hub 3158 may be secured over bushing 3160, such as with a pin through bushing 3160 and shaft 3162. In this embodiment, knob 3154 is rotatably mounted over hub 3158 and bushing 3160 such that knob 3154 can rotate independently from shaft 3162. A torsion spring 3156 may be used to couple knob 3154 to hub 3158 as shown to create a torque limiting and/or torque measuring driver. With this indirect coupling arrangement, as knob 3154 is rotated about shaft 3162, spring 3156 urges hub 3158 and shaft 3162 to rotate in the same direction. Rotational resistance applied by device 3100 to shaft tip 3164 will increase in this embodiment as gripper 3108 engages bone 3106, and flexible-to-rigid body portion 3114 compresses. As more torque is applied to knob 3154, it will advance rotationally with respect to hub 3158 as torsion spring 3156 undergoes more stress. Markings may be provided on knob 3154 and hub 3158 to indicate the torque being applied. In this manner, a surgeon can use driver 3132 to apply torque to device 3100 in a predetermined range. This can help ensure that gripper 3108 is adequately set in bone 3106, body portion 3114 is sufficiently compressed, and excessive torque is not being applied that might damage device 3100, bone 3106 or cause slippage therebetween. A slip clutch or other mechanism may be provided to allow the applied torque to be limited or indicated. For example, driver 3132 may be configured to "click" into or out of a detent position when a desired torque is reached, thus allowing the surgeon to apply a desired torque without needing to observe any indicia on the driver. In alternative embodiments, the driver knob may be selectably or permanently coupled to shaft 3162 directly.

After device 3100 is inserted in bone 3106 and deployed with tool 3138 as described above, the approximating driver portion 3144 of tool 3138 may be used to compress one or more fractures in bone 3106. Approximating driver 3144 includes knob 3166 located on sleeve 3152. Knob 3166 may be knurled on an outer circumference, and have threads on at least a portion of its axial bore. The internal threads of knob 3166 engage with mating external threads on sleeve 3152 such that when knob 3166 is rotated it advances axially with respect to sleeve 3152. When device 3100 is anchored in bone 3106, sleeve 3152 is prevented from moving away from the bone. Accordingly, as knob 3166 is advanced axially toward bone 3106, it serves to approximate bone fractures located between gripper 3108 and knob 3166. Suitable thread pitch and knob circumference may be selected to allow a surgeon to supply a desired approximating force to bone 3106 by using a reasonable rotation force on knob 3166. In alternative embodiments (not shown), a torque indicating and/or torque limiting mechanism as described above may be incorporated into approximating driver 3144.

As previously indicated, tool 3138 may also include a screw alignment portion 3146. In the embodiment depicted in the figures, alignment portion 3146 includes a removable alignment tube 3168 and two bores 3170 and 3172 through tool body 3140. In alternative embodiments (not shown), a single bore or more than two bores may be used, with or without the use of separate alignment tube(s).

In operation, alignment tube 3168 is first received in bore 3170 as shown. In this position, tube 3168 is in axial alignment with angled hole 3174 at the distal end 3102 of device 3100. As described above, the mating semicircular steps of device 3100 and sleeve 3152 position angled hole 3174 in its desired orientation. With this arrangement, a drill bit, screw driver, screw and/or other fastening device or tool may be inserted through the bore of tube 3168 such that the device(s) are properly aligned with hole 3174. The outward end of alignment tube 3168 may also serve as a depth guide to stop a drill bit, screw and/or other fastener from penetrating bone 3106 beyond a predetermined depth.

Alignment tube 3168 may be withdrawn from bore 3170 as shown, and inserted in bore 3172. In this position, tube 3168 aligns with hole 3176 of device 3100. As described above, a drill bit, screw driver, screw and/or other fastening device may be inserted through the bore of tube 3168 such that the device(s) are properly aligned with hole 3176.

Figure 33:
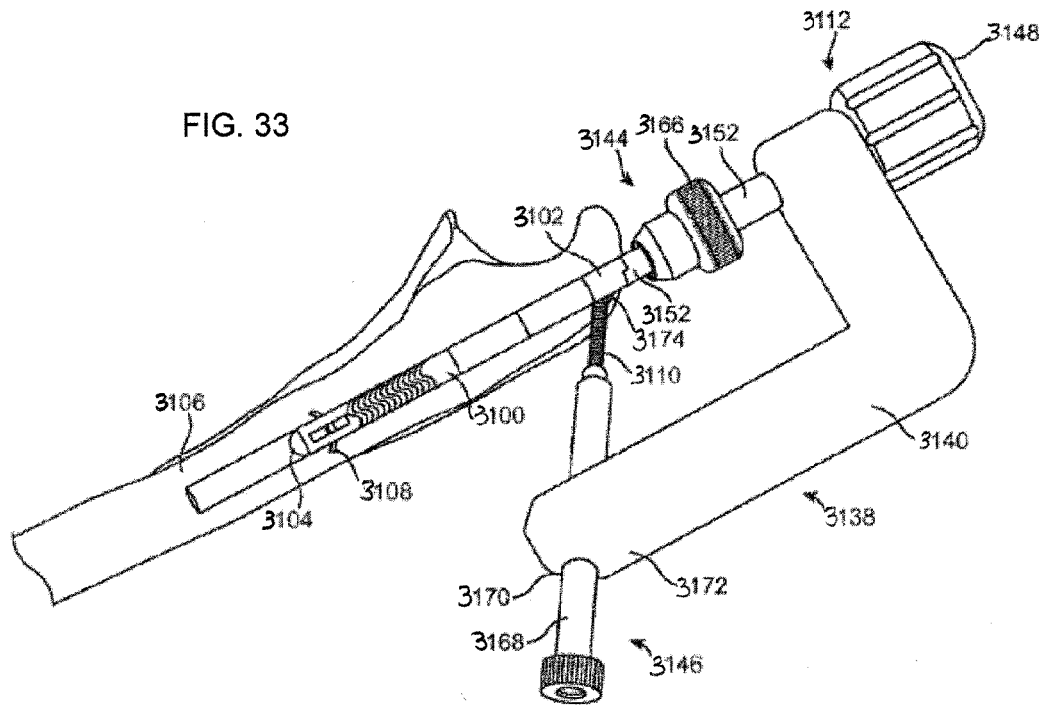
FIG. 33 is a perspective view of the tool and device shown in FIG. 31.

FIG. 33 shows alignment tube 3168 of tool 3138 aligning screw 3110 with angled hole 3174 at the distal end of device 3100, as described above.

Figure 34A:
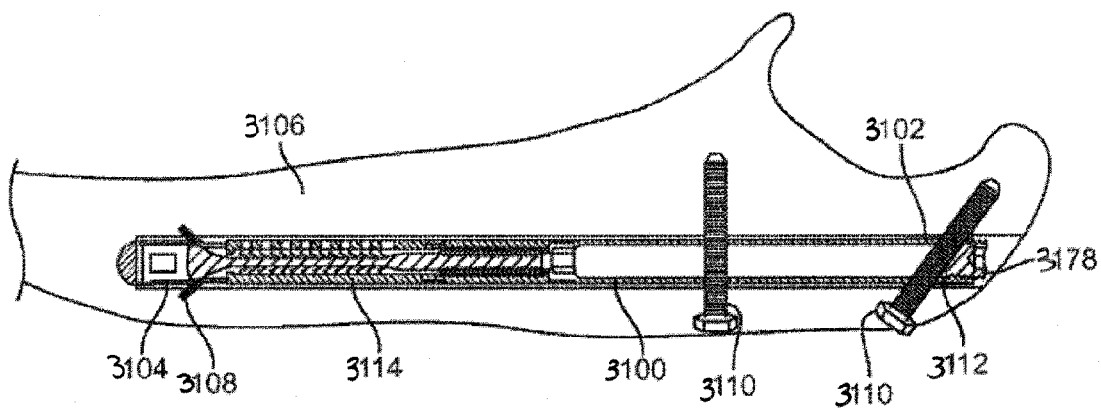
FIG. 34A is a cross-section view of the implanted device of FIG. 28.

FIG. 34A shows a first screw 3110 received through angled hole 3174 and a second screw 3110 received through hole 3176 in device 3100 and into bone 3106. Screws 3110 may be installed manually or with the aid of tool 3138 as described above. The heads of screws 3110 may be configured to be self-countersinking such that they remain substantially beneath the outer surface of the bone when installed, as shown, so as to not interfere with adjacent tissue. In this embodiment, the proximal end 3102 of device 3100 is secured to bone 3106 with two screws 3110, and the distal end 3104 is secured by gripper 3108. In this manner, any bone fractures located between the proximal screw 3110 and distal gripper 3108 may be approximated and rigidly held together by device 3100. In alternative embodiments (not shown), more than one gripper may be used, or only screws or other fasteners without grippers may be used to secure device 3100 within bone 3106. For example, the device shown in FIG. 28 could be configured with a second gripper located between screw 3110 and the middle of the device if the fracture is located more at the mid-shaft of the bone. Similarly, more than two screws or other fasteners may be used, or only grippers without fasteners may be used. In various embodiments, holes such as 3174 and 3176 as shown and described above can be preformed in the implantable device. In other embodiments, some or all of the holes can be drilled or otherwise formed in situ after the device is implanted in the bone.

Once device 3100 is secured within bone 3106, combination tool 3138 may be removed by turning knob 3148 to disengage threads of tube 3150 from threads within the proximal end 3102 of device 3100. An end plug 3178 may be threaded into the proximal end 3102 of device 3100 to preventing growth of tissue into implanted device 3100. Device 3100 may be left in bone 3106 permanently, or it may be removed by performing the above described steps in reverse. In particular, plug 3178 is removed, tool 3138 is attached, screws 3110 are removed, gripper 3108 is retracted, and device 3100 is pulled out using tool 3138.

Figure 34B:
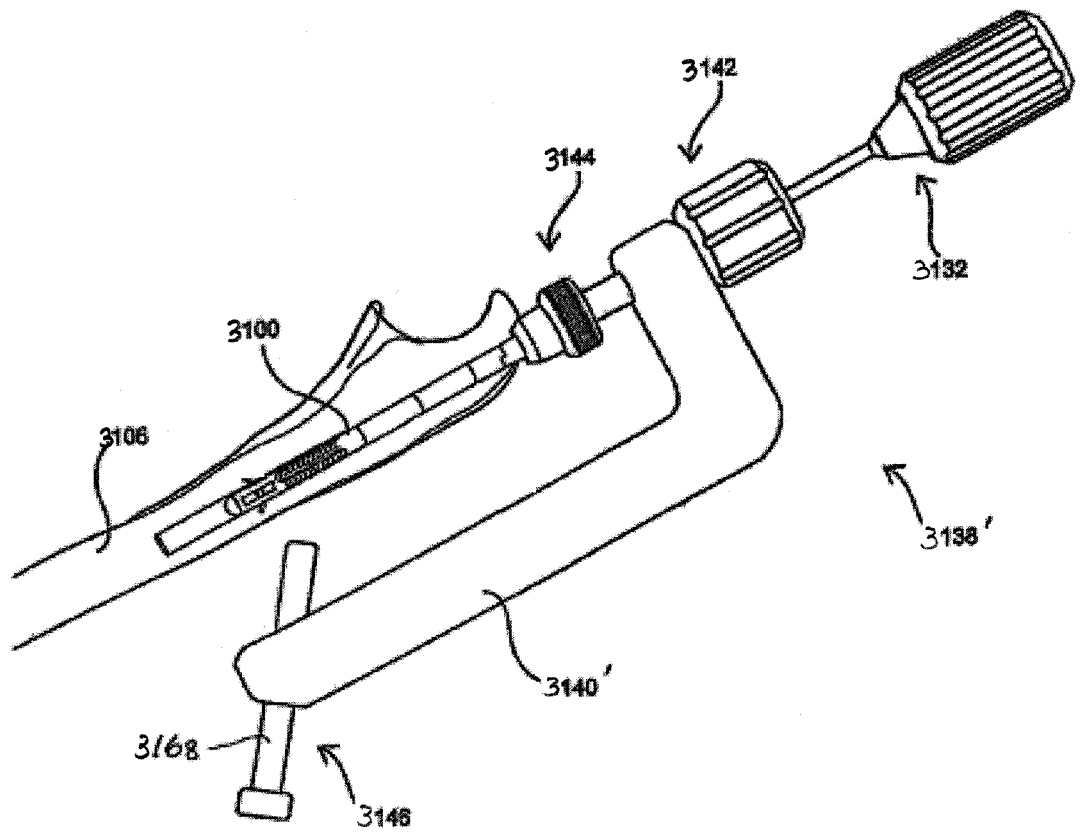
FIG. 34B is a plan view of an alternative combination deployment tool that may be used with the bone fixation device of FIG. 28.

FIG. 34B shows an alternative embodiment of a combination tool 3138' useful for inserting device 3100, actuating gripper 3108, compressing flexible-to-rigid body portion 3114, approximating the fracture in bone 3106, aligning anchor screw(s) 3110, and removing device 3100, if desired. Like tool 3138 described above, exemplary tool 3138' includes an L-shaped body 3140' that mounts the other components of the tool and also serves as a handle. The main components of tool 3138' are a device attachment portion 3142, a rotary driver 3132, an approximating driver 3144, and a screw alignment portion 3146. These components are constructed and function in a similar fashion to the components of tool 3138 described above. Tool 3138' is constructed to allow one or more screw holes to be formed in vivo, and/or allow screw(s) to be aligned with such screw holes or pre-formed screw holes, through flexible-to-rigid body portion 3114 of device 3100. Tool 3138' may be configured to allow the screw hole(s) may be formed at an angle through body portion 3114, and/or formed perpendicularly to the longitudinal axis of device 3100. Tool 3138' may also include the capability to form screw holes or align screws for insertion in the proximal hub portion of device 3100 as described above.

Tool 3138' may be used to form screw hole(s) in flexible-to-rigid body portion 3114 by guiding a drill bit with alignment tube 3168. Screw hole(s) may also be formed directly in body portion 3114 without pre-forming or drilling holes in vivo, but by placing a screw directly into body portion 3114, such as with a self-tapping screw guided with alignment tube 3168.

Internal components within device 3100, such as actuator 3126, may be configured such that screw(s) pass though it or pass around it. For example, in some embodiments the actuator comprises one or more cables, leaving enough room within body portion 3114 so that a screw can avoid the actuator(s), or move it/them out of the way when passing into or through body portion 3114. In some embodiments, the one or more actuators are large enough to allow one or more screws to pass through it/them without impeding the operation of the actuator(s). In some embodiments, the screw(s) only enter one wall of tubular body portion 3114 without entering the interior space of the body portion.

Figure 35:
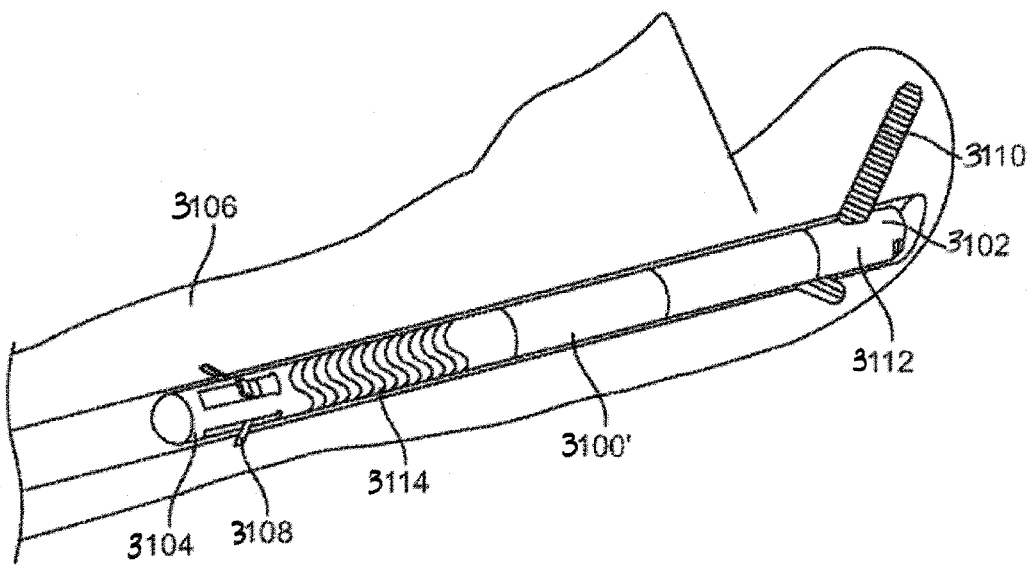
FIG. 35 is a perspective view of an alternative embodiment of the implanted device of FIG. 28.

FIGS. 35 and 36 show alternative embodiments similar to device 3100 described above. Device 3100' shown in FIG. 35 is essentially identical to device 3100 described above but is shorter in length and utilizes a single anchor screw 3110 at its proximal end 3102. Device 3100" shown in FIG. 36 is similar to device 3100', but is shorter still. In various embodiments, the devices may be configured to have a nominal diameter of 3 mm, 4 mm, 5 mm or 6 mm. It is envisioned that all three device designs 3100, 3100' and 3100" may each be provided in all three diameters such that the chosen device is suited for the particular fracture(s) and anatomy in which it is implanted.

In accordance with the various embodiments of the present invention, the device may be made from a variety of materials such as metal, composite, plastic or amorphous materials, which include, but are not limited to, steel, stainless steel, cobalt chromium plated steel, titanium, nickel titanium alloy (nitinol), superelastic alloy, and polymethylmethacrylate (PMMA). The device may also include other polymeric materials that are biocompatible and provide mechanical strength, that include polymeric material with ability to carry and delivery therapeutic agents, that include bioabsorbable properties, as well as composite materials and composite materials of titanium and polyetheretherketone (PEEK), composite materials of polymers and minerals, composite materials of polymers and glass fibers, composite materials of metal, polymer, and minerals.

Within the scope of the present invention, each of the aforementioned types of device may further be coated with proteins from synthetic or animal source, or include collagen coated structures, and radioactive or brachytherapy materials. Furthermore, the construction of the supporting framework or device may include radio-opaque markers or components that assist in their location during and after placement in the bone or other region of the musculo-skeletal systems.

Further, the reinforcement device may, in one embodiment, be osteo incorporating, such that the reinforcement device may be integrated into the bone. In a further embodiment, there is provided a low weight to volume device deployed in conjunction with other suitable materials to form a composite structure in-situ. Examples of such suitable materials may include, but are not limited to, bone cement, high density polyethylene, Kapton™, polyetheretherketone (PEEK), and other engineering polymers.

Once deployed, the device may be electrically, thermally, or mechanically passive or active at the deployed site within the body. Thus, for example, where the device includes nitinol, the shape of the device may be dynamically modified using thermal, electrical or mechanical manipulation. For example, the nitinol device may be expanded or contracted once deployed, to move the bone or other region of the musculo-skeletal system or area of the anatomy by using one or more of thermal, electrical or mechanical approaches.

It is contemplated that the inventive implantable device, tools and methods may be used in many locations within the body. Where the proximal end of a device in the anatomical context is the end closest to the body midline and the distal end in the anatomical context is the end further from the body midline, for example, on the humerus, at the head of the humerus (located proximal, or nearest the midline of the body) or at the lateral or medial epicondyle (located distal, or furthest away from the midline); on the radius, at the head of the radius (proximal) or the radial styloid process (distal); on the ulna, at the head of the ulna (proximal) or the ulnar styloid process (distal); for the femur, at the greater trochanter (proximal) or the lateral epicondyle or medial epicondyle (distal); for the tibia, at the medial condyle (proximal) or the medial malleolus (distal); for the fibula, at the neck of the fibula (proximal) or the lateral malleoulus (distal); the ribs; the clavicle; the phalanges; the bones of the metacarpus; the bones of the carpus; the bones of themetatarsus; the bones of the tarsus; the sternum and other bones, the device may be adapted and configured with adequate internal dimension to accommodate mechanical fixation of the target bone and to fit within the anatomical constraints. As will be appreciated by those skilled in the art, access locations other than the ones described herein may also be suitable depending upon the location and nature of the fracture and the repair to be achieved. Additionally, the devices taught herein are not limited to use on the long bones listed above, but can also be used in other areas of the body as well, without departing from the scope of the invention. It is within the scope of the invention to adapt the device for use in flat bones as well as long bones.

Figure 37A:
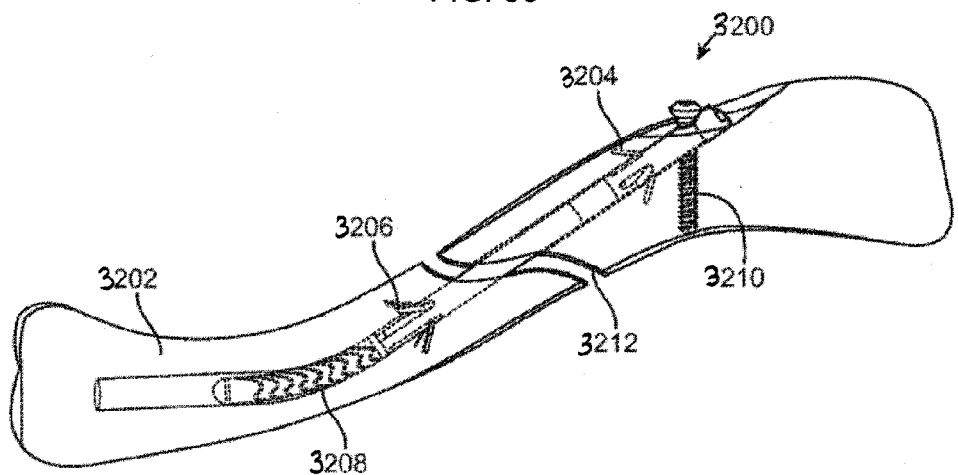
FIG. 37A is a perspective view of another embodiment of a bone fixation device shown deployed in a fractured clavicle.

FIGS. 37A-37I show another embodiment of a bone fixation device constructed according to aspects of the invention. FIG. 37A is a perspective view showing the exemplary device 3200 deployed in a fractured clavicle 3202. Device 3200 is similar to device 3100 described above and shown in FIGS. 28-34A, but has a gripper 3204 located near its proximal end, another gripper 3206 located at a more distal location, and a flexible-to-rigid body portion 3208 located near the distal end of the device. A bone screw 3210 and gripper 3204 are configured to secure device 3200 inside bone 3202 on the proximal side of fracture 3212, while gripper 3206 and flexible-to-rigid body portion 3208 are configured to secure device 3200 on the distal side of fracture 3212. In other respects, construction and operation of device 3200 is much like that of device 3100 described above.

Figure 37B:
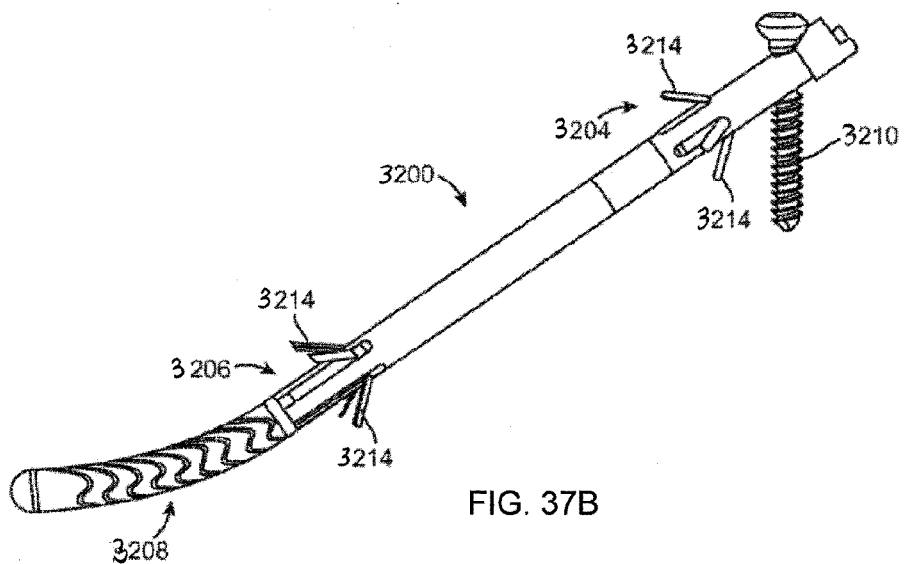
FIG. 37B is perspective view of the device shown in FIG. 37A shown in a deployed state.
Figure 37C:
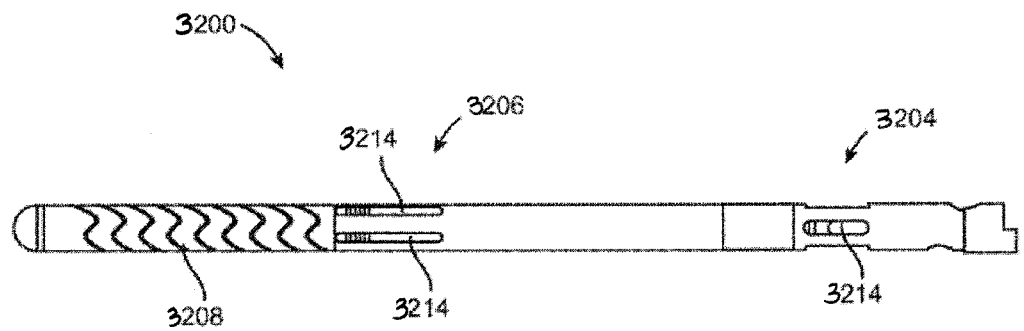
FIG. 37C is a side elevation view of the device shown in FIG. 37A shown in a retracted or undeployed state.
Figure 37D:
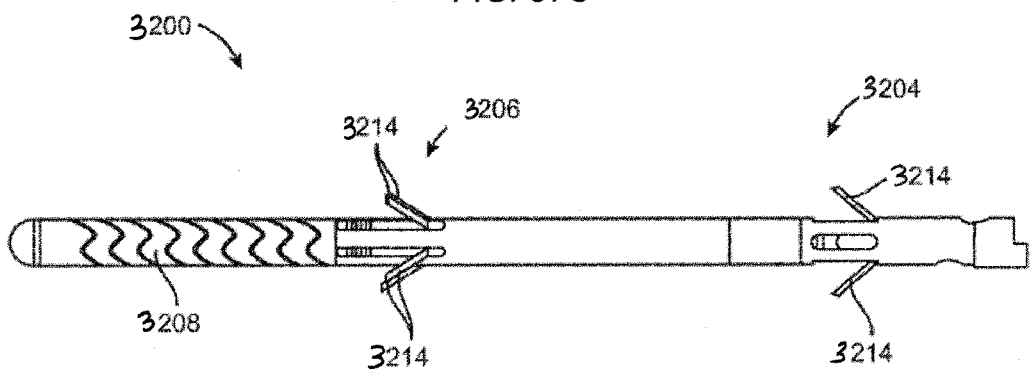
FIG. 37D is a side elevation view of the device shown in FIG. 37A shown in a deployed state.
Figure 37E:
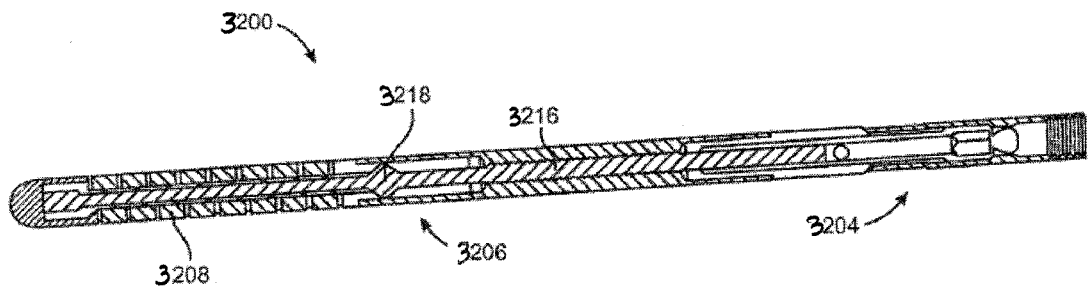
FIG. 37E is a cross-sectional view of the device shown in FIG. 37A shown in a retracted or undeployed state.
Figure 37F:
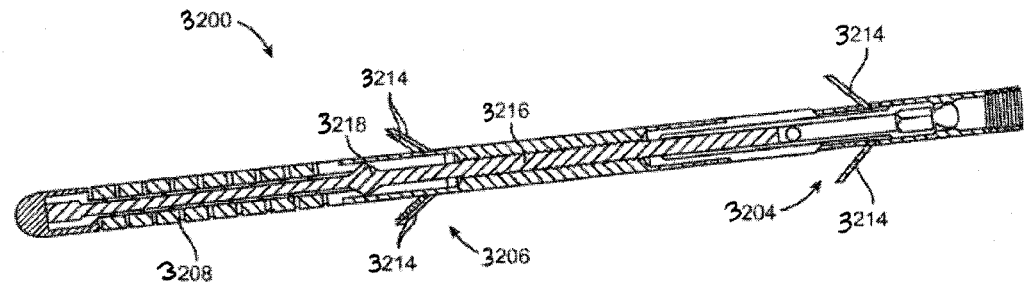
FIG. 37F is a cross-sectional view of the device shown in FIG. 37A shown in a deployed state.

In this exemplary embodiment, each of the two grippers 3204 and 3206 has four outwardly expanding arms 3214. These arms are spaced at 90 degree intervals around the circumference of the device body. The arms 3214 of gripper 3204 may be offset by 45 degrees from arms 3214 of gripper 3206 as shown in the figures to distribute the forces applied by grippers 3204 and 3206 on the bone 3202. As shown in FIGS. 37E and 37F, a single actuator 3216 may be used to deploy both grippers 3204 and 3206. Actuator 3216 may also be used to axially compress flexible-to-rigid body portion 3208 to make it substantially rigid. At least a portion of actuator 3216 may be flexible to allow flexible-to-rigid body portion 3208 to assume a curved shape, as seen in FIGS. 37A and 37B. Alternatively, it may be desirable in some embodiments to have flexible-to-rigid body portion 3208 maintain a straight or a curved configuration regardless of whether it is in a flexible or rigid state. In these embodiments, the actuator may be rigid and faulted with the desired straight and/or curved shape to match the flexible-to-rigid body portion. In some embodiments, it may also be desirable to design at least a portion of the actuator with a high degree of axial elasticity to allow the actuator to continue to expand some gripper(s) and/or compress some flexible-to-rigid body portion(s) after other gripper(s) and/or flexible-to-rigid body portion(s) have already been fully deployed.

Figure 37G:
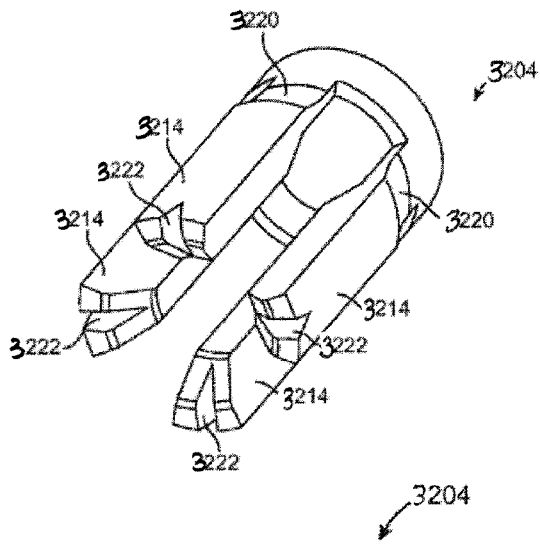
FIG. 37G is a perspective view of a gripper of the device shown in FIG. 37A shown in a retracted or undeployed state.
Figure 37H:
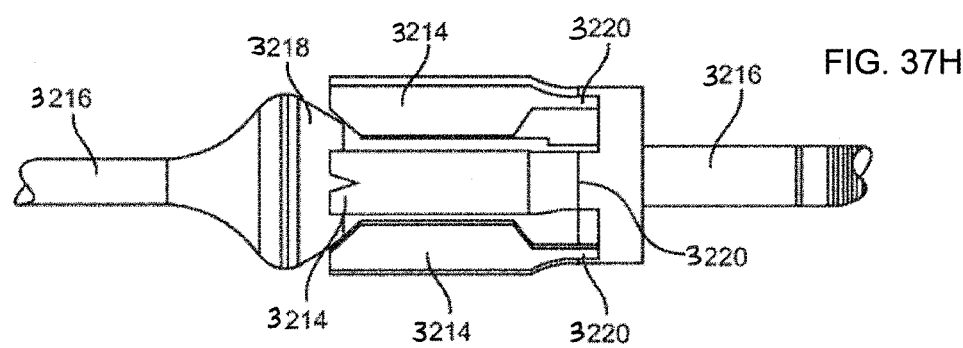
FIG. 37H is a side elevation view of a gripper and actuator of the device shown in FIG. 37A shown in a retracted or undeployed state.
Figure 37I:
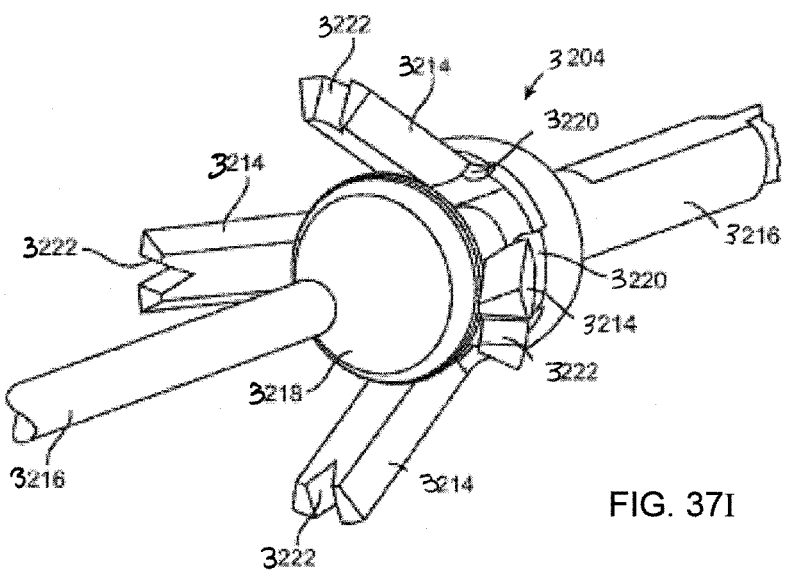
FIG. 37I is a perspective view of a gripper and actuator of the device shown in FIG. 37A shown in a deployed state.

Referring to FIGS. 37G-37I, further details of an exemplary gripper 3204 are shown. FIGS. 37G and 37H show gripper 3204 with bendable arms 3214 in a retracted state. As cam 3218 of actuator 3216 is driven axially into the distal ramped ends of arms 3214, arms 3214 bend at thinned portions 3220 to move radially outward toward the deployed position shown in FIG. 37I. Notches 3222 may be provided in the distal ends of arms 3214 as shown to allow arms 3214 to better grip interior bone surfaces. Without departing from the scope of the invention, one, two, three, or more bendable arms may be used.

Figure 38A:
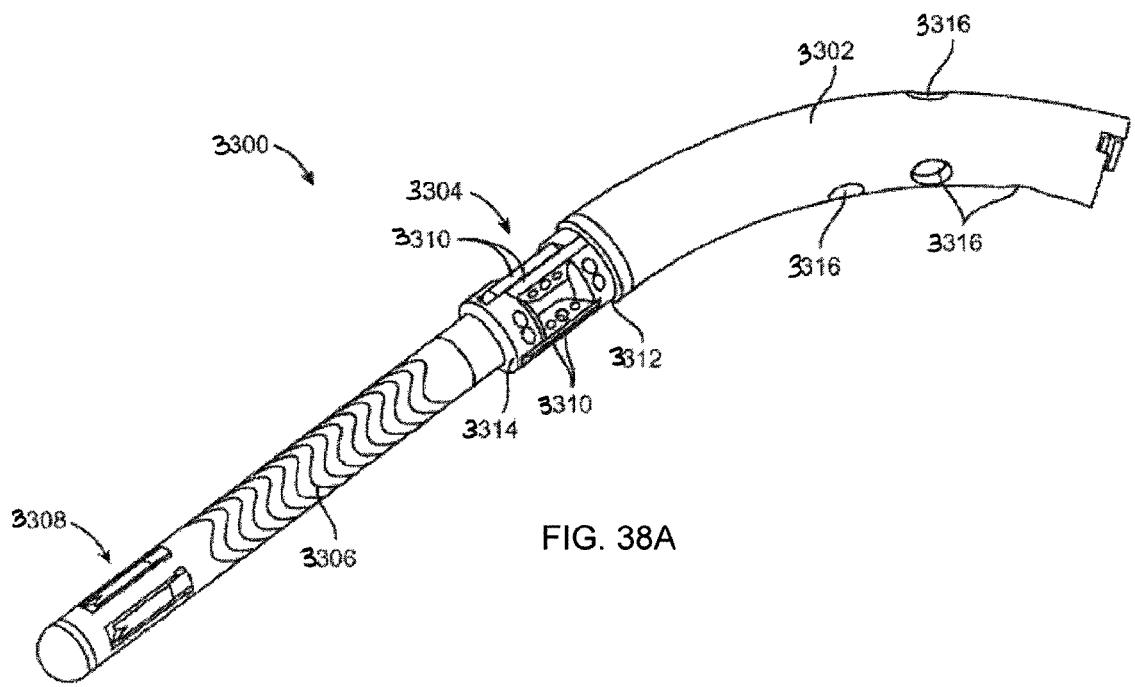
FIG. 38A is perspective view of another embodiment of a bone fixation device shown in a retracted or undeployed state.
Figure 38B:
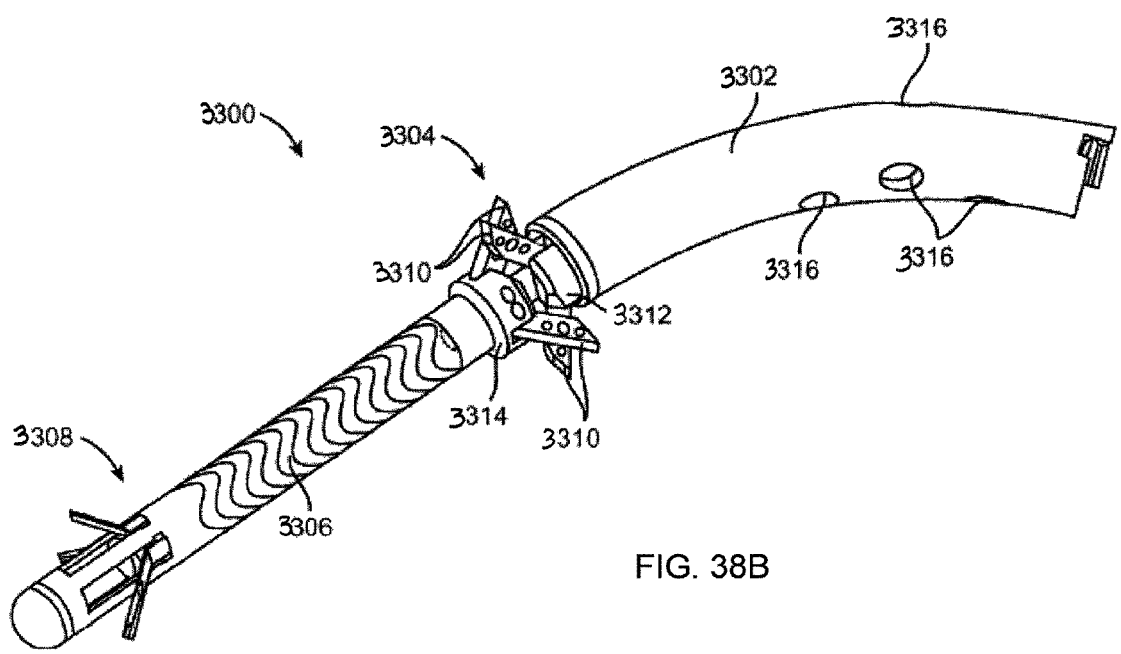
FIG. 38B is perspective view of the device shown in FIG. 38A shown in a deployed state.
Figure 38C:
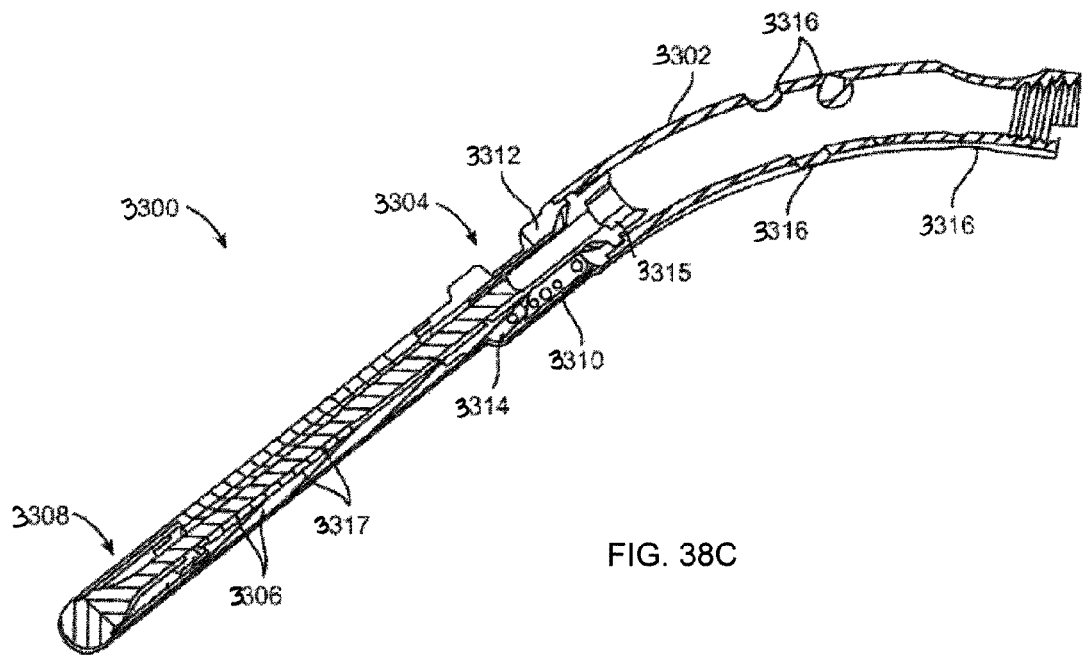
FIG. 38C is a cross-sectional view of the device shown in FIG. 38A shown in a retracted or undeployed state.
Figure 38D:
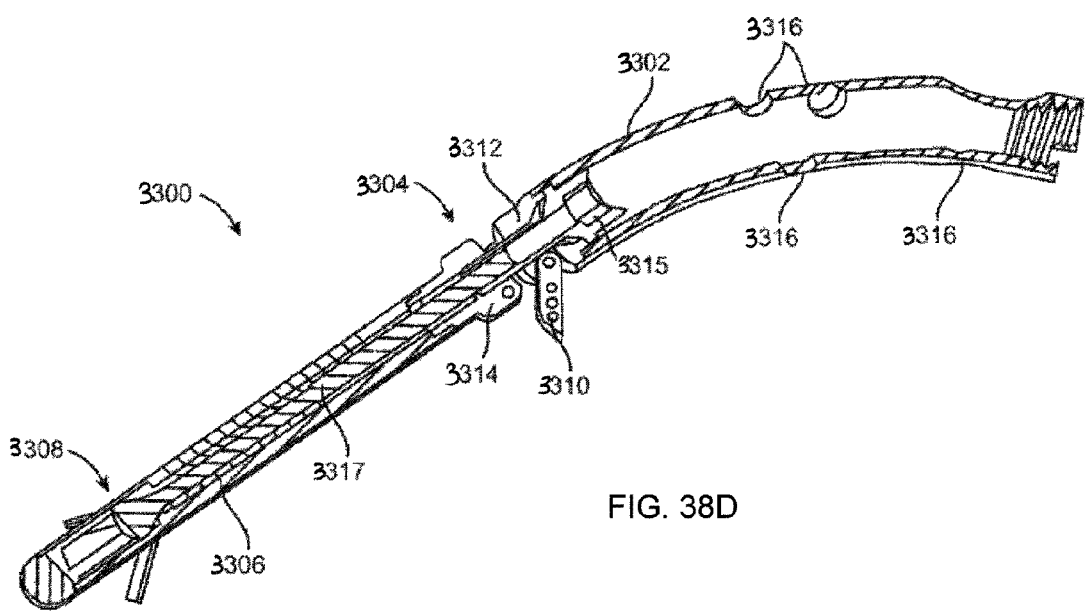
FIG. 38D is a cross-sectional view of the device shown in FIG. 38A shown in a deployed state.

Referring to FIGS. 38A-38D, another embodiment of a bone fixation device is shown. Device 3300 includes a curved hub 3302, proximal gripper 3304, flexible-to-rigid body portion 3306, and distal gripper 3308. Distal gripper 3308 is similar in construction and operation to grippers 3204 and 3206 described above. Proximal gripper 3304 is provided with three pairs of scissor arms 3310. Each pair of arms 3310 is pivotably interconnected at a mid-portion by a pin. Each arm is pivotably connected with a pin to either proximal end piece 3312 or distal end piece 3314. When end pieces 3312 and 3314 are moved closer together, arms 3310 pivot radially outward from an axially aligned retracted position, as shown in FIGS. 38A and 38C, to a deployed position, as shown in FIGS. 38B and 38D. In the deployed position, the distal ends of the six arms 3310 engage an inner surface of a bone as previously described.

In operation, device 3300, with grippers 3304 and 3308 in a retracted state, may be inserted into the intramedullary space within a bone, such as the radius. Device 3300 may be inserted through a curved opening formed in the bone, such as an opening formed through a bony protuberance on a distal or proximal end or through the midshaft of the bone. Curved hub 3302 may be configured with the same geometry of the curved opening in the bone, and when the flexible-to-rigid body portion 3306 is in its flexible state, it can assume this same geometry. Once device 3300 is in place inside the bone, actuator 3315 (shown in FIGS. 38C and 38D) may be actuated from the proximal end of device 3300 by turning drive member 3317 in a manner similar to that previously described. Longitudinal movement of actuator 3315 toward the proximal end of device 3300 causes flexible-to-rigid body portion 3306 to foreshorten and assume its rigid state, and causes grippers 3304 and 3308 to outwardly deploy against the bone. Bone screws may be inserted through holes 3316 shown in curved hub 3302 to secure the proximal end of device 3300 to the bone. Further details of the construction and operation of a device similar to device 3300 may be found in co-pending U.S. application Ser. No. 11/944,366 filed Nov. 21, 2007 and entitled Fracture Fixation Device, Tools and Methods.

Device 3300 is an example of an embodiment utilizing mixed gripper types. In other words, this device uses one scissors-arm tripod gripper 3304 and one bendable-arm gripper 3308. Other embodiments of the invention (not shown) use various combinations of gripper(s) and/or flexible-to-rigid body portion(s). Further exemplary gripper embodiments are described in detail in co-pending U.S. application Ser. No. 61/100,652 filed Sep. 26, 2008 and entitled Fracture Fixation Device, Tools and Methods. It is envisioned that virtually any combination of zero, one, two, or more grippers may be used in combination with zero, one, two or more flexible-to-rigid body portions to form a device adapted to a particular bone anatomy, fracture, disease state or fixation purpose. The grippers and/or flexible-to-rigid body portions may each be of identical or different construction, and may be placed together or at other locations along the device. Further, a straight, curved, flexible, rigid, or no hub at all may be used with the above combinations. Additionally, screws, K-wires, sutures or no additional fixation may be used with these various devices. The devices may be specially designed and constructed for a particular purpose or range of purposes. According to aspects of the invention, the components may also be designed to be interchangeable and/or produced in various sizes so that surgical kits may be provided. Such kits would allow surgical teams to select from a variety of components to build devices themselves, each suited to a particular patient's unique situation.

Referring to FIGS. 39A through 47B, further examples of the hubs discussed above are shown and will now be described.

FIGS. 39A-39F show details of a curved hub 3400 similar to hub 3302 illustrated in FIGS. 38A-38D. In this embodiment, hub 3400 has an internally threaded portion at its proximal end 3402 for engaging with an insertion and removal tool as described above. (The proximal end is referenced as the end closest to the surgeon.) The proximal end 3402 may also have a keyed feature for mating with the tool for maintaining a desired orientation of hub 3400 relative to the tool. Hub 3400 may also be provided with a counterbore at its distal end 3404 for coupling to a gripper or flexible-to-rigid body portion, such as by press fit and/or welding.

Exemplary hub 3400 includes three holes 3406, 3408 and 3410 through the wall thickness on its concave side, as seen in FIG. 39C. Similarly, hub 3400 includes four holes 3412, 3414, 3416, and 3418 through the wall thickness on its convex side, as seen in FIG. 39D. At least a portion of all seven holes may be seen in FIG. 39F. Holes 3406 and 3412 on opposite sides of hub 3400 are aligned to allow a bone screw to be inserted through the two holes across the hub to secure hub 3400 to the bone and/or to secure bone fragment(s) with the screw. Similarly, holes 3408 and 3414 are aligned to receive a second bone screw, and holes 3410 and 3416 are aligned to receive a third bone screw. A fourth screw may be inserted through the open proximal end 3402 of hub 3400 and out through hole 3418. Each screw may be passed first through cortical bone, then cancellous bone, then through the two holes of hub 3400, through more cancellous bone and possibly into more cortical bone on the opposite side of the bone from where the screw entered.

In this embodiment, the holes of hub 3400 have a diameter of 2.4 mm. In other embodiments, the holes have a diameter of 2.7 mm. In still other embodiments, the holes may have larger or smaller diameters. The holes may be threaded during the fabrication of hub 3400, or threads may be formed in vivo. Various fixtures, jigs, tools and methods may be used to align the screws with the holes, such as a tool similar to tool 3138 shown in FIGS. 31-33 and described above. Further examples of positioning aids are provided in U.S. application Ser. No. 11/944,366 filed Nov. 21, 2007 and entitled Fracture Fixation Device, Tools and Methods. The heads of the screws may be countersunk into the bone as described in U.S. application Ser. No. 61/117,901 filed Nov. 25, 2008 and entitled Bone Fracture Fixation Screws, Systems and Methods of Use.

Figure 39G:
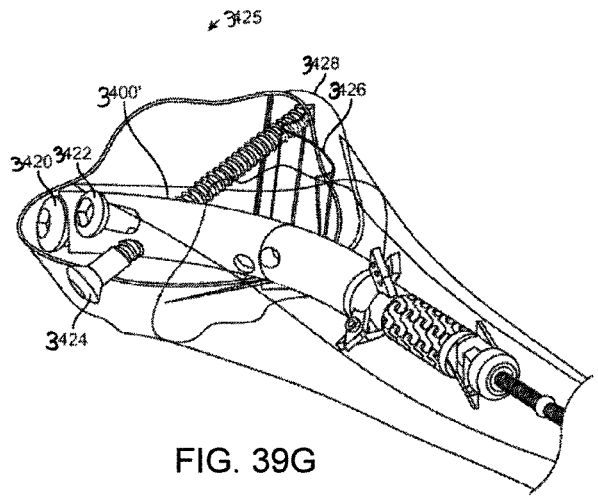
FIGS. 39G-39I show various views of an exemplary embodiment of a bone fixation device implanted in a bone.
Figure 39H:
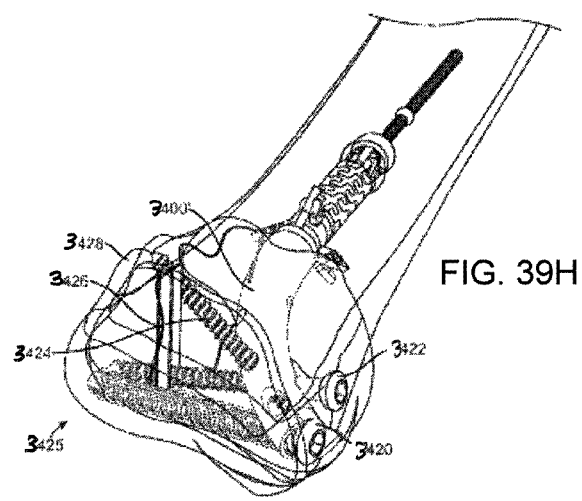
Figure 39I:
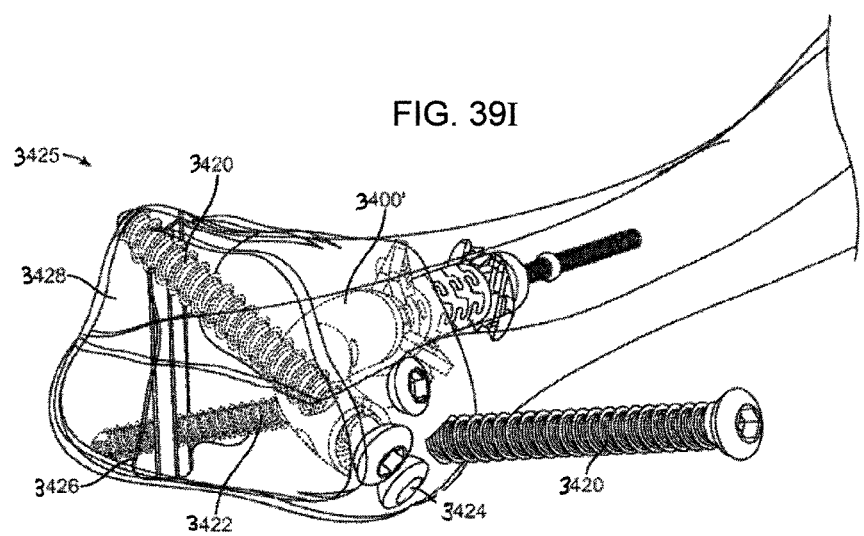

FIGS. 39G-39I illustrate an example how bone screws 3420, 3422, 3424 may be inserted through hub 3400' (which is similar to hub 3400) as described above to secure the comminuted fracture depicted at the distal end of a radius bone 3425. One, two, three, four, or more screws may be used depending on the anatomy and fracture condition of each particular case. It should be noted that in this particular embodiment, either screw 3422 or 3424 may be placed through hub 3400', but not both at the same time, as their paths intersect inside hub 3400'. It can be seen that screws 3422 and 3424 extend across fracture 3426 into bone fragment 3428. Accordingly, either screw 3422 or 3424 may be used to approximate fracture 3426 when the screw is tightened.

FIGS. 40A-40E show another exemplary embodiment of a bone fixation device hub 3450. Hub 3450 is of similar construction to hub 3400 described above and includes proximal end 3452 and distal end 3454. As seen in FIG. 40C, hub 3450 includes four holes 3456, 3458, 3460, and 3462 through the wall thickness on its concave side. Holes 3456 and 3458 are located the same longitudinal distance from distal end 3454, but are symmetrically located on opposite sides of a central longitudinal plane. As can be seen, holes 3456 and 3458 actually overlap to form a single, figure-eight shaped hole. Holes 3460 and 3462 are also located the same longitudinal distance from proximal end 3452, and are symmetrically located on opposite sides of a central longitudinal plane.

As seen in FIG. 40D, hub 3450 also includes six holes 3464, 3466, 3468, 3470, 3472, and 3474 through the wall thickness on its convex side. Holes 3464 and 3466 are located the same longitudinal distance from distal end 3454, but are symmetrically located on opposite sides of a central longitudinal plane. Holes 3464 and 3466 also overlap to form a single, figure-eight shaped hole, similar to holes 3456 and 3458 described above. Holes 3468 and 3470 are also located the same longitudinal distance from proximal end 3452, and are symmetrically located on opposite sides of a central longitudinal plane. Similarly, holes 3472 and 3474 are also located the same longitudinal distance from proximal end 3452, and are symmetrically located on opposite sides of a central longitudinal plane.

Holes 3456 and 3464 on diagonally opposite sides of hub 3450 are aligned to allow a bone screw to be inserted through the two holes across the hub, passing through a centerline of hub 3450. Similarly, holes 3458 and 3466 on diagonally opposite sides of hub 3450 are aligned to allow a bone screw to be inserted through the two holes across the hub, passing through a centerline of hub 3450. Since both of these two screw paths cross the centerline at the same location forming an X-pattern, only one screw may be placed through these two pairs of holes 3456/3464 and 3458/3466 in any particular procedure.

In a similar manner, holes 3460 and 3468 on diagonally opposite sides of hub 3450 are aligned to allow a bone screw to be inserted through the two holes across the hub, passing through a centerline of hub 3450. Holes 3462 and 3470 on diagonally opposite sides of hub 3450 are also aligned to allow a bone screw to be inserted through the two holes across the hub, passing through a centerline of hub 3450. Since both of these two screw paths cross the centerline at the same location forming an X-pattern, only one screw may be placed through these two pairs of holes 3460/3468 and 3462/3470 in any particular procedure.

A third screw may be inserted through the open proximal end 3452 of hub 3450 and out through either hole 3472 or hole 3474. Since these two screw paths also overlap, only one screw may be placed though them at a time.

As can be appreciated from FIGS. 40A-40E and the description above, exemplary hub 3450 is symmetrical about a central plane. Since hub 3450 may receive up to three screws, each in one of two positions, there are a total of eight screw patterns that may be used with hub 3450, depending on the situation. Additionally, only one or two screws, or no screws, may be used in a particular procedure, if desired. The positions and orientations of the screw holes of hub 3450 relative to previously described hub 3400 may take better advantage of cortical bone locations in some procedures for better anchoring of bone screws. In particular, a screw passing through hole pairs 3456/3464, 3458/3466, 3460/3468 or 3462/3470 of hub 3450 will have a reduced angle relative to a longitudinal axis of a bone as compared with the screw trajectories of similar screws in hub 3400. Similarly, a screw passing through either hole 3472 or 3474 will have a different angle from the same screw in hub 3400, which in many cases allows the screw of hub 3450 to hit harder bone. Additionally, screw paths of hole pairs 3460/3468 and 3462/3470 are closer to the proximal end of hub 3450 than similar screw paths in hub 3400, allowing the screws to fixate in harder bone located near the end of a bone. All of the new screw trajectories provided by hub 3450 may be used with the in vivo hole forming hubs that will be later described below. The trajectories of hole pairs 3456/3464, 3458/3466, 3460/3468 or 3462/3470 also form an angle with a central, longitudinal plane containing the curve of hub 3450 (in other words, a plane of symmetry of the hole pairs.) In some embodiments, the hole pairs each form an angle with the plane falling in a range of about 5 to 30 degrees.

Figures 41A, 41B:
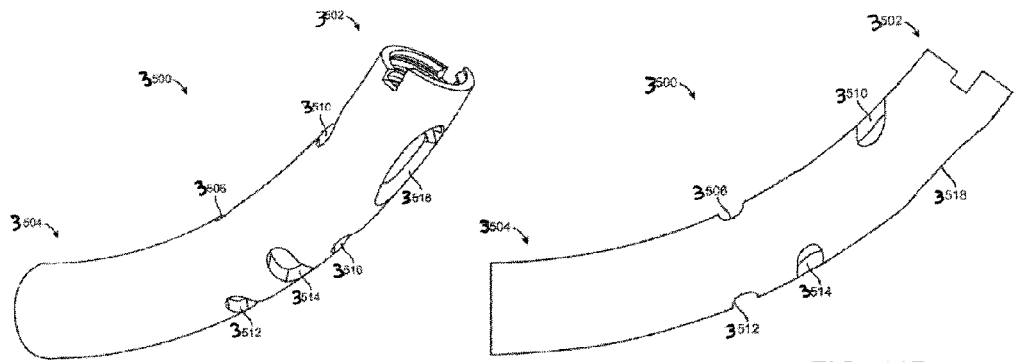
FIGS. 41A-41F show various views of another exemplary embodiment of a bone fixation device hub.
Figures 41C, 41D, 41E, 41F:
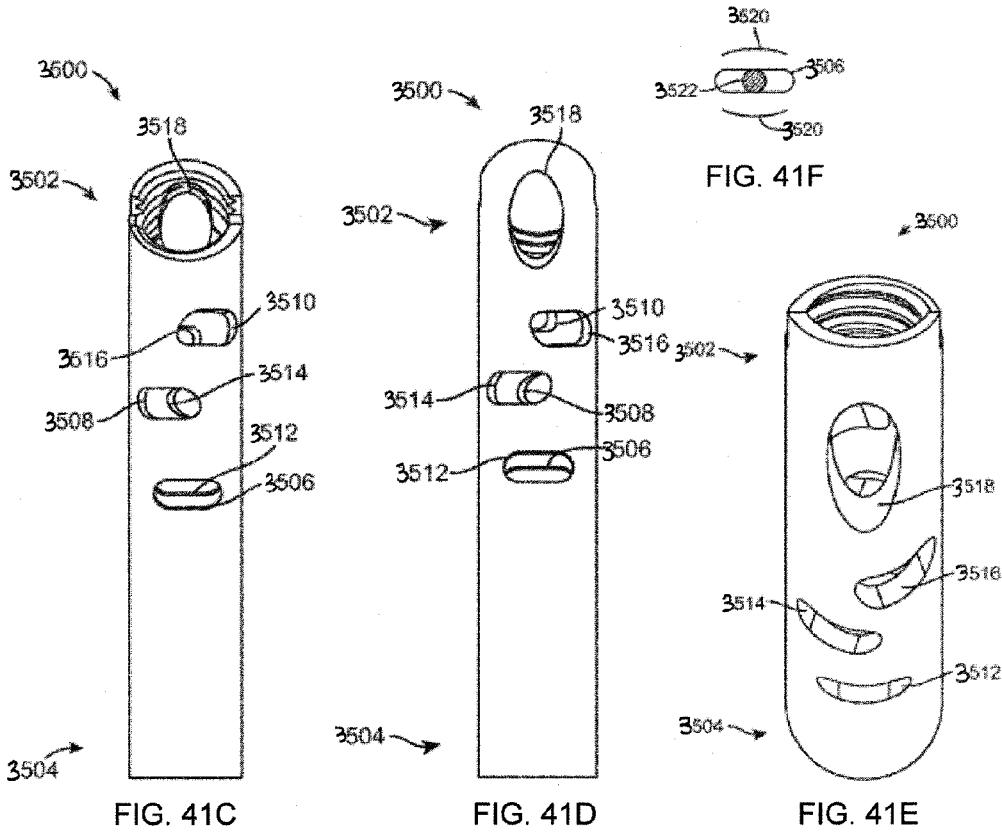

FIGS. 41A-41E show another exemplary embodiment of a bone fixation device hub 3500. Hub 3500 is of similar construction to hubs 3400 and 3450 described above and includes proximal end 3502 and distal end 3504. As seen in FIG. 41C, hub 3500 includes slotted holes 3506, 3508, and 3510 through the wall thickness on its concave side. As seen in FIG. 41D, hub 3500 also includes slotted holes 3512, 3514, and 3516, and angled hole 3518 through the wall thickness on its convex side. Holes 3506 and 3512 on opposite sides of hub 3500 are aligned to allow a first bone screw to be inserted through the two holes across the hub. Similarly, holes 3508 and 3514 are aligned to receive a second bone screw, and holes 3510 and 3516 are aligned to receive a third bone screw. Hole 3518 is aligned with the opening in the proximal end 3502 of hub 3500 to receive a fourth bone screw.

The slotted configuration of hole pairs 3506/3512, 3508/3514, and 3510/3516 allows a bone screw to be received through each of the pairs in a variety of orientations. This arrangement permits a surgeon the flexibility to place bone screws where most appropriate in a particular procedure. For example, a first bone screw may be placed through holes 3506 and 3512 such that it resides in the left, middle, or right portion of hole 3506, as viewed in FIG. 41C. The same screw will have another section that may reside in the left, middle, or right portion of hole 3512. With these various combinations, it can be appreciated that the screw can take one of nine basic orientations through holes 3506 and 3512, as well as many other orientations between these nine. In other embodiments, a slightly enlarged round hole may be provided on one side of the hub while a slotted hole on the opposite side forms the other hole of the pair.

In this exemplary embodiment, the width of slotted holes 3506, 3508, 3510, 3512, 3514, and 3516 is 2.0 mm. This provides a pilot hole in which a drill bit or screw tip may engage. Material from a portion of the sides of each hole may be removed when the drill bit forms a larger hole in one location of the slotted hole, and/or when a screw is inserted to form threads through the hole. No drilling or threading may be necessary, such as when the slot width is generally the same as the minor diameter of the screw, and the thickness of the hub walls is generally the same as the screw pitch. The slotted holes may also stretch or deform when receiving the screw. As shown in FIG. 41F, relief slit(s) 3520 may be provided adjacent to a slotted hole 3506 to allow the slot to more easily expand when receiving a screw 3522. Such slits may be formed by laser cutting, electron beam melting (EBM), electrical discharge machining (EDM), etching, stamping, milling, or other fabrication techniques.

FIGS. 42A-42D show another exemplary embodiment of a bone fixation device hub 3500'. Hub 3500' is similar to hub 3500 described above, but has slotted holes that are oriented longitudinally rather than transversely. Hub 3500' includes proximal end 3502' and distal end 3504'. As seen in FIG. 42C, hub 3500' includes slotted holes 3506', 3508', and 3510' through the wall thickness on its concave side. As seen in FIG. 42D, hub 3500' also includes slotted holes 3512', 3514', and 3516', and angled hole 3518' through the wall thickness on its convex side. Holes 3506' and 3512' on opposite sides of hub 3500' are aligned to allow a first bone screw to be inserted through the two holes across the hub. Similarly, holes 3508' and 3514' are aligned to receive a second bone screw, and holes 3510' and 3516' are aligned to receive a third bone screw. Hole 3518' is aligned with the opening in the proximal end 3502' of hub 3500' to receive a fourth bone screw. Exemplary axis lines 3524, 3526, 3528, and 3530 are shown in FIG. 42A to show examples paths for the first, second, third, and fourth screws, respectively.

FIGS. 43A-43E show another exemplary embodiment of a bone fixation device hub 3550. As seen in FIG. 43D, hub 3550 includes at its proximal end 3552 a transversely elongated hole 3554. Hole 3554 allows a screw 3556 to be located along the central axis, or off-axis in either direction as may be desired for engaging harder bone or securing additional bone fragment(s). This of arrangement of hole 3554 may be configured to hold screw 3556 tightly at all angles. This may be accomplished, for example, by using a hole 3554 slot width that is equal to or smaller than the minor diameter of screw 3556. The wall thickness of hub 3550 may fit into the screw threads, providing additional locking of screw 3556. In other embodiments, the angle of elongated hole 3554 may be oriented differently as desired.

Special screws may be used to provide additional locking. As shown in FIG. 43E, screw 3558 has a tapered edge 3560 below its head 3562. Tapered edge 3560 serves to wedge screw 3558 into slot 3554, securing the screw in place. A screw with an expanding head (not shown) may also be used. With this arrangement, a taper or other expanded section may be created once the screw is in place, thereby locking it in position.

FIGS. 44A-44C show another exemplary embodiment of a bone fixation hub 3600. Hub 3600 is provided with an array of pilot holes 3602 over most of its surface. Each hole 3602 may be 0.015 to 0.020 inches in diameter, for example, and serves as a starting point to allow a drill bit or screw tip to penetrate the wall thickness of hub 3600. This makes in vivo screw hole formation possible, while allowing the hub to remain a rigid structure. Holes 3602 may be closely spaced such that a screw or screws may be positioned in vivo virtually anywhere the surgeon desires during each particular procedure. Once the drill bit and/or screw is inserted, the hole 3602 becomes enlarged to generally the minor diameter of the screw thread, such as to 2.7 mm in diameter, for example. Screw holes may be formed in this way on both sides of hub 3600 in a continuous operation, allowing screw(s) to be positioned across the hub as previously described.

As shown in FIG. 44C, pilot holes 3602 may be placed closer to one another so that multiple perforations are consumed by the screw diameter 3604 when the screw hole is formed. This can make in vivo hole formation even easier. Other hole patterns than those shown in FIGS. 44A-44C may be used.

Holes 3602 may be fabricated in hub 3600 by laser cutting, electron beam melting (EBM), electrical discharge machining (EDM), etching, stamping, drilling, or other fabrication techniques.

FIGS. 45A and 45B show another exemplary embodiment of a bone fixation hub 3650. Hub 3650 has at least a portion that is fabricated from a mesh structure, forming a plurality of diamond or other shaped apertures 3652. Apertures 3652 may be configured with dimensions smaller than the major diameter of the threads of the bone screws to be used. Aperture dimensions may even be smaller than the minor thread diameter, such that the apertures are stretched and/or deformed as the screw enters the aperture, thereby providing an increased ability to hold the screws in place. The use of a mesh hub 3650 may reduce the amount or possibility of debris being formed and released inside the body during in vivo screw hole formation.

Apertures 3652 may be fabricated in hub 3650 by laser cutting, electron beam melting (EBM), electrical discharge machining (EDM), etching, stamping, drilling, or other fabrication techniques. Apertures 3652 may also be fabricated by forming slits in plate or tube stock and expanding the material to form the apertures. Another fabrication technique that may be used is forming wires or bands around a mandrel and then welding, brazing, soldering, pressing, melting, gluing, or otherwise joining the wires or bands to each other at their intersections. Other types of porous structures, either with or without more random aperture locations, may be used as well. Multiple layers of mesh may also be combined.

FIGS. 46A and 46B show another exemplary embodiment of a bone fixation hub 3700. Hub 3700 is provided with a plurality of thin slots 3702 along its length. Slots 3702 permit in vivo screw hole formation by acting as long pilot holes for drill bits or bone screws. A bone screw tip may be inserted into one of the slots 3702 without pre-drilling. Upon insertion, the slot and surrounding slots will deform to make way for the screw, and will provide circumferential pressure to retain the screw.

Although shown staggered and in the longitudinal direction, in other embodiments (not shown) thin slots may be provided in a transverse or other orientation, and/or in other patterns. Slots 3702 may be fabricated in hub 3700 by laser cutting, electron beam melting (EBM), electrical discharge machining (EDM), etching, stamping, drilling, or other fabrication techniques. Thin slots 3702 may generally require less material removal than other hub embodiments.

Figure 47B:
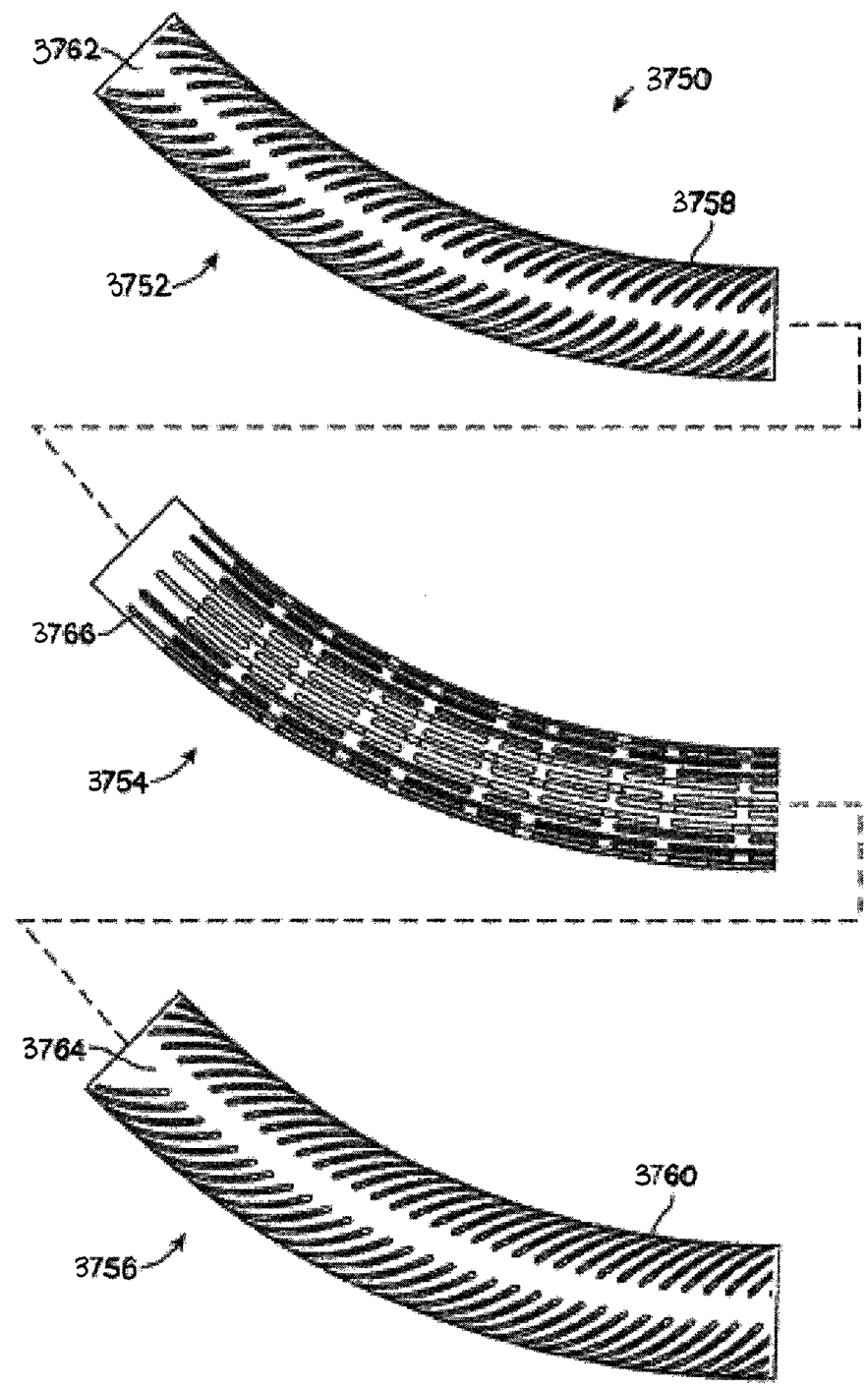

FIGS. 47A and 47B show another exemplary embodiment of a bone fixation hub 3750. Hub 3750 comprises three separately formed hubs assembled together: an inner hub 3752, a mid-hub 3754, and an outer hub 3756. Mid-hub 3754 has a larger diameter than inner hub 3752 so that mid-hub 3754 may be placed over inner hub 3752, as illustrated in FIGS. 47A and 47B. Similarly, outer hub 756 has a larger diameter than mid-hub 3754 so that outer hub 3756 may be placed over mid-hub 3754, as also illustrated in the figures. In this embodiment, all three hub components 3752, 3754, and 3756 have the same bend radius and the same arc length. Once assembled, the three hub components 3752, 3754, and 3756 may be retained at one or both ends by other components of the associated bone fixation device, and/or may be welded or otherwise fastened together.

As seen in FIG. 47B, inner hub 3752 and outer hub 3756 have spirally formed slots 3758 and 3760, respectively. Slots 3758 and 3760 may be formed such that they line up when the individual hubs are assembled. Each hub 3752 and 3756 may also be provided with an upper spine (3762 and 3764, respectively), and a lower spine (not seen in FIG. 47B). The spines are solid regions running the length of the hubs that provide rigidity, and are positioned in areas that do not typically receive screws. Mid-hub 3754 has longitudinally extending slots 3766 rather than spiral slots. When the three slot patterns are assembled in a coaxial unit, as shown in FIG. 47A, a hub is formed that may be quite rigid. Pilot holes are formed where slots 3760, 3766, and 3758 line up radially to facilitate in vivo screw hole formation. When a screw is inserted in such a pilot hole, one or more of the slots may deform to receive the screw.

One, two, three, four, or more hub layers may be used in this manner to form a single layer or composite hub. Other slot patterns and widths may be used as appropriate. Some of the layers may incorporate round or other aperture shapes instead of or in addition to the slots shown in this example.

In many of the hub embodiments described above, one or more screws may be placed into just a single side of the hub, or completely across the hub through both sides.

Referring to FIGS. 48A-48D, a tubular gripper embodiment is shown. Gripper 3800 is generally tube-shaped and has a series of slots 3802 formed through its wall thickness along the length and around the circumference of the tube. In this embodiment, each slot 3802 is helical, as shown. In other embodiments, the slots may be straight or form other patterns. Slots 3802 may be formed by laser cutting, punching, milling, etching, sawing, electro-discharge machining, or otherwise removing material from the body of the gripper. Slots 3802 may also be created by molding, extruding or otherwise forming the beam members 3804 between the slots 3802. Gripper 3800 may be formed from metal, composite, plastic, amorphous materials, shape memory alloy, and/or other suitable materials.

Figure 48A:
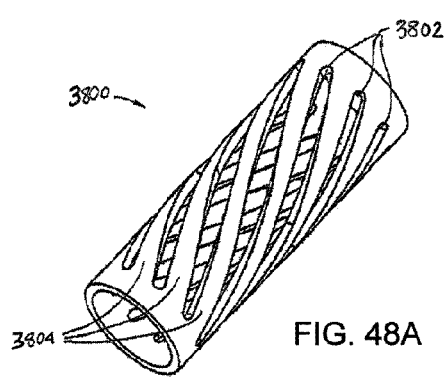
FIG. 48A is a perspective view showing another alternative gripper design in a retracted or undeployed state.
Figure 48B:
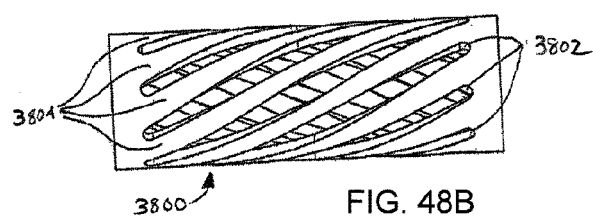
FIG. 48B is a side elevational view showing the gripper of FIG. 48A in a retracted or undeployed state.
Figure 48C:
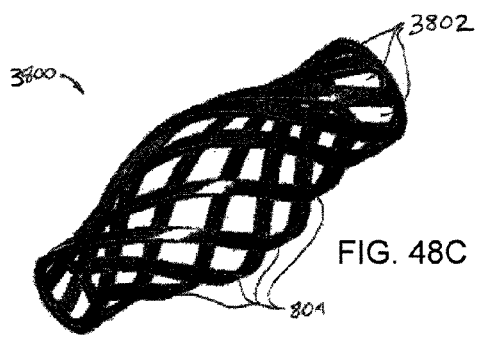
FIG. 48C is a perspective view showing the gripper of FIG. 48A in a deployed state.
Figure 48D:
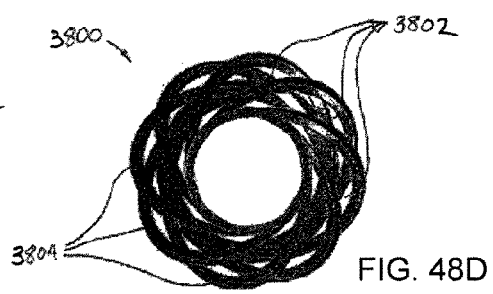
FIG. 48D is an end view showing the gripper of FIG. 48A in a deployed state.

FIGS. 48A and 48 B show gripper 3800 in a retracted state. By applying a compressive axial load to the ends of gripper 3800 as with the previously described grippers, gripper 3800 expands radially outward into a deployed state, as shown in FIGS. 48C and 48D. In the deployed state, mid-portions of beam members 3804 arc outwardly to contact an inner surface of bone to anchor an attached fixation device to the bone. By applying a tensile force to the ends of gripper 3800, it may be at least partially returned to the retracted state. In some embodiments of the invention, beam members 3804 undergo only elastic deformation when moving into the deployed state. In other embodiments, members 3804 may undergo plastic deformation.

In some embodiments, a bone fixation device incorporating gripper(s) 3800 may rotationally constrain the ends of the gripper relative to one another as the ends move axially. In other embodiments, the ends may be left unconstrained. In still other embodiments, the ends of gripper 3800 may be biased or forced to rotate relative to one another as they move axially closer and/or farther apart. Such arrangements may advantageously increase or decrease the amount of expansion that occurs when the gripper is axially compressed, and/or may similarly alter the amount of retraction that occurs when the gripper is axially pulled under tension.

Figure 49A:
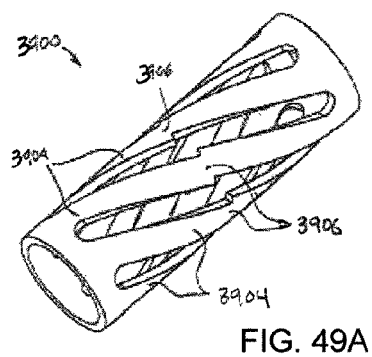
FIG. 49A is a perspective view showing another alternative gripper design in a retracted or undeployed state.
Figure 49B:
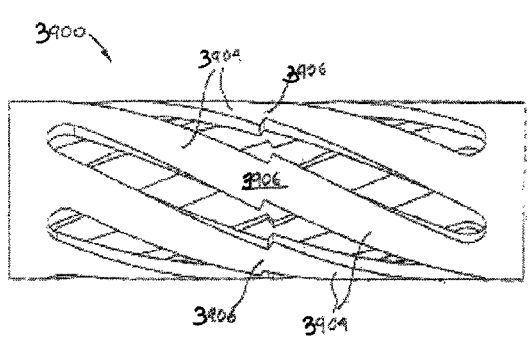
FIG. 49B is a side elevational view showing the gripper of FIG. 49A in a retracted or undeployed state.

FIGS. 49A and 49B show another tubular gripper embodiment. Gripper 3900 is similar to gripper 3800, but beam members 3904 each have an offset portion 3906 located at their mid-portions. These offset portions 3906 create a pair of sharp points on opposite sides of each beam member that can enhance the gripping effectiveness of gripper 3900 by engaging with the interior bone surface when the gripper is deployed.

Figure 50A:
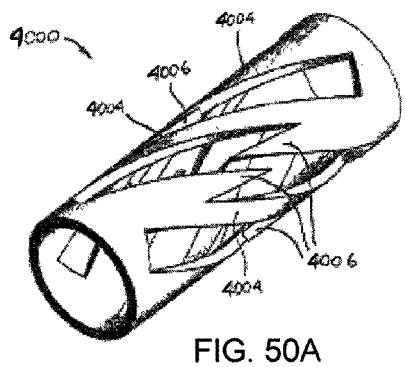
FIG. 50A is a perspective view showing another alternative gripper design in a retracted or undeployed state.
Figure 50B:
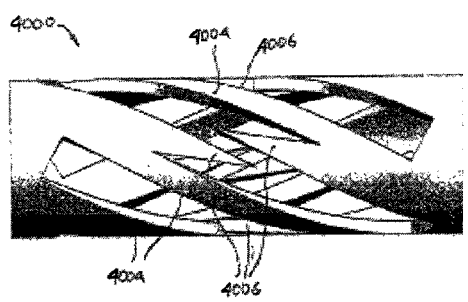
FIG. 50B is a side elevational view showing the gripper of FIG. 50A in a retracted or undeployed state.

FIGS. 50A and 50B show another tubular gripper embodiment. Gripper 4000 is similar to both grippers 3800 and 3900. Gripper 4000 includes a protruding member 4006 located along each side of each beam member 4004. Pointed ends of opposite facing protruding members 4006 provide additional gripping engagement when gripper 4000 is deployed.

Figure 51A:
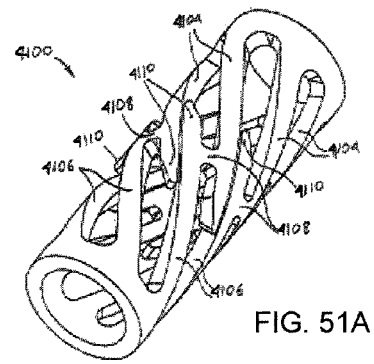
FIG. 51A is a perspective view showing another alternative gripper design in a retracted or undeployed state.
Figure 51B:
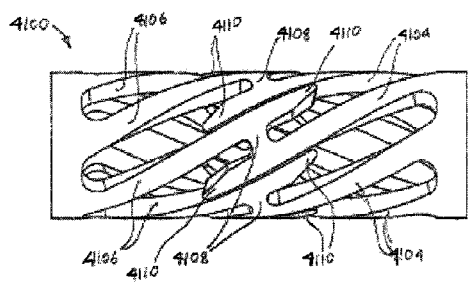
FIG. 51B is a side elevational view showing the gripper of FIG. 51A in a retracted or undeployed state.

FIGS. 51A and 51B show another tubular gripper embodiment. Gripper 4100 includes a first series of beam members 4104 helically extending from a first end of the gripper, and a second series of opposing beam members 4106 helically extending from the opposite end of the gripper and which interdigitate with the first series 4104. The first series of beam members 4104 are interconnected with the second series 4106 by a series of short leaf springs 4108 around the mid-circumference of gripper 4100. As gripper 4100 axially compresses and beam members 4104 and 4106 bend toward a deployed state, the distal ends 4110 of members 4104 and 4106 engage with the interior surface of the bone.

Figure 52A:
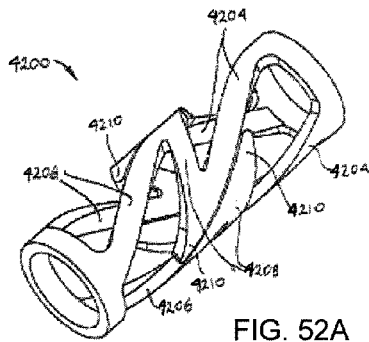
FIG. 52A is a perspective view showing another alternative gripper design in a retracted or undeployed state.
Figure 52B:
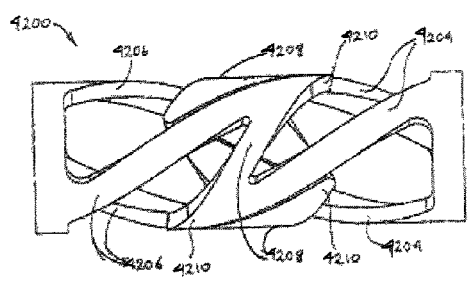
FIG. 52B is a side elevational view showing the gripper of FIG. 52A in a retracted or undeployed state.

FIGS. 52A and 52B show another tubular gripper embodiment. Gripper 4200 of this embodiment is similar to gripper 4100 of the previous embodiment, but fewer beam members 4204 and 4206 are employed in gripper 4200, and the beam members 4204 and 4206 are interconnected with longer, Z-shaped leaf springs 4208. As gripper 4200 axially compresses and beam members 4204 and 4206 bend toward a deployed state, the distal ends 4210 of members 4204 and 4206 engage with the interior surface of the bone.

Figure 53A:
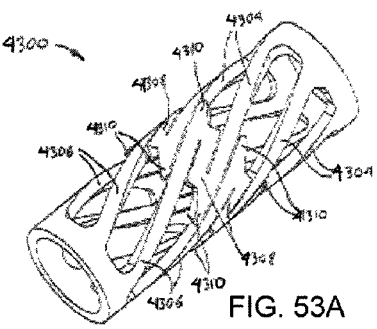
FIG. 53A is a perspective view showing another alternative gripper design in a retracted or undeployed state.
Figure 53B:
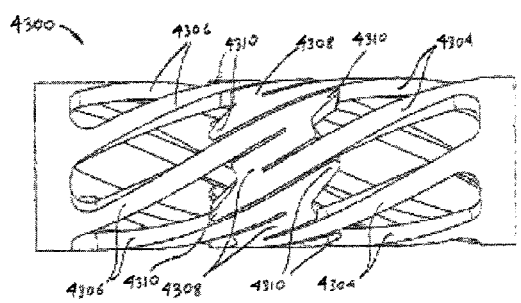
FIG. 53B is a side elevational view showing the gripper of FIG. 53A in a retracted or undeployed state.

FIGS. 53A and 53B show another tubular gripper embodiment. Gripper 4300 of this embodiment is also similar to gripper 4100 shown in FIGS. 51A and 51B, but the beam members 4304 and 4306 are interconnected with serpentine leaf springs 4308. As gripper 4300 axially compresses and beam members 4304 and 4306 bend toward a deployed state, the distal ends 4310 of members 4304 and 4306 engage with the interior surface of the bone.

In any of the above-described tubular gripper embodiments, a thinned down portion (not shown) may be provided at a predetermined location or locations along one or more of the beam members to cause the beam member to bend at that particular location during deployment under axial compressive loading.

Figure 54A:
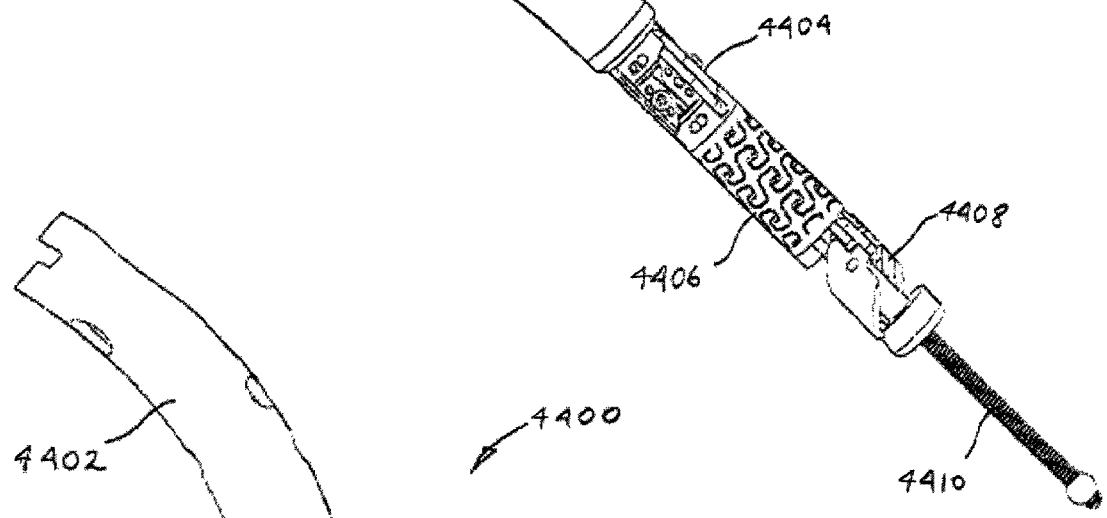
FIG. 54A is a perspective view showing another bone fixation device in a retracted or undeployed state.
Figure 54B:
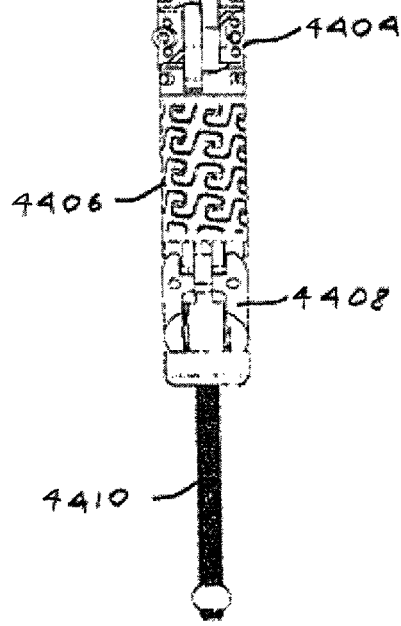
FIG. 54B is a top plan view showing the device of FIG. 54A in a retracted or undeployed state.

FIGS. 54A-54F show another exemplary embodiment of a bone fixation device 4400 constructed according to aspects of the present invention. Device 4400 includes a curved hub 4402, a proximal gripper 4404, a flexible-to-rigid body portion 4406, a distal gripper 4408, and an actuation lead screw 4410. FIGS. 54A-54C show device 4400 in an undeployed state, while FIGS. 54D-54F show device 4400 in a deployed state.

Figure 55G:
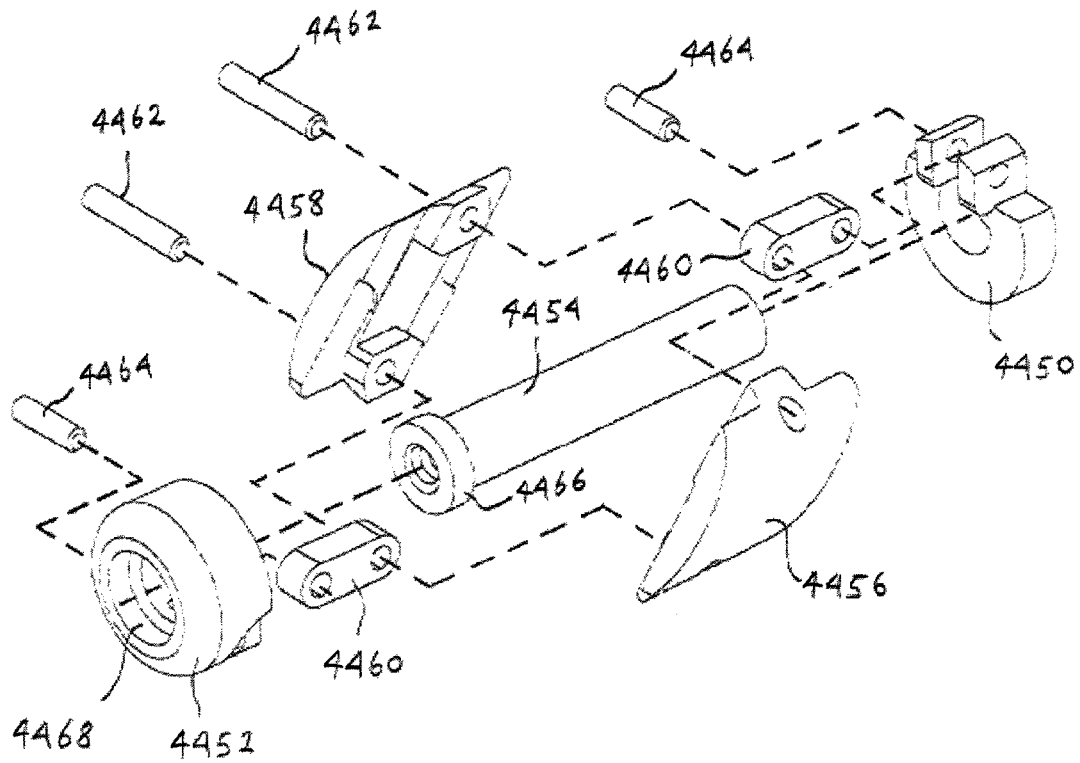
FIG. 55G is an exploded perspective view showing the gripper of FIG. 55A.

FIGS. 55A-55G show further details of distal gripper 4408 of device 4400 described above. As seen in FIG. 55G, distal gripper 4408 comprises a proximal end piece 4450, a distal end piece 4452, a tubular core 4454, a first gripper arm 4456, a second gripper arm 4458, two link bars 4460, 4460, two long pins 4462, 4462, and two short pins 4464, 4464.

Tubular core 4454 may include a flange 4466 at its distal end as shown for engaging in a circular bore 4468 in the distal side of distal end piece 4452 for transferring axial loads. Tubular core 4454 may be fastened to distal end piece 4452, such as by a press fit and/or welding. Proximal end piece 4450 includes a central opening for receiving the tubular core 4454 such that proximal end piece may freely slide along the tubular core 4454.

Upper portions of both first and second gripper arms 4456, 4458 are pivotably connected to proximal link bar 4460 by a single long pin 4462. Proximal link bar 4460 in turn is pivotably connected to proximal end piece 4450 by a short pin 4464. Similarly, lower portions of both first and second gripper arms 4456, 4458 are pivotably connected to distal link bar 4460 by the other long pin 4462. Distal link bar 4460 in turn is pivotably connected to distal end piece 4452 by the other short pin 4464.

At least a portion of tubular core 4454 may be internally threaded for engaging actuation lead screw 4410 (shown in FIGS. 54A-54F). As actuation lead screw 4410 is turned in an actuation or deployment direction, tubular core 4454 and attached distal end piece 4452 is drawn in a proximal direction. Since proximal end piece 4450 is prevented from also moving in the proximal direction by flexible-to-rigid body portion 4406 (shown in FIGS. 54A-54F), tubular core 4454 telescopes through proximal end piece 4450 into the central bore of flexible-to-rigid body portion 4406. In other words, when gripper 4408 is deployed, its distal and proximal end pieces 4452, 4450 are moved toward each other, with proximal end piece 4450 sliding along the outside surface of tubular core 4454. As this occurs, first and second gripper arms 4456, 4458 are forced to rotate from a retracted, undeployed position, as shown in FIGS. 55A-55C, toward an extended, deployed position, as shown in FIGS. 55D-55F. In the deployed position, the outward tips of gripper arms 4456, 4458 engage with bone tissue within the intramedullary space of the bone to secure gripper 4408 and device 4400 within the bone.

If desired, gripper 4408 may be moved back to the retracted, undeployed state by turning actuation lead screw 4410 (shown in FIGS. 54A-54F) in an opposite direction, causing tubular core 4454 and attached distal end piece 4452 to move in a distal direction, such that tubular core 4454 recedes from within flexible-to-rigid body portion 4406, distal and proximal end pieces 4452, 4450 separate, and gripper arms 4456, 4458 rotate back to the retracted position shown in FIGS. 55A-55C.

According to aspects of the present invention, in some embodiments the tubular core 4454 serves to isolate the threads of the actuation lead screw 4410 from corners and other geometry that could potentially damage the screw. This can improve reliability of the device and reduce or eliminate the chance of particulate matter being dislodged from the device and migrating into the patient. Tubular core 4454 may also serve to protect actuation lead screw 4410 from bending moments generated by the gripper during deployment. This in turn makes the device more robust and enables the screw to provide higher torque and higher tension performance.

Figure 56:
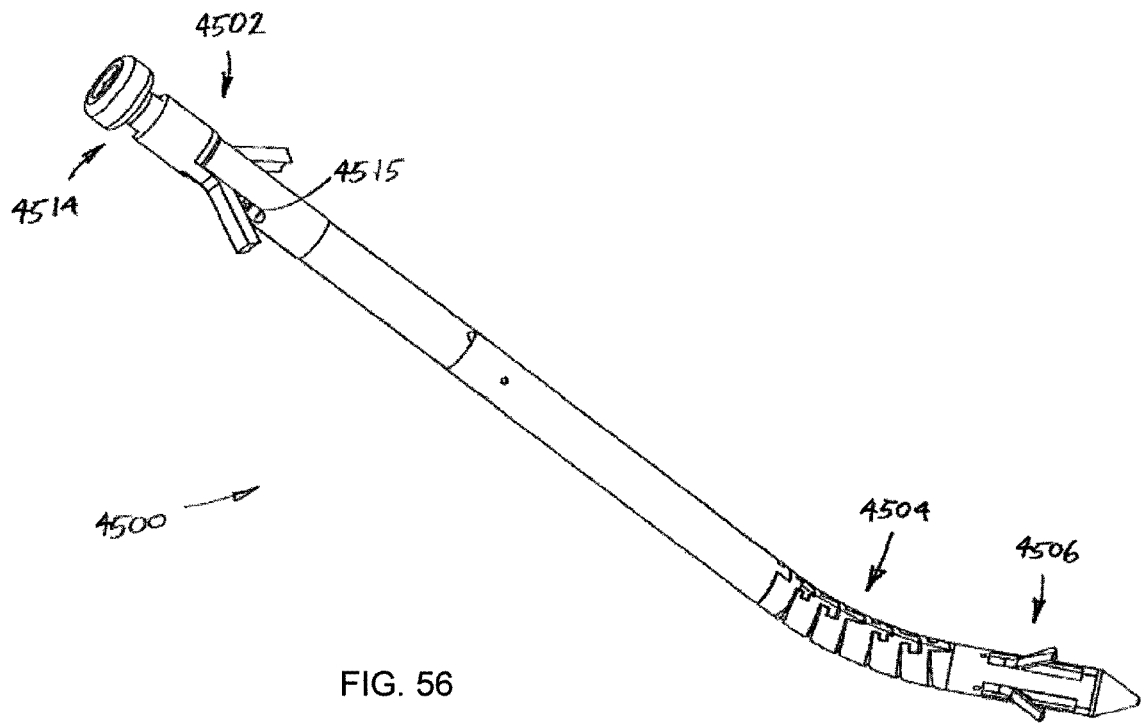
FIGS. 56-58 are various views showing another embodiment of a bone fixation device.
Figure 57:
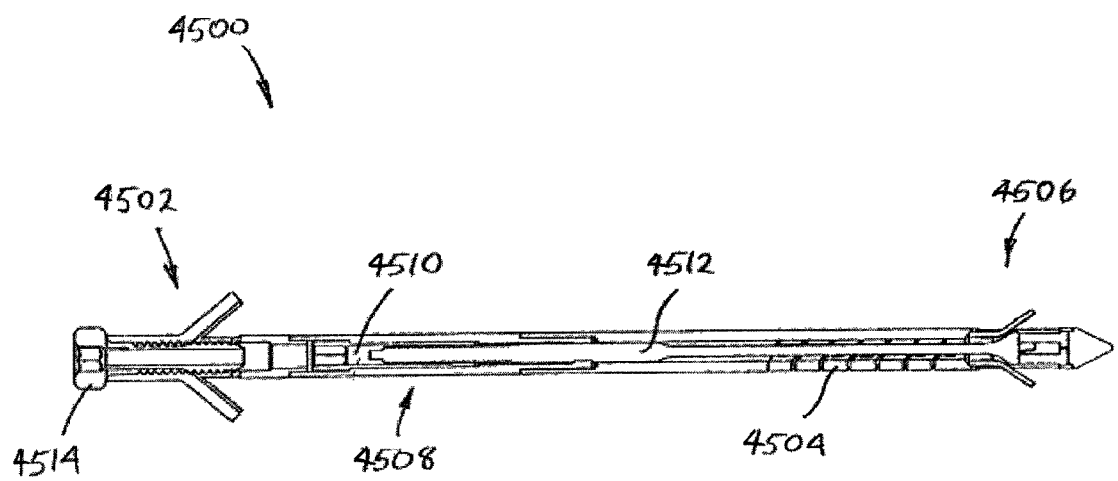
Figure 58:
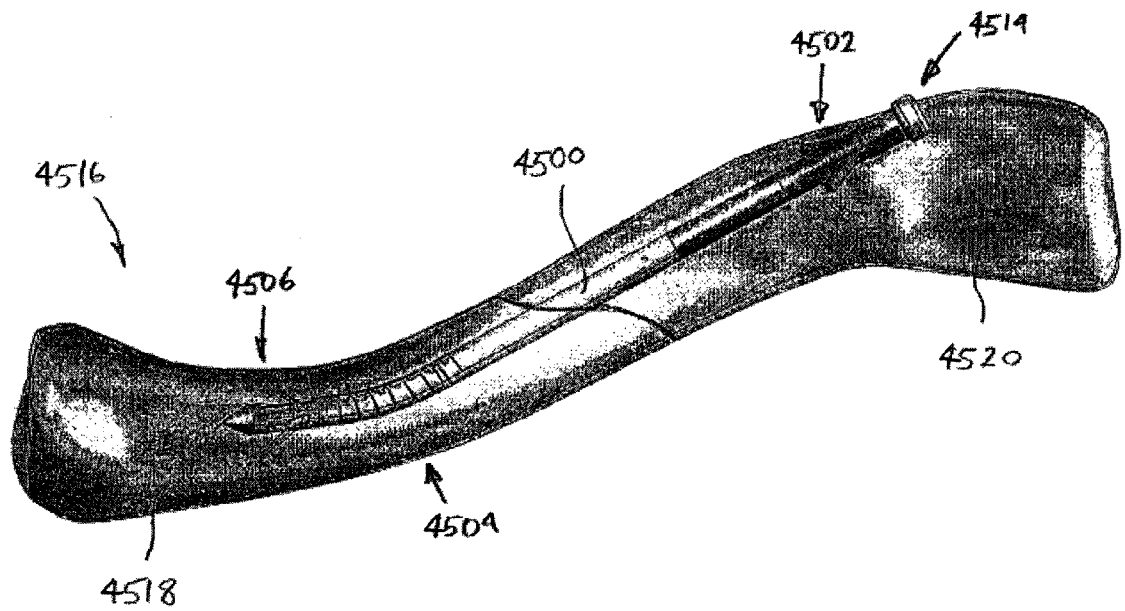

Referring to FIGS. 56-58, another embodiment of a bone fixation device with a compression screw is shown. Device 4500 has aspects that are similar in construction and operation to the previously described bone fixation devices. Device 4500 includes a proximal gripper 4502, flexible-to-rigid body portion 4504, and distal gripper 4506. As can been seen in the figures, flexible-to-rigid portion 4504 of the elongate body of device 4500 is disposed at a location on the elongate body distal to a first gripper 4502 and proximal to a second gripper 4506.

As shown in FIG. 57, one embodiment of a compression screw device 4500 includes two separate actuators. The first actuator 4508 is located internally within device 4500 and operates in similar fashion to the actuators of devices previously described herein. First actuator 4508 includes an internally threaded tube 4510 that is driven by a keyed feature at its proximal end. Tube 4510 is coupled to externally threaded rod 4512. When tube 4510 is rotated, rod 4512 is drawn in a proximal direction. Ramped surfaces at the distal end of rod 4512 cause bendable arms of distal gripper 4506 to be outwardly deployed.

In one embodiment, the second actuator 4514 of device 4500 comprises an externally threaded compression screw having a central lumen. The compression screw is coupled to internal threads within proximal gripper 4502. In some embodiments, the compression screw outwardly deploys one, two, three, four or more bendable gripper arms by driving the gripper arms distally against ramped surface(s). In some embodiments, the gripper arm(s) do not move axially when deployed. Instead, the compression screw is moved axially in a proximal direction. In one embodiment, as shown in FIG. 57, the compression screw has a variable diameter, with, for example, a larger diameter than the internal diameter of a portion the proximal gripper, so that movement of the compression screw urges the gripper arms in an outward direction. As shown in FIG. 57, the distal end of the compression screw threading has a greater diameter than the proximal threading or proximal body on the compression screw. In some embodiments, slots 4515 may be provided in the proximal end of device 4500 to resist torque from proximal gripper 4502.

In operation, device 4500, with grippers 4502 and 4506 in a retracted state, may be inserted into the intramedullary space within a bone, such as a clavicle bone 4516 as shown in FIG. 58. Once device 4500 is in place inside the bone, the first actuator 4508 may be actuated from the proximal end of device 4500 by inserting a drive tool through the central lumen of the compression screw of the second actuator 4514, engaging the distal end of the drive tool with the keyed end of tube 4510 and turning, in a manner similar to that previously described. Longitudinal movement of rod 4512 toward the proximal end of device 4500 causes flexible-to-rigid body portion 4504 to foreshorten and assume its rigid state, and causes distal gripper 4506 to outwardly deploy against the bone, such as the medial segment 4518 of the clavicle bone 4516 shown in FIG. 58. The drive tool is then removed, and a drive tool having a larger keyed end is inserted into the keyed end of the compression screw to turn the second actuator 4514, causing the bendable arms of proximal gripper 4502 to outwardly deploy against the bone, such as the lateral segment 4520 of the clavicle bone 4516.

In another embodiment, the device 4500 is configured for insertion in to a bone, such as the clavicle bone from a medial to lateral direction. Longitudinal movement of rod 4512 toward the proximal end of device 4500 causes flexible-torigid body portion 4504 to foreshorten and assume its rigid state, and causes distal gripper 4506 to outwardly deploy against the bone, such as the lateral segment 4520 of the clavicle bone 4516. The drive tool is then removed, and a drive tool having a larger keyed end is inserted into the keyed end of the compression screw to turn the second actuator 4514, causing the bendable arms of proximal gripper 4502 to outwardly deploy against the bone, such as the medial segment 4518 of the clavicle bone 4516.

In some embodiments, any of the devices for insertion into a bone for fracture fixation of a clavicle can be inserted using a medial approach. In some instances, a medial approach can be advantageous for use on fractures, taking advantage of the clavicle's S-shape curvature. For example, a medial approach can be used on the medial half of the middle third of the bone. In some embodiments, a medial approach can also be advantageous for use in small clavicles. In one embodiment, a makes it possible to flip embodiments of the procedures from a lateral to medial approach to a medial to lateral approach. In one embodiment, the medial prep becomes lateral prep and vice versa. In one embodiment, a medial exit point can be formed approximately 1-2 cm lateral to sternal end, slightly inferior, lateral to SC joint. In one embodiment, the exit point can be approximately tangent to the natural curvature of the medial side. In one embodiment, a medial approach for a medial midshaft fracture using a rapid preparation technique can include any of the following steps: a medial exit with K-Wire from fracture site, preparation of a medial fragment with a 4.5 mm drill, reduction of the fracture, driving a spade wire into the lateral fragment, reaming over a spade wire, measuring with a reamer depth gauge, insertion of the appropriate device or implant, actuation of the implant, and insertion of a cross screw or a compression screw.

In one embodiment, as shown in FIGS. 59-65, a compression screw device 4500 includes one or more actuators. In one embodiment, there are two actuators. The first actuator 4508 is located internally within device 4500 and operates in similar fashion to the actuators of devices previously described herein. In one embodiment In one embodiment, the first actuator 4508 includes a threaded rod 4512. In one embodiment, the first actuator 4508 has a pilot wire 4509 extending proximally and configured for slideably guiding or directing tools or components to the device 4500 from the proximal direction. If a pilot wire 4509 embodiment is used, the tools and/or components advanced along the pilot wire 4509 can include a pilot wire lumen.

In one embodiment, the first actuator 4508 has a keyed feature at its proximal end, such that the threaded rod 4512 can be directly driven or rotated by the first actuator tool. In one embodiment, the body of the device 4500 is internally threaded and configured to be coupled to the threaded rod 4512.

In another embodiment, the first actuator 4508 includes a threaded tube 4510 that is driven by a keyed feature 4511 at its proximal end by the first actuator tool. The threaded tube 4510 can rotate with respect to the body of the device 4500. In one embodiment, the first actuator tool includes a pilot wire lumen for sliding over the pilot wire 4509 to access the keyed feature 4511. The threaded tube 4510 is coupled to the threaded rod 4512. When tube 4510 is rotated in a first direction, the rod 4512 is drawn in a proximal direction. Ramped surfaces at the distal end of rod 4512 cause bendable arms of distal gripper 4506 to be outwardly deployed, as shown in FIGS. 59 to 60, and FIGS. 62 to 64.

In one embodiment, the second actuator 4514 of device 4500 comprises an externally threaded compression screw having a central lumen 4517. The compression screw is coupled to internal threads within proximal gripper 4502. In some embodiments, the compression screw outwardly deploys one, two, three, four or more bendable gripper arms by driving the gripper arms distally against ramped or sloped surface(s). In some embodiments, the gripper arm(s) do not move axially when deployed. In some embodiments, slots 4515 may be provided in the proximal end of device 4500 to resist torque from proximal gripper 4502. In various embodiments, a device 4500 can be inserted in a lateral to medial direction. In some embodiments, a device can be inserted in a medial to lateral direction.

In various embodiments, a surgical technique for deploying and/or removing a device 4500 can include any of the following steps.

In one embodiment, a pre-operative evaluation can comprise using AP and 45-degree cephalic tilt fluoroscopic views to evaluate the location of a clavicle fracture and associated fragments. Confirm that clear fluoroscopic images of the entire length of the clavicle can be obtained. Determine if a minimum depth of 50 mm can be achieved in the intramedullary canal of medial segment from the most medial edge of the fracture.

In one embodiment, preparation and patient positioning can involve positioning the patient in a modified beach chair position and utilizing an Allen table to gain access to posterior shoulder on the fractured side. A C-Arm can be brought in from across the body or over the top of the table. Support of the arm on the fractured side can be provided by the use of an adjustable armrest. Expose and prep the entire aspect of the clavicle from medial to lateral, including the AC joint and posterior shoulder. Alternatively, the orientation of the clavicle relative to the C-Arm can be changed by flexion or extension of the arm.

In one embodiment, surgical exposure includes making a 3 cm length horizontal or oblique incision directly over the fracture site and bluntly dissect the soft tissue structures to expose the fracture. Remove callus/scar tissue sufficiently to start medial and lateral preparation. Ensure upon reduction 50% bony apposition of the medial and lateral segments is possible.

In one embodiment, preparation of the medial segment involves elevating the medial fracture segment and secure with a bone reduction clamp. Identify the intramedullary canal with fluoroscopic guidance and use the 2 mm drill to establish a starter hole (approximately 20 mm in depth). Follow with the 3.5 mm drill or 3 mm straight trocar to increase the diameter of the starter hole. Under fluoroscopic guidance, introduce and advance a 3 mm curved trocar, followed by a 4.5 mm curved cutting awl into the medial canal, using +/−15-degree rotating hand motions until a minimum 50 mm depth is achieved. Confirm that the curve of the awl is aligned with the curvature of the clavicle.

In one embodiment, preparation of the lateral segment includes elevating the lateral fracture segment and securing it with a bone reduction clamp. The arm can be externally rotated to help access the lateral canal. Identify the intramedullary canal with fluoroscopic guidance and use the 2 mm drill to establish a starter hole to a depth of approximately 20 mm. Introduce and advance a 4.5 mm aimer awl until the awl is fully seated in the canal but has not breached the cortex. Drive a 1.6 mm K-Wire through the cannulated aimer awl under fluoroscopic guidance to exit the clavicle bone posterior lateral to the Conoid Tubercle. When viewed in the AP view, a lateral exit point in the lateral fragment is at the equator of the posterior clavicle halfway between the Conoid Tubercle and the AC Joint. Tent the skin and make a small incision over the palpable K-Wire tip to expose the exit point. Remove the aimer awl while retaining the K-Wire. Place a 4.5 mm cannulated drill bit over the K-Wire and drill a channel through the lateral segment from lateral to medial. Remove the K-Wire and leave the drill bit in place to act as a guide.

In one embodiment, fracture reduction and canal preparation can include loading the spade tip guide wire through the 4.5 mm drill bit with a spade tip directed toward the medial segment. Reduce the fracture and introduce the guide wire into the medial segment until a marker, such as a lateral gold band, on the guide wire is within the lateral end of the 4.5 mm drill bit. Remove the drill bit while retaining the guide wire. Ensure the fracture is reduced over the guide wire. Place the flexible reamer over the guide wire and under fluoro, ream from lateral to medial.

In one embodiment, a rapid preparation may be used to prepare the medial segment without using the awls. With the medial pilot hole established and the lateral segment prepared, the spade tip guide wire can be driven through the 4.5 mm drill bit into the medial segment under power. Drive the wire into the medial segment until a marker (e.g., such as a gold band) on the wire is within the lateral end of the drill. Remove the drill taking care to retain the placement of the wire. Verify the position of the wire using fluoroscopy. Use the flexible reamer to ream from lateral to medial to the tip of the spade wire.

In one embodiment, implant sizing and preparation can involve placing a reamer depth gauge over the reamer and advancing it until it contacts the lateral bone. Measure the length off of the scale. Determine the appropriate implant length by subtracting 10 mm off of the measured length to account for countersinking Devices 4500 can be available in 90, 100, 110, and 120 mm lengths. Remove the depth gauge but retain the guide wire. Use the 5 mm cannulated countersink drill to create a 10 mm deep countersink at the lateral entry. The drill has a step-off at 10 mm to limit the countersink depth. Prepare the device 4500 by aligning the notches in the hub and hub attachment tube and tightening the hub attachment screw.

In one embodiment, implant insertion and fixation involves inserting the actuation driver into the hub of the device 4500. Load a soft tissue trocar and U-shaped guide assembly through the posterior soft tissue and into the entry hole in the lateral clavicle bone. Retain the position of the U-shaped guide and remove the soft tissue trocar. In one embodiment, an optional step can be used if difficulty is encountered during implant insertion. The insertion guide can be introduced from the fracture through the lateral segment to help guide the device 4500 into the entry hole. In an embodiment, with the fracture adequately reduced, fully advance the device 4500 through the U-shaped guide into the entry hole and across the fracture. Countersink the device 4500 10 mm below the lateral entry point. Confirm positioning with fluoroscopic visualization. Position the device 4500 such that the posterior indicator pin is directed posteriorly and parallel with the top of the shoulder. This will ensure that the device 4500 is oriented correctly. Expand the grippers by turning the actuation driver in a first (e.g., clockwise or counterclockwise) direction, until markers (e.g., white lines) on the knob are collinear or match. Confirm satisfactory fixation of the device 4500 to the clavicle by gently pulling on the implant assembly and confirming position with fluoroscopic visualization.

In one embodiment, compression screw placement involves removing the actuation driver, hub attachment tube, and hub attachment screw from the device 4500. Insert the compression screw over the pilot wire extending from the device 4500. Use the 2.5 mm cannulated screw driver to tighten the compression screw until the fracture is adequately compressed. Confirm reduction under fluoroscopic visualization. Use the 2.0 mm drill bit to drill down to the edge of the anterior cortex. 4. Bend the pilot wire over approximately an inch from the end. Rotate the wire to remove.

In one embodiment, final evaluation and closure includes evaluating appropriate fixation of the device 4500 and deployment of the grippers in both AP and 45° cephalic radiographic views. Conclude the procedure with appropriate soft tissue and incision closure.

In one embodiment, post-operative care includes fitting the patient with a sling or shoulder immobilizer. Patients should avoid repetitive forward flexion or abduction past 90-degrees and have repeat x-rays at 2, 6 and 12-weeks or until healed. Once there is evidence of healing (callus formation bridging the fracture), the patient may increase activities.

In one embodiment, device 4500 removal from a bone is generally not considered less than 12-16 weeks after surgery and generally after radiographic healing can be verified. In some embodiments, it may be advantageous to remove the device 4500 from highly active individuals after radiographic healing has been verified.

Figure 66:
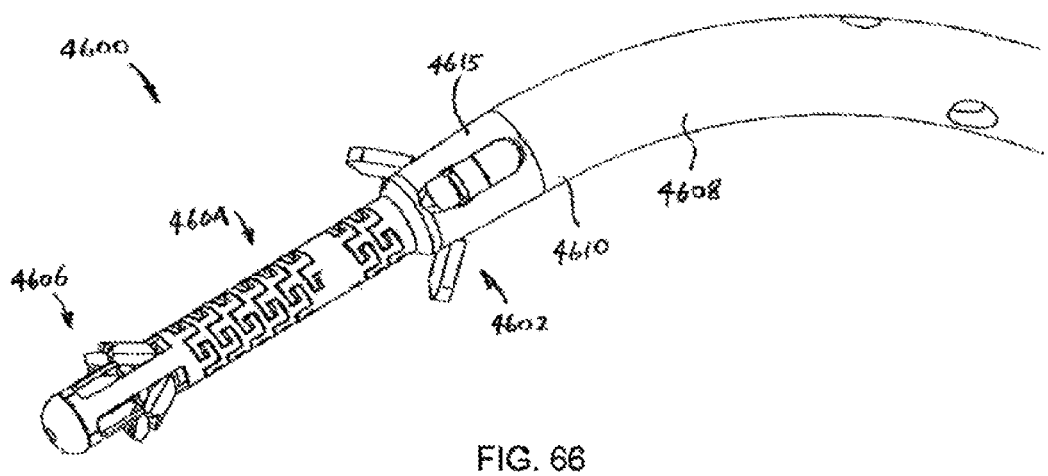
FIGS. 66-67 are views showing another embodiment of a bone fixation device.
Figure 67:
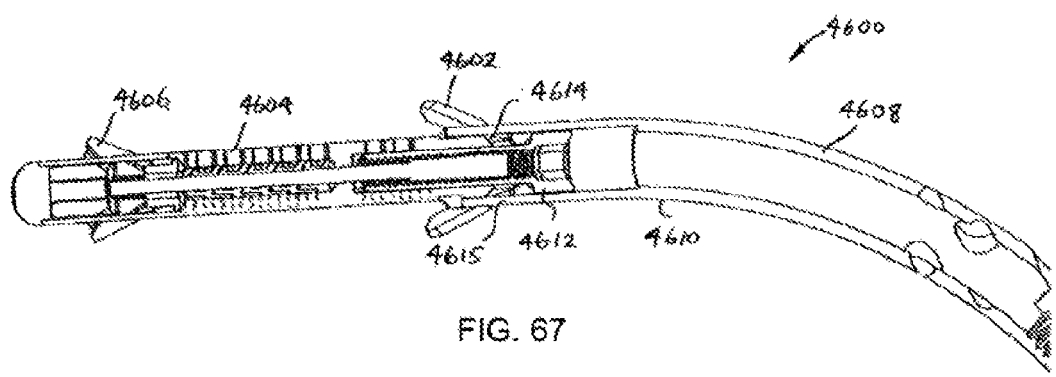
Figure 68:
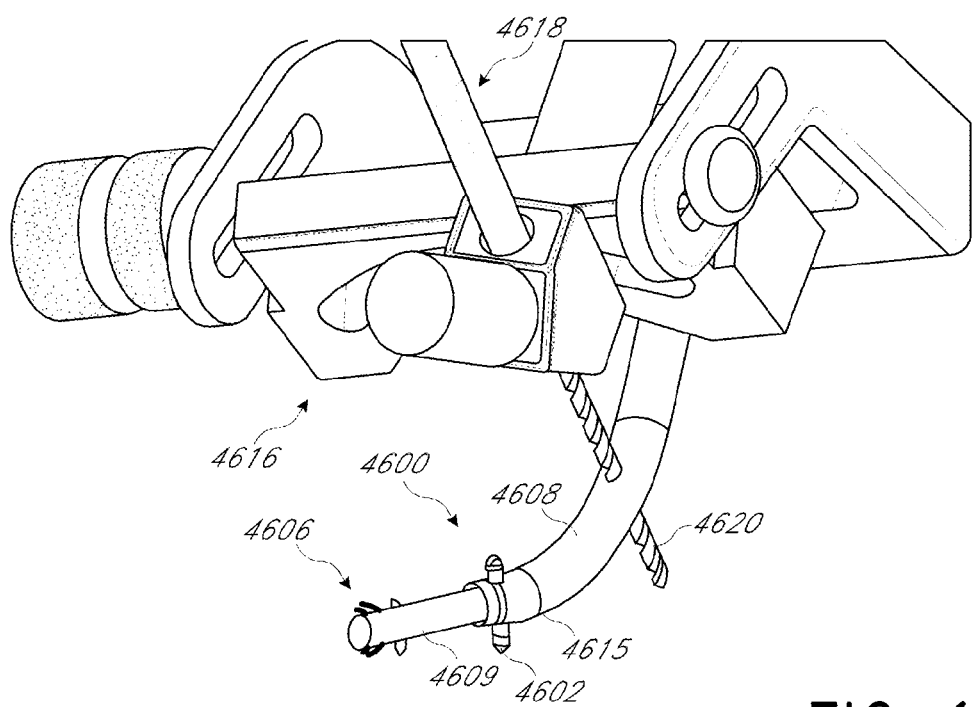
FIG. 68 is a perspective view showing the device of FIGS. 66-67 coupled with a screw hole forming guide tool.

Referring to FIGS. 66-68, another embodiment of a bone fixation device is shown. Device 4600 is similar in construction and operation to the previously described bone fixation devices. Device 4600 includes a proximal gripper 4602, flexible-to-rigid body portion 4604, and distal gripper 4606. As can been seen in the figures, flexible-to-rigid portion 4604 of the elongate body of device 4600 is disposed at a location on the elongate body distal to a first gripper 4602 and proximal to a second gripper 4606. In this embodiment, the bendable arms of proximal gripper 4602 are spaced 420 degrees apart around the axis of the device.

Device 4600 includes a curved hub 4608 having a straight section 4610 for holding inner actuation mechanism 4612. In this embodiment, the single actuation mechanism 4612 actuates both grippers 4602 and 4606. Flexible-to-rigid portion 4604 includes an interlocking cut pattern that prevents uncoiling of the body under tension. The body also has an anti-rotation feature built into it. A chamfer 4614 is provided at the proximal end of flexible-to-rigid portion 4604 to cause the bendable arms of proximal gripper 4602 to expand outwardly when body portion 4604 is driven proximally. The distal portion 4615 of curved hub 4608 maybe tapered as shown to allow for easier implantation intraoperatively.

FIG. 68 illustrates how device 4600 may be used with an external fixture 4616 to allow screw holes to be formed in hub 4608 or flexible-to-rigid portion 4604 in vivo. In some embodiments, device 4600 is devoid of any preformed screw holes before it is installed in the bone. In some embodiments, hub 4608 is made from a biocompatible material such as PEEK to allow the screw holes to be easily formed in vivo. A depth gage 4618 may be provided on the screw forming tool 4620 to aid in screw hole formation.

Figure 69:
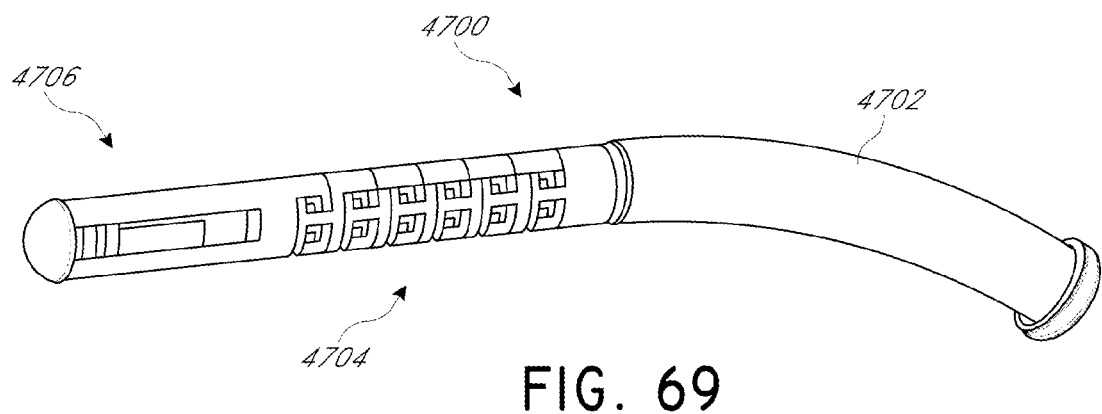
FIGS. 69-70 are various views showing another embodiment of a bone fixation device.
Figure 70:
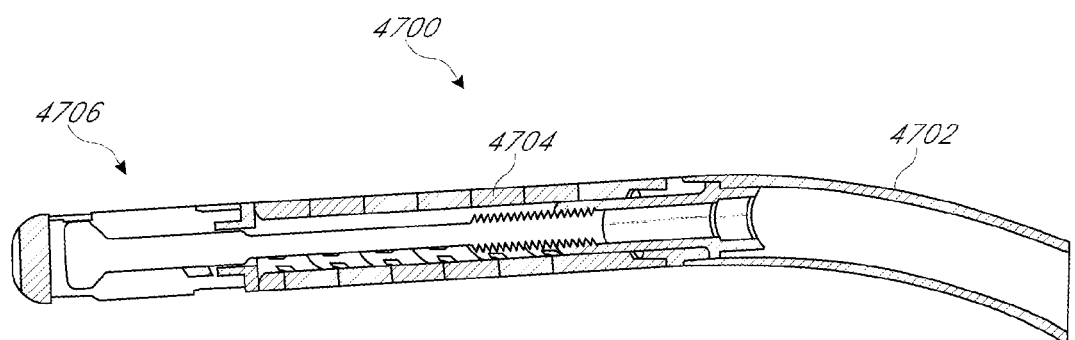
Figure 71:
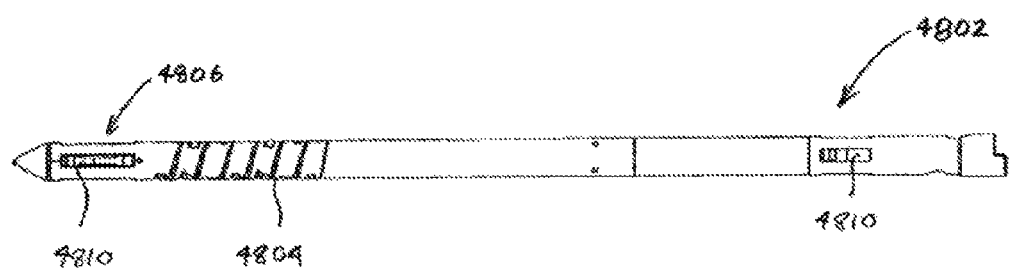
FIGS. 71-74 are various views showing another embodiment of a bone fixation device.

Referring to FIGS. 69-70, another embodiment of a bone fixation device is shown. Device 4700 is similar in construction and operation to the previously described bone fixation devices. Device 4700 includes a curved hub 4702 at its proximal end, a flexible-to-rigid body portion 4704, and a single gripper 4706 located at its distal end. As can been seen in the figures, the single actuatable bone engaging gripper 4706 is disposed on the elongate body at a location distal to the flexible-to-rigid portion 4704 of the elongate body of device 4700.

Referring to FIGS. 71-74, another embodiment of a bone fixation device is shown. Device 4800 is similar in construction and operation to the previously described bone fixation devices. Device 4800 includes a proximal gripper 4802, flexible-to-rigid body portion 4804, and distal gripper 4806. As can been seen in the figures, flexible-to-rigid portion 4804 of the elongate body of device 4800 is disposed at a location on the elongate body distal to a first gripper 4802 and proximal to a second gripper 4806. In this embodiment, each of the grippers 4802 and 4806 includes four fan-like bendable arms 4810 similar to those previously described.

Figure 72:
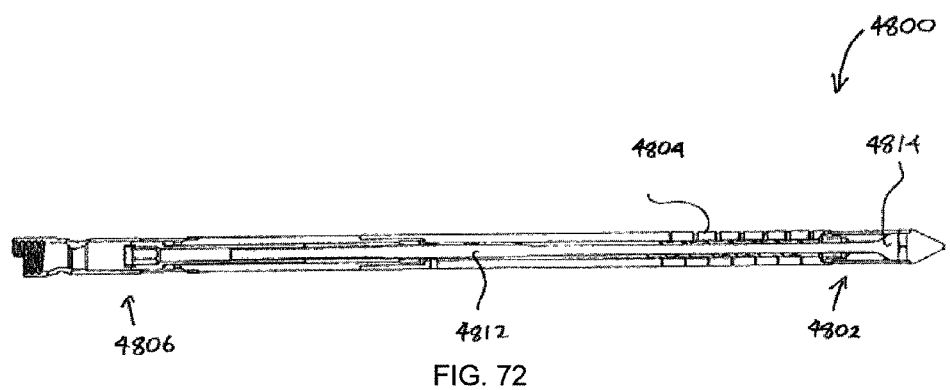
Figure 73:
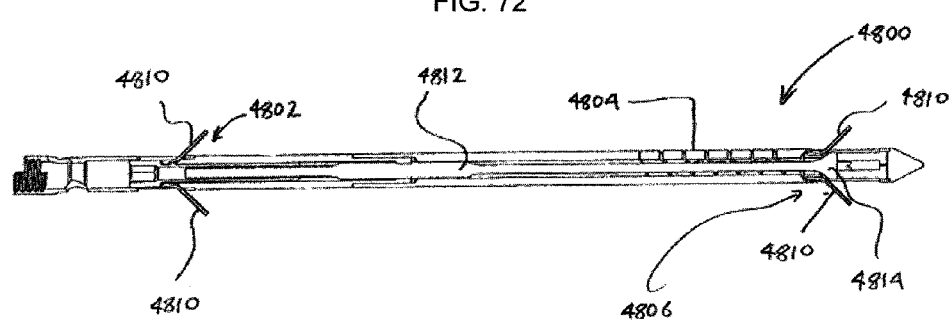
Figure 74:
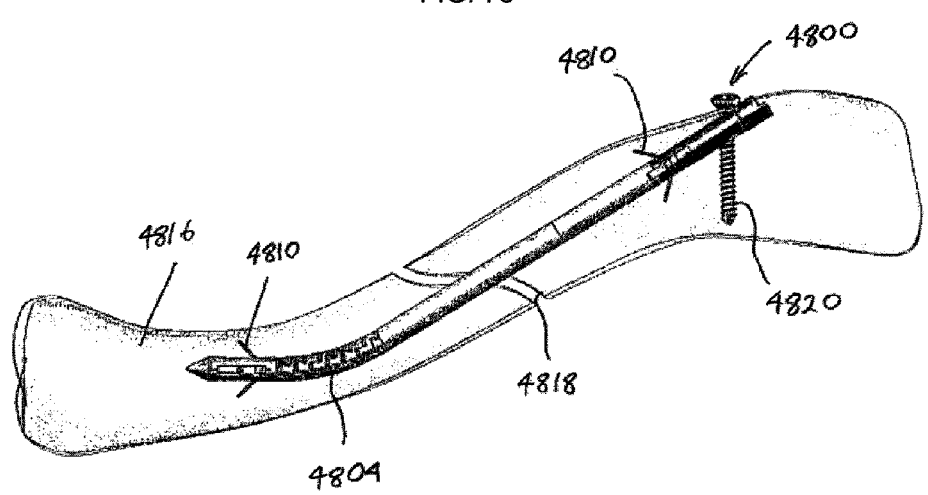
Figure 75:
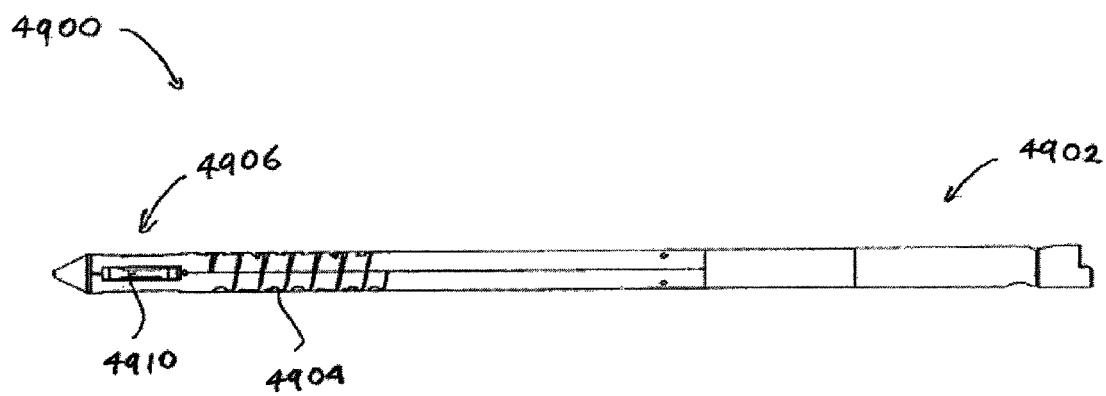
FIGS. 75-78 are various views showing another embodiment of a bone fixation device.

FIGS. 72 and 73 show cross-sections of device 4800, in which the actuator 4812 can be seen. The distal end of actuator rod 4812 is provided with a cam surface 4814 for outwardly deploying bendable arms 4810 of distal gripper 4806 from the refracted position shown in FIG. 72 to the deployed position shown in FIG. 73. FIG. 74 shows device 4800 implanted in clavicle bone 4816 across fracture 4818. One or more screws 4820 may be used to secure the proximal end of device 4800, as previously described.

Referring to FIGS. 75-78, another embodiment of a bone fixation device is shown. Device 4900 is similar in construction and operation to the previously described bone fixation devices. Device 4900 includes a straight hub 4902 at its proximal end, flexible-to-rigid body portion 4904, and distal gripper 4906. As can been seen in the figures, the single actuatable bone engaging gripper 4906 is disposed on the elongate body at a location distal to the flexible-to-rigid portion 4904 of the elongate body of device 4900. In this embodiment, single gripper 4906 includes four fan-like bendable arms 4910 similar to those previously described.

Figure 76:
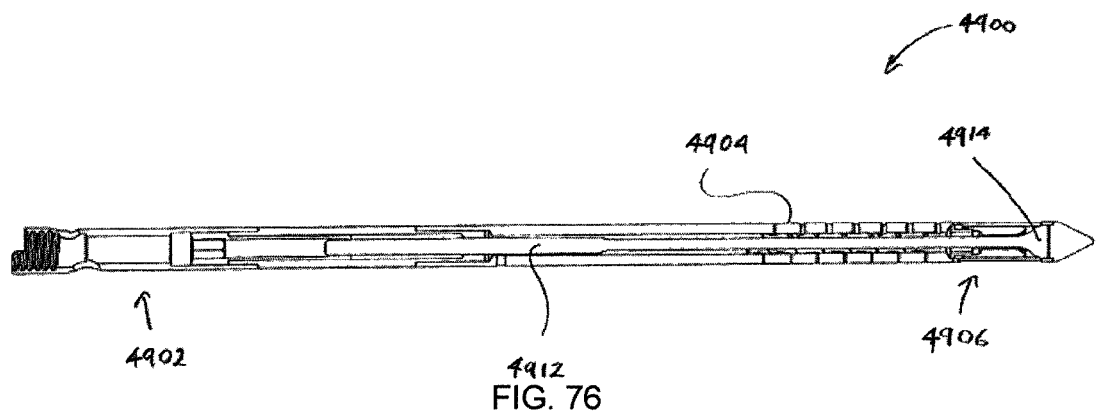
Figure 77:
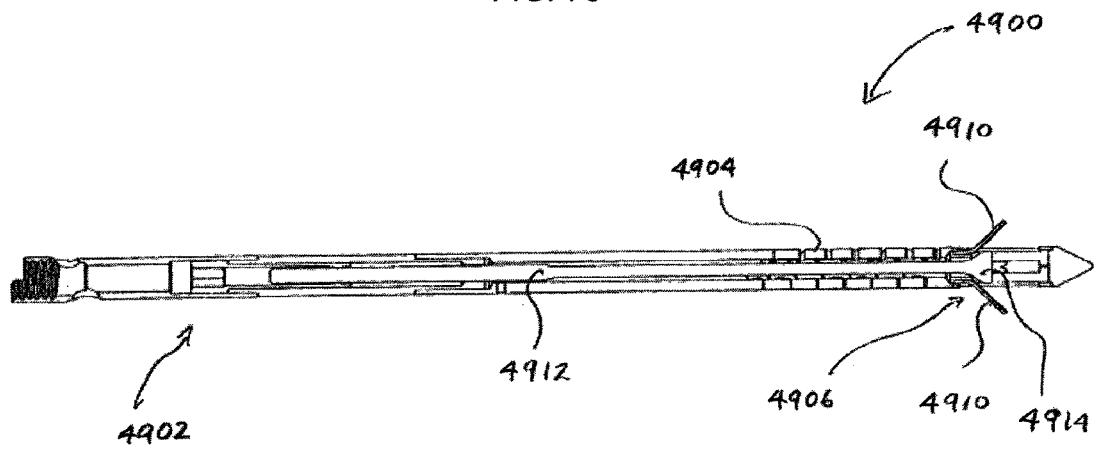
Figure 78:
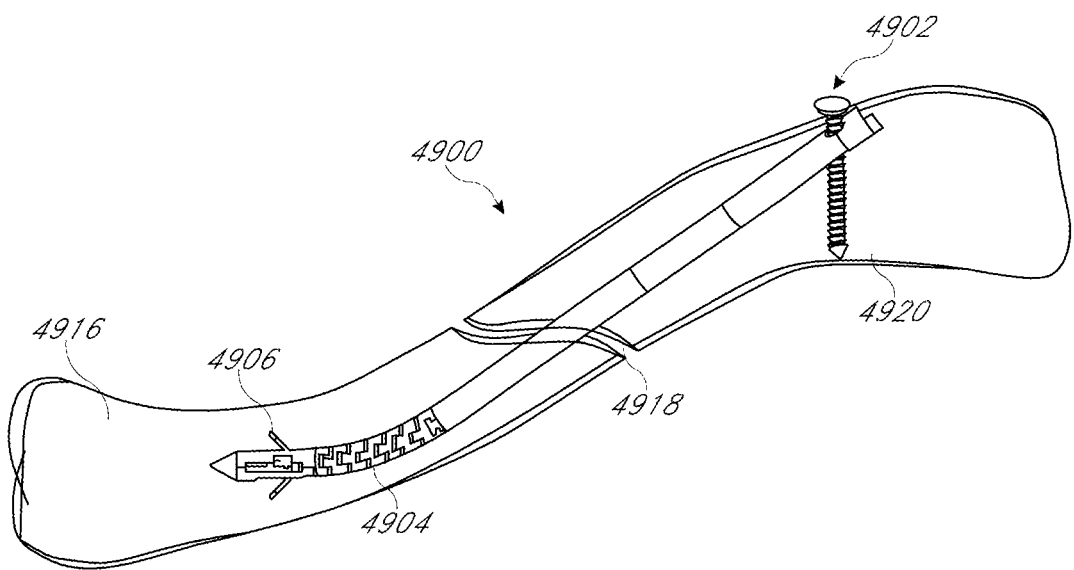

FIGS. 76 and 77 show cross-sections of device 4900, in which the actuator 4912 can be seen. The distal end of actuator rod 4912 is provided with a cam surface 4914 for outwardly deploying bendable arms 4910 of distal gripper 4906 from the retracted position shown in FIG. 76 to the deployed position shown in FIG. 77. FIG. 78 shows device 4900 implanted in clavicle bone 4916 across fracture 4918. One or more screws 4920 may be used to secure the proximal end of device 4900, as previously described.

In various embodiments, a surgical technique for deploying and/or removing any of the implants or devices, such as (but not limited to) devices 100, 3100, 3200, 3300, 3400, 3500, 4400, 4500, 4600, 4700, 4800, 4900 and other devices, can include any of the following steps.

In one embodiment, a pre-operative evaluation can comprise using AP and 45-degree cephalic tilt fluoroscopic views to evaluate the location of a clavicle fracture and associated fragments. Confirm that clear fluoroscopic images of the entire length of the clavicle can be obtained. Determine if a minimum depth of 50 mm can be achieved in the intramedullary canal of medial segment from the most medial edge of the fracture.

In one embodiment, preparation and patient positioning can involve positioning the patient in a modified beach chair position and utilizing an Allen table to gain access to posterior shoulder on the fractured side. A C-Arm can be brought in from across the body or over the top of the table. Support of the arm on the fractured side can be provided by the use of an adjustable armrest. Expose and prep the entire aspect of the clavicle from medial to lateral, including the AC joint and posterior shoulder. Alternatively, the orientation of the clavicle relative to the C-Arm can be changed by flexion or extension of the arm.

In one embodiment, surgical exposure includes making a 3 cm length horizontal or oblique incision directly over the fracture site and bluntly dissect the soft tissue structures to expose the fracture. Remove callus/scar tissue sufficiently to start medial and lateral preparation.

In one embodiment, preparation of the medial segment involves elevating the medial fracture segment and secure with a bone reduction clamp. Identify the intramedullary canal with fluoroscopic guidance and use the 2 mm drill to establish a starter hole (approximately 20 mm in depth). Follow with the 3.5 mm drill or 3 mm straight trocar to increase the diameter of the starter hole. Under fluoroscopic guidance, introduce and advance a 3 mm curved trocar, followed by a 4.5 mm curved cutting awl into the medial canal, using +/−15-degree rotating hand motions until a minimum 50 mm depth is achieved. Confirm that the curve of the awl is aligned with the curvature of the clavicle.

In one embodiment, preparation of the lateral segment includes elevating the lateral fracture segment and securing it with a bone reduction clamp. The arm can be externally rotated to help access the lateral canal. Identify the intramedullary canal with fluoroscopic guidance and use the 2 mm drill to establish a starter hole to a depth of approximately 20 mm. Introduce and advance a 4.5 mm aimer awl until the awl is fully seated in the canal but has not breached the cortex. Drive a 1.6 mm K-Wire through the cannulated aimer awl under fluoroscopic guidance to exit the clavicle bone posterior lateral to the Conoid Tubercle. When viewed in the AP view, a lateral exit point in the lateral fragment is at the equator of the posterior clavicle halfway between the Conoid Tubercle and the AC Joint. Tent the skin and make a small incision over the palpable K-Wire tip to expose the exit point. Remove the aimer awl while retaining the K-Wire. Place a 4.5 mm cannulated drill bit over the K-Wire and drill a channel through the lateral segment from lateral to medial. Remove the K-Wire and leave the drill bit in place to act as a guide.

In one embodiment, fracture reduction and canal preparation can include loading the spade tip guide wire through the 4.5 mm drill bit with a spade tip directed toward the medial segment. Reduce the fracture and introduce the guide wire into the medial segment until a marker, such as a lateral gold band, on the guide wire is within the lateral end of the 4.5 mm drill bit. Remove the drill bit while retaining the guide wire. Ensure the fracture is reduced over the guide wire. Place the flexible reamer over the guide wire and under fluoro, ream from lateral to medial.

In one embodiment, a rapid preparation may be used to prepare the medial segment without using the awls. With the medial pilot hole established and the lateral segment prepared, the spade tip guide wire can be driven through the 4.5 mm drill bit into the medial segment under power. Drive the wire into the medial segment until a marker (e.g., such as a gold band) on the wire is within the lateral end of the drill. Remove the drill taking care to retain the placement of the wire. Verify the position of the wire using fluoroscopy. Use the flexible reamer to ream from lateral to medial to the tip of the spade wire.

In one embodiment, implant sizing and preparation can involve placing a reamer depth gauge over the reamer and advancing it until it contacts the lateral bone. Determine the appropriate length implant by reading the length on the scale. In various embodiments, implants are available in 90, 100, 110, 120, and 130 mm lengths. If an implant measurement falls between two sizes, choose the longer implant. Remove depth gauge, guide wire, and reamer. Prepare the implant by inserting the hub attachment tube into the outrigger and aligning markings, (such as, e.g., an "A" to an "A" letter marking). Insert the attachment screw into the hub of the implant. Align the notches in the hub and hand tighten.

In one embodiment, implant insertion and fixation can include inserting the actuation driver into the hub of the implant. Load the soft tissue trocar and U-shaped guide assembly through the posterior soft tissue and into the entry hole in the lateral clavicle bone. Retain the position of the U-shaped guide and remove the soft tissue trocar. In one embodiment, an optional step can be used if difficulty is encountered during implant insertion: the insertion guide can be introduced from the fracture through the lateral segment to help guide the implant into the entry hole. In an embodiment, with the fracture adequately reduced, fully advance the implant through the U-shaped guide into the entry hole and across the fracture. Confirm positioning with fluoroscopic visualization. Position the outrigger in a parallel plane with the top of the shoulder, so that the direction of the screw will engage the cortex of the lateral clavicle bone. Expand the grippers by turning the actuation driver in a clockwise direction, until the white lines on the knob are collinear. Confirm satisfactory fixation of the implant to the clavicle by gently pulling on the outrigger assembly and confirming position with fluoroscopic visualization.

In one embodiment, lateral screw placement involves removing the actuation driver from the outrigger. Insert the soft tissue trocar into the external sheath. Make a small stab incision and advance the sheath and trocar until it comes in direct contact with the clavicle bone. Remove the soft tissue trocar and insert the drill guide into the external sheath. Under fluoroscopic guidance, use a 2.0 mm drill bit to drill down to the edge of the anterior cortex. Use the scale on the drill guide to measure the appropriate length 2.7 mm screw. Subtract 2 mm to allow for screw countersinking. Remove the drill guide from the external sheath and insert the screw guide. Insert the screw and tighten with a 2.5 mm hex driver. Verify that the screw has passed through the implant by reinserting the actuation driver.

In one embodiment, final evaluation and closure includes evaluating appropriate fixation of the implant and deployment of the grippers in both AP and 45° cephalic radiographic views. Cerclage techniques can be used when butterfly fragments are present and/or to provide additional compressive fixation when a significant degree of obliquity is encountered in the fracture pattern. The notched Crego elevator may be used as a guide to pass the suture needle around the clavicle. A #1 PDS suture on a CTX needle can also be used. Conclude the procedure with appropriate soft tissue and incision closure.

In one embodiment, post-operative care includes fitting the patient with a sling or shoulder immobilizer. Patients should avoid repetitive forward flexion or abduction past 90-degrees and have repeat x-rays at 2, 6 and 12-weeks or until healed. Once there is evidence of healing (callus formation bridging the fracture), the patient may increase activities.

In one embodiment, device removal from a bone is generally not considered less than 12-16 weeks after surgery and generally after radiographic healing can be verified. In some embodiments, it may be advantageous to remove the device from highly active individuals after radiographic healing has been verified.

Figure 79:
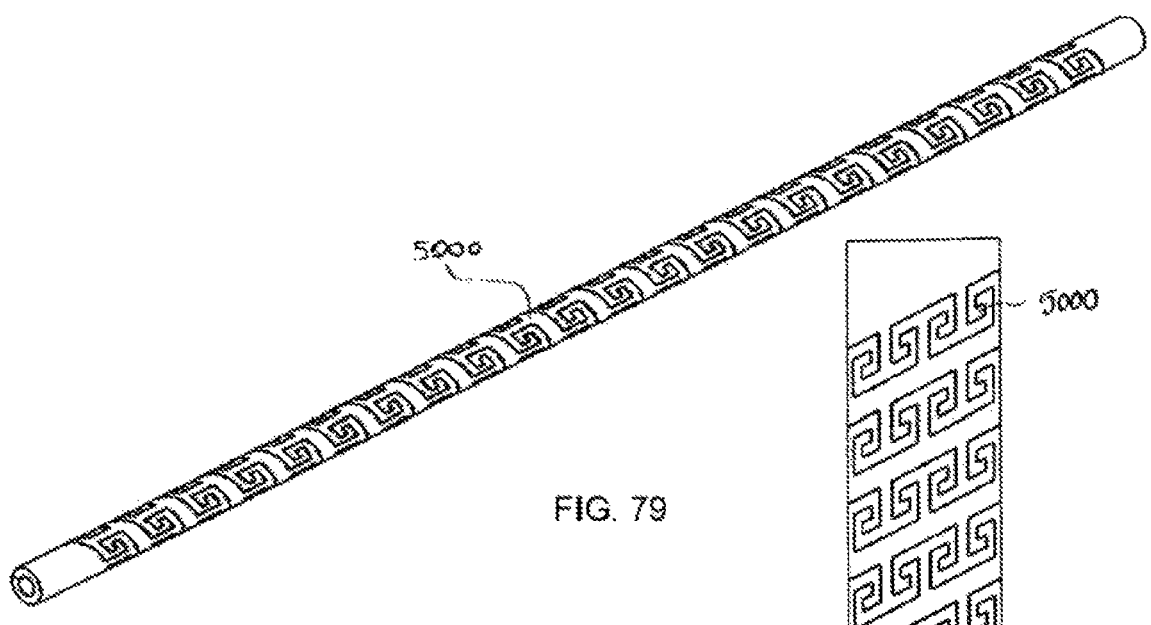
FIG. 79 is a perspective view showing another embodiment of a flexible-to-rigid body portion of a bone fixation device.
Figure 80:
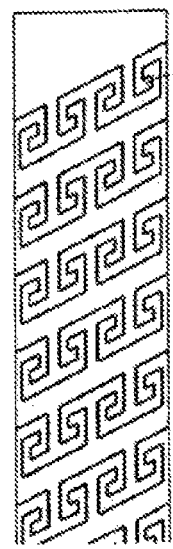
FIG. 80 is a plan view showing part of the cut pattern of the body portion of FIG. 79 laid flat.

Referring to FIGS. 79 and 80, another embodiment of a flexible-to-rigid body portion 5000 is shown. FIG. 79 shows a perspective view of body portion 5000 having a spiral cut formed through its tube wall. FIG. 80 shows a plan view of the cut pattern laid flat. Under axial compression, the extensions formed by the spiral cut collide, aiding in the rigidity of the construct.

Figure 81:
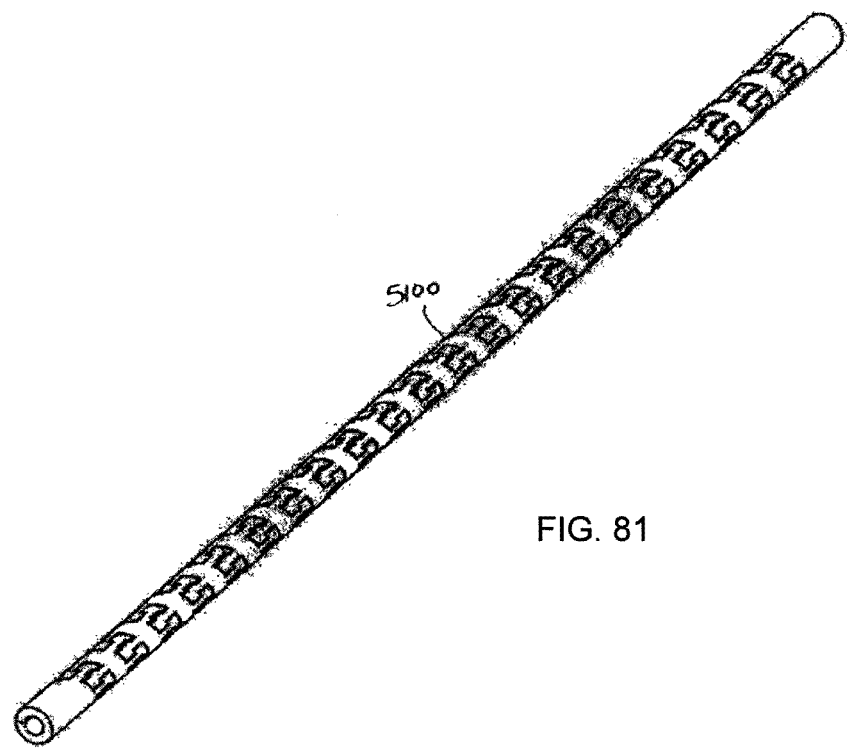
FIG. 81 is a perspective view showing another embodiment of a flexible-to-rigid body portion of a bone fixation device.
Figure 82A:
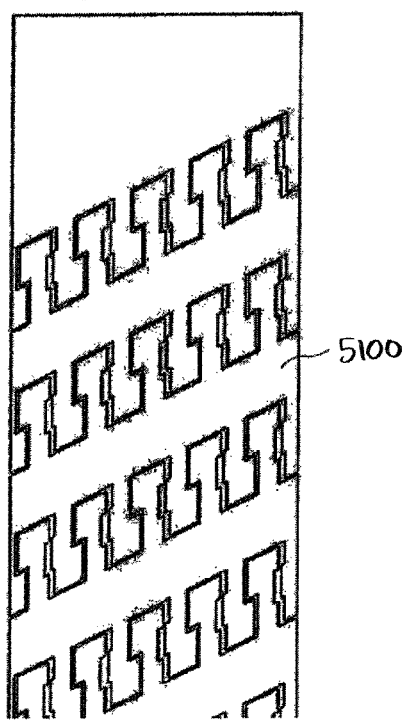
FIG. 82A is a plan view showing part of the cut pattern of the body portion of FIG. 81 laid flat.

Referring to FIGS. 81 and 82A, another embodiment of a flexible-to-rigid body portion 5100 is shown. FIG. 81 shows a perspective view of body portion 5100 having a spiral cut formed through its tube wall. FIG. 82A shows a plan view of the cut pattern laid flat. Axial compression causes the proximally and distally extending features to translate transverse to the longitudinal axis of the body portion 5100. This lateral movement causes keying features formed on the extending features to inter-engage, aiding in the rigidity of the construct.

Figure 82B:
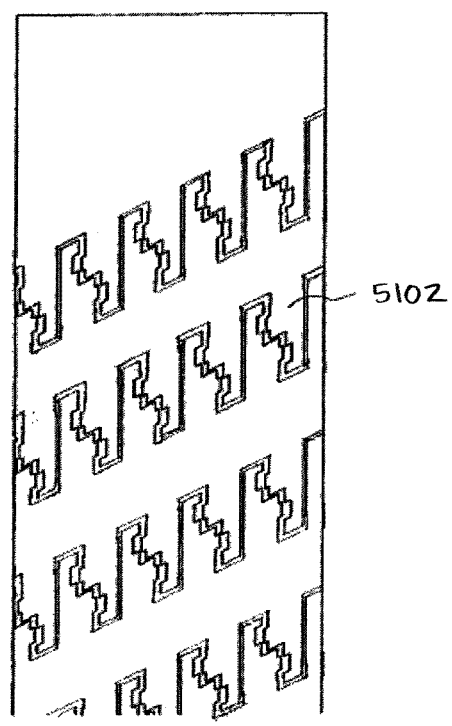
FIG. 82B is a plan view showing part of a cut pattern laid flat, similar to the one shown in FIGS. 81 and 82A.

Referring to FIG. 82B, another embodiment of a flexible-to-rigid body portion 5102 is shown in plan view, with the cut pattern laid flat. Like the pattern shown in FIG. 82A, axial compression causes the proximally and distally extending features to translate transverse to the longitudinal axis of the body portion 5102. This lateral movement causes keying features formed on the extending features to inter-engage, aiding in the rigidity of the construct.

Figure 83:
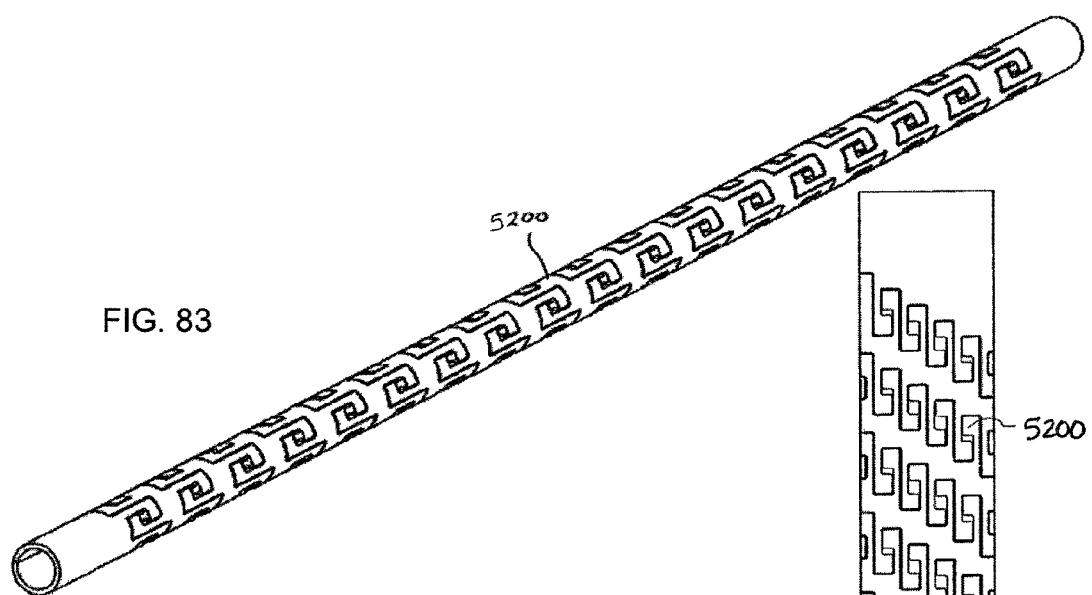
FIG. 83 is a perspective view showing another embodiment of a flexible-to-rigid body portion of a bone fixation device.
Figure 84:
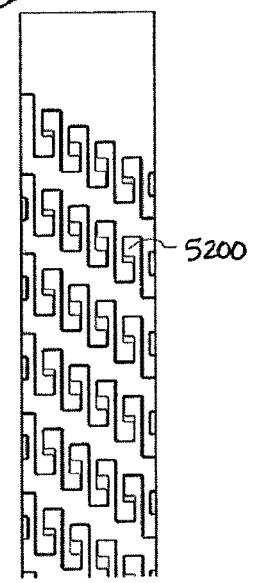
FIG. 84 is a plan view showing part of the cut pattern of the body portion of FIG. 83 laid flat.

Referring to FIGS. 83 and 84, another embodiment of a flexible-to-rigid body portion 5200 is shown. FIG. 83 shows a perspective view of body portion 5200 having a spiral cut formed through its tube wall. FIG. 84 shows a plan view of the cut pattern laid flat. The interlocking features of the spiral cut are transverse to the longitudinal axis of the body portion 5200. This maximizes contact surface in compression to aid in rigidity. The gap between the arms may be varied as shown to increase flexibility in one plane.

Figure 85:
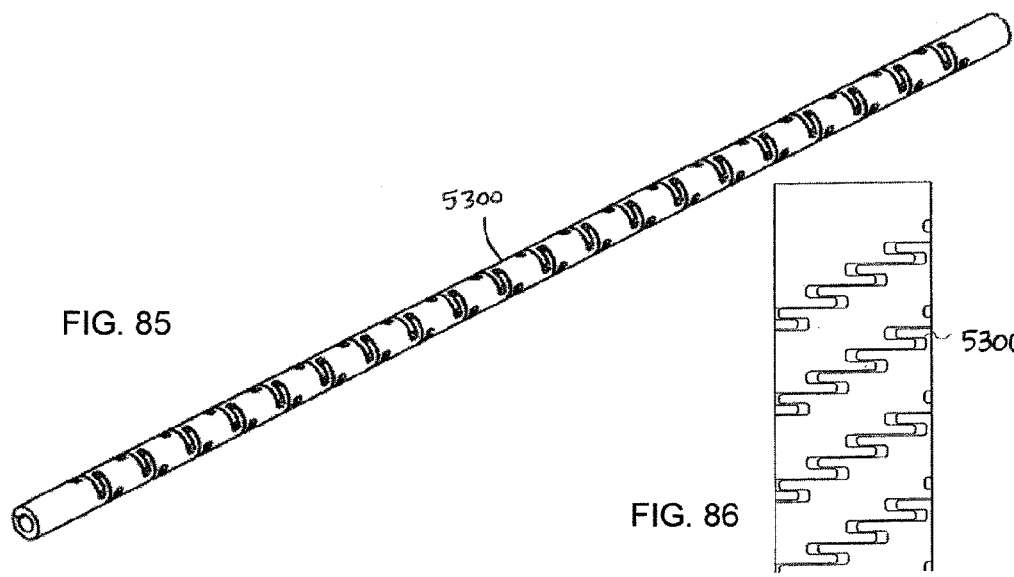
FIG. 85 is a perspective view showing another embodiment of a flexible-to-rigid body portion of a bone fixation device.
Figure 86:
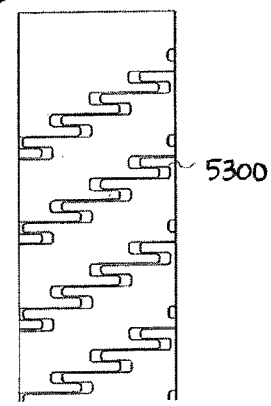
FIG. 86 is a plan view showing part of the cut pattern of the body portion of FIG. 85 laid flat.

Referring to FIGS. 85 and 86, another embodiment of a flexible-to-rigid body portion 5300 is shown. FIG. 85 shows a perspective view of body portion 5300 having a spiral cut formed through its tube wall. FIG. 86 shows a plan view of the cut pattern laid flat. The features of the spiral cut step horizontally, transverse to the longitudinal axis of the body portion 5200. This maximizes contact surface in compression. Varying gaps allow the body to twist more.

Figure 87:
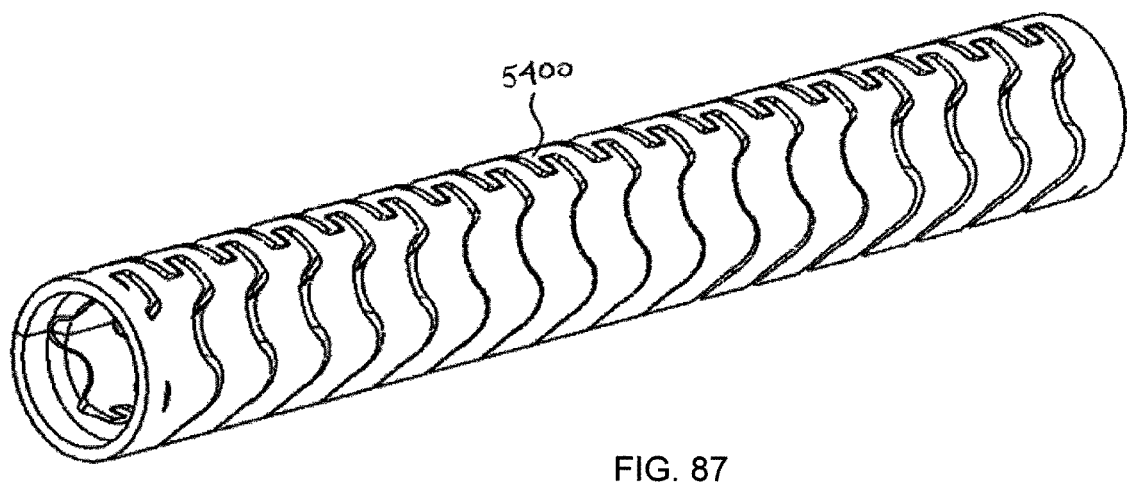
FIG. 87 is a perspective view showing another embodiment of a flexible-to-rigid body portion of a bone fixation device.
Figure 88:
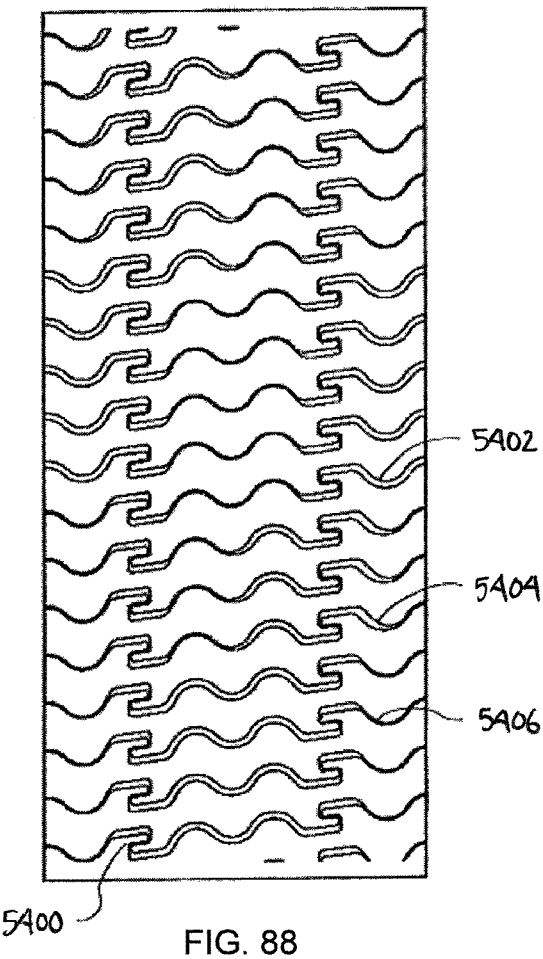
FIG. 88 is a plan view showing the cut pattern of the body portion of FIG. 87 laid flat.

Referring to FIGS. 87 and 88, another embodiment of a flexible-to-rigid body portion 5400 is shown. FIG. 87 shows a perspective view of body portion 5400 having a spiral cut formed through its tube wall. FIG. 88 shows a plan view of the cut pattern laid flat. The pattern of the spiral cut includes a sinusoidal wave interrupted by locking features. The gap formed by the cut can be varied longitudinally. For example, the gap at locations 5402, 5404 and 5406 can get progressively smaller as shown. When body portion 5400 is axially compressed, it forms a curve in each segment in which the gap is varied. The resulting shape is a curve which spirals down the length of the body, similar to the shape of a cork screw. In some embodiments, this shape aids the device in being able to grip the interior surfaces of the bone.

FIGS. 89-93 show further details of another exemplary rotary driver tool 6132', similar to the driver tool 6132 shown in FIG. 32, constructed according to aspects of the invention. Driver tool 6132' maybe used to actuate gripper 6108 and compress a flexible-to-rigid body portion after device 100 is inserted into bone 6106. Driver 6132' may also be used to allow body portion to decompress and gripper 6108 to retract if removal of device 100 from bone 6106 is desired. In the embodiment shown in FIGS. 89-93, driver 6132' includes cap 110, retaining ring 112, knob 6154', spring 6156, hub 6158', and shaft 6162. The distal end of shaft 6162 is provided with a mating tip 6164, such as one having an Allen, Torx®, Philips, or similar shape, for engaging with keyed socket 6130 of device 100, such that turning driver shaft 6162 turns actuator 6126, as previously described.

The proximal end of shaft 6162 maybe integrally formed with hub 6158', such as with an insert mold process. In this embodiment, knob 6154' is rotatably mounted over hub 6158' such that knob 6154' can rotate independently from hub 6158' and shaft 6162. Knob 6154' may be restrained from axial movement in the proximal direction (i.e. away from shaft 6162) by retaining ring 112. In this embodiment, retaining ring 112 engages with groove 114 in the proximal end of hub 6158', shown in FIG. 93. A torsion spring 6156 may be used to couple knob 6154' to hub 6158' as shown. More specifically, distal leg 116 of spring 6156 engages with slot 118 in hub 6158', and proximal leg 6120 engages with a similar feature (not shown) within knob 6154'.

With the indirect coupling arrangement just described, as knob 6154' is rotated about hub 6158' and shaft 6162, spring 6156 urges hub 6158' and shaft 6162 to rotate in the same direction. Rotational resistance applied by device 100 to shaft tip 6164 will increase in this embodiment as gripper 6108 engages bone 6106, and flexible-to-rigid body portion compresses. As more torque is applied to knob 6154', it will advance rotationally with respect to hub 6158' as torsion spring 6156 undergoes more stress.

A pair of marks 122 may be provided on knob 6154' for aligning with a corresponding pair of marks 124 on hub 6158' when a predetermined torque is applied to knob 6154'. In this manner, a surgeon can use driver 6132' to apply an exact amount of torque to device 100. This can help ensure that gripper 6108 is adequately set in bone 6106, body portion is sufficiently compressed, and excessive torque is not being applied that might damage device 100, bone 6106 or cause slippage therebetween.

Figure 89:
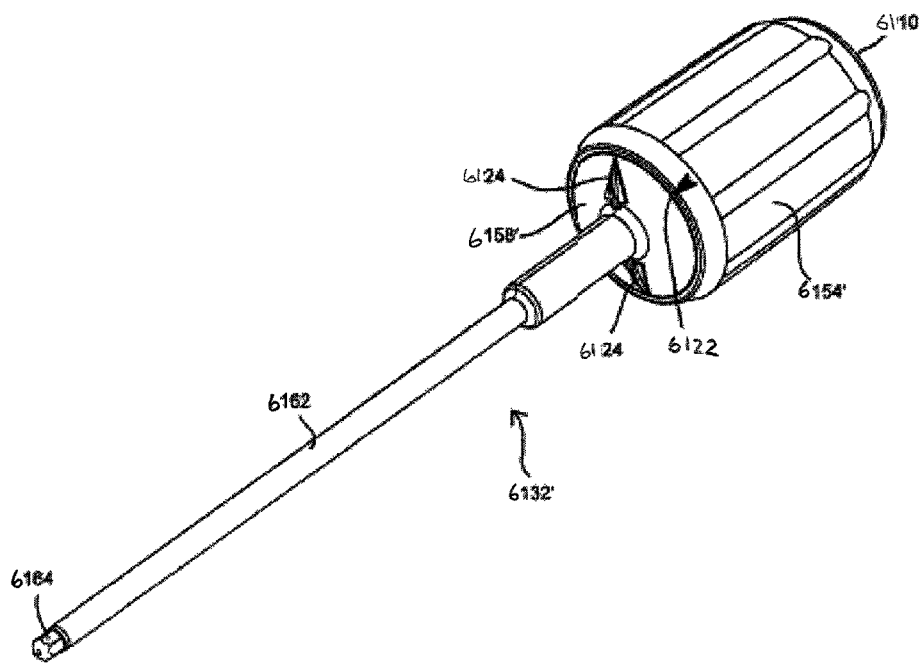
FIG. 89 is a perspective view of an exemplary rotary driver tool constructed according to aspects of the invention.
Figure 90:
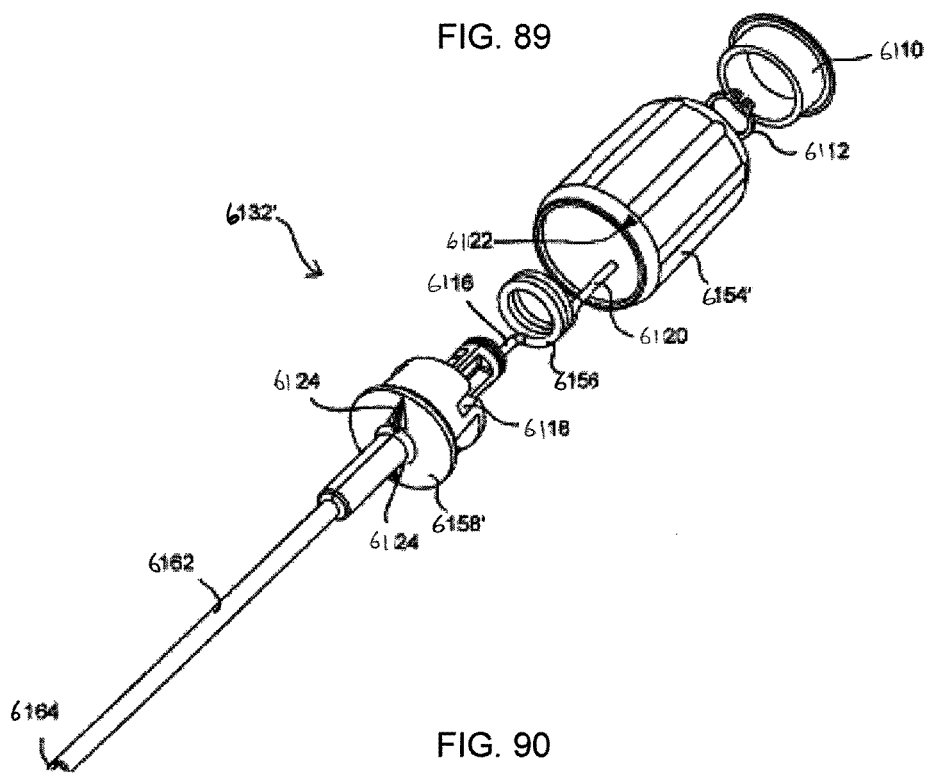
FIG. 90 is a proximally-looking exploded view showing the driver tool of FIG. 89.
Figure 91:
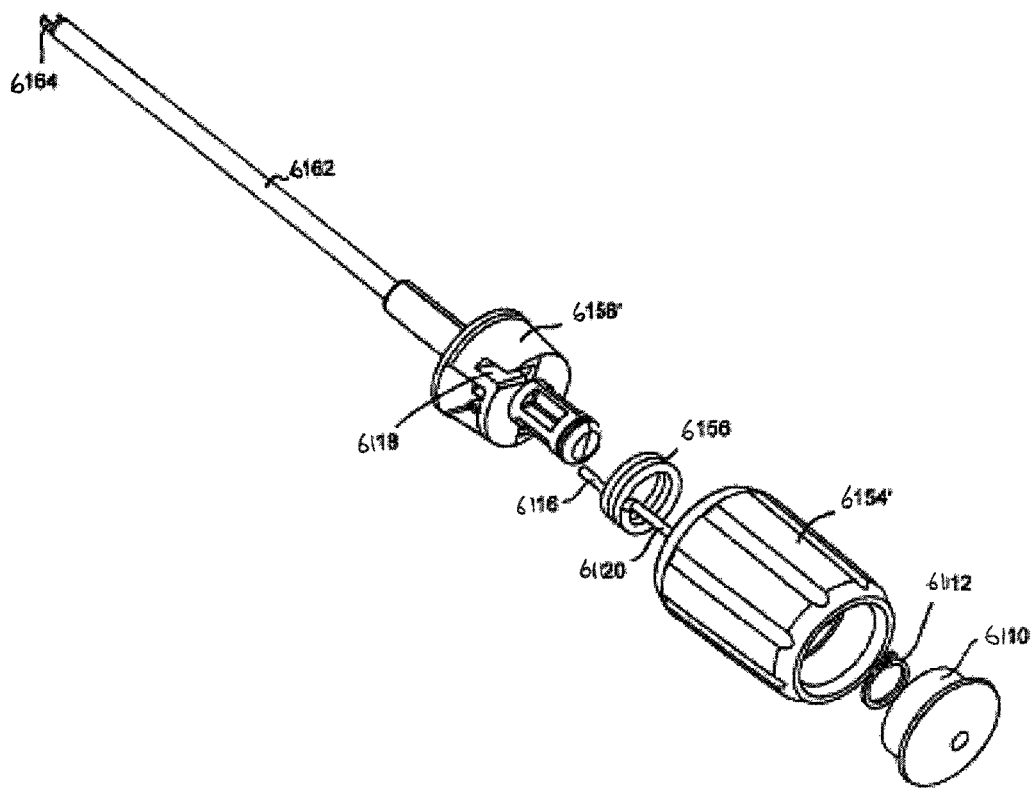
FIG. 91 is a distally-looking exploded view showing the driver tool of FIG. 89.
Figure 92:
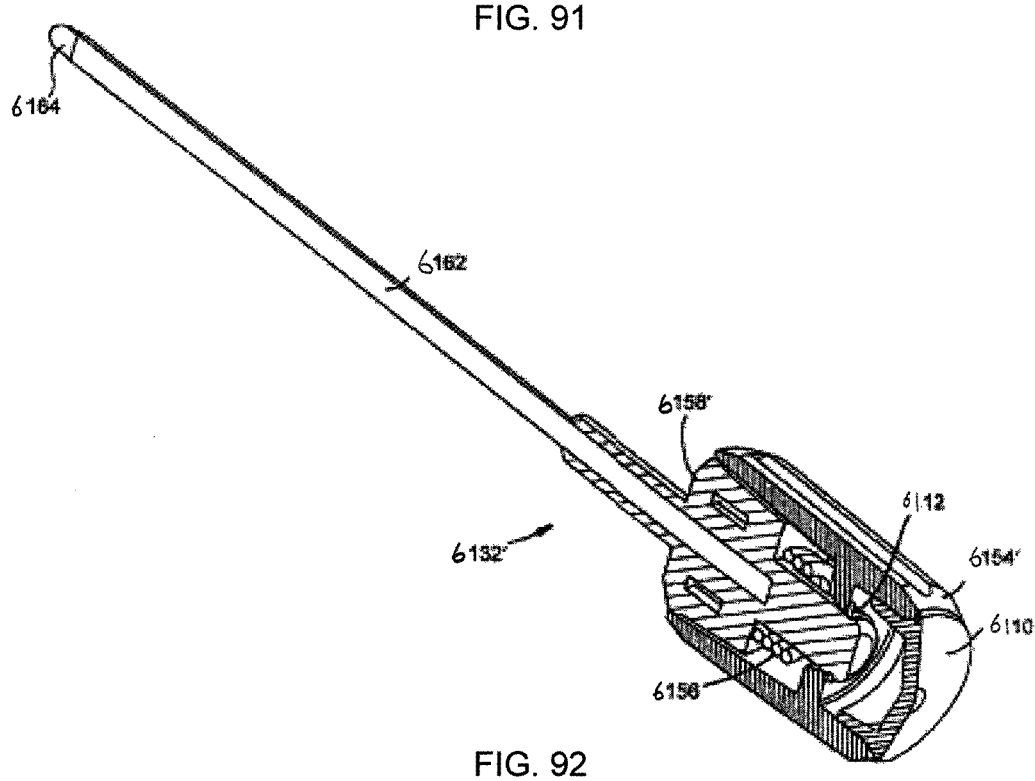
FIG. 92 is a longitudinal cross-sectional view of the driver tool of FIG. 89.
Figure 93:
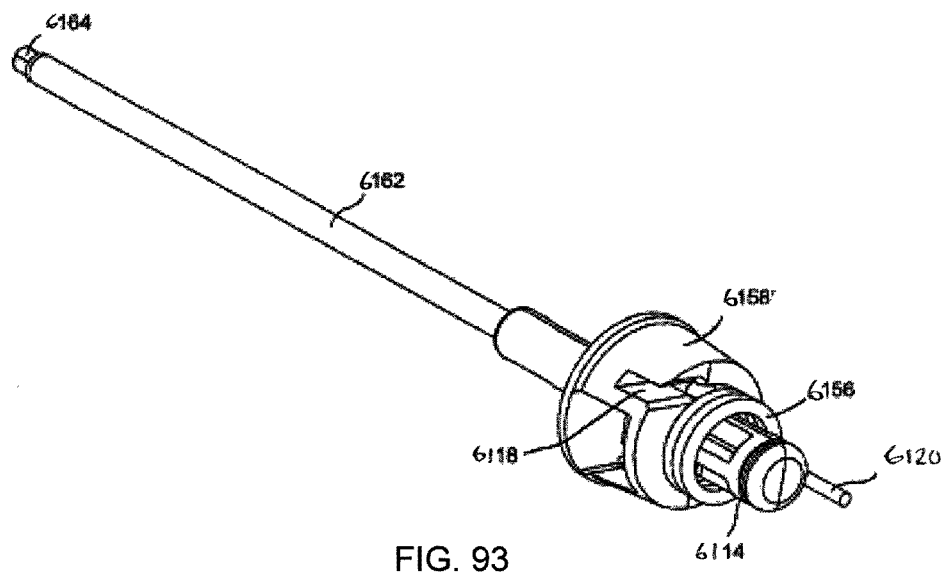
FIG. 93 is a perspective view of the driver tool of FIG. 89 with the knob, cap and retaining ring removed to more clearly show the other components of the tool.

Driver 6132' may be calibrated by not applying marks 122 to knob 6154' until after the driver is fabricated, assembled and calibrated. Marks 124 may be molded onto the distal surface of hub 6158' as shown during fabrication. After tool 6132' is assembled, either tool tip 6164 or knob 6154' can be held in a stationary position while a predetermined torque is applied to the other component, such as with a precisely calibrated torque wrench. With this known torque applied, knob 6154' will have moved rotationally relative to hub 6158' from its relaxed position. Once in this moved position, marks 122 maybe applied to knob 6154' directly adjacent to marks 124 on hub 6158'. When the predetermined torque is released, marks 122 and 124 will rotationally separate as knob 6154' returns to its relaxed position, as shown in FIG. 89. During use, the user merely needs to align marks 122 with marks 124 to obtain the precise torque desired. Marks 122 can be applied during calibration by laser etching, mechanical engraving, painting, adhering a marker, melting a portion of knob 6154', or other such means. Alternatively, other methods of calibrating driver 6132' known to those skilled in the art maybe used.

Tool shaft 6162 may be configured to be rigid for simplicity and low cost. Alternatively, shaft 6162 may be configured to be flexible so that it may access devices implanted in curved intramedullary spaces. This may be accomplished by constructing shaft 6162 from a flexible material. However, it many circumstances, it desirable that tool shaft 6162 only be flexible in a lateral bending direction, but as stiff as possible in tension, compression and torsion so that the tool is responsive during use. These goals may be accomplished by constructing shaft 6162 from one or more layers of oppositely wound wire cable, or by using other composite assembly techniques or materials.

Driver tools 6132 and 6132' described above provide ease of torque control for the user to limit the torque of device deployment. The tools increase resolution and reaction time for ceasing application of torque. These tools accurately control the tension on the implanted devices and the load on the bone when deployed, and increase patient safety. Because the tools are designed to be simple, they are inexpensive to manufacture. The tools may be designed and constructed to be sterilized for multiple uses, or they may be optimized for disposable, single-use.

Figure 94:
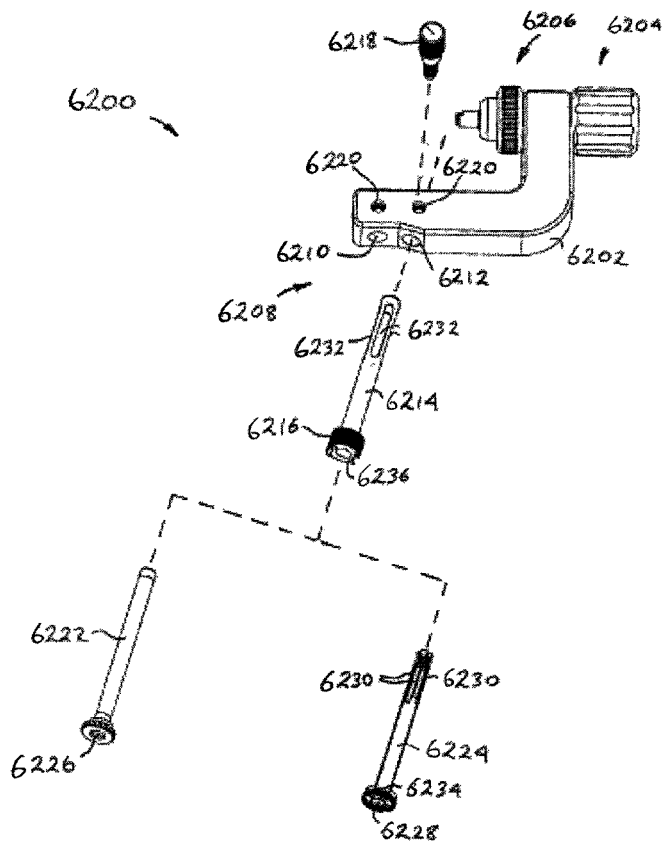
FIG. 94 is an exploded view showing a variation of the combination tool of FIG. 31.

Referring to FIG. 94, a variation of the combination tool of FIG. 31 will now be described. Combination tool 6200 includes a body 6202, a device attachment portion 6204, and an approximating driver 6206. Since these components are similar in construction and operation to those on tool 6138 described above, they will not be further described.

Figures 95, 96A:
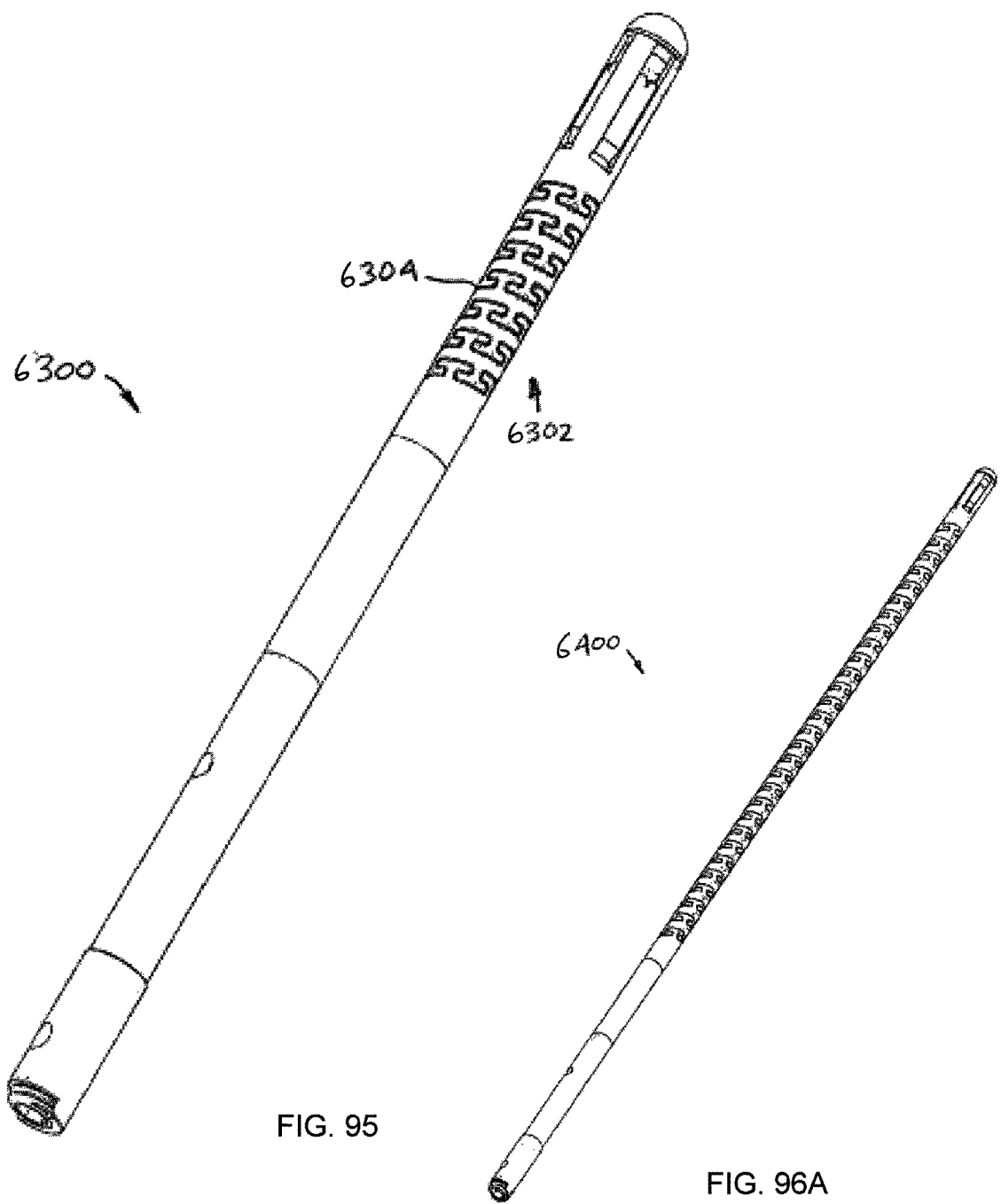
FIG. 95 is a perspective view showing a variation of the bone repair device of FIG. 28.
FIG. 96A is a perspective view showing an alternative bone repair device.

Combination tool 6200 also includes a screw alignment portion 6208, similar to that of tool 6138. In this embodiment, tool 6200 has a distal bore or aperture 6210 and a proximal bore or aperture 6212. Each of the apertures 6210 and 6212 is sized to receive an alignment sleeve 6214. In some embodiments, each aperture 6210 and 6212 has its own alignment sleeve 6214. In other embodiments, a single alignment sleeve 6214 may be alternately placed in one of the two apertures 6210 and 6212 at any given time. Retaining sleeve(s) 6214 maybe provided with an enlarged head 6216 on its proximal end to abut against tool body 6202 when inserted through apertures 6210 and 6212. A retaining device such as a knurled thumb screw 6218 may be used to thread through holes 6220 in tool body 6202 to secure alignment sleeve 6214 within apertures 6210 and 6212. In the exemplary embodiment of FIG. 94, a drill bushing 6222 and a screw bushing 6224 are provided, each to be alternately received within the central axial bore of alignment sleeve 6214. Drill bushing 6222 has an axial bore 6226 for receiving a drill bit used to drill screw holes in the bone for securing the bone fixation device, as described above. Screw bushing 6224 is configured with an axial bore 6228 for receiving a bone screw and the shaft of a screw driver. Barbed fingers 6230 longitudinally extending from the distal end of screw bushing 6224 help retain the screw while it is being driven into the bone with the screw driver. Fingers 6230 may flex radially outward when holding a screw, and may flex further outward when releasing the screw. Cutouts 6232 may be provided through the distal end of alignment sleeve 6214 to allow fingers 6230 of screw bushing 6224 to flex outward. In this embodiment, flats 6234 are provided on the proximal head of screw bushing 6224 to engage with keyway 6236 on alignment sleeve head 6216 to properly align screw bushing fingers 6230 with alignment sleeve cutouts 6232. Referring to FIG. 95, an alternative embodiment of bone fixation device 6300 is shown.

Device 6300 is similar in construction and operation to device 100 described above. Device 6300 also includes a flexible-to-rigid body portion 6302 having a generally helical slit 6304 formed through the tube wall of that portion of the body. The helical slit 6304 of this embodiment forms a T-shaped pattern such that the body portion adjacent to one side of slit 6304 interlocks with the body portion on the directly opposite side of slit 6304. The interlocking nature of this helical pattern allows device 6300 to have only limited axial movement when subjected to axial tension loads. Axial tension loads may occur when a surgeon removes device 6300 from the intramedullary space within a bone by pulling on the proximal end of device 6300. In some embodiments, device 6300 can withstand axial tension loads of up to 200 pounds or more. In some embodiments, device 6300 has an outside diameter of about 5 mm and a length of about 100 mm.

Referring to FIGS. 96A-96C, another embodiment of bone fixation device 6400 is shown. Device 6400 is similar to device 6300 described above, but has a longer flexible-to-rigid body portion. In one embodiment, devices 100 and 6300 are used with fractures of the proximal ulna. In some embodiments, device 100 or 6300 may be inserted into the intramedullary space of the proximal ulna through the olecranon. Exemplary indications for device 6400 include mid-shaft fractures of the ulna. In some embodiments, device 6400 has an outside diameter of 4 mm and a length of 200 mm. In other embodiments, device 6400 has an outside diameter of 5 mm and a length of 250 mm. Other sizes may be utilized to suit particular anatomies and injury or disease states. Other helical slit patterns on flexible-to-rigid body portions, different gripper locations, gripper types, and a different numbers of grippers (including no grippers) may also be utilized.

It is also envisioned in an alternate embodiment that a tension band in a figure-of-eight or other pattern be used to secure the entry point of the device to a position towards the hand. The tools described herein would provide for drilling one or more holes through the bone and/or the fixation device, and positioning either suture, wire, or other material so that a figure-of-eight or other pattern could be laced along the bone, through a hole in bone. In one embodiment, an elbow can be treated, with lacing along a bone, through a distal hole (toward the hand) of the shaft of the ulna and around the orifice at the proximal (elbow) end of the device. In one embodiment, one or more tension bands can be used.

FIGS. 97, 98A and 98B show various exemplary embodiments of anatomy or shape conforming body portions constructed according to aspects of the present invention. These and other body portions may be used in bone fixation devices similar to those described above. These body portions may be used in place of body portion 7114 previously described to allow the device to take on a shape that conforms to a particular anatomy when the body of the device is axially compressed when making the device substantially rigid.

Referring first to FIG. 97, flexible-to-rigid tubular body portion 7114' includes a first side 7410 which forms a solid spine and a second side 7412 which has a series of straight, V-shaped cuts 7414 in it. In this embodiment, the V-shaped cuts 7414 extend a substantial portion of the way across the diameter of tubular body portion 7114'. As body portion 7114' is axially compressed in manner similar to body portion 7114 previously described, the first side 7410 retains its original length because it is solid. The second side 7412, however, is foreshortened as V-shaped cuts 7414 begin to close. With this difference in lengths between sides 7410 and 7412, body portion 7114' takes on a curved shape, with first side 7410 becoming convex and second side 7412 becoming concave. The curved configuration of body portion 7114' can be designed to match the curve of an intramedullary bone cavity where the body portion 7114' is being implanted.

FIG. 98A shows another embodiment of a flexible-to-rigid tubular body portion 7114". Body portion 7114" has a first side 7510, a second side 7512, and a series of wavy slits 7514. Slits 7514 may be individual slits extending partially around the circumference of body portion 7114", leaving a solid spine near first side 7510, similar to first side 7410 shown in FIG. 97. Alternatively, slits 7514 may extend completely around the circumference of body portion 7114', creating a series of solid wavy rings therebetween. In yet another alternative, slits 7514 may extend completely around the circumference of body portion 7114" in spiral fashion to create one continuous helical slit.

As can be seen in FIG. 98A, slits 7514 have a varying width that increases as they extend from first side 7510 to second side 7512. With this configuration, second side 7512 will foreshorten more than first side 7510 as slits 7514 close during axial compression. This results in body portion 7114" taking on a curved shape, with first side 7510 becoming convex and second side 7512 becoming concave. The alternating curves of slits 7514 provide increased torsional rigidity, particularly when body portion 7114" is axially compressed.

FIG. 98B shows yet another embodiment of a flexible-to-rigid tubular body portion 7114'''. Body portion 7114''' has a first side 7610, a second side 7612, and a series of wavy slits 7614. First side 7610 forms a solid spine that does not axially compress. In this embodiment, slits 7614 have a generally uniform width. During axial compression, body portion 7114''' takes on a curved shape, with first side 7610 becoming convex and second side 7612 becoming concave.

Alternative designs (not shown), such as wave patterns of an interdigitating saw tooth or square wave, and the like, are also contemplated for increased torsional rigidity. As described above, these patterns may form discrete rings around body portion 7114, or these patterns may be superimposed on a helical curve to form a continuous spiral pattern.

FIGS. 99A-99J show further exemplary embodiments of anatomy or shape conforming body portions constructed according to aspects of the present invention. Similar to the body portions described above, the body portions shown in FIGS. 99A-99J may be used in place of body portion 7114 previously described to allow an implantable bone fixation device to take on a shape that conforms to a particular anatomy when the body of the device is axially compressed when making the device substantially rigid. The body portions shown in FIGS. 99A-99J have interlocking appendages or features that allow each body portion to transform from a generally flexible state to a generally rigid state when axial compression is applied. Like some of the body portions described above, these interlocking features also permit the transmission of torsional forces in both the flexible and rigid states of the device. Being able to transmit torsional forces without excessive rotational displacement from one end of the implantable device to the other can be advantageous in various situations, such as during insertion or removal of the device, or when a surgeon desires to rotate the device to properly align it during installation in a bone. Additionally, the interlocking features of the exemplary embodiments shown are designed to resist tensile forces. This allows the surgeon to pull on the proximal end of the device without the device uncoiling or extending excessively in length.

Figure 99C:
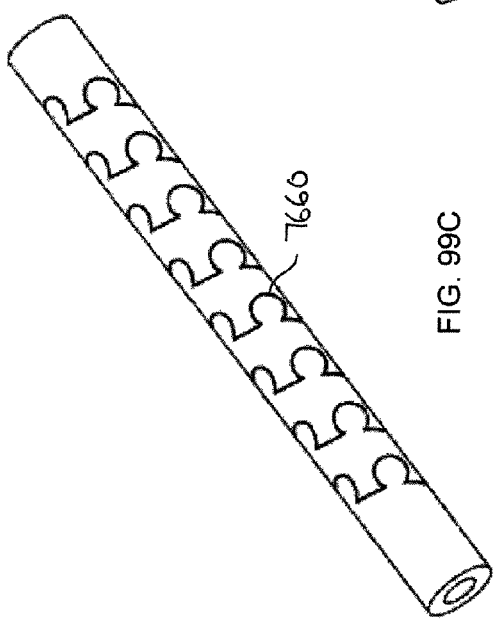
FIG. 99C is a perspective view showing another body portion embodiment having interlocking features.
Figure 99D:
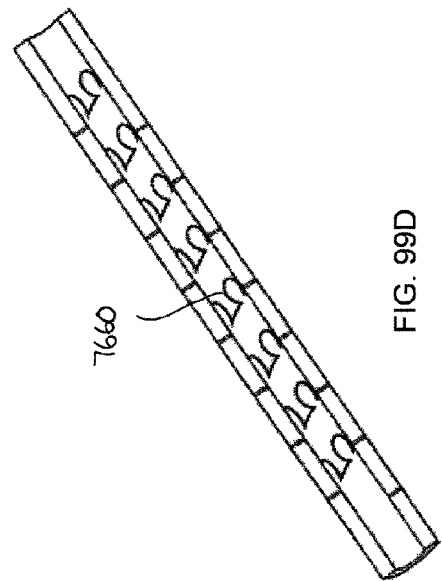
FIG. 99D is a longitudinal cross-sectional view of the body portion shown in FIG. 99C.
Figure 99E:
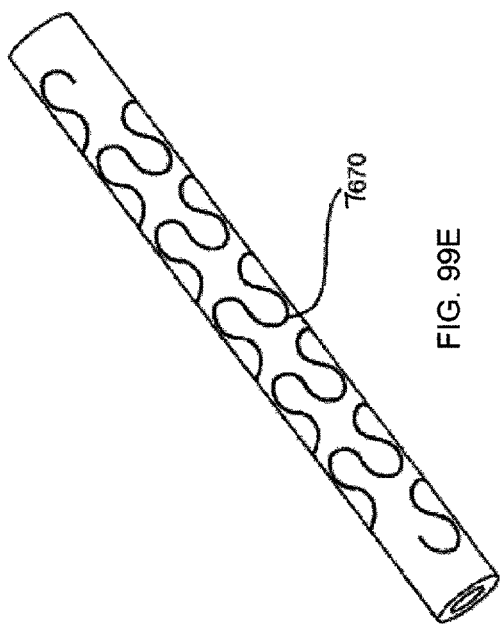
FIG. 99E is a perspective view showing another body portion embodiment having interlocking features.
Figure 99F:
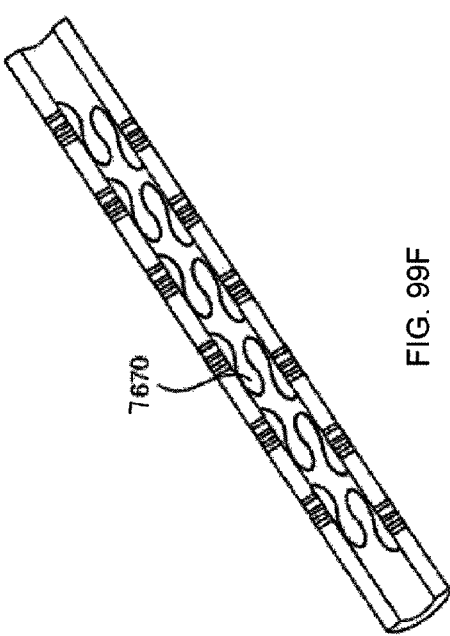
FIG. 99A is a perspective view showing another body portion embodiment having interlocking features.
FIG. 99B is a longitudinal cross-sectional view of the body portion shown in FIG. 99A.

As seen in the flexible-to-rigid body portion shown in FIGS. 99A and 99B, the interlocking features can comprise an alternating trapezoid or dovetail pattern 7650 superimposed on a helical curve. As shown in FIGS. 99C and 99D, the interlocking features can comprise an omega shape 7660. FIGS. 99E and 99F show that the interlocking features can comprise bulbous pendicles 7670. FIGS. 99G and 99H show that the interlocking features can comprise an L-shape 7680. Note that the gap 7682 between features in one column is wider than gap 7684 in the adjacent column, which in turn is wider than gap 7686 in the next column. This progressive widening of gaps from one side of the flexible to rigid body portion to the other causes the body portion to curve when compressed, as will be further described below. FIGS. 99I and 99J show an example of T-shaped interlocking features 7690. In other embodiments, a pattern of interlocking features can be continuous or intermittent. The interlocking features may also vary in a radial direction across the tube wall, and/or in an axial direction rather than, or in addition to, varying across the circumference of the tube as shown in FIGS. 99A-99J.

The body portions shown in FIGS. 99A-99J need not be curved when axially compressed as described above. Rather, they may be designed so that they compress equally on all sides of the center axis such that they form a straight segment when either flexible or rigid. Alternatively, the body portions may be designed to be curved when flexible, and compress in a uniform fashion such that they maintain their curved shape when transformed to a generally rigid state.

FIGS. 99A-99J provide exemplary geometries for a variety of cut patterns. The cross sectional geometry is shown as tubular. As discussed in more detail below, the cross sectional area can be of any shape tubular geometry or solid geometry. The specific cut pattern and cross sectional shape are selected and designed to match the anatomical shape of the bone or to provide specific fixation or reconstructive surfaces particularly suited to remediate the problem with the bone. Different cross sectional geometries are needed for the flat bones found in the face and skull, the ribs, the tibial plateau, the metacarpals, the metatarsals, and the scaphoid bone of the hand. The cut pattern can be "programmed" to reconstruct the bone into its anatomical configuration or into a modified configuration based upon the desired result of the remediation therapy. For instance, a reconstructive procedure may be prescribed to remediate a malunion of a bone. In this example the device, rather than collapsing upon activation lengthens and becomes rigid.

Although shown in the various embodiments of the figures is a device with grippers, it is also envisioned that the flexible-to-rigid member would collapse or extend such that axially successive geometries would be upset and driven radially outward. In is flexible state the cut patterns would freely bend relative to each other. Upon activation to the rigid state, for example, a crest of a wave pattern would be urged outward, thereby increasing the effective diameter of the device. The crest of the wave could be forced into the intramedullary bone and create a fixation moiety. One could envision a long tube where the crests of the wave patterns would be drive outward there by creating a high surface area of gripping power over the entire length of the device. Other pattern besides wave patterns could be made to do this.

FIGS. 100A and 100B depict the proximal end of a device 7100' which is similar to device 100 and/or 7100 previously described but incorporating the flexible-to-rigid tubular body portion 7114' of FIG. 97. FIG. 100A shows device 7100' in a flexible, undeployed state, and FIG. 100B shows device 7100' in a generally rigid, curved state. To change between states after device 7100' is inserted in the intramedullary cavity of a bone, the tip of a rotary driver tool (not shown) is inserted in keyed socket 7130 of drive member 7128' and rotated. Drive member 7128' is threadably engaged with shuttle 7710. Shuttle 7710 may be constructed in a flexible manner such that body portion 7114' remains flexible when in the undeployed state of FIG. 100A. Shuttle 7710 may include a tab 7712 at its proximal end that travels in slot 7714 in the tube wall to prevent shuttle 7710 from rotating (as seen in FIG. 101D). As drive member 7128' is rotated by the driver tool, shuttle 7710 is drawn towards the proximal end of device 7100', as shown in FIG. 100A. The proximal end of a tension wire 7716 in turn is rigidly attached to shuttle 7710. The distal end of tension wire 7716 (not shown) may be coupled to a distal gripper as previously described, or attached to the distal end of device 7100'. When tension wire 7716 is drawn proximally by shuttle 7710, V-shaped gaps 7414 on the second side 7412 of body portion 7114' are closed, causing body portion 7114' to assume a curved shape as shown in FIG. 100B.

FIGS. 101A-101C show an alternative embodiment device 7100" in various states. FIG. 101A shows device 7100" in a non-tensioned state, FIG. 101B shows a cross-section of device 7100" in the non-tensioned state, and FIG. 101C shows a cross-section of device 7100" in a tensioned state.

Device 7100" includes two flexible-to-rigid tubular body portions 7114', 7114' oriented in opposite directions. With this configuration, when shuttle 7710 and tension wire 7716 are drawn proximally by rotating drive member 7128, device 7100" assumes an S-shape, as shown in FIG. 101C. Thus, device 7100" may be used to repair S-shaped bones such as the clavicle. In a similar manner, the axial width, axial pitch and/or radial orientation of V-shaped cuts 7414 can be varied to produce compound, varying curves in three dimensions to match any desired anatomy. For obtaining smaller radii of curvature, V-shaped cuts 7414 that are more blunt may be used. The flexible to rigid body portions need not be of identical cross section. For example a round tubular section could be paired with a hexagonal tubular section. This would allow one section to rotate freely within the space it is located where the hexagonal structure would provide a form of resistance or registration.

FIGS. 101D and 101E show an S-forming device 7100''' similar to device 7100" shown in FIGS. 101A-101C, but having wavy slits 7614 instead of straight V-shaped cuts 7414.

FIG. 102 depicts an S-shaped device similar to device 7100" deployed in a clavicle bone 7910 across a mid-shaft fracture 7912. Device 7101 may be configured with a gripper 7108 and/or one or more screw holes 7914 at its proximal end to secure device 7101 to one half of clavicle 7910. Similarly, device 7101 may be configured with a gripper 7108 and/or one or more screw holes 7914 at its distal end to secure device 7101 to the other half of clavicle 7910. Body portions 7114', 7114' are configured such that they are flexible when being introduced into clavicle 7910. When grippers 7108, 7108 are deployed and body portions 7114', 7114' become rigid as described above, device 7101 assumes an S-shape that closely matches the contour of the intramedullary cavity within clavicle 7910. Such a configuration allows device 7101 to more rigidly support clavicle 7910 for healing of fracture 7912 while avoiding undue forces on clavicle 7910.

FIG. 103 shows device 7101 described above and depicted in FIG. 102 as it is being introduced into a fractured clavicle 7910.

FIG. 104 shows an alternative shape conforming device 7103. Device 7103 forms a simple curve when flexible-to-rigid body portion 7114" (also shown in FIG. 98A) is in a rigid state. Device 7103 includes a gripper 7108' at its distal end, having opposing tube segments 8110, 8110 that rotate to engage the bone when gripper 7108' is deployed. Device 7103 also has a tripod gripper 7108" at its proximal end, having three pairs of scissor arms 8112, 8112, 8112 for engaging the bone when actuated. Further details of grippers 7108' and 7108" are provided in application Ser. No. 11/944,366 referenced above.

FIG. 105 shows an alternative shape conforming device 7105. As shown, device 7105 forms an S-shape when flexible-to-rigid body portions 7114" are in a rigid state. The distal end of device 7105 may be secured to the bone by gripper 7108, and the proximal end may be secured with bone screws through the device.

In alternative embodiments, grippers 7108 and screw 7110 attachment provisions may be omitted from one or both ends of the device. In these embodiments, the curved nature of body portion(s) 7114' is enough to secure the device end(s) within the bone and hold the fracture(s) in place. In embodiments with and without grippers 7108 and screws 7110, the anatomy-conforming curve may serve to grip the bone and approximate the fracture(s). In many embodiments, the action of the closing of the slots (such as 7116) during axial compression also serves to grip the bone and/or approximate the fracture(s). In other embodiments, wire or other fastening elements may be used to secure the device in place.

Referring now to FIGS. 106-114, another exemplary embodiment of a bone fixation device constructed according to aspects of the present invention will be described. FIG. 106 shows bone fixation device 8300 attached to an insertion and removal tool 8302 and actuation tool 8304. Insertion and removal tool 8302 in turn is mounted in a fixture arm 8306.

Referring to FIG. 107, components of bone fixation device 8300 and insertion and removal tool 8302 are shown. In this exemplary embodiment, device 8300 comprises a hub 8402, actuation screw 8404, actuation shuttle 8406, flexible-to-rigid body member(s) 8408, tension member 8410, and end cap 8412. In alternative embodiments, additional, fewer, or a single flexible-to-rigid body member may be used. Insertion and removal tool 8302 comprises sleeve 8450, tube 8452, knob 8454, and may be mounted though fixture arm 8306.

Referring to FIG. 108, an enlarged perspective view of the assembled device 8300 is shown.

Referring to FIG. 109, an enlarged, cut-away perspective view shows internal components of device 8300. End cap 8412, having the same nominal outer diameter as flexible-to-rigid body member(s) 8408 (shown in FIG. 108), is rigidly connected, such as by welding, to the distal end of tension member 8410. Tension member 8410 is sized to fit within flexible-to-rigid body member(s) 8408. Tension member 8410 may include a central longitudinal lumen, the purpose of which is later described. Tension member 8410 may also be provided with a series of longitudinal slots 8610 through its wall thickness to allow it to be very flexible. Solid ring portions 8612 may be interspersed between the series of slots 8610 to retain the tubular shape and torsional rigidity of tension member 8410. In other embodiments (not shown), the tension member is formed from one or more wires or cables, which may be bundled together, to be strong in tension while being flexible in bending.

Actuation shuttle 8406 is attached to the proximal end of tension member 8410, such as by welding. Actuation shuttle 8406 includes a knobbed end 8710, as seen in FIG. 110A. Knobbed end 8710 is configured to be received within mating keyhole 8712 in one side of actuation screw 8404, as seen in FIGS. 110B and 110C. Actuation shuttle 8406 may also include a radially-protruding tab 8714, as seen in FIG. 110A. Tab 8714 is sized to slide in a longitudinal slot 8510 in device hub 8402, as seen in FIG. 108, to allow actuation shuttle 8406 to move axially without rotation. With actuation shuttle 8406 rotatably received in actuation screw 8404, which in turn is threadably engaged with hub 8402, the distal end of actuation tool 8304 may be received (as seen in FIG. 111) in a keyed recess 8716 (seen in FIG. 110C) of actuation screw 8404. Turning actuation screw 8404 with actuation driver 8304 causes actuation screw 8404, and with it actuation shuttle 8406, to move axially with respect to hub 8402. As actuation shuttle 8406 moves in a proximal direction (away from distal end cap 8412), a tensile force is imparted to tension member 8410, causing flexible-to-rigid body member(s) 8408 to be axially compressed between end cap 8412 and hub 8402 (see FIGS. 108 and 109). As previously described, this compression causes body member(s) 8408 to become substantially rigid, and to take on a predetermined shape, as will be more fully described below.

Referring to FIG. 110E, a plan view of an interlocking pattern is shown. The pattern has the same interlocking L-shaped features 7680 as the flexible-to-rigid body member 8408 shown in FIGS. 99G and 99H described briefly above. In other words, FIG. 110E represents the pattern that would result if the body member 8408 were slit along one side in a longitudinal direction, unrolled and laid flat. Arrows 8710 in FIG. 110E indicate the longitudinal or axial direction of the pattern, while arrows 8712 represent the tangential direction. As can be seen, the pattern is formed by a continuous helical cut, such that gap 8722 on one side of the pattern connects with gap 8724 on the other side of the pattern when the pattern is formed on a tubular structure. While a single helical cut is shown, other embodiments may employ two or more helical cuts running in parallel around the tube. Pattern gaps may be formed by laser cutting, punching, milling, etching, sawing, electro-discharge machining, or other material removal or material addition processes. Patterns may be formed on a tubular structure, or on a generally flat substrate which is then configured into a tubular structure.

As briefly mentioned above in conjunction with FIG. 99G, the interlocking pattern may utilize gaps that narrow along one side of the tube (shown in the center of FIG. 110E) and widen along the other side of the tube (shown at the sides of FIG. 110E). In this exemplary pattern, gaps 7682 are wider than gaps 7684, which in turn are wider than gaps 7686, which in turn are wider than gap 8726. As the pattern is compressed in an axial direction when formed on a tubular structure, the features adjacent the wider gaps (e.g. 7682) will move farther than the features adjacent the narrower gaps (e.g. 8726) as the gaps are closed. Since one side of the tube is compressing more than the opposite side, the tube forms a curve that is concave on the side having the widest gaps.

Referring again to FIGS. 107 and 108, and also to FIG. 111, if all of the flexible-to-rigid body members 8408 are oriented with their widest pattern gaps on one side of the device 8300, the flexible-to-rigid portion will take on a single curved shape. If the body members 8408 toward the distal end are all oriented with their widest pattern gaps on one side, and the body members 8408 toward the proximal end are all oriented with their widest gaps on the opposite side, a compound or S-shaped curve will result, as shown in FIG. 112. If the orientation of each successive body member is alternated from one side to the other and back again, a rapidly undulating curve will result. If the orientation of each successive body member is changed in phase, for example by 90 degrees, from the orientation of the previous body member, a helical arrangement of the overall flexible-to-rigid body portion may be achieved. It can be appreciated that by changing the orientation of the gap thicknesses, essentially any desired three-dimensional curve may be obtained to suit the particular purpose. For example, the rapidly undulating curve described above may be more useful in some circumstances for allowing a bone fixation device to gain purchase within a relatively straight intramedullary canal. A body member having a compound curve can be useful in a bone fixation device that is designed to be inserted in a radius or an ulna, as these bones curve in more than one plane simultaneously. A bone fixation device having an S-shaped curve is useful in bones that have S-shaped portions, such as the clavicle.

It should be noted that in addition to varying the gap orientation, the relative change in gap width may be varied to produce curves of different radii. For example, one portion of a flexible-to-rigid body may have the same gap width around its circumference to produce a straight section, another portion may have a relatively small change in gap width to produce a large radius of curvature, while yet another portion may have a larger change in gap width around its circumference to produce a small radius of curvature. In some embodiments, such as shown in the accompanying figures, the device may employ a series of individual body members 8408 that together form an overall flexible-to-rigid body portion. Alternatively, it should be noted again that a continuous complex pattern similar to that formed by the multiple body sections described above may be formed on a single tubular structure. Additionally, interlocking or non-interlocking features other than the L-shaped features 7680 may be used in addition to or instead of features 7680.

Referring to FIGS. 113 and 114, use of the bone fixation device 8300 and associated tools with a guide wire 9010 is described. As described above and shown in the accompanying figures, each of the central components of device 8300 has an axial lumen extending therethrough. Similarly, the central components of actuation tool 8304 have an axial lumen extending therethrough. This arrangement permits device 8300, insertion/removal tool 8302, and/or actuation tool 8304 to be slid, either individually or together, over guide wire 9010.

In some bone fixation operations, it is advantageous to first introduce a guide wire into the intramedullary space of a bone before inserting a bone fixation device 8300, and in some cases before preparing the intramedullary canal for receiving device 8300. According to aspects of the invention, in some methods an access incision or puncture is made in the tissue surrounding a bone. A pilot hole may then be drilled in the bone to gain access to the intramedullary canal. Guide wire 9010 may then be introduced through the pilot hole (or in some cases without a pilot hole) into the intramedullary space. Guide wire 9010 may be further advanced through the canal and across a fracture site or sites, lining up bone fragments along the way. Introduction of guide wire 9010 may take place with the aid of fluoroscopy or other imaging technique.

After guide wire 9010 is inserted into a target bone, various burs, cutters, reamers, trocars, and/or other bone forming or aligning tools may be alternately advanced over guide wire 9010. One an interior bone space has been prepared (if desired) to receive bone fixation device 8300, device 8300 along with insertion/removal tool 8302 and actuation tool 8304 may be advanced over guide wire 8210. Insertion/removal tool 8302 may first be inserted in fixture arm 8306, which in turn may be fastened to external fixtures or used as a handle to assist in steadying and aligning device 8300 during insertion and actuation. Device 8300 may then be advanced along guide wire 9010 and into position within the bone. The guide wire may occupy a central lumen of the device along its longitudinal axis. The guide wire may slide along openings in the outer diameter surface of the device in an analogous fashion to the eyelets of a fishing rod. These lumen may be intra-operatively or post-operatively available for the delivery of other devices, therapies to the bone, or tools.

Deployment of device 8300 may be accomplished by rotating actuation tool 8304. As previously described, such rotation moves actuation screw 8404 in a proximal direction and ultimately causes a compressive load to be placed on flexible-to-rigid body portion(s) 8408. This in turn causes flexible-to-rigid body portion(s) 8408 to take on a desired shape and become generally rigid to secure device 8300 against the interior surfaces of the bone. Actuation tool 8304 may include a torque measuring or limiting mechanism to help ensure that a predetermined or desired amount of force is being applied from deployed device 8300 against the bone. Device 8300 may be secured with additional methods, such as with bone screw(s), K-wire(s) and the like.

Actuation tool 8304 and insertion/removal tool 8302 may be removed together or individually. Actuation tool 8304 is removed be pulling in a proximal direction to disengage its distal tip from recess 8716 within actuation screw 8404. Insertion/removal tool 8302 is disengaged from device 8300 by turning the knob at the proximal end of tool 8302. This unscrews the externally threaded distal tip of tube 8452 of tool 8302 from the internally threaded bore of hub 8402, as seen in FIG. 114. The guide wire 8210 may then be removed (or at an earlier time if desired), and the access wound(s) closed. It will be appreciated that these same tools and the reverse of these methods may be used to remove device 8300, if desired, during the initial procedure or at a later time.

Referring to FIGS. 115 and 116, additional exemplary patterns are shown that may be used in the flexible-to-rigid body portions of bone fixation devices. Non-repeating pattern 9200 includes ten different interlocking shape pairs along a helical slit 9202, none of which are the same. In this example pattern 9200, there are two interlocking shape pairs located along each revolution of helical slit 9202, such that when the pattern is formed on a tube, the two pairs are on opposite sides of the tube. Alternatively, a pattern of interlocking shapes may repeat every revolution of the helical slit 9202, every partial revolution, or over the course of more than one revolution. For example, a series of six different interlocking shape pairs may repeat every three revolutions of helical slit 9202, as shown in the exemplary pattern 9300 of FIG. 116.

It can be seen in FIGS. 115 and 116 that patterns 9200 and 9300 include ramped portions 9204 along each revolution of helical slit 9202 where the slit gets progressively wider. Additionally, helical slit 9202 forms a wider gap adjacent to the lower set of interlocking shape pairs 9206 than it does adjacent to the upper set of shape pairs 9208. These ramped portions 9204 and wider gaps allow patterns 9200 and 9300 to axially compress to a greater extent in one area (the lower part of FIGS. 115 and 116) than in another area (the upper part of FIGS. 115 and 116). Accordingly, when patterns 9200 and 9300 are applied to a tubular member, the member will form a curve when axially compressed, as previously described.

Referring to FIGS. 117A-117H, an alternative flexible-to-rigid body portion pattern 9400 will now be described. Pattern 9400 is formed by superimposing a sinusoidal pattern on helical slit 9402. Helical slit 9402 may be continuous, or it may be formed in individual segments with solid sections in between, as shown in FIG. 117A. In can be seen in FIG. 117A that the peak 9404 on one side of slit 9402 nests within trough 9406 on the opposite side of slit 9402.

Referring to FIG. 117B, it can be seen that slit 9402 may be formed at an angle relative to tube wall 9408 rather than being perpendicular to tube wall 9408 and the longitudinal axis of the device. In this manner, a ramp is formed on the peak side 9404 of slit 9402 and another ramp is formed on the trough side 9406. In other embodiments, a ramp may be formed only on the peak side 9404 or only on the trough side 9406. In some embodiments, only a portion of one or both sides is ramped or rounded. When the flexible-to-rigid body portion is axially compressed, the ramps cause at least a tip portion 9410 of peak 9404 to ride up on trough 9406 and extend radially outward, as shown in FIG. 117C. This tip portion may be configured to bite into the surrounding bone. Even if each extending tip 9410 only provides a small amount of gripping force, with a large number of tips 9410 engaging the bone a large amount of gripping power can be generated to hold the device within the bone. In the embodiment shown in FIG. 117C, only a portion of the tube wall 9408 on one side of slit 9402 rides above the tube wall 9408 on the opposite side of slit 9402. In other embodiments, one side of tube wall 9408 may ride up and completely onto the opposite side.

Referring to FIGS. 117D-117G, tip 9410 need not take the shape of a sinusoidal wave. The tip may be V-shaped (FIG. 117D), semicircular (FIG. 117E), chisel-shaped (FIG. 117F), square (FIG. 117G), notched (FIG. 117H), or have another shape in order to effectively grip the surrounding bone. Tips of a particular device may have the same shape on every tip, or multiple tip shapes may be used on one device.

While bone fixation devices having circular cross-sections have been shown and described, other cross-section shapes according to aspects of the invention may be useful in some circumstances. In some embodiments, a triangular cross-section may be used, as its sharp edges can aid in gripping the surrounding bone. Non-circular cross sections may be used in applications where a particular combination of area moments of inertia is desired. Particular non-circular cross sections may be chosen for their optimization in certain anatomies, or for aiding in manufacturability of a bone fixation device. In some embodiments, the cross section of the bone fixation device is circular, oval, elliptical, triangular, square, rectangular, hexagonal, octagonal, semi-circular, crescent-shaped, star-shaped, I-shaped, T-shaped, L-shaped, V-shaped, or a combination thereof. In some embodiments, the cross section forms a polygon having any number of sides from 1 to infinity. In some embodiments, the cross-sections are tubular and in others they are solid. In some embodiments, the cross-section of the device can vary in size along it length, such as tapering from the proximal end to the distal end. FIGS. 118A-118D provide an example of an oval cross section, and FIGS. 119A-119D provide an example of a square cross-section.

In other embodiments, a solid rectangular geometry with an externally communicating stiffening member can be constructed. FIGS. 120A-120E, FIGS. 121A-121E and FIGS. 122A-122B describe three exemplary geometries. The external stiffener geometry of the device shown in FIGS. 120A-120E, and its resultant shape upon activation to its rigid state, are designed to allow insertion, match the anatomical configuration of the bone, and provide remediation of the malady of the bone, such as proximation and fixation of the fracture. The external stiffener geometry of the device allows removal upon deactivation. The devices shown in FIGS. 120 through 122 may be used for treatment of flat bones, such as those of the face, skull, scapula, and lateral clavicle.

In various embodiments, a fracture fixation system comprises a system of one or more implants, devices and instruments configured for the repair of fractures of a bone from within an intramedullary canal. As shown in FIGS. 123-150, in various embodiments, a fracture fixation system comprises a straight implant 10000 with at least one substantially straight or linear configuration. In one embodiment, a straight implant 10000 has a straight configuration and a curved configuration. In one embodiment, a straight implant 10000 has a straight configuration and no curved configuration. In various embodiments, a straight implant 10000 comprises a proximal portion 10010, a distal portion 10020 and a medial portion 10030. In various embodiments, a straight implant 10000 comprises a hub 10040, a fixation region 10050 and a shaft 10060. In one embodiment, the straight implant 10000 comprises a hub 10040 in the proximal portion 10010, a fixation region 10050 in the distal portion 10020 and a shaft 10060 in the medial portion 10030.

In various embodiments, the straight fixation implant 10000 is configured for insertion into the intramedullary canal of a long bone, the fixation region 10050 providing for at least one anchoring point for intramedullary fixation, the hub 10040 providing for at least a second anchoring point for intramedullary fixation, and the shaft 10060 providing a working length to provide structure for healing the bone fracture, spanning the fractured portion of the long bone. In various embodiments, the straight fixation implant 10000 can include any aspect of any of the embodiments of the various devices and/or implants disclosed or referenced herein. In various embodiments, the straight fixation implant 10000 can have any number of dimensions, diameters, features, materials, geometries, and/or predetermined shapes. In one embodiment, the straight fixation implant 10000 comprises Nitinol with a heat set to a predetermined shape. In one embodiment, the straight fixation implant 10000 is configured for an antegrade implanting technique. In one embodiment, the straight fixation implant 10000 is configured for a retrograde implanting technique. In one embodiment, a retrograde implant is similar to an antegrade implant in which some order of features may change.

In various embodiments, the hub 10040 comprises an interface for attaching instruments for implantation or removal of the implant 10000. In various embodiments, the hub 10040 provides for torsional resistance to the rotation of the implant 10000 in bone with one or more features, such as one or more fins, flutes, features, non-symmetrical cross section, threads, pins, locks, actuatable grippers, or other features. In one embodiment, the hub 10040 is smooth. In one embodiment, the hub has a circular cross-section. In one embodiment, the hub 10040 has the same diameter, width, depth or dimension as the shaft 10060. In one embodiment, the hub 10040 has a smaller same diameter, width, depth or dimension than the shaft 10060. In one embodiment, the hub 10040 has a same or similar diameter, width, depth or dimension as the shaft 10060. In one embodiment, the hub 10040 has a greater diameter, width, depth or dimension than the shaft 10060 such that the hub 10040 can act like a screw head and provide compression to the bone at a cortical outer surface. In one embodiment, the hub 10040 has an exterior thread with a differential pitch than a thread at the fixation region 10050 to achieve bone compression. In various embodiments, the hub 10040 can include any one or combination of one or more bone screw, cross screw, compression screw, locking feature, locking screw, slot, channel, anti-rotation feature, and/or instrument interface. In one embodiment, the hub 10040 comprises a fixation location with compression. In one embodiment, the hub 10040 comprises a fixation location without compression.

In various embodiments, the shaft 10060 is configured for providing a working length to provide structure for load bearing or load sharing to facilitate healing the bone fracture. In some embodiments, the shaft 10060 spans the fractured portion of the long bone. In one embodiment, the shaft 10060 is at least partially rigid. In one embodiment, the shaft 10060 is at least partially flexible. In one embodiment, the shaft 10060 includes a rigid portion and a flexible portion. In one embodiment, the shaft 10060 includes a flexible portion for extending through curvature of the bone. In various embodiments, the shaft 10060 can be circular in cross section, but may also have any number of various cross section shapes. In various embodiments, the shaft 10060 may be solid or cannulated. In one embodiment, the shaft 10060 is threaded.

In various embodiments, the fixation region 10050 is used to anchor the device 10000 in the intramedullary canal of a bone. In various embodiments, the fixation region 10050 comprises one or more threads various pitch, diameter or lead, corkscrews, geometries, configurations, tips, spades, deployable features, and/or deployable grippers. In one embodiment, the fixation region 10050 is at least partially rigid. In one embodiment, the fixation region 10050 is at least partially flexible. In one embodiment, the fixation region 10050 includes a rigid portion and a flexible portion. In one embodiment, the fixation region 10050 includes a flexible portion for extending through curvature of the bone.

FIGS. 123-126 illustrate a straight fixation implant 10000 configured for a cross locking screw according to an embodiment of the present invention. In one embodiment, a fixation region 10050 includes a thread 10400. In one embodiment, a hub 10040 includes a slot 10100 configured for a cross locking screw (not illustrated). In various embodiments, slot 10100 can be perpendicular or angled to a longitudinal axis of the implant 10000. As illustrated, slot 10100 is at an angle with respect to the longitudinal axis of the implant 10000. In various embodiments, the angle of the slot with respect to the longitudinal axis of the implant 10000 is 90 degrees, 80 degrees, 75 degrees, 70 degrees, 60 degrees, 50 degrees, 45 degrees, or another angle. In one embodiment, a locking screw 10110 is inserted and advanced to lock a cross locking screw in place in the slot 10100 at the hub 10040 of the implant 10000. In one embodiment, slot 10100 is threaded. In one embodiment, slot 10100 is threaded to correspond to a cross locking screw. In one embodiment, the implant 10000 has a solid shaft 10060 and a solid fixation region 10050. In various embodiments, the fixation region 10050 is threaded at a fixation region pitch and a fixation region diameter. In one embodiment, fixation region 10050 comprises a self tapping thread. In various embodiments, the length of the implant 10000 is roughly 1.5, 1.75, 2.0, 2.25, 2.5, 2.75, 3.0, 3.25, 3.5, 3.75, 4.0, 4.25, 4.5, 4.75, 5.0 inches, or any length in the range of 1-6 inches, or any subset therein. In various embodiments, the shaft 10030 diameter is roughly in the range of approximately 0.1-0.25 inches, 0.1 to 0.15 inches, and/or roughly 0.125 inches. In the embodiment illustrated at FIG. 123, the hub 10040 diameter is greater than the shaft 10060 diameter. In various embodiments, the hub 10040 diameter is roughly 0.15-0.3 inches, 0.15-0.25 inches, and/or roughly 0.2 inches. In some embodiments, the hub 10040 can have a 4, 4.2, 4.4, 4.5, 4.7, 4.8, 5.0, 5.2, 5.5, 5.8, 6.0, 6.2, or 6.5 mm diameter, or any diameter in the range of 3-7 mm, or any subset therein.

FIGS. 127-130 illustrate a straight fixation implant 10000 with a longitudinal cannula lumen 10200 according to an embodiment of the present invention. In some embodiments, the lumen 10200 is configured for sliding over a guide wire or guide device or elongate body. In some embodiments, the cannula lumen 10200 is at least partially threaded. In one embodiment, a first cannula thread 10210 is at a proximal end of the cannula lumen 10200. In one embodiment, a first cannula thread 10210 can be used in conjunction with a slot 10100 to lock a cross locking screw in place. In various embodiments, an optional second cannula thread 10220 is the same or a different pitch, diameter, and/or length as the first cannula thread 10210. In one embodiment, a compression screw (not illustrated) may be inserted into the first cannula thread 10210, and/or the second cannula thread 10220. In one embodiment, the compression screw has a head diameter large enough to provide an anchoring location on cortical bone.

FIGS. 131-133 illustrate an embodiment of a cannulated straight fixation implant with a hub 10040 dimension that is same or similar to a shaft 10060 dimension. In one embodiment, the hub 10040 diameter is the same or similar to the shaft 10060 diameter.

In one embodiment, a first cannula thread 10210 can be used in conjunction with a slot 10100 to lock a cross locking screw in place. In various embodiments, an optional second cannula thread 10220 is the same or a different pitch, diameter, and/or length as the first cannula thread 10210. In one embodiment, a compression screw (not illustrated) may be inserted into the first cannula thread 10210, and/or the second cannula thread 10220. In one embodiment, the compression screw has a head diameter large enough to provide an anchoring location on cortical bone.

FIGS. 134A-134Q illustrate hubs 10040 according to various embodiments of the present invention. Aspects, feature, characteristics in part or in whole can be combined and/or substituted with any embodiment of a hub 10040.

FIGS. 134A-134C illustrate an embodiment of a hub 10040 with a smooth exterior surface that accepts a cross screw 10230 in a slot 10100. In various embodiments, the cross screw may be angled and/or 90 degrees (perpendicular) to the longitudinal axis of the implant 10000. In various embodiments, cross screw 10230 may be locking or non-locking. In various embodiments, slot 10100 is threaded, non-threaded, partially threaded, and/or partially non-threaded.

FIG. 134D illustrates an embodiment of a hub 10040 with an off center hub feature 10240. This is a lower profile design that reduces hardware prominence. In various embodiments, cross screw 10230 may be locking or non-locking. In various embodiments, slot 10100 is threaded, non-threaded, partially threaded, and/or partially non-threaded.

FIG. 134E illustrates an embodiment of a hub 10040 with a tapered hub feature 10250. This is a lower profile design that reduces hardware prominence. In various embodiments, cross screw 10230 may be locking or non-locking. In various embodiments, slot 10100 is threaded, non-threaded, partially threaded, and/or partially non-threaded.

FIG. 134F illustrates an embodiment of a hub 10040 with an angled slot 10100 and recessed screw head cross screw 10230. This is a lower profile design that reduces hardware prominence of the hub and the screw. In one embodiment, a headless screw Low profile hub and screw design. Could also be accomplished with a headless cross screw 10230.

FIGS. 134G-134H illustrate embodiments of a hub 10040 that accepts a cross screw 10230 (not illustrated), a compression screw 10260, or both. In various embodiments, cross screw 10230 may be locking or non-locking. In various embodiments, slot 10100 is threaded, non-threaded, partially threaded, and/or partially non-threaded. In one embodiment, no slot 10100 or cross screw 10230 is present. In one embodiment, a first cannula thread 10210 is at a proximal end of the cannula lumen 10200. In one embodiment, a first cannula thread 10210 can be used in conjunction with a slot 10100 to lock a cross locking screw in place. In various embodiments, an optional second cannula thread 10220 is the same or a different pitch, diameter, and/or length as the first cannula thread 10210. In one embodiment, a compression screw 10260 may be inserted into the first cannula thread 10210, and/or the second cannula thread 10220. In one embodiment, the compression screw 10260 has a head diameter large enough to provide an anchoring location on cortical bone. In one embodiment, first cannula thread 10210 is configured for attachment to an instrument for implant 10000 delivery and/or retrieval. In one embodiment, second cannula thread 10220 is configured for attachment to an instrument for implant 10000 delivery and/or retrieval. In one embodiment, the compression screw 10260 has a lumen 10262. In one embodiment, the compression screw 10260 lumen 10262 is configured for sliding over a guidewire 10270.

FIGS. 134I-134J illustrate embodiments of a hub 10040 with one or more expandable grippers 10280. In various embodiments, the one or more grippers 10280 are the same, similar, have some or all characteristics of any embodiment of a gripper disclosed herein, including any incorporation by reference. In one embodiment, the one or more grippers 10280 expand when the compression screw 10260 is inserted into the implant 10000. In one embodiment, one or more grippers 10280 provide rotational resistance to prevent or restrict the rotation of the implant 10000 in bone. In one embodiment, one or more grippers 10280 lock the compression screw 10260, thereby preventing screw backout. In one embodiment, one or more grippers 10280 are actuated or deployed with an instrument during implant 10000 delivery. In one embodiment, one or more grippers 10280 are retracted with an instrument during implant 10000 removal or placement.

FIGS. 134K-134N illustrate various embodiments of hubs 10040 with one or more anti-rotation features 10280. In various embodiments, anti-rotation features 10280 can be a flute, fin, flat, facet, divot, slot, wedge, extension, keyed feature, or other shape to help maintain position of the hub 10040 in bone by preventing or reducing rotation of the hub 10040. In one embodiment, an anti-rotation feature 10280 is a thread.

FIG. 134O illustrates an embodiment of a hub 10040 with an external thread 10290. FIG. 134P illustrates an embodiment of a hub 10040 with a collet feature 10300. In one embodiment, the collet feature 10300 is a reverse collet configuration. In one embodiment, the collet feature 10300 includes one, two, three or more slots 10310 configured to spread apart, increasing the outer diameter of the hub 10040 when a compression screw 10260 is advanced in the hub 10040. In one embodiment the collet feature 10300 can be combined with an external thread 10290. FIG. 134Q illustrates an embodiment of a hub 10040 with a collet feature 10300 and no external thread 10290. In one embodiment, the collet feature 10300 can have a smooth external finish. In one embodiment, the collet feature 10300 can include any anti-rotation feature 10280.

FIGS. 135A-135P illustrate fixation regions 10020 according to various embodiments of the present invention. Aspects, feature, characteristics in part or in whole can be combined and/or substituted with any embodiment of a fixation region 10050.

FIG. 135A illustrates an embodiment of a fixation region 10050 with one or more threads 10400. In various embodiments, threads 10400 may be single or multiple lead. In various embodiments, threads 10400 are left-handed, right-handed, single pitch, variable pitch, constant diameter, variable diameter, continuous, discrete, self-tapping, or other characteristic. In various embodiments, the thread 10400 major diameter is greater than, less than, or equal to an outer diameter of a shaft 10060. In various embodiments, a thread 10400 pitch is configured for chip clearance to allow debris from advancement through tissue (e.g. soft tissue and/or bone). In various embodiments, a thread 10400 length is 0.1, 0.2, 0.25, 0.3, 0.4, 0.5, 0.6, 0.7, 0.75, 0.8, 0.9, 1.0, 1.25, 1.5, 1.75, 2.0 inches or more. In various embodiments, a thread 10400 major diameter is 0.05, 0.09, 0.1, 0.125, 0.15, 0.187, 0.2, 0.25 inches or more. In various embodiments, a thread 10400 minor diameter is 0.05, 0.09, 0.1, 0.125, 0.15, 0.187, 0.2, 0.25 inches or more.

FIG. 135B illustrates an embodiment of a fixation region 10050 with expanding grippers 10410. In various embodiments, the one or more grippers 10410 are the same or similar to grippers 10280 and/or are the same, similar, have some or all characteristics of any embodiment of a gripper disclosed herein, including any incorporation by reference. In one embodiment, one or more grippers 10410 provide rotational resistance to prevent or restrict the rotation of the implant 10000 in bone. In one embodiment, one or more grippers 10410 are actuated or deployed with an instrument during implant 10000 delivery. In one embodiment, one or more grippers 10410 are retracted with an instrument during implant 10000 removal or placement.

FIGS. 135C-135F illustrate various embodiments of a fixation region 10050 with a flexible region 10420. FIG. 135C illustrates an embodiment of a fixation region 10050 with threads 10400 and a flexible region 10420 configured for extending around a curvature of an intramedullary canal in bone. In one embodiment, the flexible region 10420 is present in a fixation region 10050 without a thread. In various embodiments, the flexible region 10420 may be of the same material as the shaft 10060 or a different material. In various embodiments, a fixation region 10050 may be of one piece construction or multiple component construction. In one embodiment, a fixation region 10050 includes a spade tip 10430 configured for self directing around a curvature of an intramedullary canal in bone. FIG. 135D illustrates an embodiment of a fixation region 10050 with a flexible region 10420 that includes a smooth, non-threaded portion 10440. In one embodiment, a thread 10400 is provided at the distal end of the flexible region 10420 that is designed to thread around a curvature of a bone. In one embodiment, rotation of the thread 10400 helps advance or retract the fixation region 10050 around a curvature of an intramedullary canal in bone. FIG. 135E illustrates an embodiment of a fixation region 10050 with two threaded regions 10400 located on either side of a flexible region 10420. FIG. 135F illustrates an embodiment of a fixation region 10050 with a smooth flexible region 10420. In one embodiment, the flexible region 10420 includes a spade tip 10430 configured for self directing around a curvature of an intramedullary canal in bone.

FIG. 135G illustrates an embodiment of a fixation region 10050 with a deployable member 10450. In one embodiment, deployable member 10450 has an exposed configuration and a retracted configuration. In one embodiment, deployable member 10450 has only an exposed configuration. In one embodiment, deployable member 10450 is flexible and configured for self directing around a curvature of an intramedullary canal in bone. In one embodiment, deployable member 10450 is rigid and configured for self directing around a curvature of an intramedullary canal in bone. In one embodiment, deployable member 10450 is curved and configured for self directing around a curvature of an intramedullary canal in bone. In one embodiment, deployable member 10450 is straight and configured for self directing around a curvature of an intramedullary canal in bone.

FIG. 135H illustrates an embodiment of a fixation region 10050 with a cam feature 10460 that acts as a deployable anchoring mechanism. In various embodiments, the cam feature 10460 is the same, similar, and/or has some or all characteristics of any embodiment of a cam mechanism disclosed herein, including any incorporation by reference. In one embodiment, the cam feature 10460 is a tip cam. FIG. 135I illustrates an embodiment of a fixation region 10050 with a cam feature 10460 without hinge pins.

FIGS. 135J-135K illustrate an embodiment of a fixation region 10050 with one or more scissor grippers 10470 for anchoring into the bone. In an embodiment, scissor grippers 10470 actively open and close between a deployed and retracted configuration. In various embodiments, the scissor grippers 10470 is the same, similar, and/or has some or all characteristics of any embodiment of anchors disclosed herein, including any incorporation by reference. For example, various embodiments of scissor grippers 10470, including but not limited to disclosure relating to FIGS. 12-15, are incorporated by reference from U.S. application Ser. No. 13/203,713, titled "Bone Fixation Device, Tools and Methods", filed Aug. 26, 2011 and from PCT/US2009/058632, titled "Bone Fixation Device, Tools and Methods", filed Sep. 28, 2009 and published in English as International Publication Number WO 2010/037038 A2 with International Publication Date Apr. 1, 2010. Both of these references are incorporated in their entirety herein.

FIG. 135L illustrates an embodiment of a fixation region 10050 with a cam-gripper feature 10480 that is deployable and retractable through the controlled movement of an actuation screw (not illustrated). In various embodiments, the fixation region 10050 and/or shaft 10060 include one or more fins, flutes, features, non-symmetrical cross section, threads, pins, locks, or other features for torsional resistance.

FIG. 135M illustrates an embodiment of a fixation region 10050 with a sliding wedge mechanism 10490. In one embodiment, the sliding wedge mechanism 10490 is actuated, causing the wedges to slide with respect to each other, creating a larger diameter for gripping or anchoring the fixation region 10050. In various embodiments, the fixation region 10050 and/or shaft 10060 include one or more fins, flutes, features, non-symmetrical cross section, threads, pins, locks, or other features for torsional resistance.

FIG. 135N illustrates an embodiment of a fixation region 10050 with a push rod type cam 10500 that opens one or two grippers 10510. In one embodiment, a gripper 10510 is pinned through the outer body of the fixation region 10050 with a hinge pin 10520. In one embodiment, the push rod type cam 10500 is hinged without a hinge pin using a semi spherical geometry.

FIGS. 135O-135P illustrate an embodiment of a fixation region 10050 with an expanding diameter wedge feature 10530. In one embodiment, the outer diameter of the fixation region 10050 is expanded through actuation with one or more wedges 10540. In one embodiment, an external retaining ring provides a spring force to close or reduce the diameter when the wedge feature 10530 is retracted or undeployed.

In various embodiment of an implant 10000, various combinations of embodiments of hubs 10040, shafts 10060 and/or fixation regions 10050 can include some or all aspects of any of the embodiments disclosed. FIGS. 136-140 illustrate various embodiments of straight fixation implants 10000 with combinations of features, including (but not limited to) a thread 10400, compression screw 10260 and grippers 10280 and other features. In one embodiment, the implant 10000 can be cannulated for an easier surgical technique.

FIG. 141 illustrates a fixation implant 10000 according to an embodiment of the present invention with a flexible portion 10600. In various embodiments, the flexible portion 10600 includes a flexible region 10420. In various embodiments, a fixation portion 10600 is configured for extending around a curvature of an intramedullary canal in bone. In various embodiments, a fixation portion 10600 includes one or more threads 10400. In one embodiment, the flexible region 10420 is present in a fixation region 10050 without a thread. In various embodiments, the fixation portion 10600 may be of the same material as the shaft 10060 or a different material. In various embodiments, fixation portion 10600 may be of one piece construction or multiple component construction. In one embodiment, a fixation region 10050 includes a spade tip 10430 configured for self directing around a curvature of an intramedullary canal in bone. In various embodiments, fixation portion 10600 includes a smooth, non-threaded portion 10440. In one embodiment, a thread 10400 is provided at the distal end of the flexible region 10420 that is designed to thread around a curvature of a bone. In one embodiment, rotation of the thread 10400 helps advance or retract the fixation region 10050 around a curvature of an intramedullary canal in bone. FIG. 141 illustrates an embodiment of a flexible portion 10600 with two threaded regions 10400 located on either side of a flexible region 10420. In one embodiment, once inserted into the bone, the threaded tip threads into the bone canal, following the curvature of the canal. In one embodiment, the flexible portion 10600 allows the threaded tip to deflect/bend around a corner. In one embodiment, the shaft 10060 provides rigidity to the fracture zone. In one embodiment, the hub 10040 includes features to provide compression, torsional resistance, etc. In various embodiments, the hub 10040 has provisions for a bone screw, anti-rotation features and/or connections to external instruments. FIGS. 142-143 illustrates an embodiment of a flexible fixation implant 10000 with a flexible portion 10600 implanted in a clavicle.

FIG. 144 illustrates a deployable fixation implant 10700 with a deployable member 10450 according to an embodiment of an implant 10000 of the present invention. In one embodiment, deployable member 10450 has an exposed configuration and a retracted configuration. In one embodiment, deployable member 10450 has only an exposed configuration. In one embodiment, deployable member 10450 is flexible and configured for self directing around a curvature of an intramedullary canal in bone. In one embodiment, deployable member 10450 is rigid and configured for self directing around a curvature of an intramedullary canal in bone. In one embodiment, deployable member 10450 is curved and configured for self directing around a curvature of an intramedullary canal in bone. In one embodiment, deployable member 10450 is straight and configured for self directing around a curvature of an intramedullary canal in bone. In one embodiment, the deployable fixation implant 10700 is inserted into a fractured bone with the shaft 10060 positioned across the fracture site. In one embodiment, once the deployable fixation implant 10700 is positioned correctly, the deployable member 10450 is deployed. In one embodiment, the deployable member 10450 has a predetermined shape that conforms to the curvature of the bone. In one embodiment, the deployable member 10450 is deployed into the canal, following the curvature of the canal. In one embodiment, the shaft 10060 provides rigidity to the fracture zone. In one embodiment, the hub 10040 is configured to provide compression, torsional resistance, etc. It may have provisions for a bone screw, anti-rotation features and/or connections to external instruments. In one embodiment, an instrument 10710 is used to assist in the delivery or removal of the deployable fixation implant 10700. FIG. 145 illustrates an embodiment of a deployable fixation implant 10700 with a deployable member 10450 retracted. FIG. 146 illustrates an embodiment of a deployable fixation implant 10700 with a deployable member 10450 deployed. FIG. 147 illustrates an embodiment of a deployable fixation implant 10700 with a deployable member 10450 deployed in a clavicle.

In some embodiments, any of the devices for insertion into a bone for fracture fixation of a clavicle can be inserted using a medial approach. Using some or all steps described herein with at least device 4500, an implant 10000 can be inserted in to bone with a medial approach. FIG. 148 illustrates a straight fixation implant 10000 with the proximal end exposed (or not recessed in bone) using a medial approach according to an embodiment of the present invention. FIG. 149 illustrates a straight fixation implant 10000 with a medial approach with the proximal end recessed or countersunk in the bone according to an embodiment of the present invention. Alternatively, the implant 10000 can be inserted with a lateral approach according to some or all of the steps described with at least device 4500. FIG. 150 illustrates a straight fixation implant with a lateral approach according to an embodiment of the present invention.

While various embodiments of the present invention have been shown and described herein, it will be noted by those skilled in the art that such embodiments are provided by way of example only. Numerous variations, changes, and substitutions may occur to those skilled in the art without departing from the invention. It should be understood that various alternatives to the embodiments of the invention described herein may be employed in practicing the invention. It will be understood that the foregoing is only illustrative of the principles of the invention, and that various modifications, alterations, and combinations can be made by those skilled in the art without departing from the scope and spirit of the invention. Accordingly, it is not intended that the invention be limited, except as by the appended claims.

What is claimed is:

1. A bone fixation device comprising:
an elongate body having a distal threaded fixation region, a proximal hub, a tubular surface, a longitudinal inner lumen, and a wall extending between the tubular surface and the longitudinal inner lumen,
the tubular surface being sized to fit within an intramedullary space within a bone,
a first cannula thread extending along at least a portion of the longitudinal inner lumen;
an actuatable bone engaging mechanism disposed within the elongate body, wherein the bone engaging mechanism comprises a gripper having at least one bendable member such that as the gripper is actuated, the bendable member pivots away from the longitudinal axis of the elongate body and the gripper is deployed from a retracted configuration to an engaged configuration;
an actuator operably connected to the bone engaging mechanism to actuate the bone engaging mechanism from a disengaged configuration to the engaged configuration, wherein the actuator comprises a first ramped surface that is slideably coupled to an interior surface of the bendable member of the gripper, wherein proximally moving the first ramped surface of the actuator causes the first ramped surface to slideably engage the interior surface of said bendable member at an angle thereby pivoting the bendable member of the gripper away from the longitudinal axis away from the elongate body to deploy the bone engaging mechanism into the engaged configuration; and
a compression screw rotationally engageable with the first cannula thread, the compression screw configured to apply an axial compression to the body.

2. The bone fixation device of claim 1,
wherein the bone engaging mechanism comprises at least two bendable members.

3. The bone fixation device of claim 2, wherein the actuator is a guidewire, wherein the longitudinal inner lumen is sized and configured to receive the guidewire.

4. The bone fixation device of claim 3, wherein the guidewire comprises a first guidewire surface at the distal end of the guidewire and the guidewire is disposed at least partially within the flexible-to-rigid portion of the elongate body such that the first guidewire surface is distal to the flexible-to-rigid portion of the elongate body.

5. The bone fixation device of claim 4, the elongate body further comprising a drive member threadably engaged with the guidewire.

6. The bone fixation device of claim 5, wherein by rotating the drive member, the first guidewire surface and the drive member are drawn together thereby applying a compressive force to at least a portion of the elongate body along the longitudinal axis thereby approximating a fracture in a bone.

7. The bone fixation device of claim 2, the elongate body further comprising a drive member threadably engaged with the actuator, the actuator having a first interface surface.

8. The bone fixation device of claim 7, wherein by rotating the drive member, the first interface surface of the actuator and the drive member are drawn together thereby applying a compressive force to at least a portion of the elongate body along the longitudinal axis, thereby approximating a fracture in a bone.

9. The bone fixation device of claim 2, the elongate body further comprising a drive member positioned proximally to the gripper and threadably engaged with the actuator.

10. The bone fixation device of claim 9, wherein by rotating the drive member, the first ramped surface of the actuator and the drive member are drawn together, such that the first ramped surface moves against the bendable member thereby pivoting the bendable member of the gripper away from the longitudinal axis.

11. The bone fixation device of claim 2, wherein the actuator is rotatable with respect to the bone engaging mechanism.

12. The bone fixation device of claim 2 wherein the gripper comprises more than one bendable member, such that as the gripper is actuated each member pivots away from the longitudinal axis.

13. The bone fixation device of claim 2,
wherein the gripper is a first gripper disposed at a distal location within the elongate body, and
the bone engaging mechanism further comprising a second gripper, the second gripper is disposed at a proximal location within the elongate body,
wherein the second gripper comprises at least one bendable member, the bendable member of the second gripper pivoting outside and away from the longitudinal axis of the elongate body when the second gripper is actuated.

14. The bone fixation device of claim 1, further comprising a slot extending through the proximal hub and the longitudinal inner lumen, the slot being configured for orienting a cross screw for anchoring the proximal hub.

15. The bone fixation device of claim 1, further comprising a guidewire, wherein the longitudinal inner lumen is sized and configured to receive the guidewire, wherein the guidewire is a K-wire.

16. A bone fixation device comprising:
an elongate body having a distal threaded fixation region, a proximal hub, a tubular surface, a longitudinal inner lumen, and a wall extending between the tubular surface and the longitudinal inner lumen,
the tubular surface being sized to fit within an intramedullary space within a bone,
a first cannula thread extending along at least a portion of the longitudinal inner lumen;
an actuatable bone engaging mechanism disposed within the elongate body, wherein the bone engaging mechanism comprises a gripper having at least one bendable member such that as the gripper is actuated, the bendable member pivots away from the longitudinal axis of the elongate body and the gripper is deployed from a retracted configuration to an engaged configuration;
an actuator operably connected to the bone engaging mechanism to actuate the bone engaging mechanism from a disengaged configuration to the engaged configuration, wherein the actuator comprises a first ramped surface that is slideably coupled to an interior surface of the bendable member of the gripper, wherein proximally moving the first ramped surface of the actuator causes the first ramped surface to slideably engage the interior surface of said bendable member at an angle thereby pivoting the bendable member of the gripper away from the longitudinal axis away from the elongate body to deploy the bone engaging mechanism into the engaged configuration,
wherein the actuator is a guidewire; and
a compression screw rotationally engageable with the first cannula thread, the compression screw configured to apply an axial compression to the body.

17. The bone fixation device of claim 16, the elongate body further comprising a drive member threadably engaged with the actuator, the actuator having a first interface surface.

18. The bone fixation device of claim 16, wherein by rotating the drive member, the first interface surface of the actuator and the drive member are drawn together thereby applying a compressive force to at least a portion of the elongate body along the longitudinal axis, thereby approximating a fracture in a bone.

19. The bone fixation device of claim 16 wherein the gripper comprises more than one bendable member, such that as the gripper is actuated each member pivots away from the longitudinal axis.

* * * * *